United States Patent [19]

Kleschik et al.

[11] Patent Number: 4,954,163

[45] Date of Patent: Sep. 4, 1990

[54] SUBSTITUTED 1,2,4-TRIAZOLO[1,5-A]PYRIMIDINE-2-SULFONAMIDES, COMPOSITIONS CONTAINING THEM, AND THEIR UTILITY AS HERBICIDES

[75] Inventors: William A. Kleschik, Martinez, Calif.; Robert J. Ehr, Eden Prairie, Minn.; Mark J. Costales, Concord, Calif.; Ben C. Gerwick, III, Clayton, Calif.; Richard W. Meikle, deceased, late of Walnut Creek, Calif., by Diane Meikle; William T. Monte, Corcord, Calif.; Norman R. Pearson, Walnut Creek, Calif.

[73] Assignee: The Dow Chemical Company, Midland, Mich.

[21] Appl. No.: 406,676

[22] Filed: Sep. 13, 1989

Related U.S. Application Data

[60] Division of Ser. No. 261,460, Oct. 21, 1988, Pat. No. 4,886,883, Division of Ser. No. 940,480, Dec. 10, 1986, Pat. No. 4,818,273, which is a continuation-in-part of Ser. No. 768,393, Aug. 22, 1985, abandoned, which is a continuation-in-part of Ser. No. 551,758, Nov. 14, 1983, abandoned.

[51] Int. Cl.$^5$ .................... C07D 487/04; A01N 43/54
[52] U.S. Cl. ........................ 71/92; 544/263; 560/19; 564/442
[58] Field of Search ............................. 544/263; 71/92

[56] References Cited

U.S. PATENT DOCUMENTS

| | | |
|---|---|---|
| 3,637,366 | 1/1972 | Wietelmann et al. . |
| 3,920,690 | 11/1975 | Harrington et al. . |
| 3,923,810 | 12/1975 | Harrington et al. . |
| 4,036,840 | 7/1977 | O'Brien et al. . |
| 4,349,378 | 9/1982 | Cliff et al. . |
| 4,444,774 | 4/1984 | Dusza et al. . |
| 4,605,433 | 8/1986 | Pearson et al. . |
| 4,638,075 | 1/1987 | Kleschick et al. .................. 544/263 |
| 4,727,017 | 2/1988 | Pollet et al. . |
| 4,728,601 | 3/1988 | Rauland et al. . |
| 4,772,720 | 9/1988 | Kleschick et al. .................. 544/263 |
| 4,854,964 | 8/1989 | Jelich .................................. 544/263 |
| 4,859,231 | 8/1989 | Westermann ........................... 71/90 |
| 4,904,301 | 2/1990 | Pearson .............................. 544/263 |

FOREIGN PATENT DOCUMENTS

| | | |
|---|---|---|
| 0142811 | 5/1985 | European Pat. Off. . |
| 27060 | 10/1973 | Japan . |
| 951652 | 3/1964 | United Kingdom . |

OTHER PUBLICATIONS

Broadbent et al., *J. Chem. Soc.*, 1965, pp. 3369–3372.
Okabe et al., *J. Fac. Agr.*, Kyushu University, 19, 91–102 (1975).
Okabe et al., *J. Heterocyclic Chem.*, 20, 735 (1983).
Novinson et al., *J. Med. Chem.*, 25, 420–426 (1982).
Burger, *Medicinal Chemistry*, 2nd Edition, Interscience (1960), p. 43.

*Primary Examiner*—Donald G. Daus
*Attorney, Agent, or Firm*—D. Wendell Osborne; Merlin B. Davey

[57] ABSTRACT

Novel substituted triazolo[1,5-a]pyrimidine-2-sulfonamides, e.g., 5,7-dimethyl-N-(2,6-dichlorophenyl)-1,2,4-triazolo[1,5-a]pyrimidine-2-sulfonamide and their agriculturally acceptable salt are prepared. These compounds and compositions containing them are useful for the control of unwanted vegetation. Novel substituted triazolo[1,5-a]pyrimidine-2-sulfonyl chlorides and substituted anilines and their use as intermediates are also described.

133 Claims, No Drawings

SUBSTITUTED 1,2,4-TRIAZOLO[1,5-A]PYRIMIDINE-2-SULFONAMIDES, COMPOSITIONS CONTAINING THEM, AND THEIR UTILITY AS HERBICIDES

CROSS-REFERENCE TO RELATED APPLICATION

This application is a divisional application of application Ser. No. 261,460, filed Oct. 21, 1988, U.S. Pat. No. 4,886,883 which is a divisional application of application Ser. No. 940,480, filed Dec. 10, 1986, now U.S. Pat. No. 4,818,273, which is a continuation-in-part of application Ser. No. 768,393, filed Aug. 22, 1985, now abandoned, which is a continuation in part of application Ser. No. 551,758, filed Nov. 14, 1983, now abandoned. The disclosure of the specification and claims of application Ser. No. 768,393 is hereby incorporated by reference.

BACKGROUND OF THE INVENTION

In recent years there has been a great deal of effort directed to the development of sulfonamides having herbicidal activity and several of these compounds have reached the stage of commercialization, i.e., chlorosulfuron and sulfometuron methyl. These compounds exhibit both preemergence and postemergence activity against undesirable vegetation and, in addition, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; O,O-diisopropyl phosphorodithioate-S-ester with N-(2-mercaptoethyl)benzenesulfonamide; 3-isopropyl-1H-2,1,3-benzothiadiazin-4(3H)-one-2,2-dioxide; N-[2,4-dimethyl-5-[[(trifluoromethyl)sulfonyl]amino]phenyl]acetamide and 3,5-dinitro-$N^4$, $N^4$-dipropylsulfanilamide.

It has now been found that novel compounds having the formula:

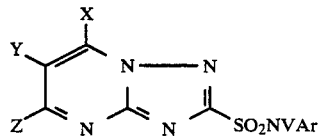

I wherein

Ar represents an aromatic or heteroaromatic ring chosen from among phenyl; 1- or 2-napthyl; 2-, 3- or 4-pyridyl; 2- or 3-thienyl; 2- or 3-furyl; 2-, 4-, or 5-thiazolyl; 2-, 4-, or 5-imidazolyl; 2-, 4-, or 5-oxazolyl; 3-, 4-, or 5-isothiazolyl; 3-, 4-, or 5-isoxazolyl; 3-, 4-, or 5-pyrazolyl; 2-benzthiazolyl; 2-benzoxazolyl; 2-benzimidazolyl: or 1-benztriazolyl; and Ar is unsubstituted except in the case of where Ar is phenyl or Ar is substituted with one to five substituents chosen from among $C_1$-$C_6$ alkyl; benzyl; halo; $C_1$-$C_6$ mono- or polyhaloalkyl; phenyl; phenyl substituted with one or more groups chosen from halo, $C_1$-$C_6$ alkyl, or $C_1$-$C_6$ haloalkyl; hydroxy; $C_1$-$C_6$ alkoxy; $C_1$-$C_6$ mono- or polyhaloalkoxy; phenoxy; phenoxy substituted with one or more groups chosen from halo, $C_1$-$C_6$ alkyl or $C_1$-$C_6$ haloalkyl; 2-pyridyloxy; 2-pyridyloxy substituted with one or more groups chosen from halo, $C_1$-$C_6$ alkyl or $C_1$-$C_6$ haloalkyl; amino; $C_1$-$C_6$ alkylamino; $C_1$-$C_6$ dialkylamino; nitro; $C_1$-$C_6$ alkylthio; $C_1$-$C_6$ polyhaloalkylthio; $C_1$-$C_6$ alkylsulfinyl; $C_1$-$C_6$ polyhaloalkylsulfinyl; $C_1$-$C_6$ alkylsulfonyl; $C_1$-$C_6$ polyhaloalkylsulfonyl; phenylthio; phenylthio substituted with one or more groups chosen from halo, $C_1$-$C_6$ alkyl or $C_1$-$C_6$ haloalkyl; phenylsulfinyl; phenylsulfinyl substituted with one or more groups chosen from halo, $C_1$-$C_6$ alkyl, or $C_1$-$C_6$ haloalkyl; phenylsulfonyl; phenylsulfonyl substituted with one or more groups chosen from halo, $C_1$-$C_6$ alkyl, or $C_1$-$C_6$ haloalkyl; cyano; carboxyl; $C_1$-$C_{10}$ alkoxycarbonyl; phenoxycarbonyl; phenoxycarbonyl substituted with one or more groups chosen from halo, $C_1$-$C_6$ alkyl or $C_1$-$C_6$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_3$-$C_6$ alkenyloxycarbonyl; COON=$C(R^{14})(R^{14})$ wherein each $R^{14}$ independently represents hydrogen, $C_1$-$C_6$ alkyl or phenyl; amino-, $C_1$-$C_6$ alkylamino-, or di $C_1$-$C_6$ alkylaminocarbonyl; $C_1$-$C_{10}$ alkoxysulfonyl; $C_1$-$C_4$ polyhaloalkoxysulfonyl; di $C_1$-$C_6$ alkylaminosulfonyl; formyl; $C_1$-$C_6$ alkylcarbonyl; $C_1$-$C_6$ mono- or polyhaloalkylcarbonyl; phenylcarbonyl; phenylcarbonyl substituted with one or more groups chosen from halo, $C_1$-$C_6$ alkyl or $C_1$-$C_6$ haloalkyl; or $C(R^{15})(R^{15})OR^{16}$ wherein each $R^{15}$ independently represents hydrogen or $C_1$-$C_6$ alkyl and $R^{16}$ represents hydrogen, $C_1$-$C_6$ alkyl, benzyl, phenylcarbonyl or $C_1$-$C_6$ alkylcarbonyl (except in the cases of thio, sulfinyl, and sulfonyl substituents where if one of these substituents is present the other one to four Ar substituents may not be chosen from among the other two; oxycarbonyl substituents where the other one to four Ar substituents may not be chosen from among different oxycarbonyl substituents; or aminocarbonyl substituents where the other one to four Ar substituents may not be chosen from among different aminocarbonyl substituents); X, Y, and Z independently represent hydroxyl; carboxyl; hydrogen; $C_1$-$C_6$ alkyl; $C_1$-$C_6$ mono- or polyhaloalkyl; $C_1$-$C_6$ alkoxy; $C_1$-$C_6$ mono- or polyhaloalkoxy; amino, $C_1$-$C_4$ alkylamino, or di $C_1$-$C_4$ alkylamino; phenyl; phenyl substituted with one or more groups chosen from halo, nitro, $C_1$-$C_6$ alkyl, or $C_1$-$C_6$ mono- or polyhaloalkyl; $C_1$-$C_6$ alkylthio; halo; or two adjacent substituents (i.e., X and Y or Y and Z) are joined together to form a five, six, or seven-membered saturated cyclic structure of carbon atoms or one said carbon atom of X,Y or Y,Z is replaced by a heteroatom chosen from among nitrogen, oxygen, or sulfur (i.e., X,Y or Y,Z is —(CH$_2$)$_n$— wherein n is 3, 4, or 5; or X,Y or Y,Z is —(CH$_2$)$_n$—A—(CH$_2$)$_m$— wherein n is 0–4, the value of m is equal to the ring size minus (n+3) and A is NH, O, or S); and V is H or R and R represents $C_1$-$C_{10}$ alkyl, $C_3$-$C_{10}$ alkenyl, $C_3$-$C_{10}$ alkynyl, phenylalkyl, $C_2$-$C_{10}$ alkanoyl, $C_1$-$C_{10}$ alkoxycarbonyl, phenoxycarbonyl, di $C_1$-$C_6$ alkylaminocarbonyl, $C_1$-$C_6$ alkylsulfonyl, phenylsulfonyl, $C_1$-$C_{10}$ alkoxythiocarbonyl or phenoxythiocarbonyl, wherein alkyl, alkenyl, alkynyl, and alkoxy in each instance is optionally substituted by halo and each phenyl moiety is optionally substituted by one or two groups selected from halo, nitro, $C_1$–$C_4$ alkyl, or $C_1$–$C_4$ haloalkyl; and, when V represents hydrogen, agriculturally acceptable salts thereof are useful pre- and post-emergence herbicides or intermediates for preparing herbicides.

Treatment of the locus of undesired vegetation or weeds with the novel compounds or with compositions containing herbicidally effective amounts of the novel compounds in admixture with one or more inert carriers can be used to obtain broad spectrum or selective weed control depending upon the specific compound and the amount applied. Broadleaf weeds are particularly susceptible to the compounds and control of undesirable vegetation in crops such as wheat, rice, corn, soybeans, and cotton can be achieved. Aquatic vegetation is controlled by the compounds.

In addition, certain novel tetrahydro derivatives of the compounds of general Formula I, which can be represented by Formula II

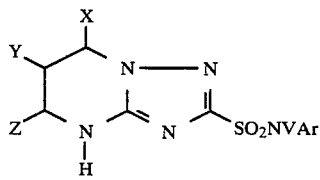

wherein X, Y, A, V, and Ar as defined hereinabove and their agriculturally acceptable salts also exhibit herbicidal activity.

The invention further encompasses certain of the novel substituted triazolo[1,5-a]pyrimidine-2-sulfonyl chlorides and certain of the novel substituted anilines which are useful in preparing the compounds of Formulae I and II.

DETAILED DESCRIPTION OF THE INVENTION

The contemplated aromatic or heteroaromatic ring systems, Ar, of Formula I include substituted or unsubstituted (except for phenyl, which must be substituted) phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidazolyl and 1-benztriazolyl. Typical examples of substituents found on the aromatic or heteroaromatic ring systems may be one, more than one, or a combination of the following: halo, $C_1$–$C_6$ alkyl, benzyl, $C_1$–$C_6$ mono- or polyhaloalkyl, phenyl (optionally substituted with one or more groups chosen from halo, $C_1$–$C_6$ alkyl, or $C_1$–$C_6$ haloalkyl), hydroxy, $C_1$–$C_6$ alkoxy, $C_1$–$C_6$ mono- or polyhaloalkoxy, phenoxy or pyridyloxy (each optionally substituted with one or more groups chosen from halo, $C_1$–$C_6$ alkyl or $C_1$–$C_6$ haloalkyl), nitro, amino, $C_1$–$C_6$ alkylamino, di $C_1$–$C_6$ alkylamino, $C_1$–$C_6$ alkylthio, $C_1$–$C_6$ polyhaloalkylthio, $C_1$–$C_6$ alkylsulfinyl, $C_1$–$C_6$ polyhaloalkylsulfinyl, $C_1$–$C_6$ alkylsulfonyl, $C_1$–$C_6$ polyhaloalkylsulfonyl, phenylthio or phenylsulfinyl or phenylsulfonyl (each phenyl optionally substituted with one or more groups chosen from halo, $C_1$–$C_6$ alkyl, or $C_1$–$C_6$ haloalkyl), cyano, carboxylic acids and derivatives of carboxylic acids (esters derived from available alcohols and amides derived from ammonia or available primary and secondary amines, which can be termed oxycarbonyl and aminocarbonyl substituents) including $C_1$–$C_{10}$ alkoxycarbonyl, phenoxycarbonyl optionally substituted with one or more groups chosen from halo, $C_1$–$C_6$ alkyl, or $C_1$–$C_6$ haloalkyl, alkoxyalkoxycarbonyl wherein the number of carbons in the alkoxyalkoxy fragment ranges from 2–10 and the number of oxygens in the alkoxyalkoxy fragment ranges from 2–4, 2-pyridylmethoxycarbonyl, dialkylaminoalkoxycarbonyl wherein the number of carbons in the dialkylaminoalkoxy fragment ranges from 3–10 and the number of oxygens in the dialkylaminoalkoxy fragment is one, $C_3$–$C_6$ alkenyloxycarbonyl, $COON=C(R^{14})(R^{14})$ wherein each $R^{14}$ independently represents hydrogen, $C_1$–$C_6$ alkyl, or phenyl, $C_1$–$C_{10}$ alkoxysulfonyl, $C_1$–$C_4$ polyhaloalkoxysulfonyl, amino- or $C_1$–$C_6$ alkylamino or di $C_1$–$C_6$ alkylaminocarbonyl, di $C_1$–$C_6$ alkylaminosulfonyl, formyl, $C_1$–$C_6$ alkylcarbonyl; $C_1$–$C_6$ mono- or polyhaloalkylcarbonyl, phenylcarbonyl (optionally substituted with one or more groups selected from halo, $C_1$–$C_6$ alkyl, or $C_1$–$C_6$ haloalkyl), or $C(R^{15})(R^{15})OR^{16}$ wherein each $R^{15}$ independently represents hydrogen or $C_1$–$C_6$ alkyl and $R^{16}$ represents hydrogen, $C_1$–$C_6$ alkyl, benzyl, phenylcarbonyl, or $C_1$–$C_6$ alkylcarbonyl. In cases where one substituent is a thio, sulfinyl, or sulfonyl moiety, other substituents may not be chosen from among the other two. Also, in cases where one substituent is an oxycarbonyl moiety, other substituents may not be chosen from among other oxycarbonyl moieties; and where one substituent is an aminocarbonyl moiety, other substituents may not be chosen from among other aminocarbonyl moieties. Halo in each instance represents fluoro, chloro, bromo, or iodo.

Compounds of Formula I wherein Ar represents substituted phenyl or substituted or unsubstituted 1- or 2-naphthyl; 2-, 3-, or 4-pyridyl; 2- or 3-thienyl; or 3-, 4-, or 5-pyrazolyl are preferred. Those wherein Ar represents substituted phenyl, substituted 1-naphthyl, or substituted 3-, 4-, or 5-pyrazolyl are more preferred.

In the case of the more preferred compounds of Formula I wherein Ar is substituted phenyl, Ar can be depicted as the formula

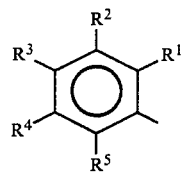

wherein $R^1$, $R^2$, $R^3$, $R^4$, and $R^5$ independently represent each of the Ar substituents (with each of the listed exceptions) noted in the Summary of the Invention and in the foregoing discussion, or hydrogen, provided not all are hydrogen. Of those substituents, the following are preferred. $R^1$ represents F, Cl, Br, I, —$NO_2$, phenyl, phenoxy (optionally substituted by one or more substituents selected from F, Cl, Br, I, $C_1$–$C_4$ alkyl, and $C_1$–$C_4$ haloalkyl), —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8R^8$, —$SO_3R^8$, or $SO_3CH_2CF_3$; $R^2$ and $R^4$ represent H, F, Cl, Br, I, $C_1$–$C_4$ alkyl, —$COOR^7$, or —$OR^8$; $R^3$ is H; and $R^5$ represents H, phenyl, $C_1$–$C_4$ alkyl, $C_1$–$C_4$ alkoxy, F, Cl, Br, I, —$NO_2$, —$CF_3$, —$OCF_3$, —$OCF_2CF_2H$, —OCF$_2$CCl$_2$H, —OCH$_2$CF$_3$, —SCF$_3$, —SCF$_2$CF$_2$H, —SCF$_2$CCl$_2$H, —SOCF$_3$, —SOCF$_2$CF$_2$H, —SOCF$_2$CCl$_2$H, —SO$_2$CF$_3$, —SO$_2$CF$_2$CF$_2$H, —SO$_2$CF$_2$CCl$_2$H, —SR$^6$, —SOR$^6$, —SOR$^6$, —CN, —COOR$^7$, —CONH$_2$, —CONHR$^8$, —CONR$^8$R$^8$, —SO$_3$R$^8$, —SO$_3$CH$_2$CF$_3$, or —CR$^6$R$^6$OR$^6$, wherein R$^6$ represents H or C$_1$–C$_4$ alkyl, R$^7$ represents C$_1$–C$_6$ alkyl, C$_3$–C$_4$ alkenyl, C$_3$–C$_4$ alkynyl, C$_1$–C$_4$ alkoxy C$_2$–C$_3$ alkyl, phenyl (optionally substituted by one or two substituents selected from F, Cl, Br, I, C$_1$–C$_4$ alkyl, and C$_1$–C$_4$ haloalkyl), or 2-pyridylmethyl and R$^8$ represents C$_1$–C$_4$ alkyl.

Compounds of Formula I in which Ar is represented by the formula

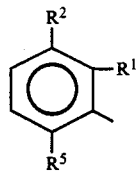

wherein R$^1$ represents C$_1$–C$_4$ alkyl, F, Cl, Br, I, —NO$_2$, —SR$^6$, —SOR$^6$, —SO$_2$R$^6$, —COOR$^7$, or —CF$_3$; R$^2$ represents H, F, Cl, Br, I, C$_1$–C$_4$ alkyl, or —COOR$^7$ and R$^5$ represents H, C$_1$–C$_4$ alkyl, C$_1$–C$_4$ alkoxy, F, Cl, Br, I, —CH$_2$OR$^6$, phenyl, —NO$_2$, or —COOR$^7$ wherein R$^6$ represents C$_1$–C$_4$ alkyl and R$^7$ represents C$_1$–C$_4$ alkyl, C$_3$–C$_4$ alkenyl, C$_3$–C$_4$ alkynyl, 2-ethoxyethyl or 2-pyridylmethyl are most especially preferred.

In the case of the more preferred compounds of Formula I wherein Ar represents 3-, 4-, or 5-pyrazolyl, Ar can be depicted as the formula

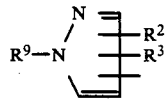

wherein R$^2$ and R$^3$ independently represent each of the substituents (with each of the listed exceptions) noted in the Summary of the Invention and in the foregoing discussions and R$^9$ represents hydrogen or C$_1$–C$_6$ alkyl. Preferred compounds of this type include those wherein R$^2$ and R$^3$ each independently represents H, C$_1$–C$_4$ alkyl, benzyl, F, Cl, Br, I, NO$_2$, CF$_3$, OCF$_3$, C$_1$–C$_4$ alkoxy, C$_1$–C$_{10}$ alkoxycarbonyl, C$_3$–C$_6$ alkenyloxycarbonyl, benzyloxycarbonyl, or amino-, C$_1$–C$_4$ alkylamino- or di C$_1$–C$_4$ alkylaminocarbonyl.

The substituents on the triazolopyrimidine fragment of Formula I are represented by X, Y, and Z. Substituents X, Y, and Z independently represent hydroxyl, carboxyl, hydrogen, C$_1$–C$_6$ alkyl, C$_1$–C$_6$ mono- or polyhaloalkyl, C$_1$–C$_6$ alkoxy, C$_1$–C$_6$ mono- or polyhaloalkoxy, amino, C$_1$–C$_4$ alkylamino, di C$_1$–C$_4$ alkylamino, phenyl (optionally substituted with one or more groups chosen from F, Cl, Br, I, nitro, C$_1$–C$_6$ alkyl, or C$_1$–C$_6$ mono- or polyhaloalkyl), C$_1$–C$_6$ alkylthio, halogen, or two adjacent substituents (i.e. X and Y or Y and Z) are joined together to form a saturated five, six, or seven-membered saturated cyclic structure of carbon atoms or up to one heteroatom chosen from among nitrogen, oxygen, or sulfur (i.e. X,Y or Y,Z is —(CH$_2$)$_n$— wherein n is 3, 4, or 5; or X,Y or Y,Z is —(CH$_2$)$_n$—A—(CH$_2$)$_m$— wherein n is 0–4, the value of m is equal to the ring size minus (n+3) and A is NH, O, or S).

Compounds of Formula I wherein X, Y, and Z independently represent H, F, Cl, Br, I, C$_1$–C$_4$ alkyl, C$_1$–C$_4$ alkoxy, C$_1$–C$_4$ alkylthio, C$_1$–C$_4$ haloalkyl are preferred.

The most highly preferred compounds of the invention are those compounds of Formula I wherein X represents H, CH$_3$, CF$_3$, OCH$_3$, OC$_2$H$_5$, or SCH$_3$; or Y represents H, Cl, or CH$_3$; or Z represents H, CH$_3$, or OCH$_3$; and Ar represents substituted phenyl wherein R$^1$ represents F, Cl, Br, CF$_3$, NO$_2$, or C$_1$–C$_4$ alkoxycarbonyl; or R$^2$ represents H or CH$_3$; or R$^5$ represents H, F, Cl, Br, OCH$_3$, or CH$_3$; and R$^3$ and R$^4$ represent hydrogen and their agriculturally acceptable salts. Additional most highly preferred compounds are those compounds of Formula I wherein X or Y or Z are as defined above and Ar represents 3-, 4-, or 5-pyrazolyl wherein R$^9$ represents H, CH$_3$, or C$_2$H$_5$; or R$^2$ and R$^3$ independently represent H, CH$_3$, CF$_3$, or C$_1$–C$_4$ alkoxycarbonyl and their agriculturally acceptable salts.

The substituent V of Formulae I and II represents any of the following: hydrogen, alkyl, alkenyl, alkynyl, phenylalkyl, substituted phenylalkyl, alkanoyl, alkoxycarbonyl, phenoxycarbonyl, dialkylaminocarbonyl, alkylsulfonyl, phenylsulfonyl, alkylthiocarbonyl, or phenylthiocarbonyl wherein alkyl, alkenyl, and alkynyl are as defined above and each phenyl group is optionally substituted as defined above.

Preferred derivatives of the invention are those compounds of Formula I wherein V represents hydrogen, C$_1$–C$_4$ alkyl, allyl, benzyl, —COR$^{13}$, —CO$_2$R$^{13}$, —CONR$^{13}$R$^{13}$, —CSOR$^{13}$, and —SO$_2$R$^{13}$, wherein R$^{13}$ is C$_1$–C$_6$ alkyl, phenyl (optionally substituted by one or more groups chosen from halo, C$_1$–C$_6$ alkyl, or C$_1$–C$_6$ haloalkyl), or C$_1$–C$_2$ haloalkyl.

The more preferred derivatives of the invention with respect to V are those wherein V represents hydrogen, C$_1$–C$_4$ alkyl, allyl, benzyl, C$_2$–C$_4$ alkanoyl, C$_2$–C$_3$ haloalkanoyl, benzoyl, C$_1$–C$_4$ alkoxycarbonyl, phenoxycarbonyl, di C$_1$–C$_4$ alkylaminocarbonyl, C$_1$–C$_4$ alkoxythiocarbonyl, C$_1$–C$_4$ alkylsulfonyl, C$_1$–C$_2$ haloalkylsulfonyl, or phenylsulfonyl, each phenyl optionally substituted by one or more groups chosen from among halo, nitro, methyl, and trifluoromethyl. The most preferred compounds in this regard are those wherein V represents hydrogen, C$_2$–C$_4$ alkanoyl, C$_1$–C$_4$ alkoxycarbonyl, or di C$_1$–C$_4$ alkylaminocarbonyl.

Substituted 1,2,4-triazolo[1,5-a]pyrimidine-2-sulfonamides and their tetrahydro derivatives behave as acids due to the presence of a sulfonamide moiety proton and consequently form salts when treated with bases. The term "agriculturally acceptable salts" is employed in this application to denote compounds wherein the acidic sulfonamide proton of the compounds of Formulae I and II and replaced by a cation which is not herbicidal, especially to crop plants, nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula

wherein R$^{10}$, R$^{11}$, and R$^{12}$ each, independently represents hydrogen or C$_1$–C$_{12}$ alkyl, C$_3$–C$_{12}$ cycloalkyl, or C$_3$–C$_{12}$ alkenyl, each of which is optionally substituted by one or more hydroxy, $C_1$–$C_8$ alkoxy, $C_1$–$C_8$ alkylthio or phenyl groups. Additionally, any two of $R^{10}$, $R^{11}$, and $R^{12}$ together represent an aliphatic difunctional moiety containing 1 to 12 carbon atoms and up to two oxygen or sulfur atoms. Sodium, potassium, ammonium, and triethanolaminium are most preferred cations.

Specifically preferred compounds include the compounds of Formula I given in the following examples and, except for examples 38 and 39, their agriculturally acceptable salts.

1. 5,7-Dimethyl-N-(2,6-dichlorophenyl)-1,2,4-triazolo[1,5-a]pyrimidine-2-sulfonamide
2. 5-Methyl-N-(2,6-dichlorophenyl)-1,2,4-triazolo[1,5-a]-pyrimidine-2-sulfonamide
3. 5-Methyl-N-(2-bromo-6-chlorophenyl)-1,2,4-triazolo[1,5-a]pyrimidine-2-sulfonamide
4. 5-Methyl-N-(2,6-difluoro-3-methylphenyl)-1,2,4-triazolo[1,5-a]pyrimidine-2-sulfonamide
5. 5-Methyl-N-(2,6-difluorophenyl)-1,2,4-triazolo[1,5-a]-pyrimidine-2-sulfonamide
6. 5,7-Dimethoxy-N-(2,6-dichloro-3-methylphenyl)-1,2,4-triazolo[1,5-a]pyrimidine-2-sulfonamide
7. 5,7-Dimethoxy-N-(2-methoxy-6-trifluoromethylphenyl)-1,2,4-triazolo[1,5-a]pyrimidine-2-sulfonamide
8. 5-Methyl-7-methylthio-N-(2,6-dichlorophenyl)-1,2,4-triazolo[1,5-a]pyrimidine-2-sulfonamide
9. 5-Methyl-7-methylthio-N-(2-trifluoromethylphenyl)-1,2,4-triazolo[1,5-a]pyrimidine-2-sulfonamide
10. 7-Ethoxy-5-methyl-N-(2,6-dichloro-3-methylphenyl)-1,2,4-triazolo[1,5-a]pyrimidine-2-sulfonamide
11. 5,7-Dimethyl-N-(2-chloro-6-phenylphenyl)-1,2,4-triazolo[1,5-a]pyrimidine-2-sulfonamide
12. 5-Methyl-N-(2-methyl-6-nitrophenyl)-1,2,4-triazolo[1,5-a]pyrimidine-2-sulfonamide
13. 5-Methyl-N-(2-chloro-6-methylphenyl)-1,2,4-triazolo[1,5-a]pyrimidine-2-sulfonamide
14. 6-Methyl-N-(2-bromo-6-methylphenyl)-1,2,4-triazolo[1,5-a]pyrimidine-2-sulfonamide
15. 6-N-(2-fluoro-6-chlorophenyl)-1,2,4-triazolo[1,5-a]pyrimidine-2-sulfonamide
16. 6-Methyl-N-(2-chloro-6-methylphenyl)-1,2,4-triazolo-[1,5-a]pyrimidine-2-sulfonamide
17. 6-Methyl-N-(2-methyl-6-nitrophenyl)-1,2,4-triazolo[1,5-a]pyrimidine-2-sulfonamide
18. 7-Ethoxy-5-methyl-N-(2-trifluoromethylphenyl)-1,2,4-triazolo[1,5-a]pyrimidine-2-sulfonamide
19. 7-Methoxy-5-methyl-N-(2,6-dichloro-3-methylphenyl)-1,2,4-triazolo[1,5-a]pyrimidine-2-sulfonamide
20. 7-Ethoxy-5-methyl-N-(2-bromo-6-chloro-3-methylphenyl)-1,2,4-triazolo[1,5-a]pyrimidine-2-sulfonamide
21. 5,7-Dimethoxy-N-(2,6-dibromo-3-methylphenyl)-1,2,4-triazolo[1,5-a]pyrimidine-2-sulfonamide
22. Methyl 3-methyl-N-(5,7-dimethyl-1,2,4-triazolo[1,5-a]pyrimidine-2-sulfonyl)anthranilate.
23. Methyl 3-methyl-N-(7-ethoxy-5methyl-1,2,4-triazolo[1,5-a]pyrimidine-2-sulfonyl)anthranilate.
24. Methyl 3-fluoro-N-(6-chloro-1,2,4-triazolo[1,5-a]-pyrimidine-2-sulfonyl)anthranilate.
25. 5,7-Dimethoxy-N-(2,6-dichlorophenyl)-1,2,4-triazolo[1,5-a]pyrimidine-2-sulfonamide.
26. 7-Methyl-N-(2,6-dichlorophenyl)-1,2,4-triazolo[1,5-a]pyrimidine-2-sulfonamide.
27. N-(2,6-dichlorophenyl)-1,2,4-triazolo[1,5-a]pyrimidine-2-sulfonamide.
28. 7-Ethoxy-5-methyl-N-(2,6-dibromo-3-methylphenyl)-1,2,4-triazolo[1,5-a]pyrimidine-2-sulfonamide.
29. 6-Chloro-N-(2,6-difluorophenyl)-1,2,4-triazolo[1,5-a]pyrimidine-2-sulfonamide.
30. 5-Methyl-7-trifluoromethyl-N-(2-methoxy-6-trifluoromethylphenyl)-1,2,4-triazolo[1,5-a]pyrimidine-2-sulfonamide.
31. 5,7-Dimethyl-N-(1,3-dimethyl-5-trifluoromethyl-4-pyrazolyl)-1,2,4-triazolo[1,5-a]pyrimidine-2-sulfonamide.
32. 5-Methyl-N-(1,3-dimethyl-5-trifluoromethyl-4-pyrazolyl)-1,2,4-triazolo[1,5-a]pyrimidine-2-sulfonamide.
33. 5,7-Dimethyl-N-(1-methyl-4-ethoxycarbonyl-4-pyrazolyl)-1,2,4-triazolo[1,5-a]pyrimidine-2-sulfonamide.
34. 5,7-Dimethoxy-N-(2-chloro-1-naphthyl)-1,2,4-triazolo[1,5-a]pyrimidine-2-sulfonamide.
35. 5-Methyl-N-(2-chloro-1-naphthyl)-1,2,4-triazolo[1,5-a]pyrimidine-2-sulfonamide.
36. 5-Methyl-7-methoxy-N-(2-chloro-1-naphthyl)-1,2,4-triazolo[1,5-a]pyrimidine-2-sulfonamide.
37. 5-Methyl-7-ethoxy-N-(2-chloro-1-naphthyl)-1,2,4-triazolo[1,5-a]pyrimidine-2-sulfonamide.
38. 5-Methyl-N-(2-methylpropanoyl)-N-(2,6-difluorophenyl)-1,2,4-triazolo[1,5a]pyrimidine-2-sulfonamide.
39. 5.Methyl-N-acetyl-N-(2,5-dichlorophenyl)-1,2,4-triazolo[1,5-a]pyrimidine-2-sulfonamide.

Specially preferred compounds of Formula II include the following and their agriculturally acceptable salts:
1. 5,7-Dimethyl-N-(2,6-dichlorophenyl)-4,5,6,7-tetrahydro-1,2,4-triazolo[1,5-a]pyrimidine-2-sulfonamide
2. 5-Methyl-N-(2,6-dichlorophenyl)-4,5,6,7-tetrahydro-1,2,4-triazolo[1,5-a]pyrimidine-2-sulfonamide
3. 5,7-Dimethyl-N-(2-trifluoromethylphenyl)-4,5,6,7-tetrahydro-1,2,4-triazolo[1,5-a]pyrimidine-2-sulfonamide Furthermore, in the compounds corresponding to general Formula II, the existence of stereoisomerism is possible. For example, stereoisomeric relationships exist when at least one of substituents X, Y, and Z does not equal hydrogen. When only one of substituents X, Y, and Z does not equal hydrogen, the compound of Formula II may exist as a mixture of enantiomers. One enantiomer will be designated as having the R-configuration and the other will be designated as having the S-configuration. Each enantiomer may exhibit different levels of herbicidal activity. When two or more of substituents X, Y, or Z in Formula II do not equal hydrogen, the material may exist as a mixture of diastereomers. For example, when two substituents among X, Y and Z do not equal hydrogen, the compound may exist as two diastereomers. When all three of substituents X, Y and Z do not equal hydrogen the compound may exist as four diastereomers. In addition all of the diastereomers described above exist as a mixture of two enantiomers. All of the stereoisomers described above, diastereomers and their enantiomeric pairs, may exhibit different levels of herbicidal activity.

The synthesis of compounds of general Formula I can be carried out in a straightforward manner as illustrated in Scheme I. Reaction of a sulfonyl chloride of Formula IV with the appropriate aromatic (substituted or unsubstituted) or heteroaromatic (substituted or unsubstituted) amino compound ($ArNH_2$) under basic conditions yields the desired product of Formula I. A wide range of solvents may be employed (i.e., $CH_2Cl_2$, CH₃CN or pyridine) at temperatures ranging from 0° C. to reflux. Bases which serve as catalysts include pyridine, 4-dimethylaminopyridine and tertiary alkylamines such as triethylamine or N-methylmorpholine. Generally the amino compound serves as the limiting reagent. Molar ratios of between 1.1 and 1.0 for the sulfonyl chloride to amino compound and molar ratios of between 5.0 and 1.1 for the base to amino compound are used most often. A wide range of concentrations may be employed (i.e., 0.1-5M). Generally concentrations in the range of 0.5-2M are used to give a homogeneous reaction which proceeds at a convenient rate. In addition it is sometimes advantageous to use a combination of pyridine derived base catalysts and tertiary amine bases. The use of pyridine as a solvent is convenient as the pyridine can serve both as the solvent and the catalyst in the transformation.

reaction mixture is generally maintained between −20° C. and 25° C. during the course of the chlorine addition. Most preferably, temperature ranges between −20° C. and 0° C. are employed to minimize unwanted side reactions such as hydrolysis of the compound of Formula IV to the corresponding sulfonic acid. Alternatively, the mercaptan of Formula V may be suspended in a two phase system of aqueous acid (i.e., HCl) and an organic solvent (i.e., CH₂Cl₂) and treated with sodium hypochlorite. This serves to convert the mercaptan to the sulfonyl chloride in a reproducibly good yield. The solubility of the product in the organic phase serves to protect it from hydrolysis to the sulfonic acid. Again, temperatures in the range of −20° C. to 25° C. are employed with temperatures in the range of −5° C. to 5° C. being most generally used.

SCHEME II

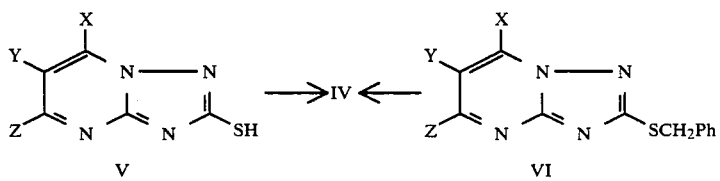

SCHEME I

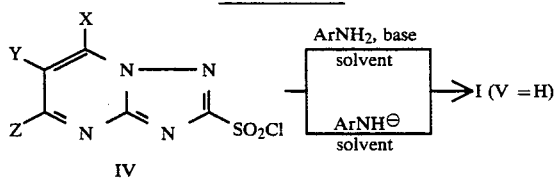

An alternative route to compounds of Formula I is also illustrated in Scheme I. In cases where the amino compound (ArNH₂) is less reactive (less nucleophic) is it advantageous to prepare a metal derivative of the amino compound by treatment with a strong base. The metal derivatives are generally prepared in ether solvents (i.e., THF) using strong bases such as alkali metal alkyls (i.e., n-BuLi) or alkali metal hydrides (i.e., NaH or KH) at temperatures ranging from −80° C. to 0° C. The amide anion thus generated in situ can be reacted with a sulfonyl chloride of Formula IV to yield the desired product of Formula I. Generally, molar ratios of the starting amino compound to sulfonyl chloride of 2 to 3 are used to ensure complete reaction.

The method of U.S. application Ser. No. 795,818, filed on Nov. 11, 1985, which method employs the condensation of N-trialkylsilylanilines with sulfonyl chlorides of Formula IV to produce compounds of Formula I, can also be used and is especially valuable in laboratory operations.

Sulfonyl chlorides of Formula IV represent key intermediates in the synthesis of sulfonamides of Formula I. Sulfonyl chlorides of Formula IV may be prepared according to routes outlined in Scheme II. Mercaptans of Formula V may be converted to sulfonyl chlorides of Formula IV by treatment with chlorine in an aqueous acidic medium. Generally the medium would be aqueous acetic acid or aqueous HCl. The temperature of the As an alternative, it is sometimes preferred to prepare sulfonyl chlorides of Formula IV from benzyl sulfides of Formula VI (Scheme II). Reaction conditions as described above for the conversion of mercaptans to sulfonyl chlorides are operable. This procedure yields by-products containing benzyl residues which are generally removed by washing the product with water and/or an appropriate organic solvent and drying in vacuo.

Compounds of general Formulae V or VI may be prepared by routes illustrated in Scheme III. Some derivatives of Formulae V and VI are known materials (i.e., V: X=Z=Me, Y=H and VI: X=Z=Me, Y=H) prepared by methods described in J. Med. Chem., 25, 420 (1982). Compounds of Formula V are prepared directly by reaction of a 1,3-diketone with commercially available 3-amino-5-mercapto-1,2,4-triazole of Formula VII in glacial acetic acid as a solvent. Generally the reaction is performed at reflux. Alternatively, the compound of Formula VII may be benzylated with benzyl chloride using an alkali earth metal alkoxide (i.e., NaOH) as a base to yield the known benzyl sulfide of Formula VIII (J. Heterocycl. Chem., 12, 1187 (1975)). The benzyl sulfide of Formula VIII can be condensed with not only 1,3-diketones but also β-keto esters, malonic esters, malonaldehyde, β-ketoaldehydes or α-formyl esters or derivatives thereof (i.e., acetals or enol ethers) to yield products of Formula VI as illustrated in Table A. Generally these reactions can be carried out under acidic conditions (i.e., glacial acetic acid as a solvent) or basic conditions (i.e., NaOR in ROH wherein R is C₁ to C₄ alkyl). In cases where the X, Y and Z substituents in Formula VI are derived from a 1,3-diketone, compounds of Formula VI may be prepared by benzylation of a compound of Formula v using an appropriate base (i.e., NaOH) and benzyl chloride in a variety of solvents (i.e., water, methanol, ethanol, THF, dioxane, acetonitrile, DMF or DMSO or combinations of the aforementioned).

SCHEME III

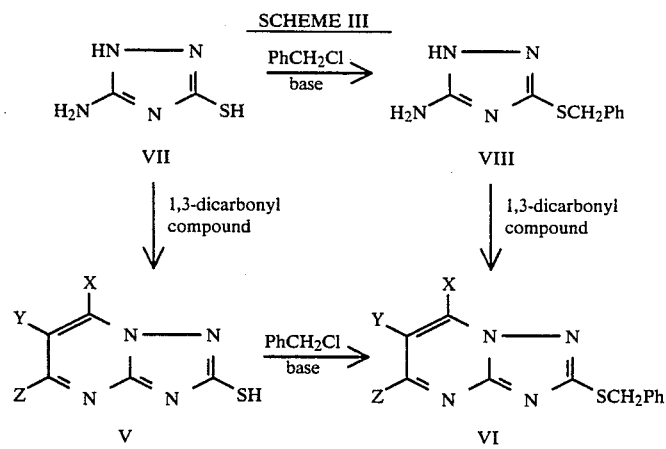

TABLE A

| 1,3-Dicarbonyl Compound or Derivative | Reaction Conditions | Compound of Formula V or VI | | |
|---|---|---|---|---|
| | | X | Y | Z |
| R-C(O)-CHR'-C(O)-R'' | acid | R | R' | R'' |
| R-C(O)-CHR'-CH(OR)(OR) | acid | H | R' | R |
| R-C(O)-CHR'-CH(OR)(OR) | base | R | R' | H |
| R-C(O)-CHR'-COOR | acid | OH* | R' | R |
| RO-CH(OR)-CHR'-CH(OR)(OR) | acid | H | H | H |
| RO₂C-CHR'-CO₂R | base | OH | R' | OH |

*In this structural representation, as well as others bearing OH groups at 5- or 7-positons of the 1,2,4-triazolo[1,5-a] pyrimidine, the enol form has been depicted. Clearly this is the equilibrium with the various keto forms.

In instances where the 1,3-dicarbonyl compound is unsymmetrical, the possibility of obtaining two different isomers from condensation with Compound VIII exists. In general, under acidic conditions the exocyclic nitrogen in Compound VIII is the first to condense with the 1,3-dicarbonyl compound. Under basic conditions the endocyclic nitrogen in Compound VIII is sometimes more reactive. Consequently, in situations where a clear difference in reactivity of the two carbonyl functionalities in the 1,3-dicarbonyl compound exists, some measure of regiochemical control may be achieved by choice of reaction conditions (i.e., entries 2 and 3 in Table I).

To prepare the alternative regioisomer to that depicted in entry 4 in Table A (i.e., VI: X=R, Y=R', and Z=OH) a route illustrated in Scheme IV was followed.

Compound VIII was condensed with 2,3-dibromoalkylcarboxylic acid esters to yield a compound of Formula VI (VI: X=R, Y=R', Z=OH). The reaction is generally carried out in refluxing pyridine.

SCHEME IV

HN—N
‖
H₂N—C—N=C—SCH₂Ph
   N

VIII

+ R'-CBr-CR(Br)-COOR →(pyridine)

R-C=C(R')
   |       
HO-C    N—N
    \\  ‖  ‖
     N—C—N—C—SCH₂Ph

VI

An additional route to compounds of Formula VI involves condensation of Compound VIII with methanaminium compounds of Formula IX as illustrated in Scheme V. The condensation is usually carried out by reaction in refluxing glacial acetic acid and is useful in the synthesis of a number of 6-substituted 1,2,4-triazolo[1,5-a]pyrimidines.

SCHEME V

HN—N
‖
H₂N—C—N=C—SCH₂Ph
   N

VIII

+

Me₂N—CH=C(Y)—CH=N⁺Me₂  X⁻

IX

→(HOAc)

SCHEME V -continued

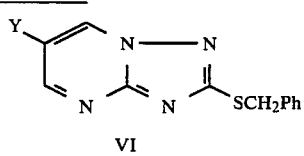

In the synthetic routes listed above, compounds of Formula VI where X and/or Z is OH are capable of undergoing further transformation (Scheme VI). For example, treatment of a compound of Formula VI (X and/or Z=OH) with phosphorus oxychloride yields the corresponding compound of Formula VI (X and/or Z=Cl). The reaction is generally carried out at reflux in neat phosphorus oxychloride or with phosphorous oxychloride in a solvent (i.e., acetonitrile). Compounds of Formula VI (X and/or Z=Cl) can be further reacted with nucelophiles (i.e., NaOCH$_3$, MeMgBr) to yield compounds of Formula VI (X and/or Z=OCH$_3$ or CH$_3$, respectively). In addition, compounds of Formula VI (X and/or Z=Cl) may be reduced to afford other compounds of Formula VI (X and/or Z=H). An effective reducing agent for this type of transformation is zinc-copper couple in the presence of acid.

SCHEME VI

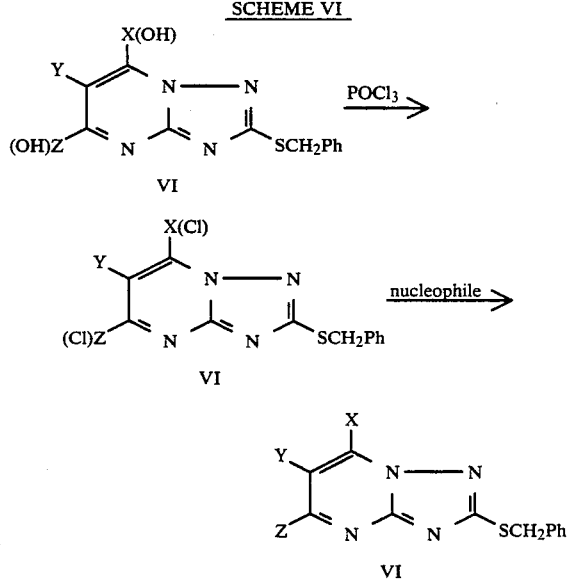

Other compounds of the present invention are best prepared in a manner illustrated in Scheme VII. Compounds such as are represented by Formula XI wherein X$^1$ and Z$^1$ are independently represented by hydrogen, C$_1$-C$_4$ alkyl, alkylthio, arylthio, or amino (including mono- and disubstituted alkylamino), can be prepared by this method. The method involves the reaction of a compound of Formula X wherein X and Z independently represent hydrogen, C$_1$-C$_4$ alkyl or an appropriate leaving group with a nucleophile in a suitable solvent. This procedure effects the substitution of the leaving group by the nucleophilic unit. A representative leaving group that is effective in this process is trifluoroethoxide (—OCH$_2$CF$_3$). Representative nucleophiles for this process include alkali metal salts of alkyl mercaptans, alkali metal salts of aryl mercaptans, ammonia, primary and secondary alkylamines, and alkali metal salts of hydroxides. These nucleophiles result in the displacement of the leaving group (X and/or Z) in Formula X to produce a compound of Formula XI containing X$^1$ and/or Z$^1$ represented as alkylthio, arylthio, amino, mono- and disubstituted alkylamino, or hydroxyl, respectively. Suitable solvents for this transformation include polar aprotic solvents (i.e., DMSO, DMF), alcohols and water. Suitable reaction temperatures range from 0° C. to 100° C. although the temperature of the reaction is usually not critical. Reaction temperatures of 20° C. to 30° C. are most frequently employed.

SCHEME VII

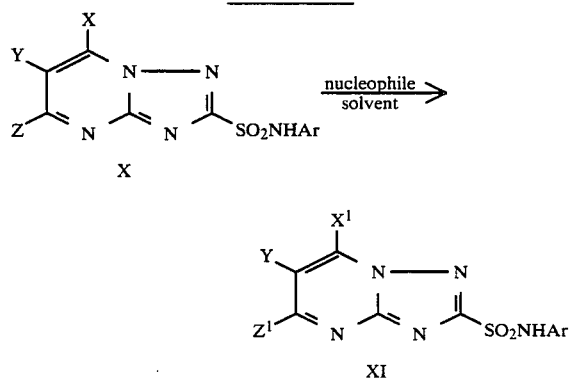

In addition certain compounds of the present invention containing a halogen in the 6-position on the 1,2,4-triazolo[1,5-a]pyrimidine ring system may be prepared by halogenation of the corresponding 6-unsubstituted compound. This is illustrated in Scheme VIII. In general, N-halo-succinimide derivatives are the halogenating agents of choice. The reactions are often performed in acid solvents at temperatures ranging from room temperature to 150° C.

SCHEME VIII

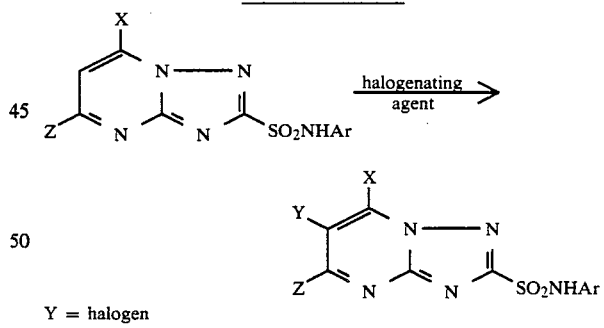

Y = halogen

Another method to prepare the compounds of the present invention is illustrated in Scheme IX. Compounds of general Formula I can be oxidized to yield compounds of Formula XII. Oxidizing agents capable of this transformation include various transition metal oxidants such as derivatives of hexavalent chromium (Cr$^{VI}$) or heptavalent manganese (<m$^{VII}$), organic peracids or peroxides. Oxidizing agents such as potassium permanganate, chromium trioxide, peracetic acid and hydrogen peroxide are frequently employed. Preferred conditions for the conversion of compounds of Formula I to compounds of Formula XII involve reaction of the former with two to five molar equivalents of potassium permanganate in 0.1N to 1.0N aqueous alkali metal hydroxide (i.e., NaOH or KOH) as a solvent. The reaction may be run at temperatures ranging from ambient temperature to reflux. Most commonly the reaction is run at 50° C. to 60° C. The product of this reaction (Formula XII) can be hydrolyzed to a compound of Formula XIII by treatment with aqueous acid in an organic co-solvent. Typical acids include hydrochloric acid, sulfuric acid, acetic acid, trifluoroacetic acid or methanesulfonic acid. Appropriate organic co-solvents include acetone, methyl ethyl ketone, ethanol, acetonitrile or tetrahydrofuran. Lastly, compounds of Formula XIII can be reconverted to a compound of general Formula I by cyclization with a 1,3-dicarbonyl compound or an equivalent of a 1,3-dicarbonyl compound. The conditions for this cyclization, the structural requirements for the 1,3-dicarbonyl compound or an equivalent and structural considerations for the product are as described previously for the conversion of compounds of Formulae VII and VIII to compounds of Formula V and VI.

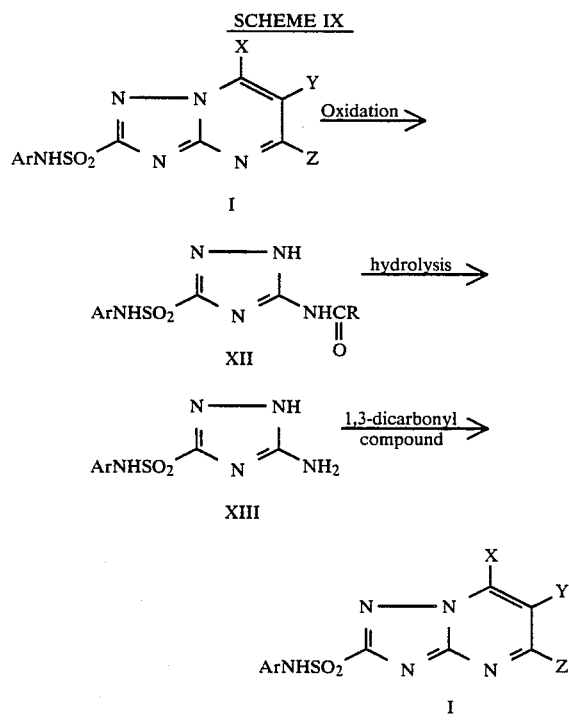

The method for the preparation of compounds of Formula I as illustrated in Scheme IX is employed advantageously in certain situations. Various functional groups present on the 1,2,4-triazolo[1,5-a]pyrimidine ring system (X, Y and Z) of Formula I which impart useful herbicidal activity can only be produced in low yield by previously described routes. The primary cause for the low yield in the previously described routes is the incompatability of the function group or the ring system which bears the functional group to the conditions required to form the required sulfonyl chlorides of Formula IV. Examples of substituents (X, Y and Z) present in compounds of Formula I which are advantageously prepared by the method outlined in Scheme IX include H, halo (F, Cl, Br and I), hydroxy, $C_1$–$C_4$ alkyl, $C_1$–$C_4$ alkoxy, $C_1$–$C_4$ alkylthio, $C_1$–$C_4$ alkysulfinyl, $C_1$–$C_4$ alkylsulfonyl, $C_1$–$C_4$ mono- or polyhaloalkyl, $C_1$–$C_4$ mono- or polyhaloalkoxy, $C_1$–$C_4$ polyhaloalkylthio, $C_1$–$C_4$ polyhaloalkylsulfinyl, $C_1$–$C_4$ polyhaloalkylsulfonyl, amino, $C_1$–$C_4$ mono- or dialkylamino, phenyl, substituted phenyl, phenoxy, substituted phenoxy, phenylthio, phenylsulfinyl, phenylsulfonyl, substituted phenylthio, substituted phenylsulfinyl, substituted phenylsulfonyl, carboxyl, and carboxyl derivatives such as esters derived from $C_1$–$C_4$ alcohols. The substituents X and Y or Y and Z can also be joined to form a ring containing a total of five to seven atoms. This ring may contain heteroatoms (i.e., nitrogen, oxygen or sulfur), unsaturation (i.e., —CO— or —C=C—) or a halogen substituent.

The compounds of Formula I which are most advantageously prepared by the method outlined in Scheme IX contain substituents (X, Y and Z) which are one or more of the following: H, halo (F, Cl, Br and I), $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, $C_1$–$C_4$ mono or polyhaloalkyl, $C_1$–$C_4$ mono- or polyhaloalkoxy, $C_1$–$C_4$ polyhaloalkylthio, $C_1''C_4$ polyhaloalkylsulfinyl, $C_1$–$C_4$ polyhaloalkylsulfonyl, amino and $C_1$–$C_4$ mono- or dialkylamino.

Specifically preferred substituent patterns of Formula I which may be prepared by the method outlined in Scheme IX are the following:
 1. X=Y=Z=H
 2. X=CF$_3$, Y=H and Z=CH$_3$
 3. X=Z=CF$_3$ and Y=H
 4. X=Cl, Y=H and Z=CH$_3$
 5. X=OCH$_3$, Y=H and Z=CH$_3$
 6. X=OC$_2$H$_5$, Y=H and Z=CH$_3$
 7. X=SCH$_3$, Y=H and Z=CH$_3$ The starting material of Formula I in the reaction sequence of Scheme IX may contain one or more of the following substituents: H, halo FF, Cl, Br and I) and $C_1$–$C_4$ alkyl. The aromatic ring in these starting materials and intermediates is defined as described previously for Formula I. The R group in intermediates of Formula XII may be H or CH$_3$.

Compounds of the present invention represented by Formula I wherein V is R are derived from compounds represented by Formula I wherein V is H as illustrated in Scheme X. The derivatization procedure involves treatment of compounds of Formula I wherein V is H with a base in a suitable solvent followed by the introduction of an appropriate electrophilic derivatizing reagent. From this process compounds of Formula I wherein V is R can be isolated in good yields. Suitable bases include tertiary alkylamines (i.e., triethylamine), pyridine, 4-dimethylaminopyridine, alkali metal carbonate (i.e., sodium carbonate or potassium carbonate) and alkali metal alkoxides (i.e., sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloroformates, aryl chloroformates, N,N-dialkylcarbamoyl chlorides, alkylsulfonyl chlorides, arylsulfonyl chlorides, alkyl chlorothioformates

(i.e., ClCOR)

and aryl chlorothioformates

SCHEME X

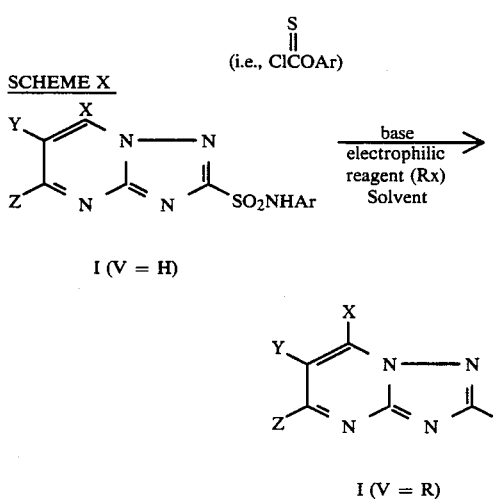

SCHEME XI

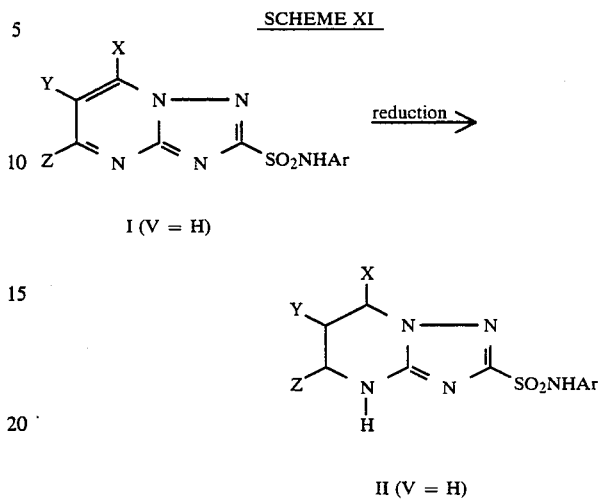

Agriculturally acceptable salts of the compounds of Formula I can be prepared by treatment of compounds of Formula I with a metal hydroxide such as sodium hydroxide, potassium hydroxide, or magnesium hydroxide, or an amine such as ammonia, dimethylamine, triethylamine, triethanolamine, diallylamine, 2-butoxyethylamine, morpholine, cyclododecylamine, or benzylamine. The reactions are typically carried out in a solvent in which one or more of the compounds of Formula I, the base, and the agriculturally acceptable salt product has appreciable solubility. Water is a preferred solvent. The agriculturally acceptable salts can be recovered from the reaction mixtures obtained by conventional means such as filtration or evaporation of the volatile components, or the reaction mixtures can be used without isolation.

In typical operations, a compound of Formula I is placed in water or other suitable solvent and an approximately equimolar quantity or an excess of base is added. The solution obtained is combined with agriculturally acceptable adjuvants and used as a herbicide.

The salts of this invention are additionally useful for purifying the compounds of Formula I. In typical operations, a contaminated compound of Formula I is combined with an excess of base in water to obtain a solution of the salt. Water insoluble contaminants are then removed by filtration or extraction with an immiscible organic solvent, such as methylene chloride or ether, and the compound of Formula I is regenerated by the addition of an acid and recovered by filtration, centrifugation, or the like. Sodium hydroxide and ammonium hydroxide are preferred bases and hydrochloric acid a preferred acid in these procedures.

Compounds of the present invention represented by Formula II are also derived from compounds represented by Formula I as illustrated in Scheme XI. The general process involves the reduction of compounds of general Formula I with an appropriate reducing agent in a suitable solvent to yield compounds of general Formula II. Reducing agents which are effective include metal hydrides (i.e., sodium borohydride) in the presence of acids (i.e., methanesulfonic acid) and hydrogen in the presence of a normal hydrogenation catalyst (i.e., palladium on carbon). For reductions with metal hydrides, polar aprotic solvents (i.e., DMSO) are most frequently used. For reductions using hydrogen and a catalyst, alcohols (i.e., ethanol) are most frequently employed as solvents.

The majority of the amino compounds (ArNH$_2$) utilized to prepare the compounds of the present invention as illustrated in Scheme I were obtained from commercial sources or prepared by known literature procedures or minor modifications of literature procedures. Others are novel compounds made by novel processes.

A number of the amino compounds (ArNH$_2$) used to prepare the compounds of the present invention are derivatives of anthranilic acid. Many of these compounds can be prepared according to conventional methods described by S. J. Holt et al., Royal Soc. Proc. Sec. B, 148, 481 (1958), P. W. Sadler et al., J. Am. Chem. Soc., 78, 1251 (1956), and G. Reissenweber et al., U.S. Pat. No. 4,310,677 (1982). Other anthranilic acid derivatives can be prepared by standard derivatizations (i.e., conversion to esters and amides) of known substituted or unsubstituted 2-nitrobenzoic acids followed by reduction of the nitro group as represented in Scheme XII.

SCHEME XII

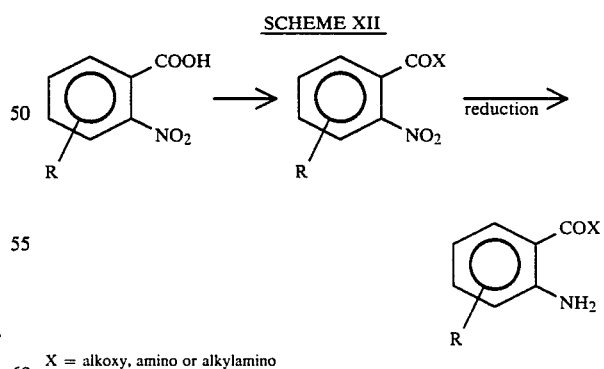

X = alkoxy, amino or alkylamino

A number of the amino compounds are prepared by reduction of anthranilic acids or esters and subsequent derivatization of the reduction product. This is outlined in Scheme XIII. The carbinol reduction products may be derivatized by reaction with base and various electrophiles (i.e., alkyl halides and carboxylic acid chlorides).

SCHEME XIII

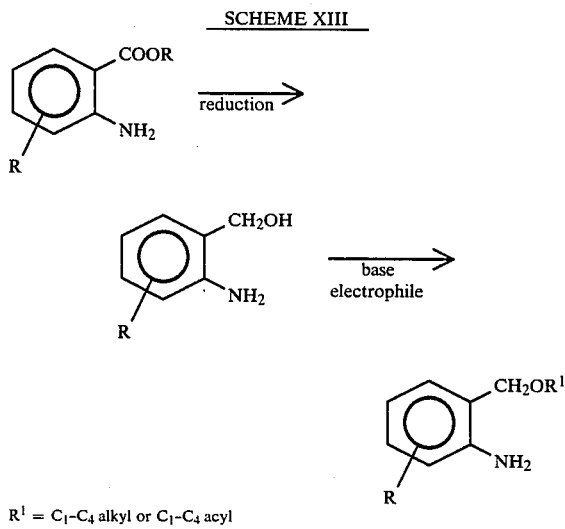

R¹ = $C_1$-$C_4$ alkyl or $C_1$-$C_4$ acyl

A large number of the amino compounds utilized in the preparation of the compounds of this invention contain halogen substituents ortho to the amino group Many of these compounds were prepared by halogenation of the corresponding material bearing no substituent in the ortho position according to a general procedure described by R. S. Neale et al., *J. Org. Chem.*, 29, 3390 (1964). The starting materials for these halogenations are commercially available or known in the literature (i.e., British Pat. No. 695,164 (1953); D. S. Noyce et al., *J. Org. Chem.* 26, 1732 (1961) and U.S. Pat. No. 3,813,234 (1974)). In certain instances to facilitate the transformation and insure ortho selectivity in the halogenation process the starting materials for the halogenation were acetamide derivatives (ArNHCOCH₃) or derivatives containing groups (i.e., Br) which would block halogenation at other positions in the molecule (i.e., para to the amino group). Following halogenation the acetamide derivatives were hydrolized back to the desired amino compound and the blocking groups were removed (i.e., Br in the para position was selectively removed by reduction in the presence of Cl in the ortho position). Other chlorine and bromine substituted amino compounds were prepared by known procedures (i.e., U.S. Pat. No. 4,188,342 (1980); C. R. Rasmussen et al. *J. Med. Chem.*, 21, 1044 (1978); H. E. Dadswell et al. *J. Chem. Soc.*, 1102 (1927); U.S. Pat. No. 3,813,234 (1974) and P. B. D. DeLaMare and J. H. Ridd, "Aromatic Substitution, Nitration and Halogenation", Academic Press, New York (1959), p. 106.

A number of the amino compounds used as starting materials for the compounds of this invention contain sulfur substituents in the ortho position These were prepared using known procedures (i.e., R. R. Gupta et al. *Heterocycles*, 16, 1527 (1981) and J. P. Chupp et. al., *J. Org. Chem.*, 49, 4711 (1984)). In some cases alkylthio groups were present and these were synthesized by alkylation of the corresponding mercaptan. Compounds having alkyl or aryl sulfinyl or sulfonyl groups were synthesized by oxidation of the appropriate alkyl or arylthio groups.

The starting amino compounds containing amino, alkylamino, aryloxy or pyridyloxy groups were prepared by catalytic reduction of the corresponding nitro compounds. The amino, alkylamino, aryloxy or pyridyloxy group were usually introduced via displacement of a leaving group ortho to the nitro group in the requisite nitrobenzene.

Other starting amino compounds were prepared by procedures involving metalation of the aromatic ring of N-substituted derivatives (i.e., t-butoxycarbonyl derivatives) of an aromatic amino compound followed by the resulting organometallic reagent with an electrophile. This general procedure is described in H. Gschwend, *Org. Reactions*, Vol. 20, 1–360 (1979) and is outlined in Scheme XIV. Suitable metalating agents are organolithium reagents (i.e., n-butyl lithium or t-butyl lithium). Typical electrophiles include alkyl halides (i.e., methyl iodide, ethyl iodide), aldehydes (i.e., formaldehyde, acetaldehyde), ketones (i.e., acetone), alkyl or aryl sulfonyl halides (i.e., methylsulfonyl chloride), and dialkyl or diaryl disulfides (i.e., dimethyl disulfide). These electrophiles are useful for the introduction of alkyl, hydroxyalkyl and alkylthio or arylthio groups to the position ortho to the amino group. After the reaction of the organometallic intermediate with the electrophile the nitrogen substituent is removed by hydrolysis.

SCHEME XIV

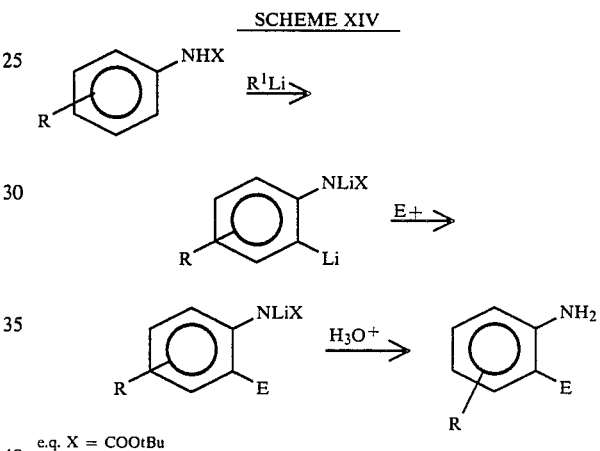

e.q. X = COOtBu

Other aromatic amino compounds used to prepare compounds of the present invention are prepared by conversion of carboxylic acid groups or derivatives of carboxylic acid groups to amino groups by standard methodology. Such a transformation is illustrated in Scheme XV and described in *J. Royal. Netherlands Chem. Soc.*, 97, 53 (1978)

Scheme XV

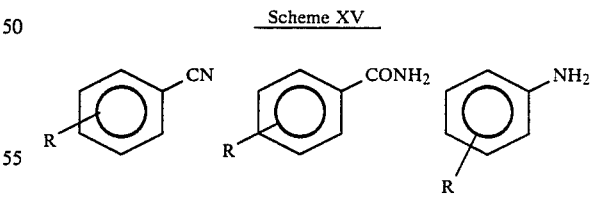

Other amino compounds such as those which are heteroaromatic amino compounds are prepared by known procedures such as those described in *Rec. Trav. Chim.*, 69, 673 (1950), T. Talik et al., *Chem. Abstracts*, 59: 8698a (1963) and L. C. Behr and R. Fusco In "Heterocyclic Compounds38", A. Weissberger, Ed. Vol 22, Interscience Publishers, New York (1967), pp. 3–174 or straightforward modification of the art described above.

Other amino compounds used to prepare compounds of the present invention are prepared by direct metalation of the aromatic ring. This is illustrated schematically in Scheme XVI. An aromatic ring bearing one to three substituents on the ring may be metalated with an alkyl lithium reagent (i.e. n-butyl lithium, s-butyl lithium or -t-butyl lithium) to form an aryl lithium intermediate. This reaction is most frequently carried out in an ethereal solvent (i.e. diethyl ether, tetrahydrofuran or 1,2-dimethoxyethane) at temperature ranging from 78° C. to ambient temperature. It is sometimes advantageous to perform the metalation reaction in the presence of additives such as tetramethylethylenediamine. The aryl lithium reagent is generated in situ and is reacted with carbon dioxide followed by protonation of the resultant carboxylate to form the carboxylic acid. The carboxylic acid can then be converted to the corresponding amino compound by standard methodology of the Hoffman, Curtius, Lossen and Schmidt reactions.

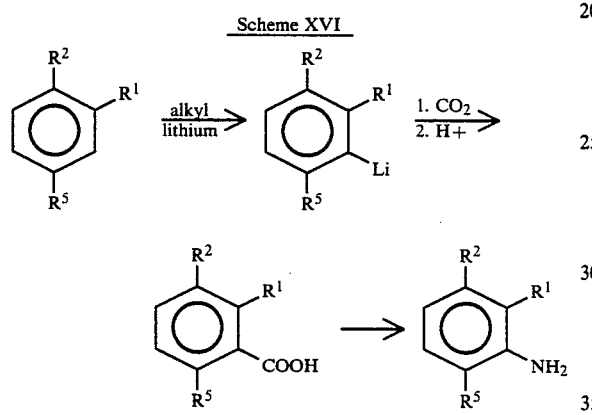

Scheme XVI

The substituents ($R^1$, $R^2$, and $R^5$), which are operable in the process illustrated in Scheme XVI are as follows: $R^1$, $R^2$, and $R^5$ may be chosen from among H, F, Cl, Br, I, $C_1$-$C_4$ alkyl, $C_1$-$C_4$ mono- or polyhaloalkyl or $C_1$-$C_4$ alkoxy. Most preferred substituents are $R^2$ is equal to H or $C_1$-$C_4$ alkyl; $R^1$ and $R^5$ are equal to F, Cl, $C_1$-$C_4$ mono- or polyhaloalkyl or $C_1$-$C_4$ alkoxy.

The intermediate carboxylic acid formed as illustrated in Scheme XVI or derivatives of the carboxylic acid (i.e. esters and amides) can be utilized to prepare other amino compounds which are useful in the preparation of compounds of Formula I of the present invention. This process is illustrated in Scheme XVII. When the carboxylic acid product contains a leaving group such as a F, Cl or Br atom at an adjacent position, the carboxylic acid may be converted to a suitable derivative and the halogen may then be replaced by displacement with a suitable nucleophile. Nucleophiles which are useful in this case include ammonia, $C_1$-$C_4$ monoalkylamines, $C_1$-$C_4$ dialkylamines, $C_1$-$C_4$ alkali metal alkoxides, $C_1$-$C_4$ alkali metal mono- or polyhaloalkoxides or $C_1$-$C_4$ alkali metal mercaptides. The use of these nucleophiles serves to replace the halogen substituent with amino, $C_1$-$C_4$ monoalkylamino, $C_1$-$C_4$ dialkylamino, $C_1$-$C_4$ alkoxy, $C_1$-$C_4$ mono- or polyhaloalkoxy or $C_1$-$C_4$ alkylthio respectively. The resultant products of the nucleophilic displacement can be converted to the corresponding amino compound by standard methodology of the Hoffman, Curtius, Lossen and Schmidt reactions.

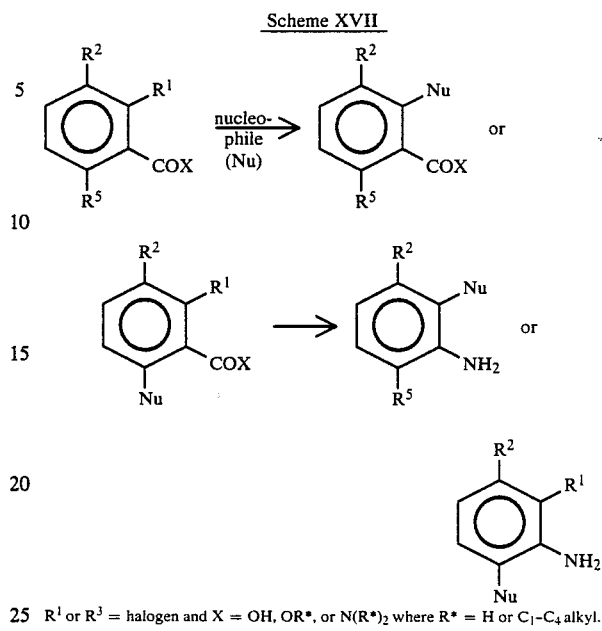

Scheme XVII $R^1$ or $R^3$ = halogen and X = OH, OR*, or N(R*)$_2$ where R* = H or $C_1$-$C_4$ alkyl.

Other amino compounds which are useful in the preparation of compounds of Formula can be prepared as illustrated in Scheme XVIII. The starting material for this procedure is 2,6-difluoroaniline. The amino group of the aniline is protected with a silyl protecting group according to a general procedure described by Magnus et al. in *Tetrahedron Lett.*, 1787 (1981) and Guggenheim et al. in *Tetrahedron Lett.*, 1253 (1984). The protected aniline can then be metalated with an alkyl lithium reagent (i.e. n-butyl lithium, s-butyl lithium or t-butyl lithium) to form the corresponding aryl lithium reagent. The metalation is best carried out in ethereal solvents such as diethyl ether, tetrahydrofuran or dimethoxyethane at temperatures ranging from −78° C. to ambient temperature. It is sometimes advantageous to carry out the metalation in the presence of additives such tetramethylethylenediamine. The aryl lithium reagent is formed in situ and can be reacted with a variety of electrophilic reagents such as $C_1$-$C_4$ alkyl halides, $C_1$-$C_4$ dialkyl disulfides or $C_1$-$C_4$ alkyl sulfenyl halides, dimethylformamide, $C_1$-$C_4$ acyl halides or $C_1$-$C_4$ N-methyl-O-methyl alkylhydroxamates, $C_1$-$C_4$ alkyl chloroformates and carbon dioxide. These electrophilic reagents serve to introduce $C_1$-$C_4$ alkyl, $C_1$-$C_4$ alkylthio, formyl, $C_1$-$C_4$ acyl, $C_1$-$C_4$ alkoxycarbonyl and carboxyl groups, respectively, directly into the 3-position of the aromatic ring. The product from electrophilic substitution can be deprotected using standard methodology as described in the literature to form the desired amino compound.

Scheme XVIII

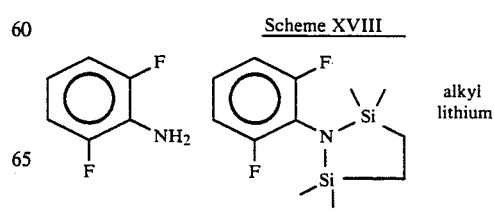

alkyl lithium

-continued
Scheme XVIII

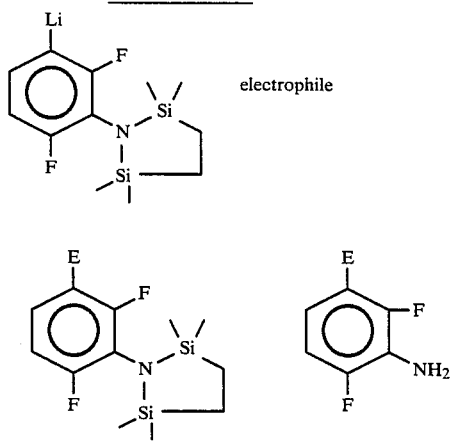

The table which follows contains a listing of some of the aromatic amino compounds prepared by methods described above and not previously described in known art, which compounds are useful in the preparation of the biologically active compounds of this invention.

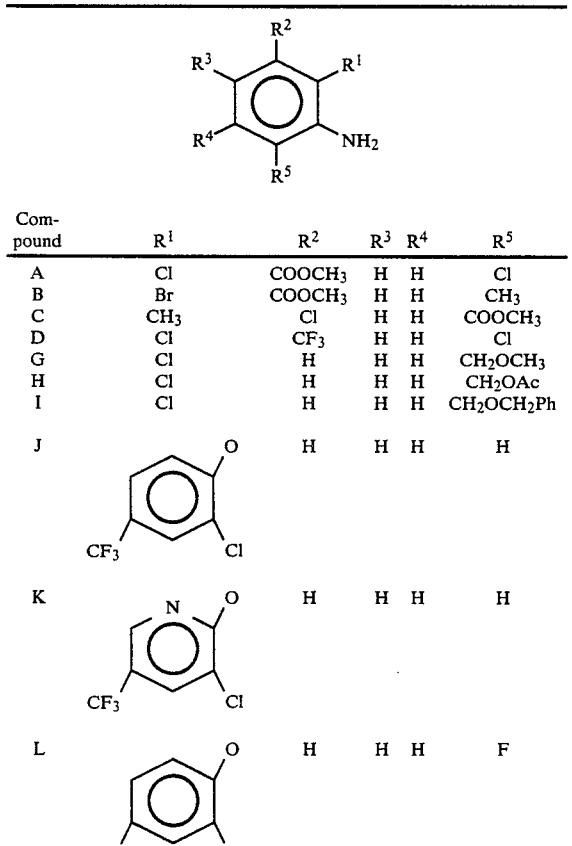

| Compound | $R^1$ | $R^2$ | $R^3$ | $R^4$ | $R^5$ |
|---|---|---|---|---|---|
| A | Cl | COOCH$_3$ | H | H | Cl |
| B | Br | COOCH$_3$ | H | H | CH$_3$ |
| C | CH$_3$ | Cl | H | H | COOCH$_3$ |
| D | Cl | CF$_3$ | H | H | Cl |
| G | Cl | H | H | H | CH$_2$OCH$_3$ |
| H | Cl | H | H | H | CH$_2$OAc |
| I | Cl | H | H | H | CH$_2$OCH$_2$Ph |
| J | (CF$_3$-phenyl-Cl-O) | H | H | H | H |
| K | (CF$_3$-pyridyl-Cl-O) | H | H | H | H |
| L | (CF$_3$-phenyl-Cl-O) | H | H | H | F |
| M | F | H | H | H | SCH$_3$ |
| N | CF$_3$ | H | H | H | OCH$_3$ |
| O | CF$_3$ | H | H | H | N(CH$_3$)$_2$ |
| P | CF$_3$ | H | H | H | OCH$_2$CH$_3$ |
| Q | CF$_3$ | H | H | H | OCH$_2$CF$_3$ |
| R | Br | CH$_3$ | H | H | Br |
| S | Br | CH$_3$ | H | H | Cl |

The novel aniline compounds that are useful for the preparation of compounds of Formulae I and II can be described by the formula

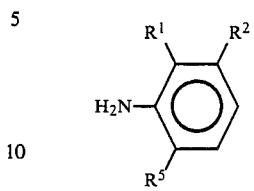

wherein (1) $R^1$ represents CF$_3$, $R^2$ represents hydrogen, and $R^5$ represents C$_1$-C$_4$ alkoxy, C$_1$-C$_4$ polyfluoroalkoxy, or C$_1$-C$_4$ alkylthio; (2) $R^1$ and $R^5$ represent F and $R^2$ represents CH$_3$ or OCH$_3$; (3) $R^1$ and $R^5$ represent Cl and $R^2$ represents CO$_2$C$_1$-C$_4$ alkyl, or CF$_3$; (4) $R^1$ represents F, $R_2$ represents hydrogen, and $R^5$ represents C$_1$-C$_4$ alkylthio or 4-trifluoromethylphenoxy or 5-trifluoromethyl-2-pyridyloxy, each optionally containing up to two fluoro, chloro, or bromo substituents; (5) $R^1$ represents Cl, $R^2$ represents hydrogen, and $R^3$ represents hydroxymethyl, C$_1$-C$_4$ alkoxymethyl, C$_1$-C$_4$ alkanoyloxymethyl, or benzyloxymethyl; (6) $R^2$ and $R^5$ represent hydrogen and $R^1$ represents 4-trifluoromethylphenoxy or 5-trifluoromethyl-2-pyridyloxy, each optionally containing up to two fluoro, chloro, or bromo substituents; (7) a C$_1$-C$_4$ alkyl 3-amino-2-bromo-4-methylbenzoate; and (8) a C$_1$-C$_4$ alkyl 4-chloro-3-methylanthranilate.

Using the routes illustrated above or minor variations based on the principles illustrated above the novel compounds of this invention can be prepared.

The invention is further illustrated by the following examples.

EXAMPLE 1

Preparation of 5,7-dimethyl-2-mercapto-1,2,4-triazolo[1,5-a]pyrimidine

A solution of 10.1 g (0.0870 mol) of 3-amino-5-mercapto-1,2,4 triazole, 8.71 g (0.0870 mol) of 2,4-pentanedione and 0.8 ml of piperidine in 300 ml of HOAc was heated at reflux for 21.5 hours. After cooling to room temperature, the solid which separated was collected by filtration and dried in vacuo to yield 13.4 g of pale yellow needles, m.p. 245°—246° C. (decomposition); $^1$H NMR (DMSO-d$_6$ —CDCl$_3$) δ 613.9 (1H, broad, SH), 7.19 (1H, broad s, H in 6-position) 2.63 and 2.51 (3H each, s, CH$_3$ groups in 5- and 7-positions), IR (KBr) ∼ 2680, 1628, 1560, 1400 and 1170 cm$^1$. An analytical sample was prepared by recrystallization from ocetir acetic acid to yield colorless plates, m.p. 243.5°–244.5° C. (decomposition).

Analysis:

Calculated for C$_7$C$_8$N$_4$S: C, 46.65; H, 4.47; N, 31.09; Found: C, 46.34; H, 4.41; N, 30.82;

EXAMPLE 2

Preparation of 2-benzylthio-5,7-dimethyl-1,2,4-triazolo[1,5-a]pyrimidine

Twenty percent NaOH (14.0 g, 70 mmol) was added dropwise to a suspension of 11.5 g (64.0 mmol) of the mercaptan prepared in Example 1 in 125 ml of H$_2$O over about 5 minutes. Benzyl chloride (7.4 ml, 8.1 g, 64 mmol) in 20 ml of CH₃OH was added and the resulting mixture was vigorously stirred at room temperature for 24 hours. The solid which began separating shortly after the addition of benzyl chloride was collected by filtration and dried in vacuo to afford 16.1 g of white solid, m.p. 134°–135° C. (lit m.p. 132°–134° C., T. Novinson et al, *J. Med. Chem.*, 25, 420 (1982)): $^1$H NMR (CDCl₃) δ 7.1–7.6 (5H, m, Ph), 6.63 (1H, s, H in 6-position), 4.50 (2H, s, —CH₂S—), 2.67 and 2.58 (3H each, s, CH₃ groups in 5- and 7-positions); IR (CHCl₃) 1620, 1447, 1339 and 1295 cm$^{-1}$. 93% yield.

Analysis:

Calculated for C₁₄H₁₄N₄S: C, 62.20; H, 5.22; N, 20.72.
Found: C, 62.21; H, 5.14; N, 20.89.

EXAMPLE 3

Preparation of 2-benzylthio-6,7-cyclopentano-5-methyl-1,2,4-triazolo[1,5-a]-pyrimidine A solution of 51.6 g (0.250 mol) of 3-amino-5-benzylthio-1,2,4-triazole and 31.5 g (0.250 mol) of 2-acetylcyclopentanone in 600 ml of HOAc was heated at reflux for 9.5 hours. The solvent was removed by evaporation, and the brown solid residue was recrystallized from EtOH to yield a light brown solid. A second recrystallization from EtOH gave 45.4 g (61 percent) of the desired product as a light brown solid, m.p. 157°–158.5° C.: $^1$H NMR (CDCl₃) δ 0–7.6 (5H, m), 4.51 (2H, s), 3.29 (2H, t), 2.97 (2H, t), 2.0–2.7 (5H, m including s at 2.52); IR (CHCl₃) 1621, 1343 and 1290 cm$^{-1}$.

Analysis:

Calculated for C₁₆H₁₆N₄S: C, 64.84; H, 5.44, N, 18.90; S, 10.82.
Found: C, 64.88; H, 5.47; N, 18.98; S, 10.72.

EXAMPLE 4

Preparation of 2-benzylthio-5,6,7-trimethyl-1,2,4-triazolo[1,5-a]pyrimidine

A solution of 51.6 g (0.250 mol) of 3-amino-5-benzylthio-1,2;4-triazole and 28.5 g (0.250 mol) of 3-methyl-2,4-pentanedione in 350 ml of glacial acetic acid was heated at reflux for 17 hours. Upon cooling to room temperature, the reaction mixture was poured onto ice. The pale yellow solid which separated was collected by filtration, washed with water and dried in vacuo to yield 67.1 g (94%) of the desired product as a pale yellow solid, m.p. 133.5°–135° C. The IR and $^1$H NMR spectra were consistent with the assigned structure.

Analysis:

Calculated for C₁₅H₁₅N₄S: C, 63.35; H, 5.67; N, 19.70; S, 11.27. Found: C, 63.07; H, 5.48; N, 19.71; S, 11.09.

EXAMPLE 5

Preparation of 2-benzylthio-6-chloro-1,2,4-triazolo[1,5-a]pyrimidine

A solution of 6.52 g (31.6 mmol) of 3-amino-5-benzylthio-1,2,4-triazole and 9.09 g (31.6 mmol) of 1,3-bis(dimethylamino)-2-chlorotrimethinium perchlorate in 100 ml of glacial acetic acid was heated at reflux for 19 hours. After cooling to room temperature, the solution was poured into 300 ml of water. The solid which separated was collected by filtration, washed with water and dried in vacuo to yield 4.12 g (48%) of the desired product as a brown solid, m.p. 119.5°–135° C., (decomposition). IR and $^1$H NMR spectra were consistent with the assigned structure.

Analysis:

Calculated for C₁₂H₉ClN₄S: C, 51.90; H, 3.20; N, 20.24. Found: C, 51.87; H, 3.42; N, 19.81.

EXAMPLE 6

Preparation of 2-benzylthio-1,2,4-triazolo-[1,5-a]pyrimidine

A solution of 2.0 g (9.6 mmol) of 3-amino-5-benzylthio-1,2,4-triazole and 2.3 ml (9.6 mmol) of malonaldehyde bis(diethylacetal) in 20 ml of glacial acetic acid was heated at reflux for 17 hours. After cooling to room temperature, the solvent was removed by evaporation at reduced pressure. The brown solid residue was recrystallized from isopropyl alcohol to afford 0.4 g (17%) of the desired product as a light brown crystalline solid, m.p. 104°–106° C. IR and $^1$H NMR spectra were consistent with the assigned structure.

Analysis:

Calculated for C₁₂H₁₀N₄S: C, 59.52; H, 4.13; N, 23.13. Found: C, 59.19; H, 4.09; N, 22.73.

EXAMPLE 7

Preparation of 2-benzylthio-5-methyl-1,2,4-triazolo[1,5-a]pyrimidine

A solution of sodium ethoxide in EtOH was prepared by dissolving 0.54 g (24 mg-atoms) of sodium metal in 120 ml of anhydrous EtOH, and 10.0 g (48 mmol) of 3-amino-5-benzylthio-1,2,4-triazole was added. After stirring for 15 minutes at room temperature, 6.4 ml (6.35 g, 48.4 mmol) of acetylacetaldehyde dimethyl acetal dissolved in 100 ml of absolute EtOH was was added dropwise. After the addition was complete the reaction mixture was stirred at room temperature for 68 hours. The product which separated from solution was collected by filtration and dried to give 10.1 g (83%) of tan solid, m.p. 128.5°–130° C. IR and $^1$H NMR spectra were in agreement with the assigned structure.

Analysis:

Calculated for C₁₃H₁₂N₄S: C, 60.94; H, 4.68; N, 21.86. Found: C, 60.69; H, 4.61; N, 21.85.

EXAMPLE 8

Preparation of 2-benzylthio-5-hydroxy-7-methyl-1,2,4-triazolo[1,5-a]pyrimidine

Ethyl 2,3-dibromobutyrate (1.33 g, 48.5 mmol) was added dropwise over 15 minutes to a solution of 10 g (49 mmol) of 3-amino-5-benzylthio-1,2,4-triazole in 20 ml of pyridine heated to °C. After the addition was complete, the reaction mixture was heated at 65° C. for 20 hours, cooled to room temperature and filtered. The filtrate was concentrated by evaporation at reduced pressure. The residue was triturated with methanol to separate 1.64 g (13%) of the desired product as a colorless crystalline solid, m.p. 219°–220° C. IR and $^1$H NMR spectra were in agreement with the assigned structure.

Analysis:

Calculated for $C_{13}H_{12}N_4OS$: C, 57.37; H, 4.41; N, 20.60. Found: C, 56.86; H, 4.41; N, 20.72.

EXAMPLE 9

Preparation of 2-benzylthio-5-methoxy-7-methyl-1,2,4-triazolo[1,5-a]pyrimidine

A solution of 2.67 g (9.80 mmol) of 2-benzylthio-5-hydroxy-7-methyl-1,2,4-triazolo[1,5-a]pyrimidine in 50 ml of phosphorous oxychloride was heated at reflux for 3 hours. The excess phosphorous oxychloride was removed by evaporation at reduced pressure The residue was partitioned between $CH_2Cl_2$ and cold water. The organic phase was separated, dried ($MgSO_4$) and concentrated by evaporation at reduced pressure. The resulting solid was added to 50 ml (0.22 mol) of a 25 weight percent solution of sodium methoxide in methanol The resulting suspension was stirred at room temperature for 30 minutes, diluted with 50 ml of water and filtered. The solid collected was dried in vacuo to yield 1.41 g (41%) of the desired product as a light brown solid, m.p. 112.5°–115° C. IR and $^1H$ NMR spectra were consistent with the assigned structure.

EXAMPLE 10

Preparation of 2-benzylthio-7-methyl-1,2,4-triazolo[1,5-a]pyrimidine

A solution of 50 g (0.24 mol) of 3-amino-5-benzylthio-1,2,4-triazole in 500 ml of glacial acetic acid was added dropwise over 3–4 hours to a solution of 34.0 g (0.25 mol) of acetylacetaldehyde dimethyl acetal in 500 ml of glacial acetic acid heated at 100° C. After the addition was complete the reaction mixture was heated at reflux overnight, cooled to room temperature and poured into an ice-water mixture. The solid which separated was collected by filtration and recrystallized from ethanol to yield 27 g (41%) of the desired product as a solid, m.p. 102°–104° C. IR and $^1H$ NMR spectra were in agreement with the assigned structure.

Analysis

Calculated for $C_{13}H_{12}N_4S$: C, 60.94; H, 4.68; N, 21.85 Found: C, 60.81; H, 4.68; N, 21.74.

EXAMPLE 11

Preparation of 2-benzylthio-6-methyl-1,2,4-triazolo[1,5-a]pyrimidine

A suspension of 14.4 g (0.124 mol) of 3-amino-5-benzyl-1,2,4-triazole and 30.0 g (0.124 mol) of 1,3-bis(dimethylamino)-2-methyltrimethinium perchlorate in 500 ml of glacial acetic acid was heated at reflux for 63 hours. The reaction mixture was subjected to the work-up described in Example 5 to yield 13.9g (68%) of the desired product as a brown solid, m.p. 254°–256° C. IR and $^1H$ NMR spectra were in agreement with the assigned structure.

Analysis:

Calculated for $C_6H_6N_4S$: C, 43.35; H 3.61; N, 33.72 Found: C, 42.71; H, 3.49; N, 33.26.

EXAMPLE 12

Preparation of 2-benzylthio-6-chloro-5,7-dimethyl-1,2,4-triazolo[1,5-a]pyrimidine To a suspension of 153 g (0.74 mol) 3-amino-5-benzylthio-1,2,4-triazole in 250 ml of glacial acetic acid was added 100 g (0.74 mol) of 3-chloro-2,4-pentanedione in a dropwise manner The reaction mixture was heated at reflux for 18 hours and cooled to room temperature. The reaction mixture was poured over ice and the oil which separated solidified upon stirring. The solid was collected by filtration and recrystallized from methanol to yield 116 g (79%) of the desired product as an off white solid, m.p. 164°–166° C. IR and $^1H$ NMR spectra were in agreement with the assigned structure.

Analysis:

Calculated for $C_{14}H_{13}ClN_4S$: C, 55 16; H, 4.30; N, 18.38. Found: C, 55.11; H, 4.30; N, 18.34.

EXAMPLE 13

Preparation of 2-benzylthio-6-ethoxy-1,2,4-triazolo[1,5-a]pyrimidine

This material was prepared in 28% yield from 3-amino-5-benzylthio-1,2,4-triazole and 1,3-bis(dimethylamino)-2-ethoxytrimethinium perchlorate following the general procedure described in Example 5. The desired product was isolated as a solid, m.p. 139°–140° C. IR and $^1H$ NMR spectra were in agreement with the assigned structure.

Analysis

Calculated for $C_{14}H_{14}N_4OS$: C, 58.73; H, 4.89; N, 19.57. Found: C, 58 68; H, 4.64; N, 19.58.

EXAMPLE 14

Preparation of 2-benzylthio-5-isopropyl-1,2,4-triazolo[1,5-a]pyrimidine

This material was prepared in 96% yield from 3-amino-5-benzylthio-1,2,4-triazole and 4-methyl-3-oxopentanal following the general procedure described in Example 7. The desired product was isolated as a solid, m.p. 65°–66° C. IR and $^1H$ NMR were in agreement with the assigned structure.

Analysis:

Calculated for $C_{15}H_{16}N_4S$: C, 63.36; H, 5.63; N, 19.71. Found: C, 63 00; H, 5.62; N, 19.62.

EXAMPLE 15

Preparation of 2-benzylthio-5,6-dimethyl-1,2,4-triazolo[1,5-a]pyrimidine

A solution of 5.0 g (24 mmol) of 3-amino-5-benzylthio-1,2,4-triazole and 5.0 g (41 mmol) of the sodium salt of 2-methyl-3-oxobutanal in 200 ml of glacial acetic acid was heated at reflux overnight. The solution was cooled to room temperature and the reaction mixture was concentrated by evaporation at reduced pressure. The residue was combined with ice and $H_2O$ to separate a tan solid. The solid was collected by filtration, dried and carefully recrystallized from ethyl acetate to yield 3.53 g (54%) of the desired product as a crystalline solid, m.p. 147°–149° C. IR and $^1$H NMR spectra were in agreement with the assigned structure.

Analysis:

Calculated for $C_{14}H_{14}N_4S$: C, 62.10; H, 5.18; N, 20.72. Found: C, 61.58; H, 5.18; N, 20.45.

EXAMPLE 16

Preparation of 2-benzylthio-6-chloro-7-hydroxy-5-methyl-1,2,4-triazolo[1,5-a]pyrimidine A solution of 16 g (77 mmol) of 3-amino-5-benzylthio-1,2,4-triazole and 10.6 g (77 mmol) of ethyl 2-chloroacetoacetate in 150 ml of glacial acetic acid was heated at 100° C. for 17 hours. Upon cooling to room temperature the solid which separated was collected by filtration. The filtrate was diluted with ice water to separate an additional quantity of solid. The solids were combined and dried to yield 14.0 g (60%) of the desired product as a solid, m.p. 258°–260° C. IR and $^1$H NMR were in agreement with the assigned structure.

Analysis:

Calculated for $C_{13}H_{11}ClN_4OS$: C, 50.89; H, 3.58; N, 18.27. Found: C, 50.51; H, 3.36; N, 18.67.

EXAMPLE 17

Preparation of 2-benzylthio-6,7-dichloro-5-methyl-1,2,4-triazolo[1,5-a]pyrimidine This material was prepared in 68% yield from 2-benzylthio-6-chloro-7-hydroxy-5-methyl-1,2,4-triazolo[1,5-a]pyrimidine and phosphorus oxychloride following the general procedure described in Example 20. The desired product was isolated as a solid, m.p. 103°–105° C. IR and $^1$H NMR spectra were in agreement with the assigned structure.

Analysis:

Calculated for $C_{13}N_{10}Cl_2N_4S$: C, 48.00; H, 3.07; N, 17.23.
Found: C, 47.40; H, 3.00; N, 17.43.

EXAMPLE 18

Preparation of 2-benzylthio-6-chloro-5-methyl-1,2,4-triazolo[1,5-a]pyrimidine This material was prepared by reduction of 2-benzylthio-6,7-dichloro-5-methyl-1,2,4-triazolo[1,5-a]pyrimidine with zinc-copper couple following the general procedure described in Example 21. The desired product was isolated in 88% yield as a solid, m.p. 160°–161° C. IR and $^1$H NMR spectra were in agreement with the assigned structure.

Analysis:

Calculated for $C_{13}H_{11}ClN_4S$: C, 53.56; H, 3.56; N, 19.27. Found: C, 53.30; H, 3.79; N, 19.28.

EXAMPLE 19

Preparation of 2-benzylthio-5,7-dihydroxy-1,2,4-triazolo[1,5-a]pyrimidine

A solution of 125 g (0.58 mol) of a 25% solution of sodium methoxide in methanol dissolved in 100 ml of absolute ethanol was treated with 66.3 ml (0.29 mol) of dimethyl malonate followed by 60.0 g (0.20 mol) of 3-amino-5-benzylthio-1,2,4-triazole. The resulting solution was heated at reflux for 5 days. On cooling to room temperature the solid which had separated was collected by filtration, washed with cold ethanol and dissolved in 1000 ml of water. The resulting yellow solution was acidified with concentrated HCl to precipitate a solid. The solid was collected by filtration and dried to yield 70.1 g (82%) of the desired product as a white solid, m.p. 199°–210° C. (decomposition). IR and $^1$H NMR spectra were in agreement with the assigned structure.

Analysis:

Calculated for $C_{12}H_{10}N_4O_2S \cdot H_2O$: C, 49.30; H, 4.14, N, 19.16. Found: C, 48.70; H, 3.89; N, 18.83.

EXAMPLE 20

Preparation of 2-benzylthio-5,7-dichloro-1,2,4-triazolo[1,5-a]pyrimidine

A suspension of 70.0 g (0.24 mol) of 2-benzylthio-5,7-dihydroxy-1,2,4-triazolo[1,5-a]pyrimidine and 67.0 ml (0.72 mol) of phosphorous oxychloride in 600 ml of acetonitrile was heated at reflux for 3 hours. The resulting orange solution was stirred at room temperature overnight (17 hours). The solution was filtered and the filtrate was concentrated by evaporation at reduced pressure. The residue was partitioned between cold water and methylene chloride, and the organic phase was separated and dried ($MgSO_4$). The organic phase was concentrated to induce crystallization. The desired product was collected by filtration to yield 98.0 g (81%) of solid, m.p. 97°–100° C. IR and $^1$H NMR spectra were in agreement with the assigned structure.

Analysis:

Calculated for $C_{12}H_8Cl_2N_4S$: C, 46.32; H, 2.59; N, 18.00. Found: C, 46.43; H, 2.57; N, 18.08.

EXAMPLE 21

Preparation of 2-benzylthio-5-chloro-1,2,4-triazolo[1,5-a]pyrimidine

A zinc-copper couple was prepared following the procedure of Bradley (J. Org. Chem. 31, 626 (1966)) by stirring 1.0 g of copper sulfate in 20 ml of water with 15.0 g of zinc dust for 2 hours. The couple was collected by filtration, washed with acetone and dried overnight under vacuum at 100° C. To a solution of 33.0 g (106 mmol) of 2-benzylthio-5,7-dichloro-1,2,4-triazolo[1,5-a]-pyrimidine in 12.5 ml (213 mmol) of acetic acid, 50 ml of methanol and 300 ml of tetrahydrofuran was added 20.5 g of Zn-Cu couple. The mixture was stirred overnight at 22°–23° C. When the reaction was complete (TLC analysis) the reaction mixture was filtered through celite and the filtrate was concentrated by evaporation at reduced pressure. The residue was triturated with hexane to separate a solid. The solid was collected by filtration to yield the desired product as 26.5 g (92%) of orange solid, m.p. 125°–127° C. IR and $^1$H NMR spectra were in agreement with the assigned structure.

Analysis:

Calculated for $C_{12}H_9ClN_4S$: C, 52.08; H, 3.25; N, 20.25. Found: C, 51.76; H, 3.00; N. 20.27.

EXAMPLE 22

Preparation of 2-benzylthio-5-methoxy-1,2,4-triazolo[1,5-a]pyrimidine

A mixture of 6.0 g (22 mmol) of 2-benzylthio-5-chloro-1,2,4-triazolo[1,5-a]pyrimidine in 25 ml of methanol was treated with 5.0 g (23.8 mmol) of a 25% solution of sodium methoxide in methanol. After stirring for 1.5 hours the reaction mixture was diluted with 100 ml of water and neutralized with 3N HCL (aq). The solid which separated was collected by filtration, washed with water and dried to afford 5.0 g (84%) of the desired product as a white solid, m.p. 126°–128° C. IR and $^1$H NMR spectra were in agreement with the assigned structure.

Analysis:
Calculated for $C_{13}H_{12}N_4OS$: C, 57.34; H, 4.41; N, 20.58. Found: C, 57.21; H, 4.42; N, 20.13.

EXAMPLE 23

Preparation of 2-benzylthio-5-(2,2,2-trifluoroethoxy)-1,2,4-triazolo[1,5-a]pyrimidine A solution of sodium 2,2,2-trifluoroethoxide in tetrahydrofuran was prepared by the addition of 1.1 g (48 mg-atom) of sodium metal to a solution of 3.5 ml (48 mmol) of 2,2,2-trifluoroethanol in 100 ml of tetrahydrofuran. To this solution was added 7.0 g (25 mmol) of 2-benzylthio-5-chloro-1,2,4-triazolo[1,5-a]pyrimidine, and the reaction mixture was stirred for 30 minutes and concentrated by evaporation at reduced pressure to approximately one quarter of the original volume Pentane (200 ml) was added to induce crystallization. The solid which separated was collected by filtration to yield 6.42 g (75%) of the desired product as a light yellow solid, m.p. 114–118° C. IR and $^1$H NMR spectra were in agreement, with the assigned structure.

Analysis:
Calculated for $C_{14}H_{11}F_3N_4OS$: C, 49.49; H, 3.23; N, 16.46. Found: C, 49.63; H, 3.09; N, 16.70.

EXAMPLE 24

Preparation of 2-benzylthio-5-ethoxy-1,2,4-triazolo[1,5-a]pyrimidine

This material was prepared by heating 2-benzylthio-5-(2,2,2-trifluoroethoxy)-1,2,4-triazolo[1,5-a]-pyrimidine in boiling ethanol. The hot mixture was filtered and the filtrate was concentrated. The crude product was recrystallized from isopropanol to yield the desired product as a solid, m.p. 115°–117° C. IR and $^1$H NMR spectra were in agreement with the assigned structure.

Analysis
Calculated for $C_{14}H_{14}N_4S$: C, 58.73; H, 4.89; N, 19.31; S, 11.20. Found: C, 57.90; H, 4.69; N, 19.30; S, 10.79.

EXAMPLE 25

Preparation of 2-benzylthio-5,7-dihydroxy-6-methyl-1,2,4-triazolo[1,5-a]pyrimidine This material was prepared in 80% yield from 3-amino-5-benzylthio-1,2,4-triazole and dimethyl 2-methyl malonate following the general procedure described in Example 19. The product was isolated as a solid, m.p. 260°–272° C. (decomposition). IR and $^1$H NMR spectra were in agreement with the assigned structure.

Analysis:
Calculated for $C_{13}H_{12}N_4O_2S$: C, 54.15; H, 4.16; N, 19.44. Found: C, 53.48; H, 4.07; N, 19.53.

EXAMPLE 26

Preparation of 2-benzylthio-5,7-dichloro-6-methyl-1,2,4-triazolo[1,5-a]pyrimidine This material was prepared in 97% yield from the reaction of 2-benzylthio-5,7-dihydroxy-6-methyl-1,2,4-triazolo[1,5-a]pyrimidine and phosphorous oxychloride following the general procedure described in Example 20. The product was isolated as a solid, m.p. 121°–123° C. IR and $^1$H NMR spectra were in agreement with the assigned structure.

Analysis:
Calculated for $C_{13}H_{10}Cl_2N_4S$: C, 48.01; H, 3.08; N, 17.23. Found: C, 47.65; H, 3.11; N, 17.70.

EXAMPLE 27

Preparation of 2-benzylthio-5-chloro-6-methyl-1,2,4-triazolo[1,5-a]pyrimidine

This material was prepared in 32% yield by reduction of 2-benzylthio-5,7-dichloro-6-methyl-1,2,4triazolo[1,5-a]pyrimidine with zinc-copper couple following the general procedure described in Example 21. The desired product was isolated as a solid, m.p. 179°–181° C. IR and $^1$H NMR spectra were in agreement with the assigned structure.

Analysis:
Calculated for $C_{13}H_{11}ClN_4S$: C, 53.70; H, 3.79; N, 19.28. Found: C, 53.33; H, 3.73; N, 19.53.

EXAMPLE 28

Preparation of 2-benzylthio-5-methoxy-6-methyl-1,2,4-triazolo[1,5-a]pyrimidine

This material was prepared in 64% yield by reaction of 2-benzylthio-5-chloro-6-methyl-1,2,4-triazolo-[1,5-a]pyrimidine with sodium methoxide following the general procedure described in Example 22. The desired product was isolated as a solid, m.p. 145°–146° C. IR and $^1$H NMR spectra were in agreement with the assigned structure.

Analysis:
Calculated for $C_{14}H_{14}N_4OS$: C, 58.73; H, 4.89; N. 19.58. Found: C, 58.34; H. 4,84; N, 19.67.

EXAMPLE 29

Preparation of 2-benzylthio-6-ethoxycarbonyl-7-methyl-1,2,4-triazolo[1,5-a]pyrimidine A solution of 15 g (73 mmol) of 3-amino-5-benzylthio-1,2,4-triazole and 15.0 g (80.0 mmol) of ethyl ethoxymethyleneacetoacetate in 250 ml of glacial acetic acid was heated at reflux for 60 hours. After cooling the volume of the reaction was reduced to approximately one quarter of the original volume by evaporation at reduced pressure. The resulting residue was poured into water, and the solid which separated was collected by filtration, washed with water and dried to yield 7.88 g (33%) of the desired product as a solid, m.p. 98°–99° C. IR and $^1$H NMR spectra were in agreement with the assigned structure.

Analysis:

Calculated for $C_{16}H_{16}N_4O_2S$: C, 58.52; H, 4.87; N, 17.07. Found: C, 58.51; H, 4.89; N. 17.03.

EXAMPLE 30

Preparation of 2-benzylthio-6-(4-nitrophenyl)-1,2,4-triazolo[1,5-a]pyrimidine

This material was prepared from 3-amino-5-benzylthio-1,2,4-triazole and 1,3-bis(dimethylamino)-2-(4-nitrophenyl)-trimethinium perchlorate following the general procedure described in Example 5. The desired product was isolated as a solid, m.p. 195°–199° C. IR and $^1$H NMR spectra were in agreement with the assigned structure.

EXAMPLE 31

Preparation of 2-benzylthio-5,6-cyclopentano-7-hydroxy-1,2,4-triazolo[1,5-a]pyrimidine A solution of 20.6 g (100 mmol) of 3-amino-5-benzylthio-1,2,4-triazole and 15 ml (16 g, 0.10 mol) of 2-carboethoxycyclopentanone in 110 ml of glacial acetic acid was heated at reflux for 23 hours. After cooling to room temperature the solid which separated from the reaction mixture was collected by filtration, washed with acetic acid and dried in vacuo to yield 22.4 g (75%) of the desired product as a colorless crystalline solid, m.p. 241°–243° C. IR and $^1$H NMR spectra were in agreement with the assigned structure.

Analysis:

Calculated for $C_{15}H_{14}N_4OS$: C, 60.38; H, 4.73; N, 18.78; S, 10.75. Found: C, 60.10; H, 4.66; N, 18.91; S, 10.72.

EXAMPLE 32

Preparation of 2-benzylthio-7-chloro-5,6-cyclopentano-1,2,4-triazolo[1,5-a]pyrimidine A solution of 5.97 g (20.0 mmol) of 2-benzylthio-5,6-cyclopentano-7-hydroxy-1,2,4-triazolo[1,5-a]pyrimidine in 250 ml of phosphorus oxychloride was heated at reflux for 50 minutes. After cooling to room temperature the excess phosphorous oxychloride was removed by distillation at aspirator pressure The residue was partitioned between ice cold water and methylene chloride. The organic phase was dried ($Na_2SO_4$) and evaporated at reduced pressure. The residue was chromatographed on silica gel eluting with EtOAc hexane (1:1, v/v) to yield 3.72 g (59%) of the desired product as a yellow solid, m.p. 119°–120° C. IR and $^1$H NMR spectra were in agreement with the assigned structure.

Analysis:

Calculated for $C_{15}H_{13}ClN_4S$: C, 56.87; H, 4 14; N, 17.68; Cl, 11.19; S, 10.12. Found: C, 56.91; H, 4.06; N, 17.83; Cl, 10.68; S; 9.65.

EXAMPLE 33

Preparation of 2-benzylthio-5,6-cyclopentano-2,4-triazolo[1,5-a]pyrimidine

A solution of 2.47 g (7.80 mmol) of 2-benzylthio-7-chloro-5,6-cyclopentano-1,2,4-triazolo[1,5-a]pyrimidine in 40 ml of dry tetrahydrofuran was cooled to 5° C. and 5.9 ml (17 mmol) of 2.9 M methyl magnesium bromide in ether was added over 5 minutes. After the addition was complete the reaction mixture was warmed to room temperature and stirred overnight (17 hours). The reaction was quenched by addition of 10 ml of saturated aqueous ammonium chloride. The organic phase was separated, dried ($Na_2SO_4$) and evaporated at reduced pressure The red oil residue was chromatographed on silica gel (HPLC) eluting with EtOAc-hexane (1:1, v/v) to yield 1.12 g (48%) of the desired product as a pale red solid, m.p. 109°–111° C. IR and $^1$H NMR spectra were in agreement with the assigned structure.

Analysis

Calculated for $C_{16}H_{16}N_4S$: C, 64.84; H, 5.44; N, 18.90; S, 10.82. Found: C, 64.99; H, 5.41; N, 18.16; S, 10.42.

EXAMPLE 34

Preparation of 2-benzylthio-5,7-bis-(tri-20 fluoromethyl)-1,2,4-triazolo[1,5-a]pyrimidine A solution of 20.8 g (0.100 mol) of 1,1,1,5,5,5-hexafluoro-2,4-pentanedione and 20.6 g (0.100 mol) of 3-amino-5-benzylthio-1,2,4-triazole in 150 ml of glacial acetic acid was heated at reflux for 14 hours. The solution was cooled to room temperature and poured over ice. The solid which separated was collected by filtration, washed with water and dried in vacuo to yield 35.5 g (94%) of the desired product as a pale yellow solid, m.p. 78.5°–80.5° C. IR, $^1$H NMR and $^{19}$F NMR spectra were in agreement with the assigned structure.

Analysis:

Calculated for $C_{14}H_8F_6N_4S$: C, 44.45; H, 2.13; N, 14.81; S, 8.48. Found: C, 44.53; H, 2.15; N, 14.97; S, 8.39.

EXAMPLE 35

Preparation of 2-benzylthio-5-methyl-7-trifluoromethyl-1,2,4-triazolo[1,5-a]-pyrimidine This material was prepared in 84% yield from 3-amino-5-benzylthio-1,2,4-triazole and 1,1,1-trifluoro2,4-pentanedione following the general procedure described in EXAMPLE 34. The product was purified by recrystallization from benzene-hexane to yield a tan solid, m.p. 83.5°–84.5° C. IR, $^1$H NMR and $^{19}$F NMR spectra were in agreement with the assigned structure.

Analysis:

Calculated for $C_{14}H_{11}F_3N_4S$: C, 51.85; H, 3.42; N, 17.27; S, 9.89. Found: C, 51.73; H, 3,44; N, 18.01; S, 10.08.

EXAMPLE 36

Preparation of
2-benzylthio-5,7-diphenyl-1,2,4-triazolo[1,5-a]pyrimidine

A solution of 8.40 g (37.5 mmol) of dibenzoylmethane and 7.73 g (37.5 mmol) of 3-amino-5-benzylthio-1,2,4-triazole in 50 ml of glacial acetic acid was heated at reflux for 24 hours. Upon cooling to room temperature the solid which separated was collected by filtration and dried. The product was chromatographed on silica gel (HPLC) eluting with EtOAc-hexane (3:7, v/v) to afford 5.08 g (34%) of the desired product as a colorless solid, m.p. 122.5°–123.5° C. IR and $^1$H NMR spectra were in agreement with the assigned structure.

Analysis:

Calculated for $C_{24}H_{18}N_4S$: C, 73.07; H, 4.60; N, 14.20; S, 8.13. Found: C, 73.48; H, 4.54; N, 14.17; S, 7.97.

EXAMPLE 37

Preparation of
2-benzylthio-5-methyl-7-phenyl-1,2,4-triazolo[1,5-a]pyrimidine and
2-benzylthio-7-methyl-5-phenyl-1,2,4-triazolo[1,5-a]pyrimidine A solution of 20.6 g (100 mmol) of 3-amino-5-benzylthio-1,2,4-triazole and 16.2 g (100 mmol) of benzoyl acetone in 100 ml of glacial acetic acid was heated at reflux for 14 hours. The solvent was removed by evaporation at reduced pressure and the residue was chromatograph on silica gel (HPLC) eluting with EtOAc-hexane (3:7, v/v) to afford 4.81 g (14%) of 2-benzylthio-7-methyl-5-phenyl-1,2,4-triazolo[1,5-a]pyrimidine as a pale yellow solid, m.p. 154°–155° C. IR and $^1$H NMR spectra were in agreement with the assigned structure.

Analysis:

Calculated for $C_{19}H_{16}N_4S$: C, 68.65; H, 4.85; N, 16.85; S, 9.65. Found: C, 68.76; H, 4.82; N, 16.98; S, 9.93.

Further elution afforded 22.8 g (69%) of 2-benzylthio-5-methyl-7-phenyl-1,2,4-triazolo[1,5-a]pyrimidine as a pale yellow solid, m.p. 110°–111° C. IR and $^1$H NMR spectra were in agreement with the assigned structure.

Analysis:

Calculated for $C_{19}H_{16}N_4S$: C, 68.65; H, 4.85; N, 16.85; S, 9.65. Found: C, 68.52; H, 4.75; N. 16.93; S, 9.61.

EXAMPLE 38

Preparation of
5,7-dimethyl-1,2,4-triazolo-[1,5-a]pyrimidine-2-sulfonyl chloride Chlorine was bubbled into a suspension of 99.0 g (0.366 mol) of 2-benzylthio-5,7-dimethyl-1,2,4-triazolo-[1,5-a]pyrimidine in 700 ml of HOAc-H$_2$O (1:1, v/v) cooled to $-1°$ C. During the course of the addition the temperature of the reaction mixture was maintained below 5° C. After 2.5 hours the chlorine addition was ceased and the reaction mixture was filtered to collect a tan solid. The filtrate was diluted with H$_2$O to separate an additional quantity of solid which was collected by filtration. The combined solid products were dried in vacuo to yield 70.4 g (78%) of crude sulfonyl chloride III (X=Z=Me, Y=H) as a tan solid. IR and $^1$HNMR spectra confirmed the structure.

Recrystallization from EtOAc produced an analytical sample as an off-white solid, m.p. 128.5°–130.5° C.

Analysis:

Calculated for $C_7H_7ClN_4O_2S$: C, 34.09; H, 2.86; N, 20.73; S, 13.00. Found: C, 34.34; H, 2.B0; N, 22.64: S, 12.85.

EXAMPLE 39

Preparation of
6,7-cyclopentano-5-methyl-5-a]pyrimidine-2-sulfonyl chloride

Chlorine gas was bubbled into a suspension of 4.45 g (15.0 mmol) of 2-benzylthio-6,7-cyclopentano- 5-methyl-1,2,4-triazolo[1,5-a]pyrimidine in 30 ml of HOAC-H$_2$O (1:1, v/v) cooled to $-4°$ C. After 30 minutes the addition was stopped and the reaction mixture was stirred for 30 minutes maintaining the temperature below 5° C. The reaction mixture was filtered and the collected solid was dried under vacuum to yield 3.46 g (85 percent) of the desired sulfonyl chloride as a cream colored solid which was used directly without further purification: IR (CHCl$_3$) 1627, 1551, 1398 and 1170 cm$^{-1}$; $^1$H NMR (CDCl$_3$) δ3.50 (2H, broad t), 3.18 (2H, broad t) and 2.2°–2.8 (5H, m including s at 2.68).

EXAMPLE 40

Preparation of
5,6,7-trimethyl-1,2,4-triazolo[1,5a]pyrimidine-2-sulfonyl chloride Chlorine was bubbled into a suspension of 28.4 g (0.100 mol) of 2-benzylthio-5,6,7-trimethyl-1,2,4-triazolo[1,5-a]pyrimidine in 200 ml of glacial acetic acid-H$_2$O (1:1, v/v) and cooled to $-5°$ C. The chlorine addition continued over 35 minutes and the temperature of the reaction mixture never exceeded 5° C. After the addition was complete, the reaction mixture was stirred for 5 minutes and filtered. The solid collected was washed twice with H$_2$O and dried in vacuo to yield 24.3 g (93%) of the crude sulfonyl chloride as a pale yellow solid. The IR and $^1$H NMR were consistent with the assigned structure. The crude sulfonyl chloride was used in subsequent transformations without further purification.

EXAMPLE 41

Preparation of
6-chloro-1,2,4-triazolo-[1,5-a]pyrimidine-2-sulfonyl chloride

A suspension of 3.75 g (13.5 mmol) of 2-benzyl-thio-6-chloro-1,2,4-triazolo[1,5-a]pyrimidine in 40 ml of AcOH-H$_2$O (1:1, v/v) was cooled to $-10°$ C. and chlorine gas was bubbled into the reaction mixture for 10 minutes. After the addition was complete, the reaction mixture was stirred for 10 minutes and diluted with 25 ml of H$_2$O. The mixture was filtered and the filtrate was extracted with CH$_2$Cl$_2$. The organic phase was evaporated at reduced pressure to afford 2.14 g of the crude sulfonyl chloride as a liquid IR and $^1$H NMR spectra were in agreement with the assigned structure.

EXAMPLE 42

Preparation of 1,2,4-triazolo[1,5-a]-pyrimidine-2-sulfonyl chloride

A suspension of 8.0 g (33 mmol) of 2-benzylthio-1,2,4-triazolo[1,5-a]pyrimidine in 60 ml of HOAc—$H_2O$ (1:1, v/v) was cooled below 0° C. and chlorine gas was bubbled into the reaction mixture for 15 minutes. The temperature of the reaction mixture was maintained below 10° C. during the course of the addition. After the addition was complete, the reaction mixture was stirred for 15 minutes, diluted with $H_2O$ and extracted with $CH_2Cl_2$. The organic phase was dried ($MgSO_4$) and evaporated at reduced pressure to yield 5.74 g of the desired crude product as a brown oil IR and $^1H$ NMR were in agreement with the assigned structure.

Recrystallization from EtOAc gave an analytical sample, m.p. 105°-109° C.

Analysis:

Calculated for $C_5H_3ClN_4O_2S$: C, 27,45; H, 1 32; N, 25.62. Found: C, 28.91; H, 1.52; N, 25.79.

EXAMPLE 43

Preparation of 5-methyl-1,2,4-triazolo-[1,5-a]pyrimidine-2-sulfonyl chloride

A suspension of 2.77 g (10.8 mmol) of 2-benzylthio-5-methyl-1,2,4-triazolo[1,5-a]pyrimidine in 40 ml of AcOH—$H_2O$ (1:1, v/v) was cooled to $-10°$ C. and chlorine gas was bubbled into the solution for 10 minutes. After the addition was complete, the reaction mixture was stirred for 5 minutes, diluted with $H_2O$ (25 ml) and filtered. The solid collected was dried in vacuo to yield 1.17 g of the desired sulfonyl chloride. IR and $^1H$ NMR were in agreement with the assigned structure.

An additional quantity of the product contaminated with by-products containing benzyl residues was obtained by extraction of the filtrate with $CH_2Cl_2$ and evaporation of the organic phase at reduced pressure.

EXAMPLE 44

Preparation of 5-methoxy-7-methyl-1,2,4-tri-azoloa]pyrimidine-2-sulfonyl chloride A suspension of 1.41 g (4.93 mmol) of 2-benzylthio-5-methoxy-7-methyl-1,2,4-triazolo[1,5-a]pyrimidine in 40 ml of AcOH-$H_2O$ (1:1, v/v) was cooled to $-20°$ C., and chlorine gas was bubbled into the reaction mixture for 5 minutes. After the addition was complete, the reaction mixture was stirred for 10 minutes, diluted with $H_2O$ (20 ml) and filtered. The solid collected was dried in vacuo to yield 0.63 g of the desired crude sulfonyl chloride as a colorless solid. IR and $^1H$ NMR were in agreement with the assigned structure.

EXAMPLE 45

Preparation of 7-methyl-1,2,4-triazolo-[1,5-a]pyrimidine-2-sulfonyl chloride

A suspension of 3.52 g (13.7 mmol) of 2-benzylthio-5-methyl-1,2,4-triazolo[1,5-a]pyrimidine in 40 ml of AcOH-$H_2O$ (1:1, v/v) was cooled to $-10°$ C., and chlorine gas was bubbled into the reaction mixture for 10 minutes. After the addition was complete, the reaction mixture was stirred for 10 minutes, diluted with $H_2O$ and filtered. The solid collected was dried in vacuo to yield 0.46 g of the desired sulfonyl chloride as a tan solid. IR and $^1H$ NMR spectra were in agreement with the assigned structure.

An additional quantity (2.2 g) of crude sulfonyl chloride contaminated with by-products containing benzyl residues was obtained by extraction of the filtrate with $CH_2Cl_2$ and evaporation at reduced pressure.

EXAMPLE 46

Preparation of 6-methyl-1,2,4-triazolo-[1,5-a]pyrimidine-2-sulfonyl chloride

A suspension of 10.0 (60 mmol) of 2-benzylthio-6-methyl-1,2,4-triazolo[1,5-a]pyrimidine in 260 ml of methylene chloride, 100 ml of water and 17 ml of concentrated HCl was cooled to $-5°$ C. and treated with 284 ml (197 mmol) of 5.25% aqueous sodium hypochlorite (commercial bleach) by dropwise addition. After the addition was complete the reaction mixture was stirred for 20 minutes at 0° C. and filtered. The organic layer was separated and the aqueous layer was extracted twice with methylene chloride. The combined organic phases were dried ($MgSO_4$) and evaporated at reduced pressure to yield 7.0 g (50%) of the desired product as a solid, m.p. 106°-108° C. IR and $^1H$ NMR spectra were in agreement with the assigned structure.

Analysis:

Calculated for $C_6H_5ClN_4O_2S$: C, 30.96; H, 2.15; N, 24.08. Found: C, 31.00; H, 2.23; N, 23.91.

EXAMPLE 47

Preparation of 6-chloro-5,7-dimethyl-1,2,4-triazolo[1,5-a]pyrimidine-2-sulfonyl chloride This material was prepared in 50% yield from 2-benzylthio-6-chloro-5,7-dimethyl-1,2,4-triazolo[1,5-a]-pyrimidine pyrimidine following the general procedure described in Examples 38–45. The product was isolated as a pale yellow solid, m.p. 131°-133° C. IR and $^1H$ NMR spectra were in agreement with the assigned structure.

EXAMPLE 48

Preparation of 6-ethoxy-1,2,4-triazolo[1,5-a]-pyrimidine-2-sulfonyl chloride

This material was prepared in 82% yield from 2-benzylthio-6-ethoxy-1,2,4-triazolo[1,5-a]pyrimidine following the general procedure described in Examples 38–45. The product was isolated as a solid, m.p. 134°-137° C. IR and $^1H$ NMR spectra were in agreement with the assigned structure.

Analysis:

Calculated for $C_8H_9ClN_4O_2S$: C, 31.96; H, 2.66; n, 21.31. Found: C, 32.64; H, 2.36; N, 21.30.

EXAMPLE 49

Preparation of 5-isopropyl-1,2,4-triazolo-[1,5-a]pyrimidine-2-sulfonyl chloride

This material was prepared in 56% yield from 2-benzylthio-5-isopropyl-1,2,4-triazolo[1,5-a]pyrimidine following the general procedure described in Example 46.

The product was isolated as a solid, m.p. 60°–62° C. IR and $^1$H NMR spectra were in agreement with the assigned structure.

Analysis:

Calculated for $C_8H_9ClN_4O_2S$: C, 36.85; H, 3.45; N, 21.49. Found: C, 37.02; H, 3.49; N, 21.71.

EXAMPLE 50

Preparation of 5,6-dimethyl-1,2,4-triazolo-[1,5-a]pyrimidine-2-sulfonyl chloride This material was prepared in 80% yield from 2-benzylthio-5,6-dimethyl-1,2,4-triazolo[1,5-a]pyrimidine following the general procedure described in Example 46. The product was isolated as a solid, m.p. 116°–120° C. IR and $^1$H NMR spectra were in agreement with the assigned structure.

Exact mass calculated for $C_7H_7ClN_4O_2S$: 245.9984. Found: 245.9981.

EXAMPLE 51

Preparation of 6-chloro-5-methyl-1,2,4-triazolo[1,5-a]pyrimidine-2-sulfonyl chloride This material was prepared in 60% yield from 2-benzylthio-6-chloro-5-methyl-1,2,4-triazolo[1,5-a]-pyrimidine following the general procedure described in Examples 38–45. The product was isolated as a solid, m.p. 99°–101° C. IR and $^1$H NMR spectra were in agreement with the assigned structure.

EXAMPLE 52

Preparation of 5-methoxy-1,2,4-triazolo-[1,5-a]pyrimidine-2-sulfonyl chloride

This material was prepared in 57% yield from 2-benzylthio-5-methoxy-1,2,4-triazolo[1,5-a]pyrimidine following the general procedure described in Examples 38–45. The product was isolated as a solid, m.p. 110°–112° C. IR and $^1$H NMR spectra were in agreement with the assigned structure.

Analysis:

Calculated for $C_6H_5ClN_4O_3S$: C, 28.97; H, 2.01: N, 22.53. Found: C, 29.90; H, 2.23; N, 22.76.

EXAMPLE 53

Preparation of 5-(2,2,2-trifluoroethoxy)-1,2,4-triazolo[1%5-a]pyrimidine-2-sulfonyl chloride This material was prepared in 74% yield from 2-benzylthio-5-(2,2,2-trifluoroethoxy)-1,2,4-triazolo-[1,5-a]pyrimidine following the general procedure described in Examples 38–45. The product was isolated as a solid, m.p. 91°–96° C. IR and $^1$H NMR spectra were in agreement with the assigned structure.

Exact mass calculated for $C_7H_4ClF_3N_4O_3S$: 315.9655 Found: 315.9650.

EXAMPLE 54

Preparation of 5-ethoxy-1,2,4-triazolo-[1,5-a]pyrimidine-2-sulfonyl chloride

This material was prepared in 74% yield from 2-benzylthio-5-ethoxy-1,2,4-triazolo[1,5-a]pyrimidine following the general procedure described in Examples 38–45. The product was isolated as a solid, m.p. 91°–96° C. IR and $^1$H NMR spectra were in agreement with the assigned structure.

EXAMPLE 55

Preparation of 5-methoxy-6-methyl-1,2,4-triazolo[1,5-a]pyrimidine-2-sulfonyl chloride This material was prepared in 80% yield from 2-benzylthio-5-methoxy-6-methyl-1,2,4-triazolo[1,5-a]pyrimidine following the general procedure outlined in Examples 38–45. The product was isolated as a solid, m.p. 154°–157° C. IR and $^1$H NMR spectra were in agreement with the assigned structure.

Analysis:

Calculated for $C_7H_7ClN_4O_3S$: C, 32.00; H, 2.67; N, 21.33. Found: C, 32.35; H, 2.61; N, 21.45.

EXAMPLE 56

Preparation of 6-ethoxycarbonyl-7-methyl-1,2,4-triazolo[1,5-a]pyrimidine-2-sulfonyl chloride This material was prepared in 82% yield from 2-benzylthio-6-ethoxycarbonyl-7-methyl-1,2,4-triazolo-[1,5-a]pyrimidine following the general procedure described in Example 46. The product was isolated as a solid, m.p. 65°–69° C. IR and $^1$H NMR spectra were in agreement with the assigned structure.

Analysis:

Calculated for $C_9H_9ClN_4O_4S$: C, 35.47; H, 2.95; N, 18.39 Found: C, 36.04; H, 3.02; N, 18.27

EXAMPLE 57

Preparation of 6-(4-nitrophenyl)-1,2,4-triazolo[1,5-a]pyrimidine-2-sulfonyl chloride This material was prepared in 71% yield from 2-benzylthio-6-(4-nitrophenyl)-1,2,4-triazolo[1,5-a]pyrimidine following the general procedure described in Examples 38–45. The product was isolated as a solid, m.p. 159°–167° C. IR and $^1$H NMR spectra were in agreement with the assigned structure.

EXAMPLE 58 of 5,7-dimethyl-N-(2-chlorophenyl)-1,2,4-triazolo[1,5-]pyrimidine-2-sulfonamide To a solution of 0.74 ml (0.90 g, 7.0 mmol) of chloroaniline in 10 ml of dry pyridine was added 1.89 g (7.66 mmol) of the sulfonyl chloride prepared in Example 38. The resulting dark solution was stirred at ambient temperature for 18 hours and evaporated to dryness. The residue was treated with 15 ml of 1N NaOH and charcoal and stirred for 15 minutes. The mixture was filtered through celite and the filtrate was acidified with 3N HCl to precipitate the product. Filtration and drying in vacuo gave the desired product (2.01 g, 85%) as a light brown solid, m.p. 188°–189.5° C. IR and $^1$H NMR spectra were in agreement with the desired compound of formula I (Ar =o-chlorophenyl, X=Z=Me, Y=H).

Analysis:

Calculated for $C_{13}H_{12}ClN_5O_2S$: C, 46.23; H, 3.58; N, 20.73; Cl, 10.50; S, 9.49. Found: C, 46.09; H, 3.58; N, 20.89; Cl, 10.34; S, 9.37.

EXAMPLE 59

Preparation of methyl N-(5,7-dimethyl-1,2,4-triazolo[1,5-a]pyrimidine-2-sulfonyl)-anthranilate To a solution of 0.91 ml (1.1 g, 7.0 mmol) of methyl anthranilate in 10 ml of dry pyridine was added 1.89 g (7.66 mmol) of the sulfonyl chloride prepared in Example 38. The resulting dark solution was stirred at room temperature for 18 hours and evaporated to dryness. The residue was treated with 15 ml of 1N NaOH and charcoal and stirred for 15 minutes. The mixture was filtered through celite, and the filtrate was acidified with 3N HCl to precipitate the product. The product was collected by filtration and dried in vacuo to yield 2.27 g (90%) of the desired product of Formula I (X=Z=Me, Y=H, Ar=o-carbomethoxyphenyl) as a cream colored solid, m.p. 169.5°–170.5° C. IR and $^1$H NMR spectra confirmed the structure of the product.

Analysis

Calculated for $C_{15}H_{15}N_5O_4S$: C, 49.86; H, 4.18; N, 19.38; S, 8.87. Found: C, 49.68; H, 4.13; N, 19.35: S, 8.69.

EXAMPLE 60

Preparation of 5,7-dimethyl-N-(2,6-dimethylphenyl)-1,2,4-triazolo[1,5-a]pyrimidine-2-sulfonamide A solution of 2.2. g (8.9 mmol) of 5,7-dimethyl-1,2,4-triazolo[1,5-a]pyrimidine-2-sulfonyl chloride, 1.01 ml (8.4 mmol) of 2,6-dimethylaniline, 0.7 ml (8.4 mmol) of dry pyridine and 4 mg of DMAP in 20 ml of $CH_2Cl_2$ was stirred at room temperature for 17 hours. The solvent was removed by evaporation and the residue was taken up in 0.5M NaOH. The solution was extracted with diethyl ether and the aqueous phase was acidified with 3N HCl to precipitate a solid. The solid was collected by filtration and dried in vacuo to yield 2.72 g (97 percent) of the desired product as a white solid, m.p. 263°–266° C. (decomp.): $^1$H NMR (DMSO—d$_6$)δ10.4 ($^1$H, broad S), 7.55 ($^1$H, s), 7.2 (3H, s), 2.7 and 2.8 (3H each, s) and 2.1 (6H, s); IR (KBr) 3100, 2980–2780, 1628, 1540 and 1355 cm$^{-1}$

Analysis:

Calculated for $C_{15}H_{17}N_5O_2S$: C, 54,31; H, 5.%, N, 21.23. Found: C, 53.59; H, 5.07; N, 20.65.

EXAMPLE 61

Preparation of 6,7-cyclopentano-5-methyl-N-(2,6-dichlorophenyl)-1,2,4-triazolo[1,5-a]-pyrimidine-2-sulfonamide A solution of 3.31 g (12.1 mmol) of crude 6,7-cyclopentano-5-methyl-1,2,4-triazolo[1,5-a]pyrimidine-2-sulfonyl chloride and 1.87 g (11.6 mmol) of 2,6-dichloroaniline in 15 ml of dry pyridine was stirred at 45°–50° C. for 23 hours. The majority of the pyridine was removed by evaporation at reduced pressure, and the residue was treated with 25 ml of 1N NaOH and ice. After stirring for 15 minutes, the mixture was filtered and the filtrate was acidified with 3N HCl to precipitate a light brown solid. The solid was taken up in 0.5N NaOH and filtered. The filtrate was acidified with 3N HCl to precipitate a solid. The solid was collected by filtration and dried in vacuo to yield 1.19 g (26 percent) of the desired sulfonamide as a light brown solid, m.p. 264°–266° C.: $^1$H NMR (DMSO-d$_6$) δ10.83 ($^1$H, broad s), 7.1–7.6 (3H, m) and 2.0–3.6 (9H, m including s at 2.57); IR (KBr) 3410, 1620, 1549, 1442, 1399, 1358 and 1167$^{-1}$.

Analysis:

Calculated for $C_{15}H_{13}Cl_2N_5O_2S$: C, 45.24; H, 3.29; N, 17.58. Found: C, 45.47; H, 3.18; N, 17.41.

EXAMPLE 62

Preparation of 5,7-dimethyl-N-(2,4,6-trichlorophenyl)-1,2,4-triazolo[1,5-a]-pyrimidine-2-sulfonamide A solution (10.7 ml, 17.1 mmol) of 1.60M N-butyllithium in hexane was added to a solution of 3.20 g (16.3 mmol) of 2,4,6-trichloroaniline in 20 ml of dry THF cooled to −78° C. The resultant solution was then allowed to warm to room temperature. This solution was added to a solution of 2.00 g (8.11 mmol) of 5,7-dimethyl-1,2,4-triazolo[1,5-a]pyrimidine-2-sulfonyl chloride in 30 ml of dry THF cooled to −10° C. The temperature of the reaction mixture was maintained between −13° C. and −9° C. during to course of the addition. After the addition was complete, the reaction mixture was stirred for 30 minutes and warmed to room temperature. After 1 hour at room temperature, THF was removed from the reaction mixture by evaporation. The residue was triturated with $H_2O$ and filtered. The filtrate was treated with charcoal and filtered through celite. The filtrate was washed with $Et_2O$, and the aqueous phase was separated and acidified with 3N HCl to precipitate a solid. The solid was collected by filtration, washed with water and dried in vacuo to yield 0.70 g (21%) of the desired product as a tan solid, m.p. >200° C. (decomp.) $^1$H NMR and IR spectra were consistent with the assigned structure.

Analysis:

Calculated for $C_{13}H_{10}N_5O_2S$: C, 38.40; H, 2.48; N, 17.22. Found: C, 38.36; H, 2.48; N, 17.14.

EXAMPLE 63

Preparation of 6-chloro-N-(2,6-difluorophenyl)-1,2,4-triazolo[1,5-a]pyrimidine-2-sulfonamide The starting 2,6-difluoroaniline (1.7 g, 13 mmol) was dissolved in 3.5 ml of pyridine and 3.5 g (14 mmol) of 6-chloro-1,2,4-triazolo[1,5-a]pyrimidine-2-sulfonyl chloride was added. After an exothermic reaction subsided the reaction mixture was heated at 60°–70° C. overnight. The solvent was removed by evaporation at reduced pressure and the residue was taken up in aqueous sodium bicarbonate. The aqueous solution was washed with ether, and acidified with aqueous HCl. The solid which separated upon acidification was collected by filtration, dried and recrystallized from methanol to afford 2.5 g (55%) of the desired product as a crystalline solid, m.p. 224°–226° C. IR and $^1$H NMR spectra were in agreement with the assigned structure.

Analysis:

Calculated for $C_{11}H_6ClF_2N_5O_2S$: C,38.21; H,1.75; N,20.26. Found: C,38.32; H,1.44; N,20.18.

EXAMPLE 64

Preparation of methyl
3-methyl-N-(6-methyl-1,2,4-triazolo[1,5-a]pyrimidine-2-sulfonyl)anthranilate Methyl 3-methylanthranilate (2.1 g, 13 mmol) was dissolved in 4 ml pyridine and 6-methyl-1,2,4-triazolo-[1,5-a]pyrimidine-2-sulfonyl chloride was added. After a mild exothermic reaction subsided the reaction mixture was stirred at 50° C. for 24 hours. The pyridine was removed by evaporation at reduced pressure and the residue was treated with in 10% aqueous sodium bicarbonate. Insoluble material was collected by filtration, washed with ether and dried to yield 2.9 (63%) of the desired product as a solid, m.p. 198.5°–205° C. An analytical sample was prepared by recrystallization from ethanol to yield a crystalline solid, m.p. 208.5°–210.5° C. IR and $^1$H NMR spectra were in agreement with the assigned structure.

Analysis:

Calculated for $C_{15}H_{15}N_5O_4S$: C, 49.85; H, 4.18; N, 19.38. Found: C, 49.96; H, 4.14; N, 19.75.

EXAMPLE 65

Preparation of
5-methyl-N-(2,6-difluorophenyl)-1,2,4-triazolo[1,5-a]pyrimidine-2-sulfonamide The starting 2,6-difluoroaniline (18.1 g, 0.140 mol) was dissolved in 45 ml of pyridine and 36.1 g (0.155 mol) of 5-methyl-1,2,4-triazolo[1,5-a]pyrimidine-2-sulfonyl chloride was added. After an exothermic reaction subsided the reaction mixture was stirred at room temperature for 15.5 hours. The pyridine was removed by evaporation at reduced pressure, and the residue was treated with 600 ml of 0.5N NaOH. After stirring to dissolve all soluble material the mixture was filtered through celite and the filtrate was acidified with 3N HCl. The precipitate which separated upon acidification was collected by filtration and dried to yield 33.0 g (73%) of the desired product as a pale red solid, m.p. 245°–247° C. IR and $^1$H NMR spectra were in agreement with the assigned structure.

Analysis:

Calculated for $C_{12}H_9F_2N_5O_2S$: C, 44.31; H, 2.79; N, 21.53. Found: C, 44.69; H, 2.80; N, 21.85.

EXAMPLE 66

Preparation of
5,7-dimethyl-N-(2-acetoxymethyl-6-chlorophenyl)-1,2,4-triazolo[1,5-a]-pyrimidine-2-sulfonamide A solution of 1.30 gm (6.50 mmol) of 2-amino-3-chlorobenzyl acetate, 4.11 gm (52.0 mmol) of pyridine and 5.0 ml of acetonitrile was treated with 1.61 gm (6.50 mmol) of 5,7-dimethyl-1,2,4-triazolo[1,5-a]pyrimidine-2-sulfonyl chloride and the resulting mixture stirred at 25° C. for 120 hours. An additional 0.53 gm (2.2 mmol) of the sulfonyl chloride was added and stirring at 25° C. continued for an additional 24 hours. The mixture was filtered and the filtrate evaporated to provide a brown oil. The oil was then dissolved in 40 ml of methylene chloride and stirred with 25 ml of 0.5M NaOH. After 5 minutes, the aqueous phase was separated, washed with ether and acidified with 3 N HCl. A light brown solid was collected, washed with water, dried and recrystallized from acetonitrile to provide 0.35 gm (13%) of the desired product as a solid, m.p. 214°–217° C., containing approximately 10% of an impurity. IR and $^1$H NMR spectra were in agreement with the assigned structure.

Analysis:

Calculated for $C_{16}H_{16}ClN_5O_4S$: C, 46.89; H, 3.94; N, 17.08. Found: C, 46.60; H, 3.80; N, 17.73.

EXAMPLE 67

Preparation of methyl
3-amino-2-bromo-4-methyl-N-(5,7-dimethyl-1,2,4-triazolo-[1,5-a]pyrimidine-2-sulfonyl)benzoate A solution of 1.50 g (6.15 mmol) of methyl 2-bromo-3-amino-4-methylbenzoate in 7 ml of pyridine was treated with 1.67 g (6.76 mmol) of 5,7-dimethyl-1,2,4-triazolo[1,5-a]pyrimidine-2-sulfonyl chloride. After stirring at 25° C. for 18 hours an additional 0.46 g (1.9 mmol) of the sulfonyl chloride was added and the reaction mixture was heated at 52°–55° C. for 3 hours. The solvent was removed by evaporation and the residue was partitioned between methylene chloride and dilute aqueous HCl. The organic phase was washed with water, dried and evaporated at reduced pressure to yield 1.85 g (66%) of the desired product as a yellow solid upon trituration with ethyl acetate. An analytical sample was prepared by recrystallization from acetonitrile-DMF to afford a crystalline solid, m.p. 229°–231° C. IR and $^1$H NMR spectra were in agreement with the assigned structure.

Analysis:

Calculated for $C_{16}H_{16}BrN_5O_4S$: C, 42.30; H, 3.55; N, 1.5.41 Found: C, 42.29; H, 3.45; N, 15.68

EXAMPLE 68

Preparation of
3-amino-2-bromo-4-methyl-N-(5,7-dimethyl-1,2,4-triazolo[1,5-a]pyrimidine-2-sulfonyl)benzoic acid A solution of 2.78 g (6.12 mmol) of methyl 3-amino-2-bromo-4-methyl-N-(5,7-dimethyl-1,2,4-triazolo[1,5-a]pyrimidine-2-sulfonyl)benzoate and 30 ml of 5% aqueous NaOH in 30 ml of water was stirred at 25° C. for 2.5 hours. The reaction mixture was filtered and the filtrate was cooled in ice and acidified to approximately pH 2 with 3N HCl. The solid which separated was collected by filtration, washed with water and dried in vacuo to yield 2.10 g (78%) of the desired product as a gold solid, m.p. 290° C. (decomposition). IR and $^1$H NMR spectra were in agreement with the assigned structure.

Analysis:

Calculated for $C_{15}H_{14}BrN_5O_4S$: C, 40.92; H, 3.21; N, 15.90 Found: C, 40.51; H, 3.11; N, 16.01

EXAMPLE 69

Preparation of
5-methylthio-N-(2,6-dichlorophenyl)-1,2,4-triazolo[1,5-a]pyrimidine-2-sulfonamide To 25 ml (13 mmol) of a 0.52M solution of sodium methyl mercaptide in DMSO prepared by bubbling methyl mercaptan into a suspension of sodium hydride in DMSO, was added 2.6 g (5.9 mmol) of 5-(2,2,2-trifluoroethoxy)-N-(2,6-dichlorophenyl)-1,2,4-triazolo[1,5-a]pyrimidine-2-sulfonamide. The solution was stirred at room temperature for 25 hours, diluted with 100 ml of ice water and neutralized with 3N aqueous HCl. The gummy solid which separated was collected and taken up in 0.5N aqueous NaOH. The mixture was filtered to remove insoluble material, and the filtrate was acidified with 6N aqueous HCl. The solid which separated was collected by filtration and dried to yield 1.5 g (66%) of the desired product as a pale yellow solid, mp 239°-243° C. IR and $^1$H NMR spectra were in agreement with the assigned structure.

Analysis:

Calculated for $C_{12}H_9Cl_2N_5O_2S_2$: C, 36.92; H, 2.31; N, 17.95. Found: C, 36.51; H, 2.41; N, 17.68.

EXAMPLE 70

Preparation of 5-dimethylamino-N-(2,6-dichlorophenyl)-1,2,4-triazolo[1,5-a]pyrimidine-2-sulfonamide The starting 5-(2,2,2-trifluoroethoxy)-N-(2,6-dichlorophenyl)-1,2,4-triazolo[1,5-a]pyrimidine-2-sulfonamide (1.5 g, 3.4 mmol) was dissolved in 5 ml (44 mmol) of 50% aqueous dimethylamine. After stirring for 48 hours at room temperature the solution was diluted with water and acidified with 6N aqueous HCl. The solid which separated was collected by filtration and treated with 0.5N aqueous NaOH and filtered to remove insoluble material. The filtrate was acidified to precipitate a solid. The solid was collected and dried to yield 1.0 g (60%) of the desired product as a solid, mp >310° C. IR and $^1$H NMR spectra were in agreement with the assigned structure.

Analysis:

Calculated for $C_{13}H_{12}Cl_2H_6O_2S$: C, 40.31; H, 3.10; N, 21.71; S, 8.28. Found: C, 40.08; H, 3.05; N, 22.33 S, 7.99.

EXAMPLE 71

Preparation of 6-bromo-5-methyl-N-(2,6-dichlorophenyl)-1,2,4-triazolo[1,5-a]pyrimidine-2-sulfonamide A suspension of 4.0 g (11 mmol) of 5-methyl-N-(2,6-dichlorophenyl)-1,2,4-triazolo[1,5-a]pyrimidine-2-sulfonamide in 50 ml of glacial acetic acid and 10 ml of acetic anhydride was stirred at 90° C. for 30 minutes. N-Bromosuccinimide (2.4 g, 13 mmol) was added to this hot solution, and the reaction mixture was stirred at 90° C. for 60 minutes. The solution was cooled and poured into 200 ml of ice water. A solid which separated was collected and dried. This crude product was purified by dissolving the sample in methylene chloride, filtering the solution through silica gel and triturating the filtrate with pentane. The desired product was obtained as a solid, mp 215°-216° C. IR and $^1$H NMR spectra were in agreement with the assigned structure.

Exact mass calculated for $C_{12}H_8BrCl_2N_5O_2S$: 438.8898 Found: 438.8899

EXAMPLE 72

Preparation of 5,7,N-trimethyl-N-(2,6-dichlorophenyl)-1,2,4-triazolo[1,5-a]-pyrimidine-2-sulfonamide A mixture of 3.00 g (8.06 mmol) of 5,7-dimethyl-N-(2,6-dichlorophenyl)-1,2,4-triazolo[1,5-a]-pyrimidine-2-sulfonamide and 0.90 g (8.1 mmol) of potassium t-butoxide in 30 ml of acetonitrile was heated at reflux for 40 minutes. After cooling to room temperature 1.14 g (8.06 mmol) of methyl iodide was added, and the reaction was heated at reflux for 1 hour. After cooling to room temperature, the reaction mixture was diluted with methylene chloride and washed with 1% aqueous NaOH. The organic phase was separated, dried (MgSO$_4$) and evaporated at reduced pressure. The brown solid residue was recrystallized from acetone to give 1.60 g (51%) the desire product as a tan solid, mp 220°-222° C. IR and $^1$H NMR spectra were in agreement with the assigned structure.

Analysis:

Calculated for $C_{14}H_{13}Cl_2N_5O_2S$: C, 43.54; H, 3.39; N, 18.13 Found: C, 43.55; H, 3.32; N, 18.03

EXAMPLE 73

Preparation of 5-methyl-N-benzoyl-N-(2,6-dichlorophenyl)-1,2,4-triazolo[1,5-a]-pyrimidine-2-sulfonamide A mixture of 3.00 g 8.37 mmol) of 5-methyl-N-(2,6-dichlorophenyl)-1,2,4-triazolo[1,5-apyrimiine-2-sulfonamide and 1.16 g (8.37 mmol) of anhydrous powdered $K_2CO_3$ in 100 ml of acetone was heated at reflux for 30 minutes. A solution of 1.18 g (8.37 mmol) of benzoyl chloride in 10 ml of acetone was added, and the reaction was heated at reflux for 115 min. The reaction was filtered, and the filtrate was evaporated at reduced pressure. The solid residue was collected by filtration, washed thoroughly with aqueous NaHCO$_3$ and H$_2$O and dried to yield 2.75 g (72%) of the desired product as a solid, mp 187°-189° C. IR and $^1$H NMR spectra were in agreement with the assigned structure.

Analysis:

Calculated for $C_{19}H_{13}Cl_2N_5O_3S$: C, 49.36; H, 2.83; N, 15.15. Found: C, 48.97; H, 2.84; N, 15.16

EXAMPLE 74

Preparation of 5-methyl-N-(2,6-dichlorophenyl)-4,5,6,7-tetrahydro-1,2,4-triazolo[1,5-a]pyrimidine-2-sulfonamide Sodium borohydride (0.6 g, 16 mmol) was added to a solution of 3.0 g (8.3 mmol) of 5-methyl-N-(2,6-dichlorophenyl)-1,2,4-triazolo[1,5-a]pyrimidine-2-sulfonamide in 25 ml of dry DMSO. An exothermic reaction occured and 2.0 ml (31 mmol) of methanesulfonic acid in 5 ml of DMSO was added at a rate to maintain the temperature of the reaction mixture at 60° C. After the addition was complete the reaction mixture was stirred for 10 minutes and carefully quenched with 0.5N aqueous NaOH. The clear yellow solution was filtered, and the filtrate was acidified with 3N aqueous HCl. The resulting precipitate was treated with dilute aqueous NaOH and filtered to remove insoluble material. The filtrate was acidified with aqueous HCl to precipitate a solid. The solid was collected by filtration and dried to yield 1.11 g (37%) of the desired product as a solid, mp 230°-235° C. IR and $^1$H NMR spectra were in agreement with the assigned structure.

Analysis:

Calculated for $C_{12}H_{12}Cl_2N_5O_2S$: C, 39.89; H, 3.32; N, 19.39. Found: C, 39.72; H, 3.42; N, 19.19.

EXAMPLE 75

Preparation of
N-(2,6-dichloro-3-methylphenyl)-5-amino-1,2,4-triazole-3-sulfonamide Potassium hydroxide (72.9 g of 85 percent pellets, 1.20 mol) was dissolved in one liter of water in a 2 liter round bottom flask and 113.3 g (0.30 mol) of wet N-(2,6-dichloro-3-methylphenyl)-5,7-dimethyl-1,2,4,-triazolo[1,5-a]pyrimidine-2-sulfonamide was added with stirring. The mixture obtained was cooled to 17° C. and 100 ml of 30 percent hydrogen peroxide solution (about 1 mole) was added with stirring over a 0.5 hour period so that the temperature did not exceed 40° C. The reaction was found to be complete after three hours by high pressure liquid chromatography. An aqueous solution of sodium bisulfite was added to quench the excess hydrogen peroxide and the solution obtained was filtered through celite and then acidified with concentrated hydrochloric acid. The precipitate that formed was collected by filtration, washed with water, and partially dried. This material, which is the $N^1$-acetyl derivative of the desired product, was dissolved in 800 ml of tetrahydrofuran and the resulting solution was combined with 100 ml of water and 100 ml of concentrated hydrochloric acid. This mixture was heated at reflux with stirring in a two liter round bottom flask overnight. The solvent was removed by evaporation under reduced pressure and the resulting aqueous suspension was filtered to collect the solid product. This was washed with water and dried to obtain 59.3 g (61 percent of theory) of the title compound as a white solid. This compound has an m.p. of 206°-8° C.

Analysis:

Calculated for $C_9H_9Cl_3N_5O_2S$: C, 30.1; H, 2.81; N, 19.3. Found: C, 29.9; H, 3.33; N, 19.0.

EXAMPLE 76

Preparation of
N-(2-trifluoromethylphenyl)-5-amino-1,2,4-triazole-3-sulfonamide

A 110.6 g (0.30 mol) portion of N-(2-trifluoromethylphenyl)-5,7-dimethyl-1,2,4-triazolo[1,5-a]pyrimidine-2-sulfonamide was added to a solution of 79 g of 85 percent potassium hydroxide (1.2 mol) in two liters of water. Another liter of water was added and then 400 ml of 30 percent hydrogen peroxide (3.9 moles) was added to the mixture with stirring and cooling with an ice bath at a rate so that the temperature did not exceed 40° C. After about 3.5 hours, the reaction was found to be complete by thin layer chromatography. About 100 ml of 12N hydrochloric acid was added dropwise to precipitate the product and then a little solid sodium bisulfite was added to destroy the excess hydrogen peroxide. The precipitate was collected by filtration washed with water and dried to obtain 94 g of the $N^1$-acetyl derivative of the desired product. This was dissolved in 750 ml of tetrahydrofuran and 375 ml of concentrated hydrochloric acid and 360 ml of water were added. The mixture was heated to reflux with stirring for about four hours The solvent was then removed by evaporation under reduced pressure. Ethanol was added and the solution obtained was treated with charcoal Ethanol was evaporated to precipitate the title compound which was collected by filtration and dried to obtain a total of 51.6 g (56.4 percent of theory) of white solid, the first 47.6 g of which melted at 227°-9° C.

Analysis:

Calculated for $C_9H_8N_5F_3SO_2$: C, 35.18; H, 2.62; N, 22.80; S, 10.43. Found: C, 34.79; H, 2.65; N, 22.53; S, 10.20.

EXAMPLE 77

Preparation of
N-(2,6-dichloro-3-methylphenyl)-7-hydroxy-5-methyl-1,2,4-triazolo[1,5-a]-pyrimidine-2-sulfonamide A solution of 32.2 g (0.10 mol) of N-(2,6-dichloro-3-methylphenyl)-5-amino-1,2,4-triazole-3-sulfonamide and 14 ml (0.11 mol) of ethyl acetoacetate in 500 ml of methanol containing 1 ml of 12N hydrochloric acid was heated to reflux with stirring for about 18 hours. The solid present was collected by filtration and the filtrate was heated to reflux for another day. The mixture obtained was cooled in an ice bath and the solid present was collected by filtration. The filtrate was concentrated to about 200 ml by evaporation of methanol and heated to reflux overnight. The mixture obtained was filtered to collect the solid present. The filtrate was concentrated to about 150 ml, treated with about 2 ml of ethyl acetoacetate, and heated at reflux for about 3 days. The solids present were collected by filtration and dried to obtain 6.4 g, 10.0 g, 8.2 g and 11.1 g crops of the title compound for a total of 35.7 g (92 percent of theory). The first obtained crop melted at 346°-7° C. with decomposition.

Analysis:

Calculated for $C_{13}H_{11}Cl_2N_5O_3S$: C, 40.2; H, 2.86; N, 18.04. Found: C, 39.6; H, 2.96; N, 17.96.

EXAMPLE 78

Preparation of
N-(2-trifluoromethylphenyl)-7-hydroxy-5-methyl-1,2,4-triazolo[1,5-a]pyrimidine-2-sulfonamide A solution of 1 ml of 12 N hydrochloric acid in 250 ml of methanol was added to a mixture of 20.0 g (65.1 mmol) of N-(2-trifluoromethylphenyl)-5-amino-1,2,4-triazole-3-sulfonamide and 9.2 ml (72.2 mmol) of ethyl acetoacetate and the mixture heated to reflux with stirring. After about 5 days, most but not all of the starting material was found to have reacted by thin layer chromatography The solution was chilled and the precipitate that formed was collected by filtration, washed with cold methanol and dried to obtain 16.5 g (67.9 percent of theory) of the title compound as a white solid hemihydrate melting at 245°-7° C.

Analysis:

Calculated for $C_{13}H_{10}F_3N_5O_3 \cdot \frac{1}{2}H_2O$: C, 40.8; H, 2.88; N, 18.31; S, 8.37. Found: C, 40.4; H, 2.76 N, 18.29; S, 7.93.

EXAMPLE 79

Preparation of
N-(2,6-dichloro-3-methylphenyl)-7-chloro-5-methyl-1,2,4-triazolo[1,5-a]pyrimidine-2-sulfonamide A solution of 100 ml of phosphoryl chloride in 400 ml of dry acetonitrile was added to 12.0 g (30.9 mmol) of N-(2,6-dichloro-3-methylphenyl)-7-hydroxy-5-methyl-1,2,4-triazolo[1,5-a]pyrimidine-2-sulfonamide and heated to reflux with stirring. After about 24 hours, the mixture became a solution which appeared to contain little or no starting material by thin layer chromatography. The volatiles were largely removed by evaporation under reduced pressure and the residue poured onto about one liter of ice and water with stirring using fresh acetonitrile as a transfer solvent. The solid in the resulting mixture was collected by filtration, washed with water, and dried under reduced pressure at 70° C. overnight. The resulting solid, which was found to be the title compound by NMR analysis, amounted to 8.4 g (67 percent of theory).

EXAMPLE 80

Preparation of
N-(2-trifluoromethylphenyl)-7-chloro-5-methyl-1,2,4-triazolo[1,5-a]pyrimidine-2-sulfonamide Phosphorus oxychloride (135 ml, 1.47 mol) was diluted with 335 ml of dry acetonitrile and added to 15 g (40 mmol) of N-(2-trifluoromethylphenyl)-7-hydroxy-5-methyl-1,2,4-triazolo[1,5-a]pyrimidine-2-sulfonamide in a one liter flask and heated to reflux with stirring. After about 3 days, the reaction was found to be complete by thin layer chromatography. Volatiles were removed by evaporation under reduced pressure until the mixture became very viscous and the residue was poured onto about one liter of ice and water with stirring. After about 30 minutes, the solid that formed was collected by filtration, washed with ice water, and dried under reduced pressure at room temperature. It was then dissolved in methylene chloride and the resulting solution dried over magnesium sulfate for about five minutes and filtered. The volatiles were removed from the filtrate by evaporation under reduced pressure to obtain the title compound as a white solid residue. The product, the structure of which was confirmed by NMR analysis, amounted to 13.4 g (85.4 percent of theory).

EXAMPLE 81

Preparation of
N-(2,6-dichloro-3-methylphenyl)-7-methoxy-5-methyl-1,2,4-triazolo[1,5-a]pyrimidine-2-sulfonamide Sodium (0.6 g, 26 mmol) was added to about 40 ml of methanol and allowed to react. N-(2,6-dichloro-3-methylphenyl)-7-chloro-5-methyl-1,2,4-triazolo[1,5-a]pyrimidine-2-sulfonamide (2.5 g, 6.9 mmol) was added with stirring. After about 20 minutes, thin layer chromatography indicated the starting material had reacted. The solution was then acidified by adding 6-N hydrochloric acid dropwise and then concentrated by evaporation under reduced pressure. The residue was triturated with water and the solid that formed was washed with water and dried to obtain 1.35 g of the title compound as a white solid, m p. 239°-42° C.

Analysis:

Calculated for $C_{14}H_{13}Cl_2N_5O_3$: C, 41.8; H, 3.26; N, 17.41; S, 7.97. Found: C, 41.4; H, 3.19; N, 17.42; S, 8.15.

EXAMPLE 82

Preparation of
N-(2,6-dichloro-3-methylphenyl)-7-ethoxy-5-methyl-1,2,4-triazolo[1,5-a]pyrimidine-2-sulfonamide Sodium (0.69 g, 30 mmol) was added to about 50 ml of ethanol and allowed to react. The mixture was allowed to cool and then 4.0 g (9.8 mmol) of N-(2,6-dichloro-3-methylphenyl)-7-chloro-5-methyl-1,2,4-triazolo[1,5-a]pyrimidine-2-sulfonamide was added with stirring. After 15 minutes no starting material remained by thin layer chromatographic analysis although complete solution was never attained. The mixture was acidified with 6N hydrochloric acid and concentrated under reduced pressure. The residue was triturated with water and the solid removed by filtration and washed with water. It was then dissolved in aqueous sodium hydroxide using a minimum amount of the base and the aqueous solution was twice extracted with ether and acidified with 6N hydrochloric acid. The solid that formed was collected by filtration, washed with water, and dried. This was extracted with about 500 ml of boiling chloroform. The chloroform solution was concentrated to about 150 ml and allowed to cool to form a precipitate which was collected by filtration and dried to obtain 1.7 g (42 percent of theory) of the title compound as a white solid, m.p. 228°-9° C.

Analysis:

Calculated for $C_{15}H_{15}Cl_2N_5O_3S$: C, 43.3; H, 3.63; N, 16.83; S, 7.70. Found: C, 42.9; H, 3.66; N, 16.92; S, 7.66.

EXAMPLE 83

Preparation of
N-(2,6-dichlorophenyl)-7-methylthio-5-methyl-1,2,4-triazolo[1,5-a]-pyrimidine-2-sulfonamide An oil dispersion of sodium hydride (1.15 g, 24 mmol) was washed three times with hexane by slurrying and decanting and was then suspended in 30 ml of dry dimethyl sulfoxide. An excess of methanethiol (greater than 1.3 ml) was added dropwise with stirring. A solution of N-(2,6-dichlorophenyl)-7-chloro-5-methyl-1,2,4-triazolo-[1,5-a]pyrimidine-2-sulfonamide (3.14 g, 8.0 mmol) was added to this dropwise with stirring. Thirty minutes after the addition was complete, about 200 ml of water were added and the solution was acidified with 6N hydrochloric acid. Nitrogen was blown through the system to remove any unreacted methanethiol (trapped in sodium hypochlorite solution) and the solid present was collected by filtration, washed with water, and dried to obtain 2.7 g (84 percent by theory) of the title compound contaminated with some 5-hydroxy analog. A 1 g portion of this was dissolved in aqueous sodium hydroxide (minimum amount of base) and the resulting solution was treated with charcoal, filtered, and then acidified with 6N hydrochloric acid The resulting precipitate was collected by filtration, washed with water, and dried to obtain 0.9 g of the title compound melting at 289°-91° C.

Analysis:

Calculated for $C_{13}H_{11}Cl_2N_5O_2S_2$ C, 38.6; H, 2.74; N, 17.32 Found: C, 38.4; H, 2.65; N, 17.20.

EXAMPLE 84

Preparation of
N-(2-trifluorophenyl)-7-methylthio-5-methyl-1,2,4-triazolo[1,5-a]-pyrimidine-2-sulfonamide Sodium hydride (1.2 g, 25 mmol) was washed three times with hexane and suspended in 50 ml of dry dimethyl sulfoxide. An excess of methanethiol (greater than 1.4 ml) was added dropwise until a clear solution formed. The solution was allowed to cool and then 2.5 g (6.4 mmol) of N-(2-trifluorophenyl)-7-chloro-5-methyl-1,2,4-triazolo[1,5-a]pyrimidine-2-sulfonamide was added. After a short time, the starting material was found to be consumed using thin layer chromatography and the solution was diluted with water and acidified with hydrochloric acid. Nitrogen was blown through the solution to remove any unreacted methanethiol. The solids in the resulting mixture were collected by filtration, washed with water, dissolved in dilute aqueous sodium hydroxide, and reprecipitated with 6N hydrochloric acid. The solid was collected by filtration, washed with water, and dried to obtain 1.4 g (54 percent of theory) of the title compound contaminated with some hydroxy analog and melting at 184°–9° C. A portion of this was extracted with boiling chloroform and the chloroform solution was concentrated by evaporation and then diluted with carbon tetrachloride and cooled to precipitate the title compound. This melted at 193°–200° C. after collection and drying.

Analysis:

Calculated for $C_{14}H_{12}F_3N_5O_2S_2$: C, 41.7; H, 3.00; N, 17.36; S, 15.90. Found C, 41.4; H, 2.95; N, 17.21 S, 15.65.

EXAMPLE 85

Preparation of N-(2,6-dichloro-3-methyl-phenyl)-5,7-dihydroxy-1,2,4-triazolo[1,5-a]-pyrimidine-2-sulfonamide Sodium (3.11 g, 135 mmol) was added to 250 ml of absolute ethanol in a 500 ml round bottom flask and allowed to react under nitrogen. N-(2,6-dichloro-3-methylphenyl)-5-amino-1,2,4-triazole-3-sulfonamide (14.5 g, 45 mmol) and then dimethyl malonate (11.9 g, 90 mmol) were added and the mixture heated at reflux with stirring for about three days. The mixture was then cooled with an ice bath and filtered to collect the solids. These were washed with hexane and dissolved in about 75 ml of cold water and the resulting solution was acidified to about pH 2 with conc. hydrochloric acid. The precipitate that formed was collected by filtration and dried to obtain 13.55 g (77.1 percent of theory) of the title compound as a white powder, which decomposes above 200° C. This was shown to be the title compound by NMR.

EXAMPLE 86

Preparation of N-(2-methoxy-6-trifluoromethylphenyl)-5,7-dihydroxy-1,2,4-triazolo[1,5-a]-pyrimidine-2-sulfonamide Sodium (5.90 g, 257 mmol) was added to 250 ml of absolute ethanol under nitrogen and allowed to react. A 28.67 g, 85.0 mmol sample of N-(2-methoxy-6-trifluoromethylphenyl)-5-amino-1,2,4-triazole-3-sulfonamide and 24.46 g (170 mmol) of dimethyl malonate were added and the mixture heated at reflux with stirring for two days. It was then cooled with an ice bath and the solids present were collected by filtration and washed with hexane. They were then dissolved in about 150 ml of ice water and acidified with conc. hydrochloric acid to obtain 11.95 g, the title compound, which was collected by filtration and dried. The ethanolic solution was concentrated by evaporation and dried by adding toluene and removing volatiles by evaporation under reduced pressure three times. The residue was taken up in ethanol and treated as before with sodium and 16.85 g of dimethyl malonate to obtain another 10.26 g of the title compound. A total of 22.21 g (64.5 percent of theory) of the title compound, which melts at 237°–243° C. with decomposition, was obtained.

EXAMPLE 87

Preparation of N-(2,6-dichloro-3-methylphenyl)-5,7-dichloro-1,2,4-triazolo[1,5-a]pyrimidine-2-sulfonamide A 29.27 g (75 mmol) sample of N-(2,6-dichloro-3-methylphenyl)-5,7-dihydroxy-1,2,4-triazolo[1,5-a]pyrimidine-2-sulfonamide was added to 250 ml of phosphorus oxychloride and 5.0 g of phosphorus pentachloride and the mixture was heated to reflux with stirring. After 2.5 hours the mixture was allowed to cool and, after standing overnight, it was further cooled in an ice bath. The solids present were removed by filtration, washed with cold toluene, triturated with cold water, and dried to obtain 11.76 g (37 percent of theory) of the title compound; m.p. 269°–271° C. Additional material was recovered from the phosphorus oxychloride by the addition of water.

Analysis:

Calculated for $C_{12}H_7Cl_4NO_2S$: C, 33.8; H, 1.65; N, 16.40. Found: C, 33.9; H, 1.70; N, 16.56.

EXAMPLE 88

Preparation of N-(2-methoxy-6-trifluoromethyl-phenyl)-5,7-dichloro-1,2,4-triazolo[1,5-a]-pyrimidine-2-sulfonamide A 2.03 g (5.0 mmol) sample of N-(2-methoxy-6-trifluoromethylphenyl)-5,7-dihydroxy-1,2,4-triazolo[1,5-a]-pyrimidine-2-sulfonamide was combined with 15 ml of phosphorus oxychloride and the mixture heated to reflux with stirring for eight hours. The mixture was allowed to cool and the solids present were collected by filtration and washed with cold toluene. They were then washed with water and dried to obtain 0.55 g (24.9 percent of theory) of the title compound. This material was homogeneous by chromatography and its NMR spectrum was compatible with the assigned structure. Additional product was obtained by quenching the phosphorus oxychloride solution with ice water.

EXAMPLE 89

Preparation of N-(2,6-dichloro-3-methylphenyl)-5,7-dimethoxy-1,2,4-triazolo[1,5-a]pyrimidine-2-sulfonamide Sodium (469 mg, 20.4 mmol) was added to 25 ml of methanol under nitrogen and allowed to react. The resulting solution was allowed to cool and then 2.14 g (5.0 mmol) of N-(2,6-dichloro-3-methylphenyl)-5,7-dichloro-1,2,4-triazolo[1,5-a]pyrimidine-2-sulfonamide were added with stirring. After about one hour, 1 ml of acetic acid was added and the mixture was poured into about 150 ml of ice water. The solid present was collected by filtration and dried to obtain 1.76 g (84.2 percent of theory) of the title compound as a white powder, m.p. 218°–221° C.

Analysis:

Calculated for $C_{14}H_{13}Cl_2N_5O_4S$: C, 40.2; H, 3.13; N, 16.74. Found: C, 39.9; H, 3.15; N, 16.76.

EXAMPLE 90

Preparation of
N-(2,6-dichlorophenyl)-5,7-dimethoxy-1,2,4-triazolo[1,5-a]pyrimidine-2-sulfonamide Sodium (683 mg, 29.7 mmol) was added to 30 ml of methanol under nitrogen and allowed to react. The resulting solution was cooled and 4.06 g (9.83 mmol) of N-(2,6-dichlorophenyl)-5,7-dichloro-1,2,4-triazolo[1,5-a]-pyrimidine-2-sulfonamide were added with stirring. After one hour, 2 ml of acetic acid was added and the mixture was poured into about 150 ml of ice water. The solids present were collected by filtration and dried to obtain 3.21 g (88 percent of theory) of the title compound, which is a white powder that melts at 232°–4° C.

EXAMPLE 91

Preparation of methyl 3-amino-2,4-dichlorobenzoate

This material was prepared by chlorination of methyl 3-amino-4-chlorobenzoate with N-chlorosuccinimide. The product was isolated as a solid, m.p. 50°–52° C. The product was characterized by IR and $^1$H NMR spectroscopy and combustion analysis.

EXAMPLE 92

Preparation of methyl
3-amino-2-bromo-4-methylbenzoate

A mixture of 16.5 g (100 mmol) of methyl 3-amino-4-methylbenzoate and 300 ml of CCl$_4$ was treated with 18.6 g (105 mmol) of N-bromosuccinimide and stirred at ambient temperature for four hours. The reaction mixture was filtered, and the filtrate was evaporated at reduced pressure to afford an amber oil. To remove material resulting from bromination at the 6-position, the crude product was taken up in 100 ml of hexane and 60 ml of ether and treated with 3.96 g (50.0 mmol) of pyridine and 3.06 g (30.0 mmol) of acetic anhydride. After stirring for three hours at 25° C., the precipitate was removed by filtration. The filtrate was evaporated at reduced pressure to yield an amber oil. The crude product was purified by HPLC to afford 14.5 g (59%) of the desired product as an amber oil. IR and $^1$H NMR spectra were in agreement with the assigned structure.

Analysis:

Calculated for C$_9$H$_{10}$BrNO$_2$: C, 44.29; H, 4.13; N, 5.74. Found: C, 44.14; H, 3.96; N, 5.72.

EXAMPLE 93

Preparation of methyl 3-methyl-4-chloroanthranilate

This material was prepared by esterification of the corresponding anthranilic acid with HCl in methanol. The product was isolated as a solid, mp 72°–74° C.

EXAMPLE 9

Preparation of 2,6-dichloro-3-trifluoromethylaniline

This material was prepared by chlorination of 2-chloro-5-trifluoromethylaniline with N-chlorosuccinimide followed by chromatographic purification. The product was isolated as a yellow oil which was characterized by IR and $^1$H NMR spectroscopy and combustion analysis.

EXAMPLE 95

Preparation of 4-bromo-2,3-dichloro-6-methylaniline

This material was prepared from 4-bromo-5-chloro-2-methylaniline by chlorination with N-chlorosuccinimide. The product was isolated as a solid, m.p. 66°–68° C. The product was characterized by IR and $^1$H NMR spectroscopy and combustion analysis.

EXAMPLE 96

Preparation of 2,3-dichloro-6-methylaniline

A slurry of 6.50 g (25.5 mmol) of 2,3-dichloro-4-bromo-6-methylaniline and 8.37 g (102 mmol) of sodium acetate in 120 ml of acetic acid-ethanol (1:1, v/v) was treated with 0.55 g of 5% palladium on carbon. The mixture was hydrogenated in a Parr hydrogenation apparatus at an initial pressure of 50 psi for 10 minutes. The reaction mixture was filtered, and the filtrate was concentrated by evaporation at reduced pressure. The residue was partitioned between ether and water, and the organic layer was washed with 5% aqueous sodium hydroxide, dried and evaporated at reduced pressure. The residue was purified by Kugelrohr distillation to afford 4.00 g (89%) of the desired product as a colorless oil, b.p. 60°–70° C. (0.15 mm). IR and $^1$H NMR spectra were in agreement with the assigned structure.

Analysis:

Calculated for C$_7$H$_7$Cl$_2$N: C, 47.76; H, 4.01; N, 7.95. Found: C, 48.11; H, 4.04; N, 8.19.

EXAMPLE 97

Preparation of 2-amino-3-chlorobenzyl alcohol

A solution of 2S.9 g (155 mmol) of methyl 3-chloroanthranilate in 100 ml of ether was added dropwise to a stirred suspension of 7.67 g (202 mmol) of lithium aluminum hydride in 400 ml of ether. After stirring for five hours at room temperature, the grey mixture was treated sequentially with 7.7 ml of water, 7.7 ml of 15% sodium hydroxide and 23 ml of water. The reaction mixture was filtered, and the filtrate was evaporated at reduced pressure. The oily residue was dissolved in ether, and precipitation of the product was induced by addition of hexane. The product was collected by filtration to yield a tan solid in 67% yield, mp 56°–68° C. IR and $^1$H NMR spectra were in agreement with the assigned structure.

Analysis:

Calculated for C$_7$H$_8$ClNO: C, 53.35; H, 5.12; N, 8.88. Found: C, 53.16; H, 4.84; N, 9.28.

EXAMPLE 98

Preparation of 2-chloro-6-methoxymethylaniline

A solution of 4.00 g (25.4 mmol) of 2-amino-3-chlorobenzyl alcohol in 30 ml of dry THF was cooled to −78° C., treated with 16.7 ml (26.7 mmol) of 1.60M n-butyllithium in hexane, warmed to 0°–5° C., treated with 3.61 g (25.4 mmol) of methyl iodide and heated at reflux for 5.5 hours. The solvent was removed by evaporation at reduced pressure. The residue was partitioned between 175 ml of ether and water, and the organic phase was separated and dried (MgSO$_4$). The solvent was removed by evaporation at reduced pressure, and the residue was purified by HPLC eluting with EtOAc (5:95, v/v) to afford 1.1 g of the desired product as a pale brown oil. IR and $^1$H NMR spectra were in agreement with the assigned structure.

Analysis:

Calculated for $C_8H_{10}ClNO$: C, 56.00; H, 5.87; N, 8.16. Found: C, 56.25; H, 5.98; N, 8.28.

EXAMPLE 99

Preparation of 2-acetoxymethyl-6-chloroaniline

This material was prepared from 2-amino-3-chlorobenzyl alcohol and acetyl chloride by the general procedure outlined in Example 98. The product was isolated as an amber oil and was characterized by IR and $^1$H NMR spectroscopy and combustion analysis.

EXAMPLE 100

Preparation of 2-benzyloxymethyl-6-chloroaniline

This material was prepared from 2-amino-3-chlorobenzyl alcohol and benzyl bromide by the general procedure outlined in Example 98. The product was purified by Kugelrohr distillation to yield an oil, b.p. 118°–125° C. (0.1 mm). The product was characterized by IR and $^1$H NMR spectroscopy.

EXAMPLE 101

Preparation of N-n-butoxycarbonyl-2-fluoroaniline

A solution of 2-fluoroaniline (30.0 g, 0.27 mol) and di-t-butyl carbonate (66.5 g, 0.30 mol) in 100 ml of THF was heated at reflux for 4 hours. The solvent was removed by evaporation at reduced pressure, and the residue was partitioned between 1M aqueous citric acid and ethyl acetate. The organic phase was washed with saturated aqueous NaCl. The solvent was removed to afford the desired product, which was used without further purification. IR and $^1$H NMR spectra were in agreement with the assigned structure.

Analysis:

Calculated for $C_{11}H_{14}FNO_2$: C, 62.55; H, 6.68; N, 6.63. Found: C, 62.45; H, 6.39; N, 6.21.

EXAMPLE 102

Preparation of 2-fluoro-6-methylaniline

A solution of 8.15 g (38.5 mmol) of N-t-butoxycarbonyl-2-fluoroaniline in 30 ml of dry THF was cooled to −70° C., and 46.3 ml (93 mmol) of 2.0 M t-butyllithium in pentane was added dropwise at a rate sufficient to maintain the temperature below −65° C. When the addition was complete the reaction mixture was stirred at −70° C. for 15 minutes, warmed to −20° C. and stirred for 2.5 hours. A solution of 6.8 g (30 mmol) of methyl iodide in THF was added and the reaction was allowed to warm to room temperature. The reaction mixture was partitioned between ether and water, and the organic layer was washed with saturated aqueous NaCl and dried (MgSO$_4$). Evaporation at reduced pressure gave a yellow solid which was added to 25 ml of 3N HCl and heated at reflux for 3 hours. After cooling to room temperature the pH of the solution was adjusted to pH 7, and the solution was extracted twice with methylene chloride. The combined organic phases were washed with water and dried (MgSO$_4$). Evaporation at reduced pressure gave a yellow oil which was Kugelrohr distilled to yield 3.8 g (80%) of the desired product as a liquid, b.p. 91°–93° C. (0.1 mm). IR and $^1$H NMR spectra were in agreement with the assigned structure.

Analysis:

Calculated for $C_7H_8FN$: C, 67.20; H, 6.45; N, 11.20. Found: C, 67.61; H, 6.09; N, 11.53.

EXAMPLE 103

Preparation of 2-fluoro-6-methylthioaniline

This material was prepared for N-t-butoxycarbonyl-2-fluoroaniline and dimethyl disulfide following the general procedure outlined in Example 102. IR and $^1$H NMR spectra of the product were consistent with the assigned structure.

EXAMPLE 104

Preparation of 2-(2-chloro-4-trifluoromethylphenoxy) nitrobenzene

A mixture of 29.4 g (0.200 mol) of 2-fluoro nitrobenzene, 41.0 g (0.200 mol) of 2-chloro-4-trifluoromethylphenol and 30.0 g (0.220 mol) of $K_2CO_3$ in 150 ml of DMSO was heated at 100° C. for six hours. The reaction mixture was poured over ice and extracted with ether. The organic phase was washed with water and saturated aqueous NaCl and dried (MgSO$_4$). The solvent was removed by evaporation at reduced pressure to yield 56.1 g (88%) of the desired product as a yellow oil. IR and $^1$H NMR spectra were in agreement with the assigned structure.

Analysis:

Calculated for $C_{13}H_7ClF_3NO_3$: C, 49.15; H, 2.22; N, 4.41. Found: C, 49.47; H, 2.07; N, 4.13.

EXAMPLE 105

Preparation of 2-(2-chloro-4-trifluoromethylphenoxy) aniline

Raney Nickel (4.0 g) was washed with water and added to 250 ml of ethanol. To this mixture under a nitrogen blanket was added 56 g (0.18 mol) of 2-(2-chloro-4-trifluoromethyl)phenoxynitrobenzene. This mixture was hydrogenated in a Parr hydrogenation apparatus at an initial pressure of 50 psi. The catalyst was removed by filtration through celite and the filtrate was evaporated at reduced pressure to yield 49.9 g (100%) of the desired product as an amber oil. IR and $^1$H NMR spectra were in agreement with the assigned structure.

Analysis:

Calculated for $C_{13}H_9ClF_3NO$: C, 54.27; H, 3.15; N, 4.87. Found: C, 54.72; H, 3.01; N, 4.61.

EXAMPLE 106

Preparation of 2-(3-chloro-5-trifluoromethyl-2-pyridyloxy)nitrobenzene

This material was prepared in 63% yield from 3-chloro-2-fluoro-5-trifluoromethylpyridine and 2-nitrophenol following the general procedure outlined in Example 104. The product was isolated as an amber oil which was characterized by IR and $^1$H NMR spectroscopy.

EXAMPLE 107

Preparation of
2-(3-chloro-5-trifluoromethyl-2-pyridyloxy)aniline

This material was prepared in 61% yield by hydrogenation of 2-(3-chloro-5-trifluoromethyl-2-pyridyloxy)-nitrobenzene following the general procedure outlined in Example 105. The crude product was recrystallized from hexane to yield the desired product as white needles, mp 133°–135° C. IR and $^1$H NMR spectra were in agreement with the assigned structure.

Analysis:

Calculated for $C_{12}H_8ClF_3N_2O$: C, 49.94; H, 2.79; N, 30.50. Found: C, 49.93; H, 2.91; N, 30.27.

EXAMPLE 108

Preparation of
2-(2-chloro-4-trifluoromethylphenoxy)-6-fluoronitrobenzene

This material was prepared in 47% yield from 2,6-difluoronitrobenzene and 2-chloro-4-trifluoromethylphenol following the general procedure outlined in Example 104. The product was isolated as an oil which was characterized by IR and $^1$H NMR spectroscopy.

EXAMPLE 109

Preparation of
2-(2-chloro-4-trifluoromethylphenxoy)-6-fluoroaniline

This material was prepared in 72% yield by hydrogenation of 2-(2-chloro-4-trifluoromethylphenoxy)-6-fluoronitrobenzene following the general procedure outlined in Example 105. The crude product was Kugelrohr 102°–103° C. (10 mm). IR and 'H NMR spectra were in agreement with the assigned structure.

Analysis:

Calculated for $C_{13}H_8ClF_4NO$: C, 51.09; H, 2.64; H, 9.17. Found: C, 51.34; H, 2.41; H, 9.16.

EXAMPLE 110

Preparation of 6-methoxy-2-trifluoromethylbenzoic acid

A solution of 3-trifluoromethylanisol (50.0 g, 0.28 mole) in tetrahydrofuran was cooled to −78° C. under nitrogen atmosphere with stirring. To this solution was added n-butyl lithium (114 ml of 2.5M, 0.28 mole), dropwise at such a rate that the temperature did not exceed −65° C. When the addition was complete, the mixture was stirred at −78° C. for three hours. The mixture was then poured over a slurry of dry ice/ether and allowed to come to room temperature. The solvent was removed under reduced pressure to give a white solid. This solid was dissolved in a minimum amount of water, extracted with diethyl ether (2×100 ml) and the aqueous phase was acidified to pH 2 with dilute hydrochloric acid. An oil formed and was extracted with diethyl ether, washed several times with water and dried over magnesium sulfate. The solvent was removed to give 45.6 g (74 percent of theory) of the title compound as a white solid of m.p. 129°–130° C.

Analysis:

Calculated for $C_9H_7F_3O_3$: C, 49.11; H, 3.21.
Found: C, 49.08; H, 3.21.

EXAMPLE 111

Preparation of 6-methoxy-2-trifluoromethylbenzamide

A mixture of 6-methoxy-2-trifluoromethylbenzamide (40.0 g, 0.18 mol) in thionyl chloride (50 ml, 0.48 mol) was heated under reflux for three hours. The formed hydrogen chloride was neutralized in an aqueous sodium hydroxide trap. When the evolution of hydrogen chloride stopped, the mixture was cooled to room temperature and the excess thionyl chloride was removed by evaporation under reduced pressure. The resulting acid chloride was added dropwise with vigorous stirring to 250 ml of 12N ammonium hydroxide while cooling to 0° C. in a salt/ice bath. When the addition was complete, the mixture was allowed to warm to ambient temperature and stir for an additional two hours. The solid that formed was collected by filtration, dried under vacuum and recrystallized from methylcyclohexane to give 32.4 g (82 percent of theory) of the title compound as a white solid of m.p. 178°–181° C.

Analysis:

Calculated for $C_9H_8F_3NO_2$: C, 49.31; H, 3.68; N, 6.39.
Found: C, 49.05; H, 3.79; N, 6.34.

EXAMPLE 112

Preparation of 6-methoxy-2-trifluoromethylaniline

Sodium hydroxide (4.6 g, 0.11 mol) was dissolved in 50 ml of water and the solution was cooled to 0° C. in a salt/ice bath. Bromine (5.87 g, 37 mmol) was slowly added to this solution and allowed to stir at 0° C. for 15 minutes. To this rapidly stirred solution was added in portions 6-methoxy-2-trifluoromethylbenzamide (6.4 g, 30.0 mmol) keeping the temperature below 5° C. The mixture was stirred at 0° C. for three hours and then heated to reflux for two hours. It was then allowed to cool to ambient temperature and was extracted with methylene chloride (2×100 ml). The organic phase was combined and dried over magnesium sulfate. The solvent was removed under reduced pressure and the resulting amber liquid distilled to give 4.1. g (71 percent of theory) of the title compound as a clear, colorless oil, b.p. 56° C. at 0.7 mm Hg.

Analysis:

Calculated for $C_8H_8F_3NO$: C, 50,28; H, 4.22; N, 7.33.
Found: C, 50.24; H, 4.12; N, 7.03.

EXAMPLE 113

Preparation of 6-fluoro-2-trifluoromethylbenzoic acid

A mixture of 3-fluorobenzotrifluoride (25.0 g, 0.15 mol) in tetrahydrofuran (200 ml) was cooled to −78° C. in a dry ice/acetone bath under nitrogen atmosphere. To this solution was added dropwise with rapid stirring N-butyl lithium (1.6M, 95.2 ml) at such rate that the temperature did not exceed −60° C. When the addition was complete, the mixture was allowed to stir at −78° C. for an additional five hours. The mixture was then poured over a slurry of dry ice/ether and allowed to come to room temperature. The solvent was removed by evaporation under reduced pressure to obtain a white solid residue. This solid was dissolved in a minimum amount of water, the solution was extracted with diethyl ether (2×100 ml) and the aqueous phase was acidified to pH 2 with dilute hydrochloric acid. An oil formed and this was dissolved in diethyl ether; the solution was washed several times with water and dried over magnesium sulfate. The solvent was removed by evaporation under reduced pressure to give a white solid. NMR analysis indicated this product was a mixture of the title compound and an isomer. A yield of 15.6 g (50 percent of theory) was obtained.

Analysis:

Calculated for $C_8H_4F_4O_2$: C, 46.17; H, 1.94.
Found: C, 46.29; H, 1.73.

EXAMPLE 114

Preparation of 6-fluoro-2-trifluoromethylbenzamide

A mixture of 6-fluoro-2-trifluoromethylbenzoic acid and its isomer (19.6 g, 0.10 mol) and thionyl chloride (35 ml) was heated under reflux for two hours. The hydrogen chloride formed was neutralized in an aqueous sodium hydroxide trap. When the evolution of hydrogen chloride stopped, the mixture was cooled to room temperature and the excess thionyl chloride was removed by evaporation under reduced pressure. This was added dropwise with vigorous stirring to 250 ml of 12N ammonium hydroxide while cooling to 0° C. in a salt/ice bath. When the addition was complete the mixture was allowed to warm to ambient temperature and stir for an additional two hours. The solid that formed was collected by filtration, dried under vacuum, and recrystallized from hexane to give two products. The first precipitated from hexane at room temperature to give 14.2 g of the desired 6-fluoro-2-trifluoromethylbenzamide which melts at 165°-6° C. and the remainder precipitated when the hexane was removed under reduced pressure to give 4.5 g of the 2-fluoro-4-trifluoromethylbenzamide, which melts at 143°-4° C. The total yield was 18.7 g which is 84 percent of theory.

Analysis:

Calculated for $C_8H_5F_4NO_2$: C, 43.06; H, 2.26; N, 6.28.
Found: C, 43.41: H, 2.13: N, 6.07.

EXAMPLE 115

Preparation of 2,6-difluoro-3-methylaniline

Sodium hydroxide (5.6 g, 0.14 mol) was dissolved in 50 ml of water and then cooled to 0° C. in a salt/ice bath. Bromine (9.60 g, 60.0 mmoles) was slowly added to this solution and allowed to stir at 0° C. for 15 minutes. To this solution was added in portions with rapid stirring 2,6-difluoro-3-methylbenzamide (7.0 g, 37.0 mmol) keeping the temperature below 5° C. The mixture was stirred at 0° C. for three hours and then heated to reflux for two hours, and was extracted with methylene chloride (2×100 ml). The organic phases were combined and dried over magnesium sulfate. The solvent was removed by evaporation under reduced pressure and the resulting amber liquid distilled to give the title compound a clear, colorless oil having a b.p. of 107° C. at 15 mm Hg and amounting to 2.1 g (36 percent of theory).

Analysis:

Calculated for $C_7H_7F_2NO$: C, 52.84; H, 4.43; N, 8.80

Found: C, 52.59; H, 4.73; N, 8.97

EXAMPLE 116

Preparation of 6-trifluoromethoxy-2-trifluoromethylaniline

Sodium hydroxide (20.0 g, 0.50 mole) was dissolved in 150 ml of water and the solution cooled to 0° C. in a salt/ice bath. Bromine (11.3 g, 70.7 mmoles) was slowly added to this solution and allowed to stir at 0° C. for 15 minutes. To this solution was added in portions with rapid stirring 6-trifluoromethoxy-2-trifluoromethylbenzamide (7.0 g, 37.0 mmoles) keeping the temperature below 5° C. The mixture was stirred at 0° C. for five hours and then heated to reflux for 18 hours. It was then allowed to cool to ambient temperature and was extracted with ether (2×100 ml). The organic phases were combined and dried over magnesium sulfate. The solvent was removed by evaporation under reduced pressure and the resulting amber liquid distilled to give the title compound a clear, colorless oil having a b.p. of 152°-153° C. at 760 mm Hg and amounting to 8.2 g (47 percent of theory).

Analysis:

Calculated for $C_8H_5F_6NO$: C, 39.20; H, 2.06; N, 5.72;
Found: C, 38.76; H, 1.99; N, 5.69

EXAMPLE 117

Preparation of 2-fluoro-6-methylthioaniline

A mixture of N-(t-butoxycarbonyl)-2-fluoroaniline (5.0 g, 24 mmoles) in anhydrous tetrahydrofuran (50 ml) was cooled to −78° C. under a nitrogen atmosphere. To this solution was added t-butyl lithium (2.0M, 57.6 mmoles, 28.8 ml) at such a rate that the temperature did not exceed −65° C. When the addition was complete, the mixture was stirred at −78° C. for an additional 15 minutes and at −20° C. for 2.5 hours. To this reaction mixture was added dimethyl disulfide (2.82 g, 30 mmoles) in 10 ml of anhydrous tetrahydrofuran while maintaining the temperature at −20° C. for an additional hour. The mixture was allowed to warm to ambient temperature and then 25 ml of 1N sodium hydroxide was added. The mixture obtained was extracted with diethyl ether (2×100 ml). The organic phase was separated and dried over magnesium sulfate and then the solvent was removed by evaporation under reduced pressure to obtain a tan solid. This was hydrolized in dilute hydrochloric acid (6N, 200 ml) by heating to reflux for three hours. The resulting solution was extracted with diethyl ether and the aqueous layer was neutralized with sodium hydroxide (6N, 200 ml), and extracted with methylene chloride, dried over magnesium sulfate and the solvent removed by evaporation under reduced pressure to obtain an amber oil. This was distilled to give 3.2 g (85% of theory) of the title compound, having a b.p. of 62°-65° C. at 0.2 mm Hg.

Analysis:

Calculated for $C_7H_8FNS$: C, 58.48; H, 5.13; N, 8.91.
Found: C, 53.84; H, 5.55; N, 8.73.

Representative compounds prepared employing the above general procedures are tabulated in the following Tables I through LII.

TABLE I

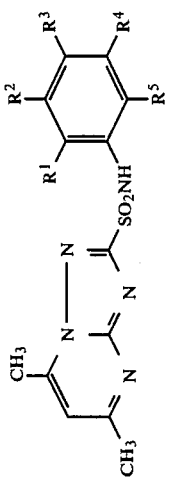

| Compound | R¹ | R² | R³ | R⁴ | R⁵ | Melting Point | Analysis | Elemental Analysis C | H | N | Cl | S |
|---|---|---|---|---|---|---|---|---|---|---|---|---|
| 1 | CF₃ | H | H | H | OCH₂CF₃ | 247–249° C. | Calcd. for C₁₆H₁₃F₆N₅O₂S: | 40.9 | 2.79 | 14.92 | | |
|   |   |   |   |   |   |   | Found: | 39.9 | 2.78 | 14.75 | | |
| 2 | CH₃ | H | H | H | H | 222–224° C. | Calcd. for C₁₄H₁₅N₅O₂S: | 52.99 | 4.76 | 22.06 | | |
|   |   |   |   |   |   |   | Found: | 52.75 | 4.79 | 22.25 | | |
| 3 | OH | H | H | H | H | >150° C. (decomp.) | Calcd. for C₁₃H₁₃N₅O₃S: | 48.90 | 4.10 | 21.92 | | |
|   |   |   |   |   |   |   | Found: | 48.45 | 4.15 | 21.77 | | |
| 4 | OCH₃ | H | H | H | H | 208°–210.5° C. | Calcd. for C₁₄H₁₅N₅O₃S: | 50.44 | 4.54 | 21.00 | | |
|   |   |   |   |   |   |   | Found: | 50.17 | 4.54 | 21.12 | | |
| 5 | NHCH₃ | H | H | H | H | 227°–228° C. | Calcd. for C₁₄H₁₆N₆O₂S: | 50.59 | 4.85 | 25.28 | | |
|   |   |   |   |   |   |   | Found: | 49.70 | 4.87 | 21.12 | | |
| 6 | I | H | H | H | H | 189°–192° C. | Calcd. for C₁₃H₁₂IN₅O₂S: | 36.38 | 2.82 | 16.31 | | |
|   |   |   |   |   |   |   | Found: | 36.61 | 2.81 | 16.15 | | |
| 7 | Cl | H | H | H | H | 188°–189.5° C. | Calcd. for C₁₃H₁₂ClN₅O₂S: | 46.23 | 3.58 | 20.73 | 10.50 | 9.49 |
|   |   |   |   |   |   |   | Found: | 46.09 | 3.58 | 20.89 | 10.34 | 9.37 |
| 8 | —F | H | H | H | H | 189°–190° C. | Calcd. for C₁₃H₁₂FN₅O₂S: | 48.59 | 3.76 | 21.79 | | 9.98 |
|   |   |   |   |   |   |   | Found: | 48.79 | 3.74 | 21.88 | | 9.86 |
| 9 | SCH₃ | H | H | H | H | 142°–144° C. | Calcd. for C₁₄H₁₅N₅O₂S₂: | 48.13 | 4.33 | 20.04 | | |
|   |   |   |   |   |   |   | Found: | 47.99 | 4.28 | 20.40 | | |
| 10 | COOCH₃ | H | H | H | H | 169.5–170.5° C. | Calcd. for C₁₅H₁₅N₅O₄S: | 49.86 | 4.18 | 19.38 | | 8.87 |
|   |   |   |   |   |   |   | Found: | 49.68 | 4.13 | 19.35 | | 8.69 |
| 11 | COOH | H | H | H | H | 247°–248° C. | Calcd. for C₁₄H₁₃N₅O₄S: | 48.41 | 3.77 | 20.16 | | 9.23 |
|   |   |   |   |   |   |   | Found: | 47.87 | 3.66 | 20.27 | | 8.87 |
| 12 | NO₂ | H | H | H | H | 140° C. | Calcd. for C₁₃H₁₂N₆O₄S: | 44.83 | 3.47 | 24.13 | | 9.21 |
|   |   |   |   |   |   |   | Found: | 44.91 | 3.48 | 24.11 | | 9.11 |
| 13 | CF₃ | H | H | H | H | 198.5–200.5° C. | Calcd. for C₁₄H₁₂F₃N₅O₂S: | 45.28 | 3.26 | 18.86 | | 8.63 |
|   |   |   |   |   |   |   | Found: | 45.39 | 3.16 | 18.74 | | 8.87 |
| 14 | —CN | H | H | H | H | 237.5–239° C. | Exact mass calcd for C₁₄H₁₂N₆O₂S: | 328.0742 | | | | |
|   |   |   |   |   |   |   | Found: | 328.0748 | | | | |
| 15 | —SO₂NMe₂ | H | H | H | H | 91° C. | Analysis Calcd. for C₁₅H₁₈N₆O₄S₂: 43.89 | C 4.42 | H 20.47 | N 20.21 | Cl 15.62 | S 15.23 |
|   |   |   |   |   |   |   | Found: | 44.25 | 4.37 | 19.80 | | 15.11 |
| 16 | —SO₂N(Me)Et | H | H | H | H | 80° C. | Calcd. for C₁₆H₂₀N₆O₄S₂: | 45.27 | 4.75 | 19.60 | | 14.77 |
|   |   |   |   |   |   |   | Found: | 45.07 | 4.64 | | | |
| 17 | H | —Cl | H | H | H | 231°–232.5° C. | Exact mass calcd. for C₁₃H₁₂ClN₅O₂S: | 337.0400 | | | | |
|   |   |   |   |   |   |   | Found: | 337.0415 | | | | |
| 18 | H | H | —Cl | H | H | 237°–239° C. | Exact mass calcd. for C₁₃H₁₂ClN₅O₂S: | 337.0400 | | | | |
|   |   |   |   |   |   |   | Found: | 337.0411 | | | | |
| 19 | Cl | Cl | H | H | H | 214.5–216.5° C. | Analysis Calcd. for C₁₃H₁₁Cl₂N₅O₂S: | C 41.95 | H 2.98 | N 18.81 | Cl 19.05 | S 8.61 |
|   |   |   |   |   |   |   | Found: | 42.02 | 3.03 | 18.99 | 18.24 | 8.30 |
| 20 | Cl | H | Cl | H | H | 176°–177.5° C. | Calcd. for C₁₃H₁₁Cl₂N₅O₂S: | 41.95 | 2.98 | 18.81 | 19.05 | 8.61 |
|   |   |   |   |   |   |   | Found: | 42.24 | 2.94 | 18.90 | 18.83 | 8.82 |

TABLE I-continued

Structure:

R² and R³ on one side, R⁴ and R⁵ on the other side of a phenyl ring, with R¹ and -SO₂NH- linked to a pyrimidine bearing two CH₃ groups and an N=N (triazine-like) system.

| Compound | R¹ | R² | R³ | R⁴ | R⁵ | Melting Point | Elemental Analysis |
|---|---|---|---|---|---|---|---|
| 21 | Cl | H | H | Cl | H | 250°–253° C. | Exact mass calcd. for $C_{13}H_{11}Cl_2N_5O_2S$: 371.0010<br>Found: 370.9997<br>Analysis — C 41.95, H 2.98, N 18.81, Cl 19.05, S 8.61 |
| 22 | Cl | H | H | H | Cl | 260.5–262.5° C. | Calcd. for $C_{13}H_{11}Cl_2N_5O_2S$: C 41.95, H 2.98, N 19.01, Cl 18.89, S 8.57<br>Found: 42.12, 2.94, 19.01, 18.89, 8.57 |
| 23 | H | Cl | Cl | H | H | 240°–242° C. | Calcd. for $C_{13}H_{11}Cl_2N_5O_2S$: C 41.95, H 2.98, N 18.81, Cl 19.05, S 8.61<br>Found: 42.32, 2.87, 18.82, 18.65, 8.42 |
| 24 | H | Cl | H | Cl | H | 273.5–275.5° C. | Calcd. for $C_{13}H_{11}Cl_2N_5O_2S$: C 41.95, H 2.98, N 18.81, Cl 19.05, S 8.61<br>Found: 42.30, 2.89, 18.42, 18.85, 8.49 |
| 25 | F | H | H | H | F | 229.5–231° C. | Exact mass calcd. for $C_{13}H_{11}F_2N_5O_2S$: 339.0630<br>Found: 339.0602<br>Analysis — C, H, N, Cl |
| 26 | COOMe | H | H | H | F | 181.5–183.5° C. | Calcd. for $C_{15}H_{14}FN_5O_4S$: C 47.49, H 3.72, N 18.46, S 8.45<br>Found: 47.65, 3.60, 18.19, 8.35 |
| 27 | COOH | H | H | H | F | 228.5–230° C. | Calcd. for $C_{14}H_{12}FN_5O_4S$: C 46.03, H 3.31, N 19.17, S 8.78<br>Found: 45.56, 3.26, 19.05, 8.50 |
| 28 | SO₂NMe₂ | H | H | CF₃ | H | 174.5–176.5° C. | Calcd. for $C_{16}H_{17}F_3N_6O_4S_2$: C 40.16, H 3.58, N 17.56, S 13.40<br>Found: 40.16, 3.49, 17.39, 13.17 |
| 29 | F | H | F | H | H | 223°–224.5° C. | Calcd. for $C_{13}H_{11}F_2N_5O_2S$: C 46.02, H 3.27, N 20.63<br>Found: 46.19, 3.37, 20.59 |
| 30 | Cl | H | F | H | H | 203°–205° C. | Calcd. for $C_{13}H_{11}ClFN_5O_2S$: C 43.89, H 3.12, N 19.68<br>Found: 44.02, 3.12, 19.89 |
| 31 | Cl | H | H | H | CH₃ | 230°–231.5° C. (decomp.) | Calcd. for $C_{14}H_{14}ClN_5O_2S$: C 47.82, H 3.98, N 19.07<br>Found: 47.87, 4.06, 19.66 |
| 32 | CH₃ | H | H | H | CH₃ | 263°–266° C. (decomp.) | Calcd. for $C_{15}H_{17}N_5O_2S$: C 54.31, H 5.23, N 21.23<br>Found: 54.59, 50.7, 20.65 |
| 33 | CH₂CH₃ | H | H | H | CH₂CH₃ | 248–249.5° C. (decomp.) | Calcd. for $C_{17}H_{21}N_5O_2S$: 56.83<br>Found: 5.84, 19.48, 19.40<br>57.06, 5.98 |
| 34 | —CF₃ | H | H | H | H | 189°–193° C. | Calcd. for $C_{14}H_{11}ClF_3N_5O_2S$: C 41.41, H 2.71, N 17.25<br>Found: 41.78, 2.73, 17.23 |
| 35 | —Cl | H | H | H | —Cl | >200 ° C. | Calcd. for $C_{13}H_{10}Cl_3N_5O_2S$: C 38.40, H 2.48, N 17.22<br>Found: 38.36, 2.48, 17.14 |
| 36 | —COOiPr | H | H | H | H | 130°–132° C. (decomp.) | Calcd. for $C_{17}H_{19}N_5O_4$ S: 52.43<br>Found: 4.92, 17.98 |
| 37 | —CONH₂ | H | H | H | H | 258°–260° C. | Calcd. for $C_{14}H_{14}N_6O_3S$: C 48.55, H 4.07, N 24.26<br>Found: 48.58, 4.00, 24.01 |
| 38 | —Br | H | H | H | —Br | 285°–287° C. | Calcd. for $C_{13}H_{11}Br_2N_5O_2S$: C 33.86, H 2.40, N 15.18<br>Found: 33.92, 2.42, 15.41 |
| 39 | —Br | H | H | H | —Cl | >230° C. (decomp.) | Calcd. for $C_{13}H_{11}BrClN_5O_2S$: C 37.47, H 2.66, N 16.80<br>Found: 37.50, 2.64, 16.87 |
| 40 | —Br | H | —Cl | H | H | 177°–179° C. | Calcd. for $C_{13}H_{11}BrClN_5O_2S$: C 37.47, H 2.66, N 16.80<br>Found: 37.45, 2.67, 16.64 |
| 41 | —Br | H | H | H | H | 188°–190° C. | Calcd. for $C_{13}H_{12}BrN_5O_2S$: C 40.85, H 3.16, N 18.32 |

TABLE I-continued

Structure: pyrimidine ring with CH₃ groups connected via N=N to sulfonamide-phenyl with substituents R¹, R², R³, R⁴, R⁵

| Compound | R¹ | R² | R³ | R⁴ | R⁵ | Melting Point | Elemental Analysis | C | H | N | S |
|---|---|---|---|---|---|---|---|---|---|---|---|
| 42 | —CONMe₂ | H | H | H | H | 193°–194° C. | Found: | 41.09 | 3.12 | 18.19 | |
| | | | | | | | Calcd. for C₁₆H₁₈N₆O₃S: | 51.33 | 4.85 | 22.44 | |
| 43 | —CONMe₂ | H | —Cl | H | H | 194°–195° C. | Found: | 51.08 | 4.65 | 22.12 | |
| | | | | | | | Calcd. for C₁₆H₁₇ClN₆O₃S: | 47.00 | 4.19 | 20.55 | |
| 44 | —Cl | H | F | H | H | 271°–273° C. (decomp.) | Found: | 47.16 | 4.07 | 20.50 | |
| | | | | | | | Calcd. for C₁₃H₁₀Cl₂FN₅O₂S: | 40.02 | 2.58 | 17.94 | |
| 45 | —SO₂Me | H | H | H | H | 181°–183° C. | Found: | 40.13 | 2.65 | 18.04 | |
| | | | | | | | Calcd. for C₁₄H₁₅N₅O₄S₂: | 44.09 | 3.96 | 18.35 | |
| 46 | —Cl | —Me | H | H | H | 280° C. (decomp.) | Found: | 43.64 | 3.84 | 18.16 | |
| | | | | | | | Calcd. for C₁₄H₁₃Cl₂N₅O₂S: | 43.54 | 3.39 | 18.13 | |
| 47 | —Cl | H | —Me | H | —Cl | 245°–248° C. | Found: | 43.45 | 3.37 | 18.15 | |
| | | | | | | | Calcd. for C₁₄H₁₃Cl₂N₅O₂S: 43.54 | 3.39 | 18.13 | | |
| 48 | —Cl | H | —Me | H | H | 229°–231° C. | Found: | 43.57 | 3.37 | 18.21 | |
| | | | | | | | Calcd. for C₁₄H₁₄ClN₅O₂S: | 48.00 | 4.01 | 19.90 | |
| 49 | —NO₂ | H | H | H | —CH₃ | 244°–246° C. | Found: | 48.01 | 3.97 | 20.05 | |
| | | | | | | | Exact mass calcd. for C₁₄H₁₄N₆O₄S: | | | 362.0799 | |
| | | | | | | | Found: | | | 362.0807 | |
| | | | | | | | Analysis | C | H | N | Cl S |
| 50 | —COOMe | H | H | H | —CH₃ | 190°–192.5° C. | Calcd. for C₁₆H₁₇N₅O₄S: | 51.19 | 4.57 | 18.65 | |
| | | | | | | | Found: | 51.22 | 4.58 | 18.46 | |
| 51 | —COO-i-Pr | H | H | H | F | 167°–168° C. | Calcd. for C₁₇H₁₈FN₅O₄S: | 50.12 | 4.45 | 17.18 | |
| | | | | | | | Found: | 50.09 | 4.39 | 17.28 | |
| 52 | —Cl | H | H | —CF₃ | H | 221.5–224° C. | Calcd. for C₁₄H₁₀ClF₃N₅O₂S: | 41.43 | 2.71 | 17.24 | |
| | | | | | | | Found: | 41.73 | 2.74 | 17.08 | |
| 53 | —I | H | H | H | —Cl | >258° C. (decomp.) | Calcd. for C₁₃H₁₁ClIN₅O₂S: | 33.68 | 2.39 | 15.10 | |
| | | | | | | | Found: | 33.66 | 2.38 | 15.03 | |
| 54* | —Cl | H | H | H | —F | 223°–225.5° C. (decomp.) | Calcd. for C₁₃H₁₁ClFN₅O₂S: | 43.89 | 3.12 | 19.68 | |
| | | | | | | | Found: | 43.20 | 2.89 | 16.61 | |
| 55 | SCF₃ | H | H | H | H | 175–178° C. | Calcd. for C₁₄H₁₂F₃N₅O₂S₂: | 41.68 | 2.97 | 17.35 | |
| | | | | | | | Found: | 40.84 | 2.95 | 16.61 | |
| 56 | COO-t-Bu | H | H | H | F | 151–153° C. (decomp.) | Calcd. for C₁₈H₂₀FN₅O₄S: | 51.30 | 4.78 | 16.61 | |
| | | | | | | | Found: | 50.90 | 4.69 | 16.49 | |
| 57 | SO₂CF₃ | H | H | H | H | 68–70° C. | Calcd. for C₁₄H₁₂F₃N₅O₄S₂: | 38.62 | 2.75 | 16.09 | |
| | | | | | | | Found: | 39.10 | 2.71 | 15.87 | |
| 58 | Br | H | H | H | CH₃ | 225–228° C. | Calcd. for C₁₄H₁₄BrN₅O₂S: | 42.44 | 3.56 | 17.67 | |
| | | | | | | | Found: | 42.56 | 3.55 | 17.66 | |
| 59 | SCF₂CF₂H | H | H | H | H | 162.5–164° C. | Calcd. for C₁₅H₁₃F₄N₅O₂S₂: | 41.38 | 3.01 | 16.08 | 14.73 |
| | | | | | | | Found: | 41.54 | 2.88 | 16.06 | 14.57 |
| 60 | SOCF₂CF₂H | H | H | H | H | 223–224° C. | Calcd. for C₁₅H₁₃F₄N₅O₃S₂: | 39.91 | 2.90 | 15.51 | 14.21 |
| | | | | | | | Found: | 39.88 | 2.83 | 15.37 | 14.15 |
| 61 | CONH₂ | H | H | H | CH₃ | 231–232° C. | Calcd. for C₁₅H₁₆N₆O₃S·H₂O: | 47.61 | 4.80 | 22.20 | |
| | | | | | | | Found: | 47.74 | 4.71 | 22.04 | |
| 62 | CONMe₂ | H | H | H | CH₃ | 225–257° C. | Calcd. for C₁₇H₁₆N₆O₃S: | 52.57 | 5.19 | 21.63 | |

TABLE I-continued

![Structure showing phenyl group with R2, R3, R4, R5 substituents and triazine/sulfonamide moiety with R1 and CH3 groups]

| Compound | R¹ | R² | R³ | R⁴ | R⁵ | Melting Point | Elemental Analysis | | |
|---|---|---|---|---|---|---|---|---|---|
| 63 | Cl | H | H | H | Ph | 256–260° C. (decomp.) | Found:<br>Calcd. for $C_{19}H_{16}ClN_5O_2S$: | 52.15<br>55.14 | 5.15<br>3.90 | 21.39<br>16.92 |
| 64 | COO-i-Pr | H | H | H | CH₃ | 178–179° C. | Found:<br>Calcd. for $C_{18}H_{21}N_5O_4S$: | 54.68<br>53.59 | 3.89<br>5.25 | 16.96<br>17.35 |
| 65 | CH₃ | Cl | H | H | CH₃ | 279–282° C. (decomp.) | Found:<br>Calcd. for $C_{15}H_{16}ClN_5O_2S$: | 53.32<br>49.25 | 5.18<br>4.41 | 17.15<br>19.14 |
| 66 | SCH₂CH=CH₂ | H | H | H | H | 113–114° C. | Found:<br>Calcd. for $C_{16}H_{17}N_5O_2S_2$: | 49.05<br>51.17 | 4.38<br>4.56 | 19.00<br>18.65 |
| 67 | SCH₂CH₂CH₃ | H | H | H | H | 124° (decomp.) | Found:<br>Calcd. for $C_{16}H_{19}N_5O_2S_2$: | 51.29<br>50.90 | 4.63<br>5.07 | 18.94<br>18.55 |
| 68 | CH₃ | Cl | H | H | H | 223–225° C. | Found:<br>Calcd. for $C_{14}H_{14}ClN_5O_2S$: | 50.41<br>47.79 | 4.76<br>4.01 | 18.79<br>19.91 |
| 69 | SCH₃ | H | H | H | Cl | 171–172° C. | Found:<br>Calcd. for $C_{14}H_{14}ClN_5O_2S_2$: | 47.52<br>43.80 | 4.31<br>3.68 | 19.84<br>18.24 |
| 70 | SCH₃ | H | H | H | H | 200–202° C. | Found:<br>Calcd. for $C_{15}H_{17}N_5O_2S_2$: | 44.00<br>Calcd.<br>for<br>49.78 | 3.74<br>49.56<br>4.49 | 17.96<br>4.71<br>19.27<br>18.68 |
| 71 | CH=NOH | H | H | H | OCH₃ | 244–246° C. | Found:<br>Calcd. for $C_{15}H_{16}N_6O_4S$: | 47.86<br>47.47 | 4.29<br>4.03 | 22.33<br>23.36 |
| 72 | CO₂CH₂CH₂OEt | H | H | H | CH₃ | 78–80° C. | Found:<br>Calcd. for $C_{19}H_{23}N_5O_5S$: | 52.65<br>51.68 | 5.35<br>5.11 | 16.16<br>16.37 |
| 73 | CO₂CH₂CH₂NMe₂ | H | H | H | CH₃ | 207–208° C. | Found:<br>Calcd. for $C_{19}H_{24}N_6O_4S$: | 52.76<br>52.06 | 5.59<br>5.48 | 19.43<br>19.18 |
| 74 | Cl | Cl | H | H | CH₃ | 287–289° C. (decomp.) | Found:<br>Calcd. for $C_{14}H_{13}Cl_2N_5O_2S$: | 43.54<br>43.74 | 3.39<br>3.46 | 18.13<br>18.48 |
| 75 | COOPh | H | H | H | CH₃ | 159.5–160.5° C. | Found:<br>Calcd. for $C_{21}H_{19}N_5O_4S$: | 57.66<br>57.17 | 4.38<br>4.38 | 16.01<br>15.74 |
| 76 | CO₂CH₂CH=CH₂ | H | H | H | CH₃ | 158–158.5° C. | Found:<br>Calcd. for $C_{18}H_{19}N_5O_4S$: | 53.86<br>53.47 | 4.46<br>4.77<br>4.63 | 17.44<br>17.54 |
| 77 | ![pyridine-CO₂CH₂ group] | H | H | H | CH₃ | 165.5–166° C. | Calcd. for $C_{21}H_{20}N_6O_4S$:<br>Found: | 55.74<br>55.82 | 4.46<br>4.43 | 18.57<br>18.32 |
| 78 | CO₂N=C(CH₃)₂ | H | H | H | CH₃ | 91–94° C. | Calcd. for $C_{18}H_{20}N_6O_4S$:<br>Found: | 51.91<br>51.51 | 4.84<br>4.68 | 20.18<br>19.70 |
| 79 | CH=N—OCH₃ | H | H | H | OCH₃ | 227–229° C. | Calcd. for $C_{16}H_{18}N_6O_4S$:<br>Found: | 49.22<br>49.00 | 4.65<br>4.63 | 21.53<br>21.24 |

TABLE I-continued

![structure with R1-R5 substituents on phenyl ring connected via N=N and sulfonamide]

| Compound | R¹ | R² | R³ | R⁴ | R⁵ | Melting Point | Elemental Analysis | | |
|---|---|---|---|---|---|---|---|---|---|
| 80 | S-t-Bu | H | H | H | H | 144-146° C. | Calcd. for C₁₇H₂₁N₅O₂S₂: | 52.15 | 5.41 | 17.89 |
| | | | | | | | Found: | 52.31 | 5.34 | 17.92 |
| 81 | Cl | H | H | COOMe | H | 175-177° C. | Calcd. for C₁₅H₁₄ClN₅O₄S: | 45.52 | 3.57 | 17.69 |
| | | | | | | | Found: | 45.42 | 3.45 | 17.66 |
| 82 | Cl | COOMe | H | H | Cl | 217-221° C. (decomp.) | Calcd. for C₁₅H₁₃Cl₂N₅O₄S: | 41.87 | 3.05 | 16.27 |
| | | | | | | | Found: | 41.96 | 3.10 | 16.22 |
| 83 | Cl | CF₃ | H | H | Cl | 286-290° C. (decomp.) | Calcd. for C₁₄H₁₀Cl₂F₃N₅O₂S: | 38.20 | 2.29 | 15.90 |
| | | | | | | | Found: | 38.36 | 2.29 | 16.63 |
| 84 | Cl | H | H | CO₂-i-Pr | H | 182-185° C. | Calcd. for C₁₇H₁₈ClN₅O₄S: | 48.17 | 4.28 | 16.52 |
| | | | | | | | Found: | 48.31 | 4.17 | 16.51 |
| 85 | NO₂ | H | H | CH₃ | CH₃ | 254-257° C. (decomp.) | Calcd. for C₁₅H₁₆N₆O₄S: | 47.87 | 4.29 | 22.32 |
| | | | | | | | Found: | 47.52 | 4.01 | 22.47 |
| 86 | Br | COOMe | H | H | CH₃ | 229-231° C. | Calcd. for C₁₆H₁₆BrN₅O₄S: | 42.30 | 3.55 | 15.41 |
| | | | | | | | Found: | 42.29 | 3.45 | 15.68 |
| 87 | Br | COO-i-Pr | H | H | CH₃ | 2088-211° C. | Calcd. for C₁₈H₂₀BrN₅O₄S: | 44.82 | 4.18 | 14.15 |
| | | | | | | | Found: | 45.09 | 4.11 | 14.39 |
| 88 | Br | COO-t-Bu | H | H | CH₃ | 181-183° C. (decomp.) | Calcd. for C₁₉H₂₂BrN₅O₄S: | 45.98 | 4.47 | 14.10 |
| | | | | | | | Found: | 45.61 | 4.17 | 13.84 |
| 89 | COMe | H | H | H | H | 166-168° C. | Calcd. for C₁₅H₁₅N₅O₃S: | 52.16 | 4.38 | 20.28 |
| | | | | | | | Found: | 52.07 | 4.19 | 20.37 |
| 90 | F | F | H | F | F | 148-149° C. (decomp.) | Calcd. for C₁₃H₉F₄N₅O₂S: | 41.60 | 2.42 | 18.66 |
| | | | | | | | Found: | 42.25 | 2.50 | 18.52 |
| 91 | CH₂OCH₃ | H | H | H | Cl | 201-202° C. | Calcd. for C₁₅H₁₆ClN₅O₃S: | 47.19 | 4.22 | 18.33 |
| | | | | | | | Found: | 47.07 | 4.16 | 18.87 |
| 92 | CH₂OCH₂Ph | H | H | H | Cl | 169-171° C. | Calcd. for C₂₁H₂₀ClN₅O₃S: | 55.08 | 4.40 | 15.29 |
| | | | | | | | Found: | 54.99 | 4.38 | 15.30 |
| 93 | CH₂OH | H | H | H | Cl | 208-209° C. | Calcd. for C₁₄H₁₄ClN₅O₃S·H₂O | 43.60 | 4.18 | 18.14 |
| | | | | | | | Found: | 43.50 | 3.75 | 18.43 |
| 94 | CH₂OAc | H | H | H | Cl | 214-217° C. | Calcd. for C₁₆H₁₆ClN₅O₄S: | 46.89 | 3.94 | 17.08 |
| | | | | | | | Found: | 46.60 | 3.80 | 17.73 |
| 95 | COPh | H | H | H | H | 169-170° C. | Calcd. for C₂₀H₁₇N₅O₃S: | 58.95 | 4.21 | 17.19 |
| | | | | | | | Found: | 58.67 | 4.14 | 17.51 |
| 96 | SO₂Ph | H | H | H | H | 152-154° C. | Calcd. for C₁₉H₁₇N₅O₄S: | 51.46 | 3.86 | 15.79 |
| | | | | | | | Found: | 51.31 | 3.81 | 15.81 |
| 97 | 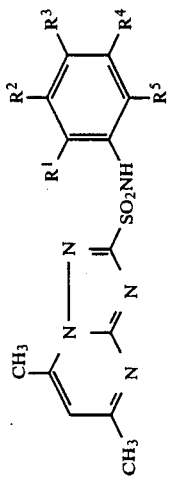 | H | H | H | H | 176-177° C. | Calcd. for C₂₀H₁₅ClF₃N₅O₃S: | 48.24 | 3.03 | 14.06 |
| | | | | | | | Found: | 48.11 | 3.09 | 14.49 |

TABLE I-continued

![structure showing R1-R5 substituted phenyl with CH3-N=N linker to pyrimidine-SO2NH]

| Compound | R¹ | R² | R³ | R⁴ | R⁵ | Melting Point | Elemental Analysis | | |
|---|---|---|---|---|---|---|---|---|---|
| 98 | (2-Cl-4-CF₃-phenoxy) | H | H | H | F | 211–213° C. | Calcd. for $C_{20}H_{14}ClF_4N_5O_3S$:<br>Found: | 46.56<br>46.02 | 2.74<br>2.74 | 13.57<br>13.40 |
| 99 | (3-Cl-5-CF₃-pyridin-2-yloxy) | H | H | H | H | 178–180° C. | Calcd. for $C_{19}H_{14}ClF_3N_6O_3S$:<br>Found: | 45.74<br>45.66 | 2.84<br>2.81 | 16.85<br>17.02 |
| 100 | Cl | H | H | COOH | H | 276–278° C. | Calcd. for $C_{14}H_{12}ClN_5O_4S$:<br>Found: | 44.04<br>44.06 | 3.17<br>3.24 | 18.34<br>18.37 |
| 101 | Br | COOH | H | H | CH₃ | 290° C.<br>(decomp.) | Calcd. for $C_{15}H_{14}BrN_5O_4S$:<br>Found: | 40.92<br>40.51 | 3.21<br>3.11 | 15.90<br>16.01 |
| 102 | CO₂Me | H | H | CO₂Me | H | 191–194° C. | Calcd. for $C_{17}H_{17}N_5O_6S$:<br>Found: | 48.68<br>48.47 | 4.09<br>4.01 | 16.70<br>16.32 |
| 103 | COOH | H | H | H | CH₃ | 268–271° C. | Calcd. for $C_{15}H_{15}N_5O_4S\cdot\frac{1}{2}H_2O$:<br>Found: | 48.64<br>48.88 | 4.35<br>4.00 | 18.90<br>19.20 |
| 104 | CF₃ | H | H | H | OCH₃ | 246–249° C. | Calcd. for $C_{15}H_{14}F_3N_5O_3S$:<br>Found: | 44.91<br>44.77 | 3.49<br>3.61 | 17.47<br>17.94 |

*This compound contains 15% where $R^1 = R^3 = Cl$ and $R^5 = F$.

TABLE II

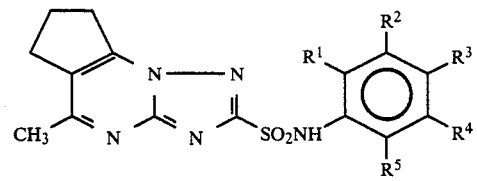

| Compound | R¹ | R² | R³ | R⁴ | R⁵ | Melting Point | Analysis | C | H | N |
|---|---|---|---|---|---|---|---|---|---|---|
| 105 | NO$_2$ | H | H | H | H | 110°–112° C. (decomp.) | Calcd. for C$_{15}$H$_{14}$N$_6$O$_4$S:<br>Found: | 48.11<br>46.96 | 3.73<br>3.54 | 22.43<br>21.62 |
| 106 | CF$_3$ | H | H | H | H | ca 200° C. | Calcd. for C$_{16}$H$_{14}$F$_3$N$_5$O$_2$S:<br>Found: | 48.35<br>48.08 | 3.52<br>3.40 | 17.61<br>17.40 |
| 107 | SO$_2$NMe$_2$ | H | H | H | H | 188°–189° C. (decomp.) | Calcd. for C$_{17}$H$_{20}$N$_6$O$_4$S$_2$:<br>Found: | 46.78<br>46.04 | 4.58<br>4.85 | 19.24<br>18.90 |
| 108 | Cl | H | H | H | H | 264°–266° C. | Calcd. for C$_{15}$H$_{13}$Cl$_2$N$_5$O$_2$S:<br>Found: | 45.24<br>45.47 | 3.29<br>3.18 | 17.58<br>17.41 |
| 109 | —COOMe | H | H | H | H | 180°–182° C. (decomp.) | Calcd. for C$_{17}$H$_{17}$N$_5$O$_4$S:<br>Found: | 52.71<br>52.19 | 4.42<br>4.28 | 18.07<br>18.12 |
| 110 | —COO-i-Pr | H | H | H | H | 170°–172° C. | Calcd. for C$_{19}$H$_{21}$N$_5$O$_4$S:<br>Found: | 54.93<br>54.82 | 5.10<br>5.01 | 16.85<br>16.59 |

TABLE III

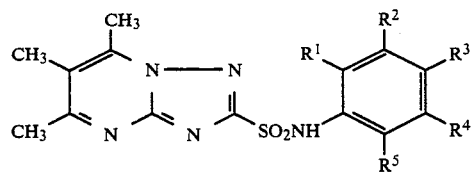

| Cmpd. | R¹ | R² | R³ | R⁴ | R⁵ | Melting Point | Analysis | C | H | N | S | Cl |
|---|---|---|---|---|---|---|---|---|---|---|---|---|
| 111 | Cl | H | H | H | Cl | 296–298° C. | Calcd. for C$_{14}$H$_{13}$Cl$_2$N$_5$O$_2$S:<br>Found: | 43.53<br>44.07 | 3.39<br>3.42 | 18.13<br>18.16 | 8.30<br>7.89 | 18.36<br>17.73 |
| 112 | CF$_3$ | H | H | H | H | 197–199° C. | Calcd. for C$_{15}$H$_{14}$F$_3$N$_5$O$_2$S:<br>Found: | 46.75<br>46.54 | 3.66<br>3.52 | 18.17<br>18.30 | 8.32<br>8.59 | |
| 113 | Cl | H | H | H | CH$_3$ | 306–309° C. | Calcd. for C$_{15}$H$_{16}$ClN$_5$O$_2$S:<br>Found: | 49.25<br>48.70 | 4.41<br>4.29 | 19.14<br>19.23 | 8.76<br>8.82 | 9.69<br>9.57 |

TABLE IV

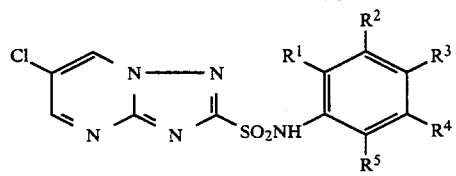

| Cmpd. | R¹ | R² | R³ | R⁴ | R⁵ | Melting Point | Analysis | C | H | N |
|---|---|---|---|---|---|---|---|---|---|---|
| 114 | —Cl | H | H | H | —Cl | 246–248° C. | Calcd. for C$_{11}$H$_6$Cl$_3$N$_5$O$_2$S:<br>Found: | 34.89<br>35.02 | 1.60<br>1.65 | 18.50<br>18.09 |
| 115 | —SMe | H | H | H | H | 159–162° C. | Calcd. for C$_{12}$H$_{10}$ClN$_5$O$_2$S$_2$:<br>Found: | 40.50<br>40.39 | 2.81<br>2.95 | 19.60<br>19.90 |
| 116 | F | H | H | H | Cl | 254–257° C. | Calcd. for C$_{11}$H$_6$Cl$_2$FN$_5$O$_2$S:<br>Found: | 36.48<br>37.21 | 1.67<br>1.91 | 19.34<br>18.74 |
| 117 | F | H | H | H | F | 224–226° C. | Calcd. for C$_{11}$H$_6$ClF$_2$N$_5$O$_2$S:<br>Found: | 38.21<br>38.32 | 1.75<br>1.44 | 20.26<br>20.18 |
| 118 | CF$_3$ | H | H | H | H | 179–180° C. | Calcd. for C$_{12}$H$_7$ClF$_3$N$_5$O$_2$S:<br>Found: | 38.15<br>38.19 | 1.87<br>1.59 | 18.54<br>18.00 |
| 119 | Cl | H | H | H | CH$_3$ | 223–226° C. | Calcd. for C$_{12}$H$_9$Cl$_2$N$_5$O$_2$S:<br>Found: | 40.23<br>40.44 | 2.53<br>2.06 | 19.55<br>19.27 |
| 120 | CF$_3$ | H | H | H | OCH$_3$ | 205–206° C. | Calcd. for C$_{13}$H$_9$ClF$_3$N$_5$O$_3$S:<br>Found: | 38.29<br>38.03 | 2.22<br>2.35 | 17.18<br>17.39 |
| 121 | Cl | H | H | H | H | 188–189° C. | Calcd. for C$_{11}$H$_7$Cl$_2$N$_5$O$_2$S:<br>Found: | 38.39<br>38.26 | 2.05<br>1.84 | 20.35<br>19.98 |
| 122 | COOMe | H | H | H | H | 187–188° C. | Calcd. for C$_{13}$H$_{10}$ClN$_5$O$_4$S:<br>Found: | 42.46<br>42.54 | 2.74<br>2.79 | 19.04<br>19.13 |
| 123 | SO$_2$NMe$_2$ | H | H | H | H | 164–165° C. | Calcd. for C$_{13}$H$_{13}$ClN$_6$O$_4$S$_2$:<br>Found: | 37.46<br>37.42 | 3.14<br>3.21 | 20.16<br>20.25 |

TABLE IV-continued

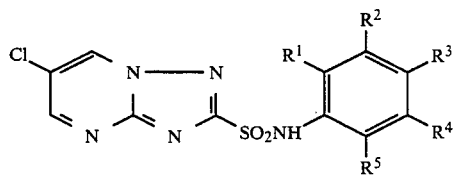

| Cmpd. | R¹ | R² | R³ | R⁴ | R⁵ | Melting Point | Analysis | C | H | N |
|---|---|---|---|---|---|---|---|---|---|---|
| 124 | H | Br | H | H | H | 245–247° C. | Calcd. for $C_{11}H_7BrClN_5O_2S$: | 34.00 | 1.82 | 18.02 |
|  |  |  |  |  |  |  | Found: | 34.49 | 1.90 | 18.31 |
| 125 | H | H | CF₃ | H | H | 239–241° C. | Calcd. for $C_{12}H_7F_3ClN_5O_2S$: | 38.16 | 1.87 | 18.54 |
|  |  |  |  |  |  |  | Found: | 38.54 | 1.83 | 18.83 |
| 126 | CONMe₂ | H | H | H | H | 162–163° C. | Calcd. for $C_{14}H_{13}ClN_6O_3S$: | 44.16 | 3.44 | 22.07 |
|  |  |  |  |  |  |  | Found: | 44.57 | 3.47 | 22.43 |
| 127 | COOiPr | H | H | H | H | 158–160° C. | Calcd. for $C_{15}H_{14}ClN_5O_4S$: | 45.52 | 3.57 | 17.69 |
|  |  |  |  |  |  |  | Found: | 45.54 | 3.49 | 17.93 |
| 128 | Cl | H | H | H | Ph | 243–245° C. | Calcd. for $C_{17}H_{11}Cl_2N_5O_2S$: | 48.58 | 2.64 | 16.66 |
|  |  |  |  |  |  |  | Found: | 49.24 | 2.62 | 16.65 |
| 129 | CH₃ | H | H | H | H | 170–171° C. | Calcd. for $C_{12}H_{10}ClN_5O_2S$: | 44.52 | 3.11 | 21.63 |
|  |  |  |  |  |  |  | Found: | 44.66 | 3.04 | 21.96 |
| 130 | H | H | n-Bu | H | H | 233–235° C. | Calcd. for $C_{15}H_{16}ClN_5O_2S$: | 49.25 | 4.41 | 19.14 |
|  |  |  |  |  |  |  | Found: | 49.10 | 4.30 | 19.30 |
| 131 | H | OCH₃ | H | H | H | 212–215° C. | Calcd. for $C_{12}H_{10}ClN_5O_3S$: | 42.42 | 2.97 | 20.61 |
|  |  |  |  |  |  |  | Found: | 42.33 | 2.97 | 20.65 |
| 132 | SO₂N(Me)Et | H | H | H | H | 155–157° C. | Calcd. for $C_{14}H_{15}ClN_6O_4S_2$: | 39.02 | 3.51 | 19.50 |
|  |  |  |  |  |  |  | Found: | 39.17 | 3.47 | 19.54 |
| 133 | F | H | H | H | H | 171–172° C. | Calcd. for $C_{11}H_7ClFN_5O_2S$: | 40.32 | 2.15 | 21.37 |
|  |  |  |  |  |  |  | Found: | 41.00 | 2.18 | 21.55 |
| 134 | H | SCH₃ | H | H | H | 210–212° C. | Calcd. for $C_{12}H_{10}ClN_5O_2S_2$: | 40.51 | 2.83 | 19.68 |
|  |  |  |  |  |  |  | Found: | 39.29 | 2.77 | 19.70 |

TABLE V

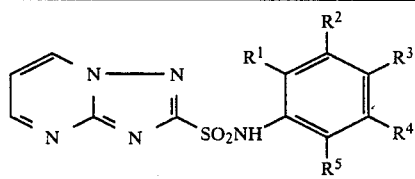

| Cmpd. | R¹ | R² | R³ | R⁴ | R⁵ | Melting Point | Analysis | C | H | N |
|---|---|---|---|---|---|---|---|---|---|---|
| 135 | —SCH₃ | H | H | H | H | 162.5–165° C. (decomp.) | Calcd. for $C_{12}H_{11}N_5O_2S_2$: | 44.85 | 3.43 | 21.78 |
|  |  |  |  |  |  |  | Found: | 44.35 | 3.43 | 22.08 |
| 136 | —CF₃ | H | H | H | H | 168.5–171° C. (decomp.) | Calcd. for $C_{12}H_8F_3O_2S$: | 42.11 | 2.33 | 20.45 |
|  |  |  |  |  |  |  | Found: | 41.93 | 2.28 | 19.99 |
| 137 | Cl | H | H | H | Cl | 278–280° C. | Calcd. for $C_{11}H_7Cl_2N_5O_2S$: | 38.38 | 2.03 | 20.35 |
|  |  |  |  |  |  |  | Found: | 38.28 | 1.70 | 20.75 |
| 138 | F | H | H | H | F | 296–299° C. (decomp.) | Calcd. for $C_{11}H_7F_2N_5O_2S$: | 42.46 | 2.25 | 22.52 |
|  |  |  |  |  |  |  | Found: | 42.27 | 2.30 | 22.60 |
| 139 | Cl | CH₃ | H | H | Cl | 252–255° C. (decomp.) | Calcd. for $C_{12}H_9Cl_2N_5O_2S$: | 40.23 | 2.51 | 19.55 |
|  |  |  |  |  |  |  | Found: | 40.00 | 2.65 | 19.75 |
| 140 | F | CH₃ | H | H | F | 280–283° C. (decomp.) | Calcd. for $C_{12}H_9F_2N_5O_2S$: | 44.32 | 2.77 | 21.55 |
|  |  |  |  |  |  |  | Found: | 44.10 | 2.81 | 21.55 |
| 141 | CF₃ | H | H | H | OCH₃ | 230–232° C. | Calcd. for $C_{13}H_{10}F_3N_5O_3S$: | 41.80 | 2.68 | 18.78 |
|  |  |  |  |  |  |  | Found: | 41.40 | 2.77 | 18.69 |

TABLE VI

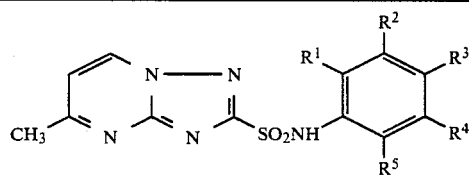

| Cmpd. | R¹ | R² | R³ | R⁴ | R⁵ | Melting Point | Analysis | C | H | N |
|---|---|---|---|---|---|---|---|---|---|---|
| 142 | —SCH₃ | H | H | H | H | 166°–169° C. | Calcd. for $C_{13}H_{13}N_5O_2S_2$: | 45.67 | 3.77 | 20.11 |
|  |  |  |  |  |  |  | Found: | 47.34 | 3.90 | 19.86 |

TABLE VI-continued

Structure: methyl-pyrimidine-triazolo core with SO₂NH-phenyl substituted at R¹(ortho), R²,R³,R⁴ and R⁵(other ortho).

| Cmpd. | R¹ | R² | R³ | R⁴ | R⁵ | Melting Point | Elemental Analysis | | | |
|---|---|---|---|---|---|---|---|---|---|---|
| 143 | —Cl | H | H | H | —Cl | 228.5°–230° C. | Calcd. for C₁₂H₉Cl₂N₅O₂S: Found: | 40.24 40.34 | 2.51 2.52 | 19.54 19.09 |
| 144 | —Cl | H | H | H | —CH₃ | 211–215° C. (decomp.) | Calcd. for C₁₃H₁₂ClN₅O₂S: Found: | 46.19 45.91 | 3.55 3.43 | 20.72 20.70 |
| 145 | CF₃ | H | H | H | H | 144–145° C. | Calcd. for C₁₃H₁₀F₃N₅O₂S: Found: | 43.67 43.67 | 2.79 2.74 | 19.59 19.52 |
| 146 | COOMe | H | H | H | CH₃ | 184–186° C. | Calcd. for C₁₅H₁₅N₅O₄S: Found: | 49.84 49.65 | 4.15 4.13 | 19.38 19.45 |
| 147 | Cl | CH₃ | H | H | Cl | 140° C. (decomp.) | Calcd. for C₁₁H₁₁Cl₂N₅O₂S: Found: | 41.91 41.92 | 2.95 2.83 | 18.80 18.45 |
| 148 | Br | H | H | H | CH₃ | 106° C. (decomp.) | Calcd. for C₁₃H₁₂BrN₅O₂S: Found: | 40.83 40.36 | 3.14 3.14 | 18.32 18.30 |
| 149 | SOCF₂CF₂H | H | H | H | H | 180°0 C. (decomp.) | Calcd. for C₁₄H₁₁F₄N₅O₃S₂: Found: | 38.40 36.70 | 2.52 2.50 | 16.03 14.69 |
| 150 | SCH₃ | H | H | H | CH₃ | 234° C. (decomp.) | Calcd. for C₁₄H₁₅N₅O₂S₂: Found: | 48.12 47.89 | 4.33 4.17 | 20.04 20.31 |
| 151 | NO₂ | H | H | H | CH₃ | 120° C. (decomp.) | Calcd. for C₁₃H₁₂N₆O₄S: Found: | 44.82 45.94 | 3.47 3.30 | 24.13 23.75 |
| 152 | Br | H | H | H | Cl | 230–235° C. | Calcd. for C₁₂H₉BrClN₅O₂S: Found: | 35.79 35.50 | 2.25 2.19 | 17.39 17.97 |
| 153 | I | H | H | H | Cl | 210–215° C. | Calcd. for C₁₂H₉ClIN₅O₂S: Found: | 32.05 32.36 | 2.02 2.29 | 15.58 15.31 |

| Cmpd. | R¹ | R² | R³ | R⁴ | R⁵ | Melting Point | Elemental Analysis | C | H | N | S |
|---|---|---|---|---|---|---|---|---|---|---|---|
| 154 | Cl | H | H | H | Ph | 233–234° C. (decomp.) | Analysis Calcd. for C₁₈H₁₄ClN₅O₂S: Found: | 54.07 53.49 | 3.53 3.45 | 17.52 17.82 | 8.02 8.49 |
| 155 | Cl | Cl | H | H | CH₃ | 256–259° C. (decomp.) | Calcd. for C₁₃H₁₁Cl₂N₅O₂S: Found: | 41.95 42.00 | 2.98 2.96 | 18.81 18.75 | 8.61 8.63 |
| 156 | COOCH₃ | H | H | Cl | CH₃ | 75–80° C. | Calcd. for C₁₄H₁₅ClN₅O₄S: Found: | 45.52 45.28 | 3.57 3.57 | 17.69 17.41 | 8.10 8.07 |

| Cmpd. | R¹ | R² | R³ | R⁴ | R⁵ | Melting Point | Elemental Analysis | C | H | N |
|---|---|---|---|---|---|---|---|---|---|---|
| 157 | F | H | H | H | F | 245–247° C. | Analysis Calcd. for C₁₂H₉F₂N₅O₂S: Found: | 44.30 44.69 | 2.79 2.80 | 21.53 21.85 |
| 158 | F | H | H | H | Cl | 243–248° C. | Calcd. for C₁₂H₉ClFN₅O₂S: Found: | 42.17 42.14 | 2.65 2.63 | 20.49 20.18 |
| 159 | COOMe | H | H | H | F | 159–163° C. | Calcd. for C₁₄H₁₂FN₅O₄S: Found: | 46.03 45.56 | 3.31 3.08 | 19.16 19.25 |
| 160 | NO₂ | H | H | CH₃ | CH₃ | 225–230° C. | Exact mass calcd. for C₁₄H₁₄N₆O₄S: Found: | | 262.0799 262.0802 | |
| 161 | F | H | H | H | SCH₃ | 190–192° C. | Analysis Calcd. for C₁₃H₁₂FN₅O₂S₂: Found: | 44.18 44.02 | 3.42 3.41 | 19.82 19.51 |
| 162 | F | H | H | H | CH₃ | 241° C. (decomp.) | Calcd. for C₁₃H₁₂FN₅O₂S: Found: | 48.59 48.31 | 3.76 3.51 | 21.80 21.62 |
| 163 | F | F | H | F | F | 209°0 C. (decomp.) | Calcd. for C₁₂H₇F₄N₄O₂S: Found: | 39.89 38.41 | 1.95 2.21 | 19.39 19.04 |
| 164 | CH₂OCH₃ | H | H | H | Cl | 186–191° C. (decomp.) | Calcd. for C₁₄H₁₄ClN₅O₃S: Found: | 45.72 45.46 | 3.84 3.88 | 19.03 18.97 |

| Cmpd. | R¹ | R² | R³ | R⁴ | R⁵ | Melting Point | Elemental Analysis | C | H | N | S |
|---|---|---|---|---|---|---|---|---|---|---|---|
| 165 | CN | H | H | H | CH₃ | 240–245° C. (decomp.) | Analysis Calcd. for C₁₄H₁₂N₆O₂S: Found: | 51.22 49.43 | 3.68 3.58 | 25.59 24.55 | 9.77 9.47 |
| 166 | COCH₃ | H | H | H | CH₃ | 204–207° C. | Calcd. for C₁₅H₁₅N₅O₃S: Found: | 52.17 51.82 | 4.38 4.25 | 20.27 20.95 | 9.28 9.19 |

| Cmpd. | R¹ | R² | R³ | R⁴ | R⁵ | Melting Point | Elemental Analysis | C | H | N |
|---|---|---|---|---|---|---|---|---|---|---|
| 167 | CN | H | H | H | F | 201–203° C. | Analysis Calcd. for C₁₃H₉FN₆O₂S: Found: | 46.98 46.41 | 2.73 2.81 | 25.29 26.01 |
| 168 | CF₃ | H | H | H | F | 214–216° C. | Calcd. for C₁₃H₉F₄N₅O₂S: Found: | 41.60 41.33 | 2.42 2.61 | 18.66 18.74 |
| 169 | CH₃ | H | Cl | H | H | 170–171° C. | Calcd. for C₁₃H₉ClF₃N₅O₂S: Found: | 39.85 39.96 | 2.32 2.29 | 17.88 17.30 |
| 170 | Cl | OCH₃ | H | H | Cl | 229–231° C. (decomp.) | Calcd. for C₁₃H₁₁Cl₂N₅O₃S: Found: | 40.21 40.18 | 2.86 2.99 | 18.04 17.71 |
| 171 | F | H | H | H | OCH₃ | 212–214° C. | Calcd. for C₁₃H₁₂FN₅O₃S: Found: | 46.28 46.26 | 3.58 3.56 | 20.76 20.49 |
| 172 | F | OCH₃ | H | H | F | 219–221° C. | Calcd. for C₁₃H₁₁F₂N₅O₃S: Found: | 43.94 43.79 | 3.12 3.29 | 19.71 19.48 |
| 173 | F | H | H | H | NO₂ | 227° C. (decomp.) | Calcd. for C₁₂H₉FN₆O₂S: Found: | 44.99 44.63 | 2.83 2.51 | 26.24 26.46 |
| 174 | F | CH₃ | H | H | F | 219–221° C. | Calcd. for C₁₃H₁₁F₂N₅O₂S: Found: | 46.01 46.27 | 3.27 3.47 | 20.64 20.27 |
| 175 | CF₃ | H | H | H | OCH₃ | 209–211° C. | Calcd. for C₁₄H₁₂F₃N₅O₃S: | 43.41 | 3.12 | 18.08 |

TABLE VI-continued

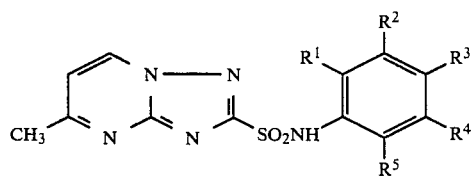

| Cmpd. | R¹ | R² | R³ | R⁴ | R⁵ | Melting Point | Elemental Analysis | | | |
|---|---|---|---|---|---|---|---|---|---|---|
| | | | | | | | | | | |
| 176 | $CF_3$ | H | H | H | $CH_2SCH_3$ | 227–229° C. | Found:<br>Calcd. for $C_{15}H_{14}F_3N_5O_2S_2$: | 43.31<br>43.16 | 3.07<br>3.38 | 17.97<br>16.78 |
| 177 | $CF_3$ | H | H | H | $CH_3$ | 219–220° C. | Found:<br>Calcd. for $C_{14}H_{12}F_3N_5O_2S$: | 43.24<br>48.41 | 3.71<br>3.48 | 16.37<br>20.17 |
| | | | | | | | Found: | 48.14 | 3.71 | 20.34 |

TABLE VII

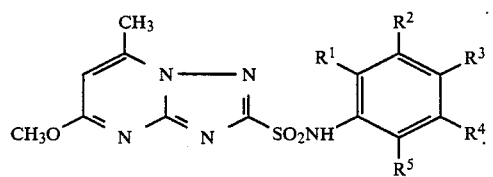

| Cmpd. | R¹ | R² | R³ | R⁴ | R⁵ | Melting Point | Analysis | Elemental Analysis | | |
|---|---|---|---|---|---|---|---|---|---|---|
| | | | | | | | | C | H | N |
| 178 | Cl | H | H | H | Cl | 133°–134.5° C. | Calcd. for $C_{13}H_{11}Cl_2N_5O_3S$:<br>Found: | 40.22<br>40.05 | 2.83<br>2.88 | 18.03<br>17.86 |
| 179 | Cl | H | H | H | H | 195–196° C. | | | | |

TABLE VIII

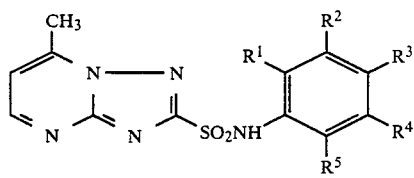

| Cmpd | R¹ | R² | R³ | R⁴ | R⁵ | Melting Point | Analysis | Elemental Analysis | | |
|---|---|---|---|---|---|---|---|---|---|---|
| | | | | | | | | C | H | N |
| 180 | Cl | H | H | H | Cl | 268°–269.5° C.<br>(decomp.) | Calcd. for $C_{12}H_9Cl_2N_5O_2S$:<br>Found: | 40.24<br>40.19 | 2.51<br>2.68 | 19.54<br>19.06 |
| 181 | F | H | H | H | Cl | 270–273° C. | Calcd. for $C_{12}H_9ClFN_5O_2S$:<br>Found: | 42.17<br>42.09 | 2.65<br>2.63 | 20.49<br>19.91 |
| 182 | Cl | $CH_3$ | H | H | Cl | 257–263° C. | Calcd. for $C_{13}H_{11}Cl_2N_5O_2S$:<br>Found: | 41.91<br>41.88 | 2.98<br>2.86 | 18.82<br>18.30 |
| 183 | $CF_3$ | H | H | H | H | 171–185° C. | Calcd. for $C_{13}H_{10}F_3N_5O_2S$:<br>Found: | 42.70<br>42.33 | 2.82<br>2.66 | 19.60<br>19.36 |
| 184 | $NO_2$ | H | H | H | $CH_3$ | 200–205° C. | Calcd. for $C_{13}H_{12}N_6O_4S$:<br>Found: | 44.82<br>44.43 | 3.47<br>3.43 | 24.13<br>23.81 |
| 185 | F | H | H | H | F | 255–257° C. | Calcd. for $C_{12}H_9F_2N_5O_2S$:<br>Found: | 44.30<br>44.08 | 2.79<br>3.08 | 21.53<br>21.32 |
| 186 | Cl | H | H | H | $CH_3$ | 229.5–233° C. | Calcd. for $C_{13}H_{12}ClN_5O_2S$:<br>Found: | 46.22<br>45.56 | 3.58<br>3.93 | 20.74<br>20.27 |
| 187 | $COOCH_3$ | H | H | H | F | 200–201° C. | Calcd. for $C_{14}H_{12}FN_5O_4S$:<br>Found: | 46.03<br>45.75 | 3.31<br>3.25 | 19.17<br>19.20 |
| 188 | $NO_2$ | H | H | $CH_3$ | $CH_3$ | 233–236° C. | Calcd. for $C_{14}H_{14}N_6O_4S$:<br>Found: | 46.40<br>46.29 | 3.89<br>3.67 | 23.19<br>22.84 |
| 189 | $COOCH_3$ | H | H | H | $CH_3$ | 167–167.5° C. | Calcd. for $C_{15}H_{15}N_5O_4S$:<br>Found: | 49.86<br>49.78 | 4.18<br>4.10 | 19.38<br>19.16 |
| 190 | F | $CH_3$ | H | H | F | 256–258° C. | Calcd. for $C_{13}H_{11}F_2N_5O_2S$:<br>Found: | 46.02<br>44.95 | 3.27<br>3.00 | 20.64<br>20.00 |
| 191 | $CF_3$ | H | H | H | $OCH_3$ | 260–262° C. | Calcd. for $C_{14}H_{12}F_3N_5O_3S$:<br>Found: | 43.41<br>42.83 | 3.12<br>3.18 | 18.08<br>19.74 |

TABLE IX

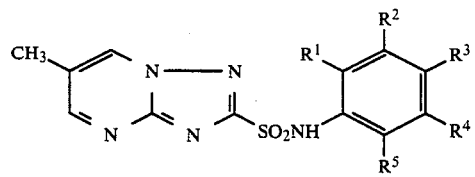

| Cmpd | R¹ | R² | R³ | R⁴ | R⁵ | Melting Point | Analysis | C | H | N | S |
|---|---|---|---|---|---|---|---|---|---|---|---|
| 192 | Cl | H | H | H | Cl | 249° C. (decomp.) | Calcd. for $C_{12}H_{10}Cl_2N_5O_2S$: Found: | 40.21 39.99 | 2.51 2.66 | 19.56 19.62 | 8.94 8.70 |
| 193 | F | H | H | H | F | 263–265° C. | Calcd. for $C_{12}H_9F_2N_5O_2S$: Found: | 44.30 44.37 | 2.79 2.92 | 21.53 20.98 | 9.86 9.85 |
| 194 | Cl | CH₃ | H | H | Cl | 276–280° C. | Calcd. for $C_{13}H_{11}Cl_2N_5O_2S$: Found: | 41.94 41.59 | 2.98 2.97 | 18.82 19.13 | 8.61 8.46 |
| 195 | Cl | H | H | H | CH₃ | 227–232° C. | Calcd. for $C_{13}H_{12}ClN_5O_2S$: Found: | 46.22 45.73 | 3.58 3.47 | 20.74 20.94 | 9.49 9.49 |
| 196 | NO₂ | H | H | H | CH₃ | 251–253° C. | Calcd. for $C_{13}H_{12}N_6O_4S$: Found: | 44.82 43.84 | 3.47 3.39 | 24.13 24.05 | 9.20 9.28 |
| 197 | COOMe | H | H | H | CH₃ | 208.5–210.5° C. | Calcd. for $C_{15}H_{15}N_5O_4S$: Found: | 49.85 49.96 | 4.18 4.14 | 19.38 19.75 | |

TABLE X

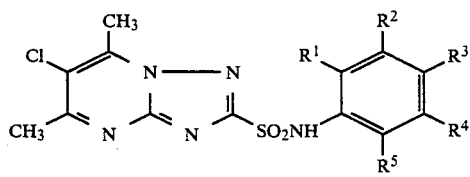

| Cmpd. | R¹ | R² | R³ | R⁴ | R⁵ | Melting Point | Analysis | C | H | N |
|---|---|---|---|---|---|---|---|---|---|---|
| 198 | Cl | H | H | H | H | 174–176° C. | Calcd. for $C_{13}H_{11}Cl_2N_5O_2S$: Found: | 41.95 41.64 | 2.98 2.84 | 18.82 18.54 |
| 199 | Cl | CH₃ | H | H | Cl | 231–233° C. | Calcd. for $C_{14}H_{12}Cl_3N_5O_2S$: Found: | 39.96 39.94 | 2.88 2.88 | 18.65 18.15 |
| 200 | Cl | H | H | H | Cl | 171° C. (decomp.) | Calcd. for $C_{13}H_{10}Cl_3N_5O_2S$: Found: | 38.39 38.47 | 2.48 2.66 | 17.22 17.37 |

TABLE XI

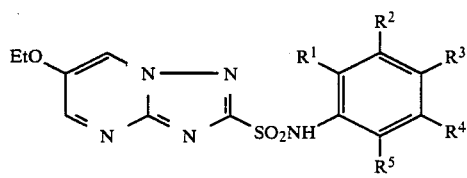

| Cmpd. | R¹ | R² | R³ | R⁴ | R⁵ | Melting Point | Analysis | C | H | N |
|---|---|---|---|---|---|---|---|---|---|---|
| 201 | CF₃ | H | H | H | H | 75–78° C. (decomp.) | Calcd. for $C_{14}H_{12}F_3N_5O_3S$: Found: | 43.36 43.53 | 3.09 3.17 | 18.06 17.50 |
| 202 | Cl | H | H | H | CH₃ | 105–110° C. (decomp.) | Calcd. for $C_{14}H_{14}ClN_5O_3S$: Found: | 45.66 43.74 | 3.80 3.80 | 19.02 18.76 |
| 203 | Cl | H | H | H | Cl | 215–216° C. | Calcd. for $C_{12}H_{12}Cl_2N_5O_2S$: Found: | 40.21 40.13 | 2.83 2.96 | 18.04 17.99 |

TABLE XII

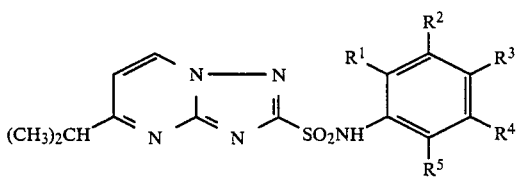

| Cmpd. | R¹ | R² | R³ | R⁴ | R⁵ | Melting Point | Analysis | Elemental Analysis C | H | N | S |
|---|---|---|---|---|---|---|---|---|---|---|---|
| 204 | Cl | H | H | H | Cl | 214–216° C. | Calcd. for $C_{14}H_{13}Cl_2N_5O_2S$: | 43.51 | 3.37 | 18.13 | 8.30 |
| | | | | | | | Found: | 43.50 | 3.28 | 17.63 | 7.96 |

TABLE XIII

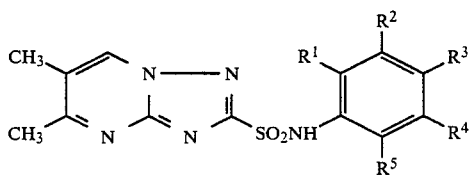

| Cmpd. | R¹ | R² | R³ | R⁴ | R⁵ | Melting Point | Analysis | Elemental Analysis C | H | N |
|---|---|---|---|---|---|---|---|---|---|---|
| 205 | Cl | H | H | H | Cl | 235–237° C. | Calcd. for $C_{13}H_{11}Cl_2N_5O_2S$: | 41.93 | 2.95 | 18.81 |
| | | | | | | | Found: | 41.80 | 3.08 | 18.65 |

TABLE XIV

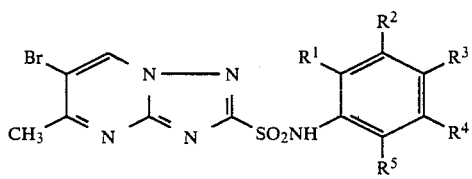

| Cmpd. | R¹ | R² | R³ | R⁴ | R⁵ | Melting Point | Elemental Analysis | |
|---|---|---|---|---|---|---|---|---|
| 206 | Cl | H | H | H | Cl | 215–216° C. | Exact mass calcd. for $C_{12}H_8BrCl_2N_5O_2S$: | 438.8898 |
| | | | | | | | Found: | 438.8899 |

TABLE XV

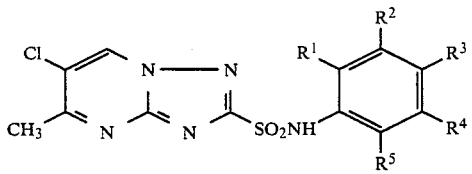

| Cmpd. | R¹ | R² | R³ | R⁴ | R⁵ | Melting Point | Analysis | Elemental Analysis C | H | N |
|---|---|---|---|---|---|---|---|---|---|---|
| 207 | Cl | H | H | H | Cl | 105–110° C. | Calcd. for $C_{12}H_8Cl_3N_5O_2S$: | 36.69 | 2.04 | 17.80 |
| | | | | | | | Found: | 36.28 | 2.15 | 18.41 |

TABLE XVI

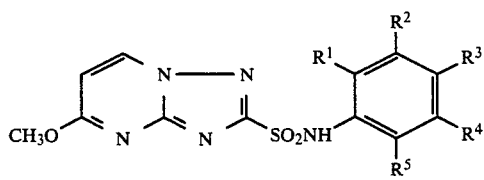

| Cmpd. | R¹ | R² | R³ | R⁴ | R⁵ | Melting Point | Analysis | C | N | H |
|---|---|---|---|---|---|---|---|---|---|---|
| 208 | Cl | H | H | H | Cl | 235–237° C. | Calcd. for $C_{12}H_9Cl_2N_5O_3S$: | 38.51 | 2.41 | 18.72 |
| | | | | | | | Found: | 38.29 | 2.44 | 18.92 |

TABLE XVII

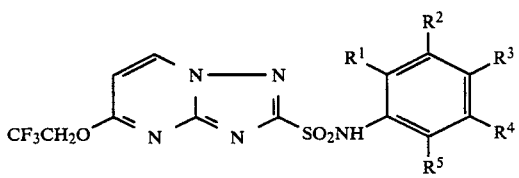

| Cmpd. | R¹ | R² | R³ | R⁴ | R⁵ | Melting Point | Analysis | C | H | N |
|---|---|---|---|---|---|---|---|---|---|---|
| 209 | Cl | H | H | H | Cl | 266–269° C. | Calcd. for $C_{13}H_8Cl_2F_3N_5O_3S$: | 35.29 | 1.81 | 15.84 |
| | | | | | | | Found: | 35.14 | 1.72 | 15.65 |

TABLE XVIII

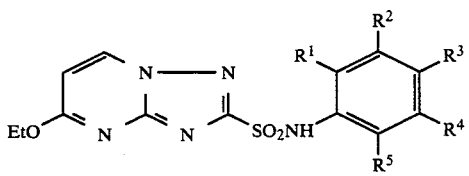

| Cmpd. | R¹ | R² | R³ | R⁴ | R⁵ | Melting Point | Analysis | C | H | N |
|---|---|---|---|---|---|---|---|---|---|---|
| 210 | Cl | H | H | H | Cl | 230–233° C. | Calcd. for $C_{13}H_{11}Cl_2N_5O_3S$: | 40.21 | 2.83 | 18.03 |
| | | | | | | | Found: | 40.10 | 2.76 | 17.87 |

TABLE XIX

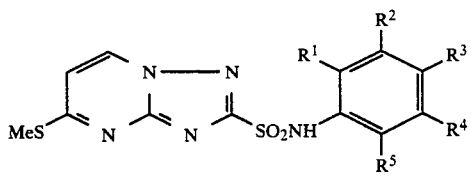

| Cmpd. | R¹ | R² | R³ | R⁴ | R⁵ | Melting Point | Analysis | C | H | N |
|---|---|---|---|---|---|---|---|---|---|---|
| 211 | Cl | H | H | H | Cl | 239–243° C. (decomp.) | Calcd. for $C_{12}H_9Cl_2N_5O_2S_2$: | 36.92 | 2.31 | 17.95 |
| | | | | | | | Found: | 36.51 | 2.41 | 17.68 |

TABLE XX

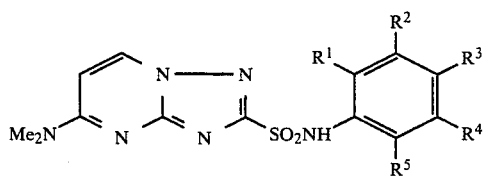

| Cmpd. | R¹ | R² | R³ | R⁴ | R⁵ | Melting Point | Analysis | C | N | H | S |
|---|---|---|---|---|---|---|---|---|---|---|---|
| 212 | Cl | H | H | H | Cl | >310° C. | Calcd. for $C_{13}H_{12}Cl_2N_6O_2S$: | 40.31 | 3.10 | 21.71 | 8.28 |
|  |  |  |  |  |  |  | Found: | 40.31 | 3.05 | 22.31 | 7.99 |

TABLE XXI

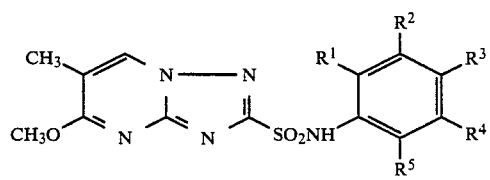

| Cmpd. | R¹ | R² | R³ | R⁴ | R⁵ | Melting Point | Analysis | C | H | N |
|---|---|---|---|---|---|---|---|---|---|---|
| 213 | Cl | H | H | H | Cl | 235–242° C. (decomp.) | Calcd. for $C_{13}H_{11}Cl_2N_5O_3S$: | 40.21 | 2.84 | 18.04 |
|  |  |  |  |  |  |  | Found: | 40.37 | 2.78 | 18.06 |
| 214 | F | H | H | H | F | 230–232° C. | Calcd. for $C_{13}H_{11}F_2N_5O_3S$: | 43.94 | 3.12 | 19.71 |
|  |  |  |  |  |  |  | Found: | 43.80 | 3.10 | 20.11 |
| 215 | COOCH₃ | H | H | H | F | 195–197° C. | Calcd. for $C_{15}H_{14}FN_5O_5S$: | 45.57 | 3.57 | 17.71 |
|  |  |  |  |  |  |  | Found: | 45.26 | 3.51 | 18.12 |
| 216 | COOCH₃ | H | H | H | CH₃ | 197–198° C. | Calcd. for $C_{16}H_{17}N_5O_5S$: | 49.10 | 4.38 | 17.89 |
|  |  |  |  |  |  |  | Found: | 48.95 | 4.28 | 17.88 |
| 217 | CF₃ | H | H | H | H | 213–215° C. | Calcd. for $C_{14}H_{12}F_3N_5O_3S$: | 43.41 | 3.12 | 18.08 |
|  |  |  |  |  |  |  | Found: | 41.64 | 3.28 | 17.56 |
| 218 | Cl | CH₃ | H | H | Cl | 240.5–241.5° C. | Calcd. for $C_{14}H_{13}Cl_2N_5O_3S$: | 41.80 | 3.26 | 17.41 |
|  |  |  |  |  |  |  | Found: | 41.64 | 3.28 | 17.56 |
| 219 | F | CH₃ | H | H | F | 230–231° C. | Calcd. for $C_{14}H_{13}F_2N_5O_3S$: | 45.53 | 3.55 | 18.96 |
|  |  |  |  |  |  |  | Found: | 45.16 | 3.55 | 19.37 |
| 220 | Cl | H | H | H | CH₃ | 213–214° C. | Calcd. for $C_{14}H_{14}ClN_5O_3S$: | 45.72 | 3.84 | 19.04 |
|  |  |  |  |  |  |  | Found: | 45.96 | 3.90 | 19.40 |
| 221 | NO₂ | H | H | H | CH₃ | 226–228° C. | Calcd. for $C_{14}H_{14}N_6O_5S$: | 44.44 | 3.73 | 22.21 |
|  |  |  |  |  |  |  | Found: | 44.52 | 3.75 | 22.50 |
| 222 | NO₂ | H | H | CH₃ | CH₃ | 230–231° C. | Calcd. for $C_{15}H_{16}N_6O_5S$: | 45.91 | 4.11 | 21.42 |
|  |  |  |  |  |  |  | Found: | 45.49 | 4.04 | 21.64 |
| 223 | CF₃ | H | H | H | OCH₃ | 232–233° C. | Calcd. for $C_{15}H_{14}F_3N_5O_4S$: | 43.17 | 3.38 | 16.78 |
|  |  |  |  |  |  |  | Found: | 43.10 | 3.42 | 16.92 |

TABLE XXII

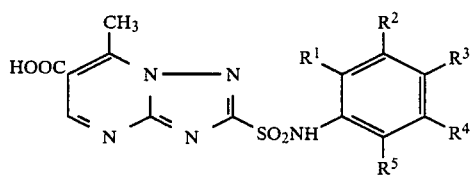

| Cmpd. | R¹ | R² | R³ | R⁴ | R⁵ | Melting Point | Analysis | C | H | N |
|---|---|---|---|---|---|---|---|---|---|---|
| 224 | Cl | H | H | H | Cl | 220° C. (decomp.) | Calcd. for $C_{13}H_9Cl_2N_5O_4S$: | 38.80 | 2.24 | 17.41 |
|  |  |  |  |  |  |  | Found: | 39.30 | 2.66 | 17.41 |

TABLE XXIII

HO–[ring with N–N, N]–N—N–C(=SO₂NH–Ar)

where Ar = phenyl with R¹, R², R³, R⁴, R⁵

| Cmpd. | R¹ | R² | R³ | R⁴ | R⁵ | Melting Point | Analysis | C | H | N |
|---|---|---|---|---|---|---|---|---|---|---|
| 225 | Cl | H | H | H | Cl | 310–320° C. (decomp.) | Calcd. for $C_{11}H_7Cl_2N_5O_3S$: | 36.65 | 1.94 | 19.40 |
| | | | | | | | Found: | 36.79 | 1.76 | 19.14 |

TABLE XXIV

| Cmpd. | R¹ | R² | R³ | R⁴ | R⁵ | Melting Point | Analysis | C | H | N |
|---|---|---|---|---|---|---|---|---|---|---|
| 226 | Cl | H | H | H | Cl | 285–287° C. | Calcd. for $C_{17}H_{10}Cl_2N_6O_4S$: | 43.84 | 2.15 | 18.00 |
| | | | | | | | Found: | 44.12 | 2.43 | 17.45 |

TABLE XXV

| Cmpd. | R¹ | R² | R³ | R⁴ | R⁵ | Melting Point | Analysis | C | H | N |
|---|---|---|---|---|---|---|---|---|---|---|
| 227 | Cl | H | H | H | Cl | 237–239° C. | Calcd. for $C_{13}H_8Cl_2F_3N_5O_2S$: | 36.63 | 1.88 | 16.42 |
| | | | | | | | Found: | 36.74 | 1.52 | 16.94 |
| 228 | F | H | H | H | F | 234–237° C. | Calcd. for $C_{13}H_8F_5N_5O_2S$: | 39.74 | 2.04 | 17.83 |
| | | | | | | | Found: | 39.49 | 2.08 | 18.11 |
| 229 | Cl | CH₃ | H | H | Cl | 252–254° C. | Calcd. for $C_{14}H_{10}Cl_2F_3N_5O_2S$: | 38.21 | 2.27 | 15.97 |
| | | | | | | | Found: | 38.09 | 2.34 | 16.40 |
| 230 | F | CH₃ | H | H | F | 243–245° C. | Calcd. for $C_{14}H_{10}F_5N_5O_2S$: | 41.32 | 2.46 | 17.23 |
| | | | | | | | Found: | 41.21 | 2.51 | 17.49 |
| 231 | CF₃ | H | H | H | OCH₃ | 226–229° C. | Calcd. for $C_{15}H_{11}F_6N_5O_3S$: | 39.61 | 2.42 | 15.40 |
| | | | | | | | Found: | 39.50 | 2.52 | 15.60 |
| 307 | Cl | H | H | H | CH₃ | 234–235° C. | Calcd. for $C_{14}H_{11}ClF_3N_5OS$: | 41.14 | 2.73 | 17.26 |
| | | | | | | | Found: | 41.03 | 2.77 | 17.14 |
| 308 | Cl | H | H | H | CH₂OCH₃ | 206–207° C. | Calc. for $C_{15}H_{13}ClF_3N_5O_3S$ | 41.34 | 3.01 | 16.07 |
| | | | | | | | Found: | 41.19 | 2.97 | 16.02 |

TABLE XXVI

| Cmpd. | R¹ | R² | R³ | R⁴ | R⁵ | Melting Point | Analysis | C | H | N |
|---|---|---|---|---|---|---|---|---|---|---|
| 232 | Cl | H | H | H | Cl | >310° C. | Calcd. for $C_{12}H_9Cl_2N_5O_3S$: | 38.51 | 2.41 | 18.72 |
| | | | | | | | Found: | 38.28 | 2.44 | 19.03 |

TABLE XXVII

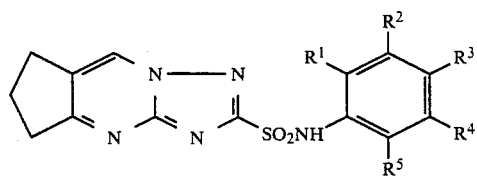

| Cmpd. | $R^1$ | $R^2$ | $R^3$ | $R^4$ | $R^5$ | Melting Point | Analysis | Elemental Analysis C | H | N |
|---|---|---|---|---|---|---|---|---|---|---|
| 233 | Cl | H | H | H | CH₃ | 221–224° C. (decomp.) | Calcd. for $C_{15}H_{14}ClN_5O_2S$: Found: | 49.52 49.56 | 3.85 3.85 | 19.27 18.90 |

TABLE XXVIII

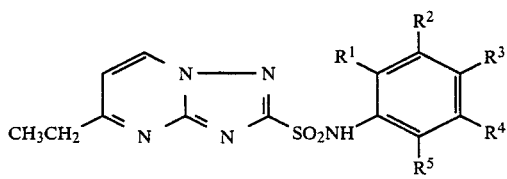

| Cmpd. | $R^1$ | $R^2$ | $R^3$ | $R^4$ | $R^5$ | Melting Point | Elemental Analysis | |
|---|---|---|---|---|---|---|---|---|
| 234 | Cl | H | H | H | Cl | 80–92° C. (decomp.) | Exact mass calcd. for $C_{13}H_{11}Cl_2N_5O_2S$: Found: | 327.9981 327.9994 |

TABLE XXIX

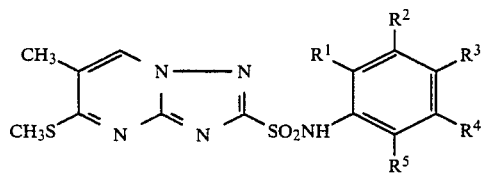

| Cmpd. | $R^1$ | $R^2$ | $R^3$ | $R^4$ | $R^5$ | Melting Point | Analysis | Elemental Analysis C | H | N |
|---|---|---|---|---|---|---|---|---|---|---|
| 235 | Cl | H | H | H | Cl | 254–258° C. (decomp.) | Calcd. for $C_{13}H_{11}Cl_2N_5O_2S_2$: Found: | 36.96 36.92 | 2.60 2.44 | 16.58 16.57 |

TABLE XXX

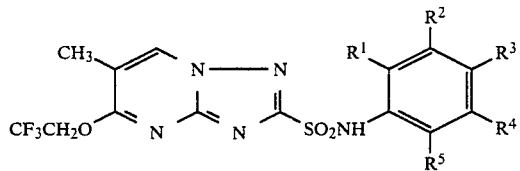

| Cmpd. | $R^1$ | $R^2$ | $R^3$ | $R^4$ | $R^5$ | Melting Point | Analysis | Elemental Analysis C | H | N |
|---|---|---|---|---|---|---|---|---|---|---|
| 236 | Cl | H | H | H | Cl | 250–253° C. (decomp.) | Calcd. for $C_{14}H_{10}Cl_2F_3N_5O_3S$: Found: | 36.85 36.44 | 2.19 2.07 | 15.35 15.62 |

TABLE XXXI

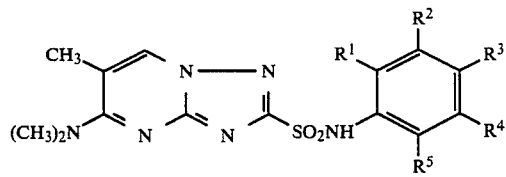

| Cmpd. | R¹ | R² | R³ | R⁴ | R⁵ | Melting Point | Analysis | | Elemental Analysis | |
|---|---|---|---|---|---|---|---|---|---|---|
| | | | | | | | | C | H | N |
| 237 | Cl | H | H | H | Cl | 270–274° C. (decomp.) | Calcd. for $C_{14}H_{14}Cl_2N_6O_2S$: Found: | 41.89 41.87 | 3.49 3.49 | 20.95 21.03 |

TABLE XXXII

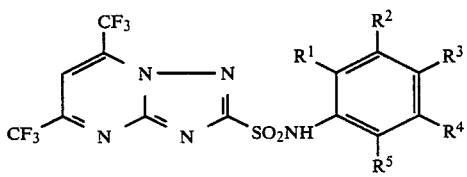

| Cmpd | R¹ | R² | R³ | R⁴ | R⁵ | Melting Point | Analysis | | Elemental Analysis | |
|---|---|---|---|---|---|---|---|---|---|---|
| | | | | | | | | C | H | N |
| 238 | Cl | H | H | H | Cl | 286–287° C. | Calcd. for $C_{13}H_5Cl_2F_6N_5O_2S$: Found: | 32.56 32.98 | 1.04 0.70 | 14.59 14.71 |

TABLE XXXIII

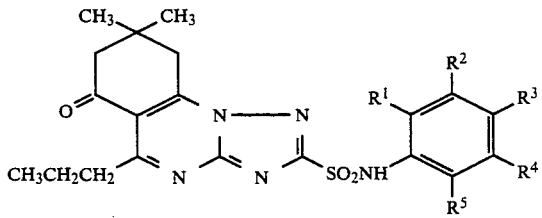

| Cmpd. | R¹ | R² | R³ | R⁴ | R⁵ | Melting Point | Analysis | | Elemental Analysis | |
|---|---|---|---|---|---|---|---|---|---|---|
| | | | | | | | | C | H | N |
| 239 | Cl | H | H | H | Cl | 284–286° C. | Calcd. for $C_{20}H_{21}Cl_2N_5O_3S$: Found: | 49.90 49.81 | 4.36 4.22 | 14.52 14.28 |

TABLE XXXIV

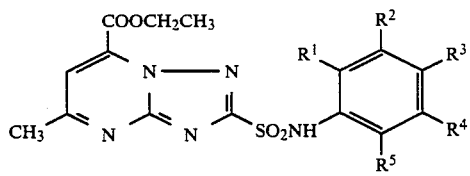

| Cmpd. | R¹ | R² | R³ | R⁴ | R⁵ | Melting Point | Analysis | | Elemental Analysis | |
|---|---|---|---|---|---|---|---|---|---|---|
| | | | | | | | | C | H | N |
| 240 | Cl | H | H | H | Cl | 236–239° C. (decomp.) | Calcd. for $C_{15}H_{13}Cl_2N_5O_4S$: Found: | 41.86 41.75 | 3.02 2.79 | 16.28 16.16 |

TABLE XXXV

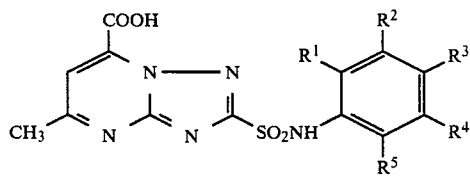

| Cmpd. | R¹ | R² | R³ | R⁴ | R⁵ | Melting Point | Analysis | Elemental Analysis C | H | N |
|---|---|---|---|---|---|---|---|---|---|---|
| 241 | Cl | H | H | H | Cl | 120–130° C. (decomp.) | Calcd. for $C_{13}H_9Cl_2N_5O_4S \cdot H_2O$: Found: | 37.15 37.03 | 2.38 2.02 | 16.70 17.16 |

TABLE XXXVI

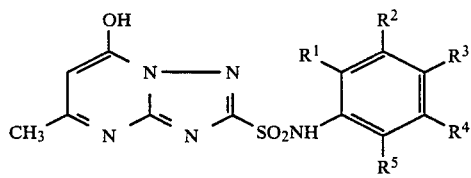

| Cmpd. | R¹ | R² | R³ | R⁴ | R⁵ | Melting Point | Analysis | Elemental Analysis C | H | N |
|---|---|---|---|---|---|---|---|---|---|---|
| 242 | Cl | H | H | H | Cl | 280–304° C. (decomp.) | Calcd. for $C_{12}H_9Cl_2N_5O_3S$: Found: | 38.51 38.52 | 2.41 2.49 | 18.72 19.03 |
| 309 | F | CH₃ | H | H | F | 304–305° C. | Calcd. for $C_{13}H_{11}F_2N_5O_3S$: Found: | 43.94 43.86 | 3.12 2.91 | 19.71 19.79 |
| 310 | CF₃ | H | H | H | H | 245–247° C. | Calcd. for $C_{13}H_{10}F_3N_5O_3S$: Found: | 40.37 40.41 | 3.00 2.76 | 8.29 7.93 |

TABLE XXXVII

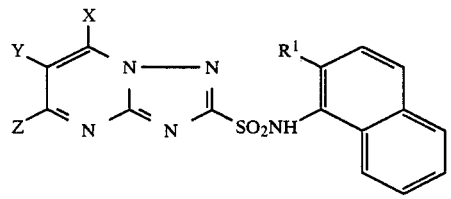

| Cmpd. | R¹ | X | Y | Z | Melting Point | Analysis | Elemental Analysis C | H | N |
|---|---|---|---|---|---|---|---|---|---|
| 243 | Cl | CH₃ | H | CH₃ | 303–306° C. (decomp.) | Calcd. for $C_{17}H_{14}ClN_5O_2S$: Found: | 52.65 52.10 | 3.64 3.65 | 18.05 18.51 |
| 244 | Cl | H | H | CH₃ | 262–265° C. (decomp.) | Calcd. for $C_{16}H_{12}ClN_5O_2S$: Found: | 51.41 50.97 | 3.24 3.29 | 18.73 18.99 |

TABLE XXXVIII

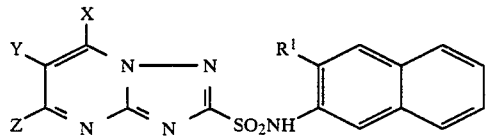

| Cmpd. | R¹ | X | Y | Z | Melting Point | Analysis | Elemental Analysis C | H | N |
|---|---|---|---|---|---|---|---|---|---|
| 245 | COOMe | CH₃ | H | CH₃ | 206–208° C. | Calcd. for $C_{19}H_{17}N_5O_4S \cdot \frac{1}{2}H_2O$: Found: | 54.28 53.98 | 4.32 4.12 | 16.65 16.83 |

TABLE XXXIX

| Cmpd. | Pyrazole | $R^2$ | $R^3$ | X | Y | Z | Melting Point | Analysis | C | H | N |
|---|---|---|---|---|---|---|---|---|---|---|---|
| 246 | A | $CF_3$ | $CH_3$ | H |  | $CH_3$ | 273–274° C. (decomp.) | Calcd. for $C_{12}H_{12}F_3N_7O_2S$: Found: | 38.39 38.73 | 3.22 3.23 | 26.12 25.92 |
| 247 | A | $CF_3$ | $CH_3$ | $CH_3$ |  | $CH_3$ | 288–288.5° C. (decomp.) | Calcd. for $C_{13}H_{14}F_3N_7O_2S$: Found: | 40.09 40.22 | 3.62 3.49 | 25.18 25.17 |
| 248 | A | COOMe | $CH_3$ | H |  | $CH_3$ | 174–175° C. | Calcd. for $C_{13}H_{15}N_7O_4S$: Found: | 42.73 42.39 | 4.14 4.21 | 26.84 26.91 |
| 249 | A | H | COOMe | $CH_3$ | $CH_3$ | $CH_3$ | 208–210° C. | Calcd. for $C_{14}H_{17}N_7O_4S$: Found: | 44.32 44.07 | 4.52 4.31 | 25.85 25.72 |
| 250 | A | H | $CH_3$ | COOMe | $CH_3$ | $CH_3$ | 228–230° C. | Calcd. for $C_{14}H_{17}N_7O_4S$: Found: | 44.32 44.06 | 4.52 4.82 | 25.85 25.97 |
| 311 | B | H | COOEt | $CH_3$ | H | $CH_3$ | 217–219° C. | Calcd. for $C_{14}H_{17}N_7O_4S$: Found: | 44.31 44.29 | 4.52 4.73 | 25.85 25.63 |
| 312 | B | $CH_3$ | Br | $CH_3$ | H | $CH_3$ | 188° C. (decomp.) | Calcd. for $C_{12}H_{14}BrN_7O_2S$: Found: | 36.01 36.07 | 3.53 3.74 | 24.50 24.27 |

TABLE XL

| Cmpd. | $R^1$ | $R^2$ | $R^3$ | $R^4$ | Melting Point | Elemental Analysis | | | |
|---|---|---|---|---|---|---|---|---|---|
| 251 | Cl | H | Cl | H | 159°–161° C. | Exact mass calcd. for $C_{12}H_{10}Cl_2N_6O_2S$: Found: Analysis | 371.9963 371.9973 C | H | N |
| 252 | Cl | H | H | H | >210° C. (decomp.) | Calcd. for $C_{12}H_{11}ClN_6O_2S$: Found: | 42.55 42.19 | 3.27 3.28 | 24.80 24.27 |

TABLE XLI

| Cmpd. | $R^1$ | $R^2$ | $R^3$ | $R^4$ | Melting Point | Analysis | C | H | N |
|---|---|---|---|---|---|---|---|---|---|
| 253 | H | H | H | H | >250° C. (decomp.) | Calcd. for $C_{12}H_{12}N_6O_2S \cdot H_2O$: Found: | 44.72 44.88 | 4.38 4.19 | 26.06 26.37 |
| 254 | H | Cl | H | H | >260° C. (decomp.) | Calcd. for $C_{12}H_{11}ClN_6O_2S$: Found: | 42.55 42.48 | 3.27 3.40 | 24.80 24.49 |

TABLE XLII

| Cmpd. | $R^1$ | $R^2$ | $R^3$ | $R^4$ | Melting Point | Elemental Analysis | |
|---|---|---|---|---|---|---|---|
| 255 | Cl | H | H | H | 207.5°–208.5° C. | Exact mass calcd. for $C_{12}H_{11}ClN_6O_2S$: Found: | 338.0352 338.0342 |

TABLE XLIII

[Structure: pyrimidine with CH₃ groups connected via N—N to triazole bearing SO₂NHAr]

| Cmpd. | Ar | Melting Point | Analysis | C | H | N |
|---|---|---|---|---|---|---|
| 256 | 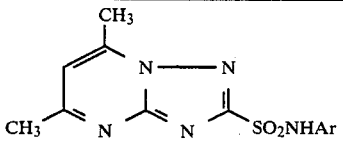 (thiazole) | 120–125° C. | Calcd. for C$_{10}$H$_{10}$N$_6$O$_2$S$_2$:<br>Found: | 38.66<br>38.48 | 3.22<br>3.28 | 27.06<br>26.92 |
| 257 | 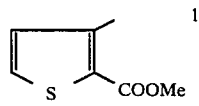 (3-methyl-2-COOMe-thiophene) | 160–168° C. | Calcd. for C$_{13}$H$_{13}$N$_5$O$_4$S$_2$:<br>Found: | 42.49<br>42.04 | 3.53<br>3.40 | 19.05<br>18.81 |
| 258 | 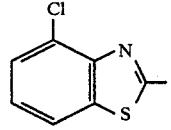 (4-chloro-benzothiazole) | 224–226° C.<br>(decomp.) | Calcd. for C$_{14}$H$_{11}$ClN$_6$O$_2$S$_2$:<br>Found: | 42.58<br>43.10 | 2.78<br>2.79 | 21.27<br>20.74 |
| 259 | 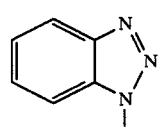 (1-methylbenzotriazole) | 195° C.<br>(decomp.) | Calcd. for C$_{13}$H$_{11}$N$_8$O$_2$S:<br>Found: | 47.41<br>47.01 | 3.37<br>3.31 | 29.78<br>30.78 |

TABLE XLIV

| Cmpd. | $R^1$ | $R^2$ | V | X | Z | Melting Point | Analysis | Elemental Analysis C | H | N | S | Cl |
|---|---|---|---|---|---|---|---|---|---|---|---|---|
| 260 | Cl | Cl | $CH_3$ | $CH_3$ | $CH_3$ | 220–222° C. | Calcd. for $C_{14}H_{13}Cl_2N_5O_2S$: Found: | 43.54 43.55 | 3.39 3.32 | 18.13 18.03 | | |
| 261 | COOMe | $CH_3$ | $CH_3$ | $CH_3$ | $CH_3$ | 175.5–177° C. | Calcd. for $C_{17}H_{19}N_5O_4S$: Found: | 52.43 52.31 | 4.92 4.93 | 17.98 17.94 | | |
| 262 | Cl | Cl | $COCH_3$ | $CH_3$ | $CH_3$ | 214–217° C. | Calcd. for $C_{15}H_{13}Cl_2N_5O_3S$: Found: | 43.49 43.44 | 3.16 3.16 | 16.90 16.77 | | |
| 263 | Cl | Cl | $CH_2CH=CH_2$ | $CH_3$ | $CH_3$ | 182–184° C. | Calcd. for $C_{16}H_{15}Cl_2N_5O_2S$: Found: | 46.61 46.74 | 3.67 3.67 | 16.98 16.86 | | |
| 264 | Cl | Cl | $CH_2COOEt$ | $CH_3$ | $CH_3$ | 173–176° C. | Calcd. for $C_{17}H_{17}Cl_2N_5O_4S$: Found: | 44.55 44.74 | 3.74 3.74 | 15.27 15.08 | | |
| 265 | Cl | Cl | $CH_2Ph$ | $CH_3$ | $CH_3$ | >240° C. (decomp.) | Calcd. for $C_{20}H_{17}Cl_2N_5O_2S.\frac{1}{2}H_2O$: Found: | 50.97 50.93 | 3.85 3.66 | 14.85 14.85 | | |
| 266 | COOMe | $CH_3$ | $CH_2COOEt$ | $CH_3$ | $CH_3$ | 152–155° C. | Calcd. for $C_{20}H_{23}N_5O_6S$: Found: | 52.05 51.64 | 5.02 4.94 | 15.17 15.39 | | |
| 267 | COOMe | $CH_3$ | $CH_2Ph$ | $CH_3$ | $CH_3$ | 174–176° C. | Calcd. for $C_{23}H_{23}N_5O_4S$: Found: | 59.34 59.00 | 4.98 4.89 | 15.04 15.18 | | |
| 268 | Cl | Cl | $COCH_3$ | H | $CH_3$ | 176–181° C. | Calcd. for $C_{14}H_{11}Cl_2N_5O_3S$: Found: | 42.02 42.28 | 2.77 2.90 | 17.49 17.16 | | |
| 269 | Cl | Cl | $COiPr$ | H | $CH_3$ | 193–194.5° C. | Calcd. for $C_{16}H_{15}Cl_2N_5O_3S$: Found: | 44.87 45.26 | 3.53 3.53 | 16.35 16.39 | | |
| 270 | Cl | Cl | $COC_{11}H_{23}$ | H | $CH_3$ | 105.5–106.5° C. | Calcd. for $C_{24}H_{31}Cl_2N_5O_3S$: Found: | 53.33 53.40 | 5.78 5.77 | 12.96 12.84 | | |
| 271 | Cl | Cl | (2,4-dichlorobenzoyl) | H | $CH_3$ | 234–235° C. | Calcd. for $C_{19}H_{11}Cl_4N_5O_3S$: Found: | 42.96 43.31 | 2.09 2.29 | 13.18 13.04 | | |
| 272 | Cl | Cl | $CO_2Et$ | H | $CH_3$ | 189–191° C. | Calcd. for $C_{15}H_{15}Cl_2N_5O_4S$: Found: | 41.87 42.51 | 3.05 3.25 | 16.28 16.02 | | |
| 273 | Cl | Cl | $CON(CH_3)_2$ | H | $CH_3$ | 225–228° C. (decomp.) | Calcd. for $C_{15}H_{14}Cl_2N_6O_3S$: Found: | 41.97 42.08 | 3.29 3.27 | 19.58 20.18 | | |
| 274 | Cl | Cl | $COPh$ | H | $CH_3$ | 187–189° C. | Calcd. for $C_{19}H_{13}Cl_2N_5O_3S$: Found: | 49.36 48.97 | 2.83 2.84 | 15.15 15.16 | | |
| 275 | F | F | $COCH_3$ | H | $CH_3$ | 195–200° C. | Calcd. for $C_{14}H_{11}F_2N_5O_3S$: Found: | 45.77 45.59 | 3.02 3.12 | 19.07 19.16 | 8.73 8.91 | |
| 276 | F | F | $COEt$ | H | $CH_3$ | 154–160° C. | Calcd. for $C_{15}H_{13}F_2N_5O_3S$: Found: | 47.24 47.05 | 3.44 3.44 | 18.37 18.49 | 8.41 8.27 | |
| 277 | F | F | $COiPr$ | H | $CH_3$ | 182–184° C. | Calcd. for $C_{16}H_{15}F_2N_5O_3S$: Found: | 48.60 | 3.82 | 17.71 | | |

TABLE XLIV-continued

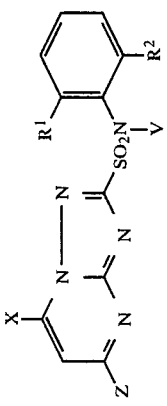

| Cmpd. | R¹ | R² | V | X | Z | Melting Point | Analysis | C | H | N | S | Cl |
|---|---|---|---|---|---|---|---|---|---|---|---|---|
| 278 | F | F | COCH₂tBu | H | CH₃ | 158–162° C. | Found:<br>Calcd. for $C_{18}H_{19}F_2N_5O_3S$: | 48.41<br>51.05 | 3.93<br>4.52 | 17.43<br>16.54 | 7.57<br>7.83 | |
| 279 | F | F | COnBu | H | CH₃ | 131–134° C. | Found:<br>Calcd. for $C_{17}H_{17}F_2N_5O_3S$: | 51.15<br>49.87 | 4.62<br>4.19 | 16.38<br>17.11 | | |
| 280 | F | F | COtBu | H | CH₃ | 185–186° C.<br>(decomp.) | Found:<br>Calcd. for $C_{17}H_{17}F_2N_5O_3S$: | 49.10<br>49.87 | 4.04<br>4.19 | 17.05<br>17.11 | 7.83<br>7.10 | |
| 281 | F | F | COCH₂Ph | H | CH₃ | 178–185° C. | Found:<br>Calcd. for $C_{20}H_{15}F_2H_5O_3S$: | 49.93<br>54.17 | 3.89<br>3.41 | 16.82<br>15.80 | | |
| 282 | F | F | COCH₂CH₂Cl | H | CH₃ | 195° C.<br>(decomp.) | Found:<br>Calcd. for $C_{15}H_{12}ClF_2N_5O_3S$: | 53.60<br>43.33 | 3.18<br>2.91 | 15.56<br>16.84 | 7.71<br>7.47 | 8.53<br>8.45 |
| 283 | F | F | COnPr | H | CH₃ | 130–135° C. | Found:<br>Calcd. for $C_{16}H_{15}F_2N_5O_3S$: | 43.21<br>48.60 | 2.95<br>3.82 | 17.31<br>17.71 | 8.11<br>7.98 | |
| 284 | F | F | COCH₂iPr | H | CH₃ | 154–159° C. | Found:<br>Calcd. for $C_{17}H_{17}F_2N_5O_3S$: | 48.42<br>49.87 | 3.81<br>4.19 | 17.91<br>17.11 | 7.83<br>7.68 | |
| 285 | F | F | COCH₂Cl | H | CH₃ | 156–158° C. | Found:<br>Calcd. for $C_{14}H_{10}ClF_2N_5O_3S$: | 49.45<br>41.85 | 4.04<br>2.51 | 17.15<br>17.43 | | |
| 286 | F | F | COCHCH₃=CH₂ | H | CH₃ | 171.5–174° C. | Found<br>Calcd. for $C_{16}H_{13}F_2O_3S$: | 42.19<br>48.85 | 2.68<br>3.33 | 17.43<br>17.81 | 8.15<br>7.94 | |
| 287 | F | F | COnC₉H₁₉ | H | CH₃ | 97–99° C. | Calcd. for $C_{22}H_{27}F_2N_5O_3S$:<br>Found | 48.36<br>55.10 | 3.51<br>5.68 | 17.91<br>14.61 | 6.69<br>6.63 | |
| 288 | F | F | COCH=CHCH₃ | H | CH₃ | 154–156° C. | Calcd. for $C_{16}H_{13}F_2N_5O_3S$:<br>Found: | 55.22<br>48.85 | 5.60<br>3.33 | 14.85<br>17.81 | | 8.15<br>8.49 |
| 289 | F | F | COcycloC₃H₅ | H | CH₃ | 200.5–203° C. | Calcd. for $C_{16}H_{13}F_2N_5O_3S$:<br>Found: | 48.41<br>48.32 | 3.41<br>3.34 | 17.94<br>18.03 | 8.15<br>8.34 | |
| 290 | F | F | COPh | H | CH₃ | 186–189° C. | Calcd. for $C_{19}H_{13}F_2N_5O_3S$:<br>Found: | 53.14<br>53.74 | 3.05<br>3.16 | 16.31<br>16.63 | 7.47<br>7.11 | |
| 291 | F | F | COcycloC₆H₁₁ | H | CH₃ | 178–180° C. | Calcd. for $C_{19}H_{19}F_2N_5O_3S$:<br>Found: | 52.40<br>51.40 | 4.40<br>4.28 | 16.08<br>16.08 | 7.36<br>7.78 | |
| 292 | F | F | COCH₂OPh | H | CH₃ | 141–144° C. | Calcd. for $C_{20}H_{15}F_2N_5O_4S$:<br>Found: | 52.28<br>51.77 | 3.29<br>3.38 | 15.25<br>15.28 | 6.98<br>6.76 | |
| 293 | F | F | COCH=CHPh | H | CH₃ | oil | Calcd. for $C_{21}H_{15}F_2N_5O_3S$:<br>Found: | 55.38<br>55.55 | 3.32<br>3.45 | 15.38<br>15.29 | 7.04<br>6.98 | |
| 294 | F | F | COCH₂CH₂—<br>—CO₂CH₂CH₃ | H | CH₃ | 157–162° C. | Calcd. for $C_{18}H_{17}F_2N_5O_5S$:<br>Found: | 47.68<br>47.32 | 3.78<br>3.78 | 15.45<br>15.68 | 7.07<br>7.03 | |
| 295 | F | F | CO(2-furyl) | H | CH₃ | 120° C.<br>(decomp.) | Calcd. for $C_{17}H_{11}F_2N_5O_4S$:<br>Found: | 48.69<br>48.49 | 2.64<br>2.75 | 16.70<br>17.03 | 7.65<br>7.83 | |
| 296 | F | F | COcycloC₄H₇ | H | CH₃ | 161–170° C. | Calcd. for $C_{17}H_{15}F_2N_5O_3S$:<br>Found: | 50.12<br>49.58 | 3.71<br>3.89 | 17.19<br>17.21 | 7.87<br>8.07 | |
| 297 | F | F | SO₂CH₃ | H | CH₃ | 193–195° C. | Calcd. for $C_{13}H_{11}F_2N_5O_4S_2$:<br>Found: | 38.71<br>38.98 | 2.75<br>2.92 | 17.36<br>17.18 | 15.90<br>15.72 | |
| 298 | F | F | SO₂Ph | H | CH₃ | 182–190° C. | Calcd. for $C_{18}H_{13}F_2N_5O_4S_2$: | 46.45 | 2.82 | 15.05 | 13.78 | |

TABLE XLIV-continued

| Cmpd. | R¹ | R² | V | X | Z | Melting Point | Analysis | Elemental Analysis C | H | N | S | Cl |
|---|---|---|---|---|---|---|---|---|---|---|---|---|
| 299 | F | F | CH₂Ph | H | CH₃ | 170–177° C. | Found: Calcd. for $C_9H_{15}F_2N_5O_2S$: | 46.41 54.93 | 3.03 3.64 | 14.79 16.86 | 14.01 7.72 | |
| 300 | F | F | C=O(SEt) | H | CH₃ | 197–199° C. | Found: Calcd. for $C_{15}H_{13}F_2N_5O_3S_2$: | 54.45 43.58 | 3.73 3.17 | 16.63 16.94 | 7.77 15.51 | |
| 301 | F | F | CH₂(4-NO₂Ph) | H | CH₃ | 194–200° C. | Found: Calcd. for $C_{19}H_{14}F_2N_6O_4S$: | 43.45 49.64 | 3.19 3.07 | 17.12 18.26 | 15.64 6.96 | |
| 302 | F | F | CH₂(4-MeOPh) | H | CH₃ | 156–158° C. | Found: Calcd. for $C_{20}H_{17}F_2N_5O_3S$: | 49.64 53.92 | 3.25 3.85 | 18.40 15.72 | 6.88 7.20 | |
| 303 | F | F | CH₂(2-furyl) | H | CH₃ | 177–180° C. | Found: Calcd. for $C_{17}H_{13}F_2N_5O_3S$: | 53.65 50.37 | 3.98 3.23 | 15.95 17.28 | 7.46 7.91 | |
| 313 | F | F | CH₂SCH₃ | H | CH₃ | 195–200° C. | Found: Calcd. for $C_{14}H_{13}F_2N_5O_2S_2$: | 50.50 43.63 | 3.30 3.40 | 17.33 18.16 | 7.74 | |
| 314 | F | F | CH₂CH—CH₂ (epoxide) | H | CH₃ | 132–135° C. | Found: Calcd. for $C_{15}H_{13}F_2N_5O_3S$: | 44.04 47.24 47.15 | 3.53 3.44 3.58 | 18.37 18.36 18.11 | | |
| 315 | F | F | CH₂OCH₂CH₂OCH₃ | H | CH₃ | 127–131° C. | Found: Calcd. for $C_{16}H_{17}F_2N_5O_4S$: | 46.49 46.40 | 4.15 4.17 | 16.93 17.11 | | |
| 316 | F | F | (CH₂)₄COOCH₂CH₃ | H | CH₃ | 96–100° C. | Found: Calcd. for $C_{19}H_{21}F_2N_5O_4S$: | 50.33 49.70 | 4.67 4.61 | 15.44 15.57 | | |

TABLE XLV

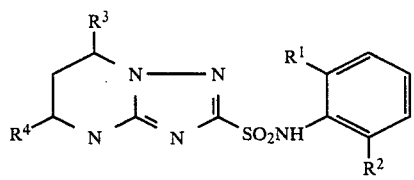

| Cmpd. | R¹ | R² | R³ | R⁴ | Melting Point | Elemental Analysis | | | |
|---|---|---|---|---|---|---|---|---|---|
| 304 | Cl | Cl | Me | Me | 198–205° C. | Analysis | C | H | N |
| | | | | | | Calcd. for $C_{13}H_{15}Cl_2N_5O_2S$: | 41.49 | 3.98 | 18.50 |
| | | | | | | Found: | 41.27 | 3.81 | 18.28 |
| 305 | CF₃ | H | Me | Me | 74.5–84° C. | Exact mass calcd. for $C_{14}H_{16}F_3N_5O_2S$: | | | 375.0979 |
| | | | | | | Found: | | | 375.0978 |
| 306 | Cl | Cl | H | Me | 230–235° C. | Analysis | C | H | N |
| | | | | | | Calcd. for $C_{12}H_{13}Cl_2N_5O_2S$: | 39.89 | 3.32 | 19.39 |
| | | | | | | Found: | 39.72 | 3.42 | 19.90 |

TABLE XLVI

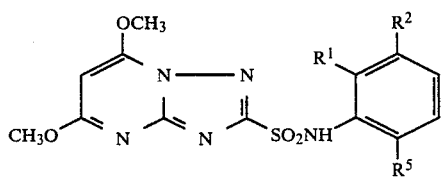

| Cmpd. | R¹ | R² | R⁵ | Melting Point | Analysis | Elemental Analysis | | |
|---|---|---|---|---|---|---|---|---|
| | | | | | | C | H | N |
| 317 | Cl | H | Cl | 232–234° C. (decomp.) | Calcd. for $C_{13}H_{11}Cl_2N_5O_4S$: Found: | 38.62 38.39 | 2.74 2.83 | 17.30 16.70 |
| 318 | CF₃ | H | OCH₃ | 205–210° C. (decomp.) | Calcd. for $C_{15}H_{14}F_3N_5O_5S$: Found: | 41.57 41.19 | 3.26 3.27 | 16.16 15.98 |
| 319 | Cl | CH₃ | Cl | 206–208° C. (decomp.) | Calcd. for $C_{14}H_{13}Cl_2N_5O_4S$: Found: | 40.20 39.89 | 3.13 3.09 | 16.75 16.58 |
| 320 | F | H | Cl | 229–230° C. (decomp.) | Calcd. for $C_{13}H_{11}ClFN_5O_4S$: Found: | 40.26 39.87 | 2.86 2.86 | 18.06 17.83 |
| 321 | Br | H | Cl | 231–233° C. (decomp.) | Calcd. for $C_{13}H_{11}BrClN_5O_4S$: Found: | 34.80 34.41 | 2.47 2.02 | 15.61 15.48 |
| 322 | Cl | H | CH₃ | 204–206° C. (decomp.) | Calcd. for $C_{14}H_{14}ClN_5O_4S$: Found: | 43.81 43.62 | 3.68 3.63 | 18.25 18.38 |

TABLE XLVII

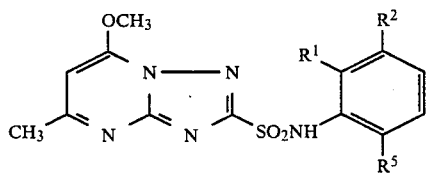

| Cmpd. | R¹ | R² | R⁵ | Melting Point | Analysis | Elemental Analysis | | | |
|---|---|---|---|---|---|---|---|---|---|
| | | | | | | C | H | N | S |
| 323 | Cl | H | Cl | 214–215° C. (decomp.) | Calcd. for $C_{13}H_{11}Cl_2N_5O_3S$: Found: | 40.21 39.84 | 2.84 3.08 | 18.04 17.99 | |
| 324 | CF₃ | H | OCH₃ | 205–210° C. (decomp.) | Calcd. for $C_{15}H_{14}F_3N_5O_4S$: Found: | 43.16 42.92 | 3.38 3.44 | 16.78 16.88 | |
| 325 | Cl | CH₃ | Cl | 239–242° C. (decomp.) | Calcd. for $C_{14}H_{13}Cl_2N_5O_3S$: Found: | 41.80 41.35 | 3.26 3.19 | 17.41 17.42 | 7.97 8.15 |
| 326 | Cl | H | F | 246–247° C. (decomp.) | Calcd. for $C_{13}H_{11}ClFN_5O_3S$: Found: | 42.00 41.67 | 2.98 3.10 | 18.84 18.57 | |
| 327 | CF₃ | H | H | 181–183° C. (decomp.) | Calcd. for $C_{14}H_{12}F_3N_5O_3S$: Found: | 43.41 43.20 | 3.12 3.13 | 18.08 17.88 | 8.28 8.18 |
| 328 | F | H | F | 226–235° C. (decomp.) | Calcd. for $C_{13}H_{11}F_2N_5O_3S$: Found: | 43.94 43.50 | 3.12 3.09 | 19.71 19.32 | 9.02 8.81 |

TABLE XLVIII

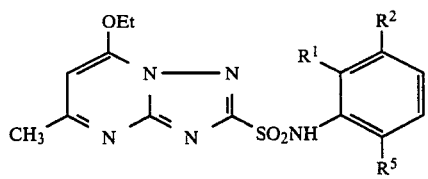

| Cmpd. | $R^1$ | $R^2$ | $R^5$ | Melting Point | Analysis | C | H | N | S |
|---|---|---|---|---|---|---|---|---|---|
| 329 | Cl | H | Cl | 222–225° C. | Calcd. for $C_{14}H_{13}Cl_2N_5O_3S$: | 41.80 | 3.26 | 17.41 | 7.97 |
|  |  |  |  |  | Found: | 41.56 | 3.37 | 17.24 | 7.76 |
| 330 | $CF_3$ | H | $OCH_3$ | 210–213° C. | Calcd. for $C_{16}H_{16}F_3N_5O_4S$: | 44.54 | 3.74 | 16.24 | 7.43 |
|  |  |  |  |  | Found: | 43.89 | 3.68 | 16.00 | 7.70 |
| 331 | Cl | $CH_3$ | Cl | 228–229° C. | Calcd. for $C_{15}H_{15}Cl_2N_5O_3S$: | 43.28 | 3.63 | 16.83 | 7.70 |
|  |  |  |  |  | Found: | 42.87 | 3.66 | 16.92 | 7.66 |
| 332 | Cl | H | F | 211–212° C. | Calcd. for $C_{14}H_{13}ClFN_5O_3S$: | 43.58 | 3.40 | 18.15 |  |
|  |  |  |  |  | Found: | 43.36 | 3.41 | 18.01 |  |
| 333 | $CF_3$ | H | H | 187–188° C. | Calcd. for $C_{15}H_{14}F_3N_5O_3$: | 44.88 | 3.52 | 17.45 | 7.99 |
|  |  |  |  |  | Found: | 44.67 | 3.49 | 17.48 | 8.10 |
| 334 | F | H | H | 208.5–210.5° C. | Calcd. for $C_{14}H_{13}F_2N_5O_3S$: | 45.52 | 3.55 | 18.96 | 8.68 |
|  |  |  |  |  | Found: | 45.28 | 3.56 | 19.31 | 8.60 |
| 335 | F | $CH_3$ | F | 192–195° C. | Calcd. for $C_{15}H_{15}F_2N_5O_3S$: | 46.99 | 3.94 | 18.27 | 8.36 |
|  |  |  |  |  | Found: | 46.76 | 3.96 | 18.10 | 8.19 |

TABLE XLIX

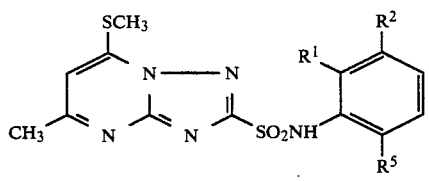

| Cmpd. | $R^1$ | $R^2$ | $R^5$ | Melting Point | Analysis | C | H | N | S |
|---|---|---|---|---|---|---|---|---|---|
| 336 | Cl | H | Cl | 300–304° C. (decomp.) | Calcd. for $C_{13}H_{11}Cl_2N_5O_2S_2$: | 38.61 | 2.72 | 17.32 |  |
|  |  |  |  |  | Found: | 38.99 | 2.93 | 17.34 |  |
| 337 | $CF_3$ | H | $OCH_3$ | 245–249° C. (decomp.) | Calcd. for $C_{15}H_{14}F_3O_3S_2$: | 41.56 | 3.26 | 16.16 |  |
|  |  |  |  |  | Found: | 41.42 | 3.25 | 16.30 |  |
| 338 | $CF_3$ | H | H | 193–200° C. | Calc. for $C_{14}H_{12}F_3N_5O_2S_2$: | 41.68 | 3.00 | 17.36 | 15.90 |
|  |  |  |  |  | Found: | 41.39 | 2.95 | 17.21 | 15.65 |
| 339 | $NO_2$ | H | $CH_3$ | 266–267° C. | Calcd. for $C_{14}H_{14}N_6O_4S_2$: | 42.63 | 3.58 | 21.31 | 16.26 |
|  |  |  |  |  | Found: | 42.32 | 3.64 | 21.46 | 15.98 |

TABLE L

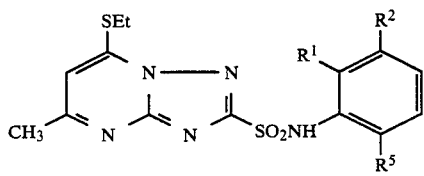

| Cmpd. | $R^1$ | $R^2$ | $R^5$ | Melting Point | Analysis | C | H | N | S |
|---|---|---|---|---|---|---|---|---|---|
| 340 | $CF_3$ | H | $OCH_3$ | 228–235° C. | Calcd. for $C_{16}H_{16}F_3N_5O_3S_2$: | 42.95 | 3.60 | 15.65 |  |
|  |  |  |  |  | Found: | 42.55 | 3.53 | 15.53 |  |
| 341 | $CF_3$ | H | H | 202–202.5° C. | Calcd. for $C_{15}H_{14}F_3N_5O_2S_2$: | 43.16 | 3.38 | 16.78 | 15.36 |
|  |  |  |  |  | Found: | 43.09 | 3.42 | 16.69 | 15.41 |
| 342 | Cl | H | $CH_3$ | 231–233° C. | Calcd. for $C_{15}H_{16}ClN_5O_2S_2$: | 45.16 | 4.04 | 17.56 | 16.07 |
|  |  |  |  |  | Found: | 45.31 | 4.10 | 17.44 | 16.17 |
| 343 | F | $CH_3$ | F | 233–235° C. | Calcd. for $C_{15}H_{15}F_2N_5O_2S_2$: | 45.16 | 3.78 | 17.52 | 16.03 |
|  |  |  |  |  | Found: | 44.77 | 3.89 | 17.14 | 16.42 |

TABLE LI

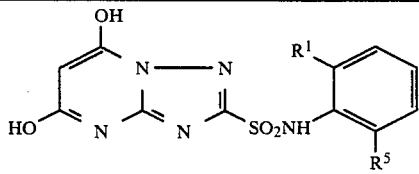

| Cmpd. | $R^1$ | $R^5$ | Melting Point | Analysis | C | H | N | Cl | S |
|---|---|---|---|---|---|---|---|---|---|
| 344 | Cl | Cl | 306–308° C. (decomp.) | Calcd. for $C_{11}H_7ClN_5O_4S.H_2O$: Found: | 39.90 40.36 | 3.35 3.32 | 16.60 16.08 | | |
| 345 | F | Cl | 240–242° C. (decomp.) | Calcd. for $C_{11}H_7ClFN_5O_4S.H_2O$: Found: | 34.98 33.87 | 2.40 2.36 | 18.54 18.01 | | |
| 346 | Br | Cl | 200–203° C. (decomp.) | Calcd. for $C_{11}H_7ClBrN_5O_4S.H_2O$: Found: | 30.12 28.65 | 2.07 2.09 | 15.97 16.21 | | |
| 347 | Cl | $CH_3$ | >250° C. (decomp.) | Calcd. for $C_{12}H_{10}ClN_5O_4S.H_2O$: Found: | 38.56 38.13 | 3.24 2.97 | 18.74 18.32 | 9.29 9.58 | 8.58 8.54 |

TABLE LII

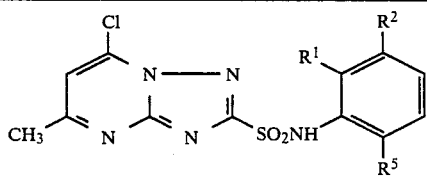

| Cmpd. | $R^1$ | $R^2$ | $R^5$ | Melting Point | Analysis | C | H | N | S |
|---|---|---|---|---|---|---|---|---|---|
| 348 | Cl | H | Cl | 217–221° C. | Calcd. for $C_{12}H_8Cl_3N_5O_2S$: Found: | 36.70 36.69 | 2.04 2.13 | 17.84 17.93 | |
| 349 | $CF_3$ | H | $OCH_2CH_3$ | 212° C. (decomp.) | Calcd. for $C_{15}H_{13}ClF_3N_5O_3S$: Found: | 41.34 41.14 | 3.01 3.21 | 16.07 16.41 | |
| 350 | F | $CH_3$ | F | 185–187° C. (decomp.) | Calcd. for $C_{13}H_{10}ClF_2N_5O_2S.H_2O$: Found: | 39.85 39.98 | 3.09 2.87 | 17.88 17.52 | 8.18 8.02 |

TABLE LIII

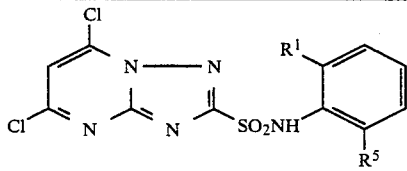

| Cmpd. | $R^1$ | $R^5$ | Melting Point | Analysis | C | H | N |
|---|---|---|---|---|---|---|---|
| 351 | Cl | Cl | 184–210° C. (decomp.) | Calcd. for $C_{11}H_5Cl_4N_5O_2S$: Found: | 31.98 31.54 | 1.22 1.70 | 16.96 17.41 |
| 352 | Cl | $CH_3$ | 222–224° C. | Calcd. for $C_{12}H_8Cl_3N_5O_2S$: Found: | 36.71 37.05 | 2.05 2.04 | 17.84 17.73 |

The compounds of the present invention are highly effective herbicides when applied to the locus of vegetation, herein defined as encompassing pre-emergent (soil) applications as well as post-emergent (foliar) applications. They have utility for broad spectrum pre- and/or post-emergence weed control in areas where complete vegetation control is desired. Certain of these compounds are effective for the control of nutsedge (cyperus spp.). The subject compounds are also useful for selective pre- and/or postemergence weed control in crops such as wheat corn, soybeans, rice, and cotton. While none of the compounds are selective for use in all crops, by all methods of application, and at all rates of application, each is active as a herbicide and most are selective for use in one or more crops at some application rates and by some methods of application. The data provided herein in the examples can be used as a guide in choosing appropriately selective compounds from the compounds of Formulae I and II, appropriate application methods, and appropriate application rates for controlling unwanted vegetation in various crops. It is well within the skill of those in the art to select appropriate compounds of Formulae I and II not mentioned in the examples using the information herein and routine procedures.

Certain of the compounds of Formula I, notably those wherein X and Z represent $C_1$–$C_4$ alkyl, are resistant to degradation in the environment and, therefore, have limited utility as selective herbicides in crops where crop rotation programs are practiced except where the soil and climate are especially favorable for degradation. These compounds, on the other hand, are particularly useful as industrial herbicides where multi-year control is desired.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylalyl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat ® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic ® 61 (molecular weight about 1000), polyethylene glycol ester of tall oil acids, sodium octophenoxyethoxyethyl sulfate, tris(polyoxyethylene)sorbitan monostearate (Tween ® 60), and sodium dihexylsulfosuccinate.

The herbicidally effective concentration of the active ingredients in solid or liquid compositions generally is from about 0.00003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including, for example, the substituted urea herbicides such as 3-(3,4-dichlorophenyl)-1,1-dimethylurea, 3-(3,4-dichlorophenyl)-1-methoxy-1-methylurea (Lorox ®)) and 1,1-dimethyl-3-($\alpha,\alpha,\alpha$-trifluoro-m-tolyl)urea (Cotoran ®); the triazines such as 2-chloro-4-(ethylamino)-6-(isopropylamino)-s-triazine and 2-chloro-4-(1-cyano-1-methylethylamino)-6-ethylamino-s-triazine (Bladex ®); the uracils such as 5-bromo-3-sec-butyl-6-methyluracil; N-(phosphonomethyl)glycine; the phenoxies such as 2,4-dichlorophenoxyacetic acid; picolinic acids such as 4-amino-3,5,6-trichloropicolinic acid (Tordon ®) and 3,6-dichloropicolinic acid (Lontrel ®); 4-chloro-2-butynyl-3-chlorophenyl carbamate (Carbyne ®); diisopropylthiocarbamic acid, ester with 2,3-dichloroallyl alcohol (Avadex ®); diisopropylthiocarbamic acid, ester with 2,3,3-trichloroallyl alcohol (Avadex ® BVD); ethyl-N-benzoyl-N-(3,4-dichlorophenyl)-2-aminopropionate (Suffix ®); 1,2-dimethyl-3,5-diphenyl-pyrazolium methylsulfate (Avenge ®); methyl (2-[4-

(2,4-dichlorophenoxy)phenoxy]propanoate) (Hoelon®); butyl 2-[4-[(5-(trifluoromethyl)-2-pyridinyl)oxy]phenoxy]propanoate (Fusilade®); esters of 2-[4-[(3-chloro-5-trifluoromethyl)-2-pyridinyl)oxy]phenoxy]propionic acid; 4-amino-6-tertbutyl-3-(methylthio)-1,2,4-triazin-5-(4H)-one (Lexone®); 3-isopropyl-1H-2,1,3-benzothiadiazin-(4)-3H-one 2,2-dioxide; $\alpha,\alpha,\alpha$-trifluoro-2,6-dinitro-N,N-dipropyl-p-toluidine; 1,1'-dimethyl-4,4'-bipyridinium ion; 2-chloro-2',6'-diethyl(-methoxymethyl)acetanilide; and 2-[1-(ethoxyimino)-butyl]-5-[(2-ethylthio)propyl]-3-hydroxy-2-cyclohexen-1-one (Poast®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.01 to about 10 pounds/acre. In pre- and postemergence operations for selective uses, a dosage of about 0.01 to about 10 pounds/acre is generally applicable, a rate of 0.01 to 4 pounds/acre being preferred.

The following example illustrates the effect of the compounds of this invention applied postemergently.

Plant species in this and other tests were the following:

|   | Common Name | Scientific Name |
|---|---|---|
| A. | cotton | Gossypium spp. |
| B. | rape | Brassica napus |
| C. | soybean | Glycine max. |
| D. | sugar beet | Beta saccharifera |
| E. | cocklebur | Xanthium spp. |

-continued

|   | Common Name | Scientific Name |
|---|---|---|
| F. | jimsonweed | Datura stramonium |
| G. | annual morning glory | Ipomoea spp. |
| H. | pigweed | Amaranthus spp. |
| I. | velvetleaf | Abutilon theophrasti |
| J. | corn | Zea mays |
| K. | rice | Oryza sativa |
| L. | sorghum | Sorghum vulgare |
| M. | wheat | Triticum aestivum |
| N. | barnyardgrass (watergrass) | Echinochloa crusgalli |
| O. | crabgrass | Digitaria spp. |
| P. | yellow foxtail | Setaria lutescens |
| Q. | johnson grass | Sorghum halepense |
| R. | wild oats | Avena fatua |
| S. | sprangletop | Leptochloa filiformis |
| T. | yellow nutsedge | Cyperus esculentus |

EXAMPLE 118

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–4 leaf stage in soil of gold nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species test compound and dosage and the percent postemergent control obtained at one or more dosages tested are set forth in the table below. Control refers to the reduction in growth compared to the observed results of the same untreated species.

POSTEMERGENT CONTROL OF PLANT SPECIES

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 1 | 15.6 | 90 | 100 | 95 | — | 95 | 60 | 85 | 98 | 100 | 100 | 98 | 100 | 100 | 95 | — | 95 | 98 | 90 | 70 |
| 2 | 1000 | 10 | 50 | 40 | 90 | 80 | 90 | 10 | 0 | 50 | 0 | 20 | 0 | 0 | 0 | 0 | 0 | 90 | 0 | 0 |
| 4 | 500 | 10 | 40 | 40 | 70 | 40 | 60 | 0 | 0 | 60 | 0 | 40 | 40 | 0 | 0 | 20 | 0 | 80 | 0 | 0 |
| 6 | 500 | 60 | 80 | 70 | 90 | 90 | 30 | 80 | 30 | 90 | 0 | 20 | 80 | 0 | 35 | 20 | 25 | 80 | 0 | 90 |
| 7 | 500 | — | 90 | 55 | 100 | 100 | 20 | 90 | 60 | 65 | 0 | 15 | 65 | 0 | 35 | 10 | 25 | 50 | 0 | 65 |
| 8 | 500 | — | 90 | 75 | 60 | 90 | 90 | 70 | 50 | 75 | 0 | 40 | 70 | 10 | 0 | 0 | 10 | 90 | 0 | 60 |
|  | 62.5 | — | 60 | 40 | 80 | 70 | 15 | 35 | 40 | 20 | 20 | 30 | 20 | 0 | 5 | 40 | 0 | 20 | 0 | 0 |
| 9 | 1000 | 50 | 60 | 65 | 75 | 90 | 90 | 20 | 80 | 40 | 0 | 0 | 90 | 0 | 20 | 0 | 0 | 30 | 0 | 40 |
| 10 | 2000 | 15 | 30 | 50 | 60 | 15 | 0 | 0 | 100 | 15 | 10 | — | 10 | 0 | 0 | 25 | 0 | 0 | 0 | 60 |
| 12 | 500 | 0 | 10 | 20 | 60 | 100 | 0 | 0 | 20 | 0 | 0 | 25 | 75 | 0 | 80 | 0 | 20 | 55 | 0 | 0 |
|  | 125 | — | 100 | 80 | 95 | 100 | 70 | 100 | 100 | 95 | 10 | 10 | 60 | 0 | 10 | 0 | 0 | 25 | 0 | 90 |
|  | 15.6 | — | 95 | 60 | 95 | 90 | 20 | 60 | 90 | 75 | 0 | 0 | 90 | 0 | 90 | 20 | 0 | 90 | 0 | 40 |
| 13 | 250 | 95 | 100 | 95 | 100 | 100 | 90 | 90 | 100 | 95 | 15 | 15 | 80 | 0 | 100 | 0 | 70 | 85 | 0 | 90 |
|  | 62.5 | 95 | 100 | 95 | 95 | 100 | 50 | 90 | 100 | 80 | 0 | 0 | 80 | 0 | 0 | 20 | 50 | 70 | 0 | 75 |
|  | 15.6 | 60 | 90 | 85 | 90 | 100 | 30 | 85 | 70 | 70 | 0 | 0 | 80 | 0 | 0 | 75 | 0 | 0 | 0 | 0 |
| 14 | 1000 | 20 | — | 25 | 40 | 80 | 0 | 10 | 60 | 0 | 15 | 0 | 40 | 0 | 0 | 0 | 0 | 0 | 0 | 10 |
| 15 | 1000 | — | 70 | 25 | 15 | 80 | 0 | 70 | 40 | 60 | 0 | 30 | 50 | 10 | 0 | 15 | 10 | 85 | 0 | 0 |
| 17 | 1000 | 20 | 95 | 15 | 10 | 10 | 0 | 0 | 60 | 85 | 0 | 35 | 30 | 0 | 0 | 0 | 20 | 60 | 0 | 0 |
|  | 500 | 15 | 70 | 15 | 10 | 10 | 0 | 0 | 50 | 70 | 30 | 0 | 40 | 30 | 20 | 20 | 0 | 20 | 0 | 85 |
| 19 | 1000 | 90 | 90 | 90 | 100 | 90 | 95 | 40 | 100 | 80 | 0 | 20 | 50 | 0 | 0 | 0 | 10 | 65 | 0 | 85 |
| 21 | 1000 | 100 | 100 | 70 | 100 | 95 | 0 | 45 | 80 | 30 | 25 | 50 | 30 | 0 | 20 | 20 | 20 | 20 | 20 | 80 |
| 22 | 250 | 95 | 100 | 95 | 100 | 100 | 100 | 100 | 100 | 95 | 15 | 20 | 90 | 0 | 100 | 90 | 100 | 100 | 0 | 40 |
|  | 62.5 | 85 | 95 | 90 | 100 | 90 | 80 | 80 | 95 | 95 | 0 | 0 | 75 | 0 | 100 | 75 | 95 | 85 | 0 | 0 |
|  | 15.6 | 40 | 90 | 40 | 70 | 90 | — | 0 | — | 50 | 0 | 20 | 10 | 30 | 0 | — | — | 10 | 0 | 80 |
| 24 | 1500 | 100 | 100 | 90 | 100 | 100 | 100 | 80 | 100 | 95 | 70 | 60 | 85 | 0 | 90 | 90 | 95 | 100 | 0 | 60 |
| 25 | 250 | 90 | 100 | 80 | 100 | 100 | 100 | 35 | 100 | 60 | 40 | 10 | 80 | 0 | 70 | 70 | 90 | 90 | 0 | 0 |
|  | 62.5 | 30 | 100 | 70 | 100 | 100 | 100 | 20 | 100 | 40 | 80 | 80 | 60 | 0 | 20 | 90 | 70 | 75 | 0 | 90 |
|  | 15.6 | 100 | 100 | 95 | 100 | 100 | 100 | 90 | 100 | 100 | 80 | 40 | 90 | 30 | 100 | 80 | 90 | 60 | 0 | 80 |
| 26 | 500 | 100 | 100 | 85 | 100 | 90 | 60 | 85 | 100 | 90 | 20 | 0 | 85 | 0 | 20 | 20 | 75 | 95 | 0 | 80 |
|  | 125 | 90 | 40 | 80 | 95 | 40 | 0 | 60 | 0 | 40 | 0 | 20 | 50 | 0 | 0 | 0 | 30 | 60 | 0 | 0 |
| 30 | 31.25 | 0 | 100 | 30 | 0 | 90 | 100 | 40 | 85 | 40 | 40 | 0 | 90 | 0 | 40 | 80 | 90 | 100 | 0 | 75 |
| 31 | 500 | 90 | 95 | 95 | 100 | 75 | 80 | 45 | 80 | 90 | 50 | 20 | 80 | 0 | 20 | 75 | 80 | 100 | 0 | 80 |
|  | 125 | 75 | 60 | 75 | 90 | 60 | 60 | 100 | 55 | 95 | 30 | 0 | 50 | 0 | 0 | 0 | 60 | 95 | 0 | 50 |
|  | 31.25 | 60 | 0 | 15 | 100 | 15 | 60 | 60 | 0 | 85 | 0 | 10 | 0 | 0 | 0 | 10 | 10 | 80 | 0 | 0 |
|  | 7.8 | 20 | 0 | 15 | 30 | 0 | 30 | 40 | 0 | 50 | 25 | 20 | 80 | 0 | 0 | 0 | 0 | 95 | 0 | 10 |
| 32 | 500 | 30 | 60 | 40 | 0 | 60 | 40 | 60 | 10 | 40 | 0 | 0 | 60 | 0 | 10 | 10 | 0 | 80 | 0 | 60 |
| 33 | 250 | 50 | 100 | 90 | 40 | 100 | 50 | 75 | 100 | 80 | 0 | 20 | 20 | 0 | 0 | 5 | 0 | 20 | 0 | 0 |
| 34 | 500 | 70 | 100 | 70 | 100 | 95 | 30 | 40 | 90 | 100 | 0 | 0 | 60 | 0 | 50 | 70 | 0 | 90 | 0 | 30 |
| 35 | 500 | 0 | 70 | 80 | 80 | 98 | 60 | 80 | 100 | 0 | 0 | 0 | 20 | 0 | 40 | 0 | 0 | 0 | 0 | 10 |
| 38 | 62.5 | 80 | 98 | 70 | 100 | 95 | 50 | 50 | 98 | 98 | 0 | 0 | 65 | 0 | 10 | 0 | 95 | 90 | 0 | 40 |
| 39 | 15.6 | 10 | 98 | 80 | 98 | 98 | 90 | 95 | 80 | 40 | 0 | 0 | 80 | 0 | 0 | 5 | 80 | 50 | 0 | 20 |
|  | 62.5 | 98 | 98 | 98 | 98 | 95 | 40 | 70 | 100 | 98 | 0 | 0 | 5 | 0 | 50 | 70 | 97 | 90 | 0 | 20 |
|  | 15.6 | 80 | 95 | 98 | 98 | 100 | 90 | 20 | 95 | 40 | 0 | 0 | 20 | 0 | 40 | 0 | 90 | 80 | 0 | 95 |
|  | 3.9 | 40 | 90 | 40 | 90 | 95 | 40 | 20 | 70 | 20 | 0 | 0 | 5 | 0 | 0 | 0 | 80 | 0 | 0 | 0 |
| 40 | 1000 | 25 | — | 25 | — | — | — | 60 | — | 98 | — | — | 20 | — | 80 | 40 | 40 | 0 | — | 20 |
| 41 | 4000 | 30 | 20 | — | 0 | 0 | 0 | 0 | — | 0 | 0 | 0 | 0 | 0 | 0 | 25 | 0 | — | 0 | 95 |
| 43 | 2000 | 0 | 20 | 15 | 0 | 0 | 0 | 0 | — | 0 | 0 | 0 | 0 | 0 | 0 | 0 | 40 | 20 | 0 | 0 |
| 44 | 250 | 40 | 80 | 75 | 80 | 85 | 20 | 75 | 90 | 80 | 0 | 0 | 20 | 0 | 0 | 0 | 40 | 0 | 0 | 60 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 45 | 500 | 0 | 70 | 60 | 70 | 25 | 0 | 10 | — | 50 | 0 | 50 | 0 | 0 | 0 | 0 | 0 | 0 | 0 | 0 |
| 46 | 31.3 | 95 | 98 | 98 | 98 | 98 | 95 | 98 | 100 | 98 | 15 | 0 | 0 | 0 | 0 | 10 | 80 | 50 | 0 | 40 |
|  | 7.8 | 80 | 95 | 98 | 98 | 98 | 80 | 98 | 100 | 98 | 15 | 0 | 0 | 0 | 0 | 0 | 0 | 0 | 0 | 20 |
|  | 1.9 | 60 | 98 | 95 | 95 | 95 | 30 | 90 | 90 | 95 | 15 | 0 | 0 | 0 | 0 | 0 | 0 | 0 | 0 | 10 |
| 47 | 62.5 | 70 | 90 | 98 | 100 | 98 | 20 | 98 | 90 | 98 | 0 | 0 | 0 | 0 | 0 | 0 | 0 | 0 | 0 | 10 |
| 48 | 500 | 10 | 75 | 55 | 70 | 70 | 30 | 60 | — | 40 | 0 | 0 | 0 | 0 | 0 | 0 | 0 | 0 | 0 | 0 |
| 49 | 250 | 90 | 100 | 95 | 100 | 100 | 100 | 95 | 90 | 100 | 0 | 10 | 80 | 0 | 90 | 80 | 95 | 80 | 20 | 90 |
|  | 62.5 | 95 | 100 | 100 | 100 | 100 | 100 | 95 | 80 | 100 | 0 | 0 | 70 | 0 | 80 | 60 | 90 | 100 | 0 | 90 |
| 50 | 62.5 | 98 | 100 | 98 | 100 | 98 | 98 | 98 | 98 | 100 | 93 | 97 | 90 | 0 | 95 | 95 | 99 | 97 | 90 | 80 |
|  | 15.6 | 90 | 98 | 98 | 90 | 98 | 90 | 80 | 90 | 100 | 70 | 97 | 50 | 0 | 80 | 80 | 97 | 95 | 10 | 80 |
| 51 | 62.5 | 98 | 98 | 98 | 98 | 100 | 95 | 98 | 90 | 100 | 40 | 40 | 90 | 0 | 20 | 0 | 93 | 20 | 10 | 80 |
|  | 7.8 | 30 | 70 | 80 | 95 | 95 | 60 | 90 | 20 | 70 | 0 | 0 | 50 | 0 | 0 | 0 | 25 | 0 | 0 | 70 |
| 52 | 2000 | 70 | 10 | 70 | 50 | 70 | 0 | — | 0 | 0 | 0 | 0 | 0 | 0 | 0 | 0 | 0 | 0 | 0 | 0 |
| 53 | 62.5 | 90 | 100 | 98 | 100 | 100 | 98 | 90 | 100 | 100 | 0 | 10 | 90 | 0 | 70 | 50 | 95 | 97 | 15 | 60 |
|  | 15.6 | 60 | 98 | 98 | 98 | 98 | 98 | 90 | 100 | 98 | 0 | 0 | 90 | 0 | 65. | 20 | 97 | 93 | 0 | 80 |
| 54 | 62.5 | 98 | 98 | 98 | 100 | 98 | 95 | 98 | 100 | 100 | 30 | 40 | 93 | 20 | 50 | 30 | 95 | 97 | 0 | 30 |
|  | 7.8 | 30 | 70 | 80 | 95 | 98 | 60 | 40 | 20 | 70 | 0 | 0 | 25 | 0 | 0 | 0 | 25 | 60 | 0 | 0 |
| 55 | 125 | 70 | 10 | 70 | 50 | 70 | 0 | — | 0 | 0 | 0 | 0 | 0 | 0 | 0 | 0 | 0 | 0 | 15 | 0 |
| 56 | 62.5 | 90 | 98 | 98 | 100 | 100 | 98 | 90 | 100 | 100 | 85 | 0 | 55 | — | 95 | 0 | 75 | 95 | 0 | 60 |
| 57 | 125 | 20 | 95 | 90 | 85 | 98 | 98 | 80 | 100 | 98 | 75 | 60 | 70 | 60 | 90 | 40 | 0 | 85 | 0 | 80 |
| 58 | 125 | 90 | 100 | 95 | 100 | 99 | 85 | 80 | 95 | 50 | 0 | 50 | 95 | 0 | 0 | 90 | 90 | 100 | 0 | 30 |
|  | 31.25 | 90 | 100 | 95 | 100 | 100 | 95 | 0 | 0 | 20 | 0 | 0 | 90 | 0 | 95 | 95 | 90 | 95 | 0 | 0 |
| 59 | 250 | 0 | 70 | 10 | 40 | 75 | 50 | 95 | 100 | 100 | 0 | 0 | 10 | 0 | 90 | 0 | 0 | 0 | — | 15 |
| 60 | 2000 | 60 | — | 15 | — | — | 50 | 0 | 0 | 80 | — | 15 | 0 | — | — | 70 | 25 | — | — | 5 |
| 61 | 125 | 40 | 75 | 90 | 90 | 30 | 75 | 80 | 100 | 40 | 0 | 15 | 45 | 0 | — | 10 | 10 | 35 | 0 | 15 |
| 62 | 125 | 40 | 80 | 90 | 70 | 80 | 75 | 5 | 60 | 80 | 0 | 15 | 60 | 0 | 50 | 40 | 25 | 80 | 0 | 15 |
| 63 | 62.5 | 90 | 90 | 90 | 90 | 95 | 95 | 65 | 75 | 80 | 0 | 10 | 80 | 0 | 0 | 90 | 10 | 60 | 0 | 60 |
| 64 | 125 | 90 | 99 | 90 | 90 | — | 95 | 80 | 90 | 100 | 85 | 70 | 70 | 80 | 50 | 70 | 65 | 90 | 0 | 80 |
| 65 | 250 | 100 | 85 | 75 | 60 | — | 10 | 0 | 100 | 50 | 70 | 0 | 20 | 0 | 50 | 40 | 80 | 80 | 0 | 15 |
| 66 | 125 | — | 80 | 0 | 30 | — | 0 | 0 | 40 | 30 | 0 | 0 | 0 | 0 | 0 | 90 | 0 | 90 | 0 | 0 |
| 67 | 1000 | 50 | 70 | 0 | 100 | — | 0 | 50 | 95 | 30 | 0 | 25 | 0 | 20 | 30 | 20 | 20 | 0 | 0 | 75 |
| 68 | 1000 | 40 | 80 | 60 | 30 | 100 | 75 | 0 | 100 | 90 | 0 | 0 | 80 | 0 | 80 | 80 | 95 | 75 | 0 | 20 |
| 69 | 125 | 70 | 50 | 40 | 100 | 60 | 25 | 80 | 65 | 50 | 0 | 25 | 25 | 0 | 0 | 0 | 50 | 60 | 0 | 80 |
|  | 62.5 | 80 | 90 | 40 | 100 | — | 90 | 60 | 100 | 85 | 90 | 0 | 80 | 0 | 30 | 80 | 90 | 95 | 0 | 60 |
| 70 | 250 | 90 | 80 | 5 | 40 | — | 50 | 80 | 100 | 50 | 40 | 0 | 40 | 0 | 80 | 80 | 70 | 30 | 0 | 90 |
| 71 | 250 | 75 | 95 | 70 | 90 | 95 | 95 | 0 | 50 | 70 | 0 | 0 | 0 | 0 | 0 | 75 | 08 | 80 | 0 | 85 |
| 72 | 500 | 75 | 70 | 35 | 70 | 0 | 60 | 85 | 70 | 100 | 0 | 0 | 50 | 0 | 0 | 20 | 40 | 0 | 0 | 25 |
| 73 | 62.5 | 100 | 100 | 85 | 90 | 100 | 90 | 20 | 40 | 50 | 0 | 35 | 0 | 0 | 50 | 0 | 0 | 70 | 0 | 95 |
| 74 | 500 | 0 | 50 | 50 | 70 | 80 | 70 | 85 | 70 | 80 | 0 | 0 | 80 | 0 | 0 | 0 | 60 | 0 | 0 | 5 |
| 75 | 125 | 70 | 100 | 80 | 90 | 75 | 90 | 0 | 100 | 100 | 0 | 20 | 0 | 0 | 70 | 0 | 0 | 50 | 0 | 95 |
| 76 | 125 | 25 | 65 | 40 | 0 | 90 | 40 | 90 | 40 | 98 | 0 | 80 | 40 | 20 | 10 | 65 | 98 | 60 | 10 | 80 |
| 77 | 31.25 | 80 | 95 | 90 | 90 | 70 | 100 | 80 | 95 | 80 | 40 | 70 | 50 | 0 | 35 | 50 | 85 | 30 | 0 | 15 |
|  | 125 | 60 | 100 | 80 | 60 | 85 | 50 | 50 | 20 | 100 | 30 | 30 | 20 | 0 | 30 | 20 | 98 | 20 | 10 | 15 |
|  | 15.6 | 50 | — | 75 | 20 | 50 | 100 | 15 | 100 | 80 | 10 | 15 | 40 | 0 | 40 | 0 | 40 | 0 | 0 | 75 |
| 78 | 125 | 75 | 95 | 90 | 85 | 40 | 80 | 0 | 30 | 90 | 0 | 50 | 50 | 0 | 10 | 10 | 50 | 60 | 0 | 0 |
| 79 | 2000 | 80 | 90 | 70 | 90 | 75 | 85 | 15 | 30 | 75 | 0 | 0 | 0 | 0 | 10 | 0 | 0 | 0 | 25 | 75 |
| 81 | 2000 | 50 | — | 10 | 0 | — | 20 | 0 | 30 | 40 | 0 | 0 | 50 | 0 | 0 | 0 | 0 | 60 | 0 | 40 |
| 82 | 500 | 85 | 100 | 85 | 95 | 85 | 90 | 85 | 100 | 85 | 0 | 0 | 75 | 0 | 0 | 0 | 0 | 0 | 0 | 0 |
| 83 | 62.5 | 50 | 60 | 10 | 60 | 20 | 0 | 0 | 0 | 30 | 0 | 0 | 0 | 0 | 0 | 0 | 0 | 0 | 0 | 0 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 84 | 2000 | 30 | 100 | 40 | 100 | — | — | 0 | 100 | 98 | 0 | 0 | 0 | 0 | 0 | 0 | 0 | 0 | 0 | 30 |
| 85 | 62.5 | 70 | — | 80 | 100 | 70 | 70 | 75 | 100 | 80 | 0 | 0 | 40 | 0 | 50 | 50 | 75 | 0 | 0 | 60 |
|  | 7.8 | 50 | — | 80 | 100 | 55 | 80 | 55 | 100 | 80 | 0 | 0 | 20 | 0 | 30 | 0 | 70 | 0 | 0 | 50 |
| 86 | 125 | 50 | 80 | 80 | 100 | 60 | — | 0 | 100 | 65 | 0 | 0 | 40 | 0 | 0 | 50 | 70 | 0 | 0 | 20 |
| 87 | 250 | 50 | 80 | 75 | 100 | 40 | 50 | 40 | 70 | 60 | 0 | 10 | 20 | 0 | 0 | — | 40 | 20 | 20 | 20 |
| 88 | 2000 | 50 | — | 35 | 80 | 70 | 85 | 20 | 100 | 90 | 0 | 0 | 30 | 0 | 0 | 0 | 70 | 20 | 0 | 30 |
| 89 | 500 | 0 | 70 | 50 | — | 75 | 70 | 30 | 100 | 50 | 0 | 0 | 0 | 0 | 0 | 50 | 95 | 0 | 0 | 50 |
| 90 | 62.5 | 100 | 100 | 90 | 100 | 100 | 100 | 90 | 100 | 100 | 40 | 0 | 0 | 0 | 20 | 0 | 0 | 20 | 0 | 0 |
| 91 | 62.5 | 25 | 50 | 80 | 0 | — | 90 | 80 | 60 | 50 | 0 | 30 | 0 | 0 | 20 | 0 | 0 | 20 | 0 | 95 |
| 92 | 500 | 0 | 70 | 90 | 70 | 80 | 80 | 0 | 70 | 20 | 0 | 0 | 25 | 80 | 0 | 0 | 0 | 60 | 0 | 0 |
| 93 | 2000 | 0 | 60 | 85 | 100 | 80 | 70 | 0 | 70 | 70 | 0 | 30 | 55 | 50 | 20 | 30 | 70 | — | 80 | 15 |
| 94 | 1000 | 70 | 90 | 70 | 90 | 90 | 20 | 50 | 100 | 80 | 0 | 0 | 0 | 20 | 0 | 0 | 98 | 0 | 50 | 80 |
| 97 | 4000 | 60 | — | 60 | — | — | 60 | 100 | 90 | 0 | — | — | — | 0 | 0 | 0 | 0 | — | 30 | 0 |
| 98 | 2000 | 25 | 80 | 50 | 65 | 0 | 80 | 0 | 50 | 20 | 0 | 20 | 0 | 0 | 0 | 0 | 80 | 0 | 20 | 0 |
| 99 | 2000 | 40 | — | — | 100 | 50 | — | 0 | 100 | 35 | — | 30 | — | — | 20 | 30 | — | — | — | 0 |
| 101 | 4000 | 0 | — | — | — | 85 | — | 0 | 100 | 80 | — | — | — | — | 100 | — | — | — | — | 50 |
| 103 | 125 | 65 | 95 | 90 | 100 | 70 | 100 | 100 | 100 | 100 | 100 | 100 | 100 | 80 | 100 | 100 | 100 | 100 | 80 | 80 |
| 104 | 3.9 | 35 | 85 | 80 | 100 | 100 | 75 | 90 | 60 | 90 | 85 | 85 | 95 | 50 | 20 | — | 100 | 95 | 50 | 60 |
| 105 | 500 | 30 | 40 | 95 | 90 | 70 | 60 | 70 | 40 | 0 | 80 | 20 | 0 | 20 | 30 | 0 | 0 | 90 | 30 | 0 |
| 106 | 500 | 0 | 40 | 90 | 0 | 100 | 0 | 80 | 20 | 0 | 90 | 30 | 40 | 60 | 0 | 0 | 0 | 80 | 20 | 0 |
| 107 | 250 | 0 | 20 | 90 | 0 | 90 | 0 | 80 | 40 | 0 | 50 | 10 | 30 | 0 | 0 | 0 | 0 | 75 | 0 | 0 |
| 108 | 1000 | 0 | 50 | 85 | 15 | 40 | 30 | 0 | 40 | 25 | 0 | 0 | 40 | 0 | 0 | 0 | 0 | 100 | 0 | 0 |
| 111 | 500 | 70 | 40 | 75 | 70 | 80 | 15 | 10 | 0 | 90 | 80 | 0 | 80 | 60 | 100 | 0 | 0 | 80 | 0 | 35 |
| 112 | 125 | 60 | 25 | 75 | 35 | 80 | 50 | 80 | 70 | 20 | 85 | 0 | 90 | 0 | 100 | 0 | 0 | 50 | 0 | 5 |
| 113 | 250 | 25 | 90 | 70 | 90 | 70 | 65 | 80 | 60 | 85 | 0 | 0 | 10 | 0 | 0 | 0 | 40 | 15 | 0 | 60 |
| 114 | 250 | 0 | 90 | 85 | 90 | 95 | 50 | 80 | 70 | 85 | 50 | 0 | 60 | 0 | 0 | 0 | 65 | 10 | 0 | 40 |
| 116 | 1000 | 30 | 70 | 15 | 90 | 95 | 80 | 80 | 60 | 75 | 85 | 0 | 50 | 85 | 0 | 0 | 65 | 30 | 0 | 60 |
| 117 | 62.5 | 25 | 95 | 40 | 0 | 90 | 50 | 0 | 70 | 90 | 0 | 0 | 25 | 0 | 10 | 0 | 40 | 75 | 0 | 75 |
| 118 | 250 | 0 | 50 | 25 | 0 | 20 | 60 | 25 | 0 | 60 | 0 | 0 | 0 | 0 | 0 | 60 | 20 | 0 | 0 | 0 |
| 119 | 500 | 100 | 100 | 45 | 100 | 95 | 90 | 80 | 95 | 100 | 0 | 0 | 60 | 0 | 0 | 0 | 40 | 75 | 50 | 50 |
| 120 | 500 | 90 | 75 | 35 | 80 | 100 | 100 | 50 | 75 | 80 | 0 | 0 | 15 | 0 | 0 | 0 | 20 | 25 | 0 | 25 |
| 133 | 62.5 | 60 | 80 | 0 | 100 | 100 | 100 | 70 | 40 | 80 | 0 | 0 | 0 | 0 | 0 | 0 | 40 | 80 | 30 | 0 |
| 135 | 500 | 0 | 100 | 0 | 100 | 100 | 100 | 30 | 70 | 70 | 0 | 0 | 35 | — | 0 | 60 | 0 | 0 | 20 | 70 |
| 136 | 500 | 0 | 90 | 0 | 50 | 70 | 90 | 30 | 0 | 80 | 30 | 0 | — | 0 | 0 | 0 | 0 | — | 0 | 40 |
| 137 | 250 | 100 | 100 | 98 | 80 | 98 | 90 | 100 | 100 | 75 | 0 | 98 | 35 | 0 | 0 | 0 | 70 | 0 | 0 | 70 |
| 138 | 4000 | 20 | 90 | 40 | 90 | 75 | 75 | 40 | — | 70 | — | 0 | — | 0 | 0 | 0 | 0 | — | 0 | 0 |
| 139 | 2000 | 30 | 50 | 30 | 80 | 98 | 30 | 40 | 90 | 80 | 0 | 100 | 10 | 0 | 0 | 0 | 0 | 0 | 0 | 0 |
| 140 | 500 | 40 | 80 | 50 | 100 | 70 | 100 | 50 | 100 | 85 | 0 | 50 | 50 | 0 | 75 | 98 | 80 | 80 | 0 | 50 |
|  | 1000 | 70 | — | 35 | 80 | 30 | 70 | 50 | 100 | 65 | 0 | 30 | 50 | 25 | 60 | 20 | 75 | 20 | 0 | 20 |
| 141 | 62.5 | 40 | 100 | 40 | 100 | 80 | 80 | 0 | 100 | 100 | 0 | 80 | 0 | 30 | 80 | 0 | 85 | 70 | 0 | 0 |
|  | 125 | 70 | 98 | 50 | 100 | 100 | 50 | 90 | 100 | 100 | 0 | 0 | 65 | 0 | 20 | 20 | 75 | 70 | 50 | 70 |
|  | 31.2 | 40 | 98 | 65 | 100 | 100 | 85 | 100 | 100 | 85 | 70 | 100 | 95 | 20 | 80 | 80 | 80 | 80 | 0 | 40 |
| 142 | 125 | 60 | 100 | 50 | 100 | 100 | 95 | 100 | 100 | 100 | 0 | 55 | 70 | 30 | 20 | 50 | 98 | 100 | 50 | 35 |
|  | 31.2 | 95 | 100 | 65 | 100 | 100 | 80 | 100 | 100 | 85 | 0 | 80 | 65 | 0 | 75 | 95 | 100 | 90 | 0 | 0 |
| 143 | 2000 | 60 | 100 | 50 | 100 | 70 | 98 | 80 | 100 | 98 | 0 | 80 | 55 | 50 | 0 | 0 | 80 | 80 | 70 | 80 |
|  | 62.5 | 80 | 75 | 75 | 95 | 65 | 50 | 75 | 100 | 95 | 0 | 0 | 55 | 0 | 60 | 50 | 80 | 80 | 0 | 60 |
|  | 15.6 | 80 | 100 | 50 | 100 | 100 | 20 | 100 | 100 | 35 | 70 | 93 | 75 | 93 | 50 | 97 | 97 | 97 | 0 | 90 |
| | | 98 | 98 | 60 | 100 | 95 | 50 | 100 | 100 | 0 | 50 | 30 | 0 | 35 | 60 | 80 | 80 | 80 | 0 | 70 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 144 | 3.9 | 80 | 70 | 0 | 98 | 40 | 0 | 60 | 90 | 0 | 0 | 0 | 0 | 0 | 10 | 70 | 70 | 0 | 0 | 0 |
| | 62.5 | 80 | 95 | 15 | 100 | 99 | 99 | 80 | 100 | 100 | 0 | 75 | 80 | 0 | 80 | 100 | 95 | 100 | 0 | 85 |
| 145 | 7.8 | 55 | 70 | 0 | 100 | 85 | 70 | 35 | 95 | 95 | 0 | 15 | 25 | 0 | 50 | 40 | 90 | 10 | 0 | 55 |
| | 62.5 | 75 | 90 | 35 | 100 | 100 | 90 | 95 | 100 | 100 | 0 | — | 80 | 0 | 15 | 25 | 75 | 75 | 0 | 20 |
| 146 | 7.8 | 50 | 65 | 0 | 95 | 95 | 55 | 65 | 100 | 75 | 0 | — | 45 | 0 | 0 | 95 | 0 | 0 | 0 | 0 |
| | 62.5 | 50 | 95 | 85 | 100 | 100 | 95 | 95 | 100 | 100 | 15 | 90 | 75 | 0 | 95 | 0 | 95 | 65 | — | 85 |
| 147 | 3.9 | 20 | 50 | 5 | 70 | 90 | 75 | 60 | 75 | 75 | 0 | 40 | 10 | 0 | 20 | 0 | 75 | 90 | 0 | 55 |
| | 15.6 | 80 | 90 | 45 | 100 | — | 90 | 80 | 100 | 100 | 0 | 0 | 0 | 0 | 0 | 0 | 80 | 25 | 0 | 80 |
| 148 | 3.9 | 25 | 70 | 5 | 100 | — | 60 | 60 | 100 | 90 | 0 | — | 0 | 0 | 0 | 20 | 0 | 40 | 0 | 15 |
| 149 | 25 | 75 | — | 0 | — | — | 80 | 0 | 90 | 10 | — | — | 70 | 0 | — | 60 | 95 | 0 | — | 90 |
| 150 | 2000 | 0 | — | 0 | — | — | 0 | 0 | 100 | 0 | 0 | — | 0 | 0 | — | 0 | 90 | — | — | 0 |
| 151 | 125 | 10 | 70 | 0 | 90 | 90 | 90 | 35 | 70 | 80 | 0 | 0 | 0 | 0 | 10 | 0 | 80 | 25 | 0 | 65 |
| | 62.5 | 95 | 100 | 25 | — | 100 | 100 | 95 | 100 | 95 | 0 | 25 | 40 | 0 | 80 | 0 | 85 | — | 0 | 95 |
| 152 | 15.6 | 80 | 75 | 0 | — | 100 | 100 | 90 | 100 | 95 | 0 | 0 | 0 | 0 | 30 | 0 | 85 | — | 0 | 90 |
| | 125 | 100 | 100 | 45 | 100 | 100 | 100 | 100 | 100 | 100 | 0 | 50 | 80 | 0 | 100 | 0 | 100 | 90 | 0 | 95 |
| 153 | 7.8 | 90 | 90 | 0 | 90 | 80 | 80 | 85 | 100 | 100 | 0 | 0 | 0 | 0 | 55 | 0 | 90 | 65 | 0 | 90 |
| | 125 | 90 | 100 | 35 | 100 | 100 | 100 | 85 | 100 | 100 | 0 | 50 | 40 | 0 | 90 | 25 | 100 | 80 | 0 | 90 |
| 154 | 7.8 | 70 | 90 | 0 | 100 | 60 | 70 | 55 | 40 | 90 | 0 | 50 | 20 | 0 | 70 | 0 | 55 | 0 | 0 | 80 |
| | 62.5 | 40 | 90 | 20 | 80 | 95 | 90 | 50 | 100 | 90 | 0 | 25 | 0 | 0 | 0 | 0 | 0 | 0 | 0 | 30 |
| 155 | 125 | 90 | 100 | 0 | 100 | 100 | 95 | 85 | 100 | 100 | 0 | 20 | 75 | 10 | 15 | 0 | 75 | 75 | 0 | 95 |
| | 15.6 | 75 | 90 | 20 | 100 | 50 | 80 | 15 | 80 | 95 | 0 | 0 | 15 | 0 | 0 | 0 | 50 | 10 | 0 | 80 |
| 156 | 31.25 | 75 | 90 | 0 | 80 | 90 | 100 | 85 | 100 | 100 | 0 | 40 | 20 | 0 | 0 | 50 | 75 | 10 | 0 | 85 |
| 157 | 15.6 | 70 | 90 | 0 | 100 | 50 | 90 | 40 | 80 | 90 | 0 | 0 | 80 | 0 | 10 | 30 | 70 | 80 | 0 | 0 |
| 158 | 31.25 | 75 | 95 | 20 | 80 | 90 | 80 | 60 | 70 | 95 | 0 | 0 | 50 | 0 | 0 | 0 | 70 | 50 | 0 | 0 |
| | 7.8 | 45 | 80 | 10 | 100 | 40 | 80 | 10 | 40 | 65 | 0 | 0 | 0 | 0 | 10 | 0 | 25 | 0 | 0 | 0 |
| 159 | 125 | 100 | 100 | 25 | 100 | 100 | 100 | 100 | 100 | 100 | 0 | 35 | 75 | 0 | 100 | 0 | 75 | 100 | 0 | 90 |
| | 15.6 | 50 | 100 | 0 | 90 | 70 | 70 | 70 | 70 | 95 | 0 | 15 | 50 | — | 50 | 50 | 60 | 40 | 0 | 10 |
| 160 | 62.5 | 65 | 80 | 30 | 100 | 75 | 100 | 60 | 100 | 100 | 0 | 0 | 50 | 0 | 30 | 30 | 70 | 30 | 0 | 100 |
| 161 | 250 | 80 | 85 | 65 | 80 | 65 | 80 | 75 | 80 | 60 | 0 | 40 | 65 | 0 | 15 | 0 | 50 | 10 | 0 | 50 |
| 162 | 62.5 | 40 | 80 | 40 | — | 10 | 50 | 20 | 95 | 80 | 15 | 0 | 55 | 0 | 15 | 0 | 70 | 0 | 0 | 0 |
| 163 | 500 | 0 | 70 | 0 | 100 | 40 | 70 | 0 | 90 | 20 | 0 | 0 | 0 | 0 | 0 | 0 | 50 | 0 | 0 | 70 |
| 164 | 125 | 90 | 95 | 30 | 100 | 80 | 95 | 80 | 100 | 90 | 0 | 0 | 85 | 0 | 65 | 0 | 70 | 75 | 0 | 85 |
| | 31.25 | 60 | 90 | 0 | 90 | 50 | 50 | 10 | 80 | 90 | 80 | 0 | 15 | 0 | 0 | 80 | 60 | 0 | 0 | 80 |
| 165 | 62.5 | 70 | 70 | 30 | 100 | 50 | 50 | 60 | 100 | 45 | 0 | 0 | 0 | 0 | 50 | 0 | 50 | 20 | 0 | 60 |
| | 15.6 | 45 | 40 | 0 | 90 | 20 | 60 | 40 | 80 | 90 | 0 | 0 | 0 | 0 | 20 | 80 | 70 | 30 | 0 | 70 |
| 166 | 62.5 | 60 | 65 | 55 | 70 | 70 | 50 | 75 | 100 | 80 | 25 | 0 | 0 | 0 | 80 | 80 | 85 | 25 | 30 | 60 |
| | 15.6 | 40 | 40 | 40 | 60 | 20 | 60 | 50 | 80 | 80 | 0 | 0 | 0 | 0 | 65 | 0 | 50 | 100 | 0 | 80 |
| 168 | 62.5 | 60 | — | 80 | — | 70 | — | 98 | 70 | 60 | 0 | 0 | 0 | — | 0 | 90 | 75 | 0 | 0 | 0 |
| | 15.6 | 20 | 90 | 0 | 100 | 50 | 70 | 75 | 100 | 60 | 0 | 0 | 20 | 0 | 0 | 0 | 80 | 0 | 0 | — |
| 169 | 125 | 50 | 80 | 0 | 80 | 30 | 70 | 0 | 70 | 65 | 0 | 0 | 25 | 0 | 75 | 60 | 70 | 0 | 80 | 98 |
| 170 | 500 | 50 | — | 30 | 95 | 25 | 90 | 70 | 100 | 90 | 0 | 35 | 50 | 0 | 40 | 60 | 50 | 85 | 40 | 0 |
| 171 | 125 | 50 | 100 | 0 | 90 | 15 | 80 | 60 | 100 | 80 | 0 | 30 | 0 | 0 | 0 | 0 | 80 | 80 | 0 | — |
| 172 | 2000 | 60 | 30 | — | 80 | 0 | 50 | 20 | 0 | 50 | 0 | 0 | 0 | 0 | 0 | — | 0 | 0 | 0 | 50 |
| 173 | 1000 | 40 | 80 | 50 | 90 | 20 | 70 | 0 | 100 | 70 | 0 | 25 | 0 | 25 | 0 | 0 | 40 | 50 | 0 | 0 |
| 174 | 125 | 0 | 80 | 40 | 80 | 0 | 85 | 0 | 80 | 0 | 20 | 70 | 0 | 0 | 80 | 98 | 20 | 40 | 0 | 90 |
| | 62.5 | 80 | — | 70 | 90 | 80 | 80 | 100 | 100 | 90 | 0 | 30 | 0 | 0 | 40 | 20 | 80 | 80 | 85 | 0 |
| 175 | 62.5 | 100 | 80 | 50 | 90 | 40 | 80 | 70 | 100 | 80 | 0 | 30 | 20 | 0 | 100 | 100 | 80 | 100 | 40 | 100 |
| 176 | 250 | 0 | — | 65 | 80 | 100 | 80 | 50 | 100 | 80 | 25 | 0 | 80 | 0 | 0 | 0 | 20 | 0 | 0 | 20 |
| 177 | 62.5 | 90 | 98 | 80 | 90 | 98 | 85 | 80 | 100 | 100 | 50 | 98 | 90 | 50 | 100 | 80 | 98 | 98 | 60 | 65 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 178 | 7.8 | 50 | 85 | 60 | 80 | 50 | 40 | 0 | 100 | 100 | 0 | 80 | 50 | 0 | 80 | 50 | 95 | 80 | 20 | 45 |
| 179 | 250 | 50 | 90 | 50 | 80 | 90 | 85 | 35 | — | 80 | 0 | 75 | 0 | 0 | 0 | 0 | 0 | 0 | 0 | 0 |
| 180 | 62.5 | 0 | 50 | 10 | 75 | 50 | 15 | 0 | 0 | 0 | 0 | 0 | 0 | 0 | 0 | 0 | 0 | 0 | 0 | 90 |
|  | 500 | 100 | 100 | 100 | 100 | 100 | 100 | 90 | — | 100 | 0 | 10 | 50 | 0 | 10 | 90 | 75 | 20 | 0 | 40 |
| 181 | 125 | 95 | 100 | 90 | 90 | 80 | 100 | 90 | — | 95 | 0 | 0 | 40 | 0 | 0 | 40 | 60 | 0 | 0 | 0 |
| 182 | 125 | 90 | 99 | 95 | — | 100 | 98 | 80 | 100 | 98 | 0 | 0 | 50 | 0 | 0 | 20 | 95 | 40 | 0 | 20 |
| 183 | 125 | 90 | 98 | 95 | 98 | 80 | 90 | 60 | 95 | 90 | 0 | 0 | 0 | 0 | 0 | 20 | 95 | 20 | 0 | 0 |
| 184 | 125 | 65 | 95 | 0 | — | 50 | 100 | 0 | 100 | 100 | 0 | 0 | 20 | 0 | 0 | 20 | 80 | 20 | 30 | 50 |
|  | 62.5 | 95 | 100 | 90 | 95 | 90 | 90 | 85 | 100 | 90 | 0 | 0 | 50 | 0 | 0 | 20 | 20 | 30 | 0 | 0 |
| 185 | 62.5 | 90 | 98 | — | — | 90 | — | 50 | — | 100 | 0 | — | — | 0 | 50 | — | — | — | 100 | 50 |
| 186 | 4000 | 100 | — | — | — | — | — | 80 | 100 | 90 | 0 | — | 0 | 0 | 0 | 70 | 90 | 0 | 30 | 0 |
| 187 | 125 | 40 | 80 | 90 | 85 | 80 | 80 | 80 | 98 | 90 | 0 | 50 | 50 | 20 | 70 | 0 | 70 | 60 | 0 | 90 |
| 188 | 125 | 90 | 100 | 95 | 85 | 60 | 80 | 80 | 100 | 90 | 0 | 25 | 50 | 0 | 70 | 80 | 80 | 40 | 70 | 70 |
| 189 | 125 | 80 | 80 | 85 | 100 | 25 | 80 | 100 | 90 | 90 | 0 | 0 | 40 | 0 | 70 | 50 | 70 | 40 | 25 | 70 |
| 190 | 125 | 98 | 80 | 85 | 100 | 80 | — | 20 | 90 | 85 | 0 | 80 | 70 | 0 | 100 | 20 | 85 | 90 | 0 | 70 |
| 191 | 125 | 60 | 100 | 80 | 95 | 70 | 100 | 80 | 98 | 98 | 15 | 50 | 70 | 30 | 75 | 60 | 100 | 80 | 65 | 50 |
|  | 31.2 | 40 | 100 | 80 | 80 | 20 | 80 | 80 | 100 | 70 | 0 | 0 | 0 | 0 | 0 | 20 | 40 | 0 | 50 | 30 |
| 192 | 125 | 80 | 100 | 20 | 100 | — | 90 | 90 | 100 | 20 | 0 | 0 | 0 | 0 | 0 | 0 | 0 | 0 | 0 | 30 |
|  | 31.25 | 40 | 90 | 0 | 100 | 30 | 80 | 40 | 100 | 98 | 0 | 20 | 10 | 0 | 60 | 60 | 90 | 75 | 0 | 98 |
| 193 | 250 | 80 | 100 | 40 | 100 | 70 | 100 | 80 | 98 | 100 | 0 | 0 | 0 | 0 | 0 | 30 | 80 | 25 | 0 | 90 |
| 194 | 250 | 50 | 100 | 60 | 100 | 25 | 85 | 10 | 98 | 95 | 0 | 0 | 50 | 0 | 20 | 20 | 80 | 30 | 70 | 65 |
| 195 | 250 | 80 | 90 | 65 | 100 | 80 | 100 | 80 | 100 | 100 | 0 | 0 | 40 | 0 | 20 | 70 | 80 | 40 | 25 | 60 |
| 196 | 250 | 70 | 100 | 40 | 100 | 65 | 100 | 100 | 100 | 100 | 0 | 0 | 70 | 10 | 15 | 30 | 80 | 10 | 0 | 70 |
| 197 | 250 | 80 | 85 | 40 | 80 | 0 | — | 75 | 30 | 60 | 0 | 0 | 0 | 0 | 0 | 0 | 50 | 0 | 0 | 50 |
| 198 | 2000 | 80 | 100 | 0 | 90 | — | 40 | 50 | 98 | 80 | 15 | 30 | 30 | 0 | 0 | 0 | 0 | 0 | 65 | 30 |
| 199 | 62.5 | 60 | 100 | 90 | 90 | 20 | 30 | 0 | 40 | 50 | 0 | 65 | 0 | 0 | 0 | 0 | 0 | 0 | 50 | 98 |
| 200 | 62.5 | 40 | 100 | 35 | 95 | 50 | 70 | 10 | 98 | 80 | 0 | 0 | 0 | 0 | 0 | 0 | 0 | 0 | 0 | 90 |
| 201 | 500 | 0 | 95 | 0 | 50 | 70 | 50 | 0 | 40 | 50 | 0 | 0 | 10 | 0 | 0 | 0 | 0 | 0 | 0 | 65 |
| 204 | 1000 | 0 | 20 | 15 | 60 | 70 | 60 | 0 | 90 | 60 | 0 | 20 | 80 | 0 | 40 | 95 | 95 | 100 | 0 | 0 |
| 205 | 250 | 70 | 60 | 60 | 95 | 70 | 90 | 40 | 100 | 90 | 45 | 0 | 0 | 0 | 20 | 20 | 20 | 80 | 10 | 10 |
| 206 | 250 | — | 75 | 20 | 100 | 70 | 95 | 98 | 30 | — | 0 | 0 | 15 | 0 | 0 | 50 | 50 | 40 | 60 | 60 |
| 207 | 1000 | 40 | 100 | 25 | 100 | 25 | 70 | 50 | 100 | 98 | 0 | 35 | 80 | 70 | 40 | 95 | 0 | 0 | 80 | 80 |
| 208 | 62.5 | 90 | 100 | 65 | 80 | 90 | — | 0 | 30 | 80 | 0 | 30 | 0 | 20 | 20 | 20 | 20 | 0 | 70 | 70 |
| 209 | 250 | 80 | 100 | 0 | 100 | 65 | — | 0 | 100 | 50 | 0 | 30 | 15 | 40 | 80 | 80 | 50 | 40 | 25 | 25 |
| 210 | 62.5 | 0 | 70 | 20 | 40 | 80 | 80 | 0 | 0 | 60 | 0 | 0 | 0 | 0 | 0 | 80 | 60 | 0 | 0 | 0 |
| 211 | 1000 | 35 | 30 | 55 | 40 | 20 | — | 0 | 75 | 55 | 0 | 0 | 10 | 0 | 0 | 70 | 25 | 0 | 0 | 0 |
| 212 | 2000 | 20 | — | 90 | 98 | 50 | — | 0 | 100 | 70 | 0 | 0 | 50 | 25 | 70 | 50 | 85 | 25 | 0 | 0 |
| 213 | 125 | 95 | 100 | 90 | 100 | 70 | 100 | 0 | 100 | 100 | 98 | 20 | 85 | 0 | 35 | 90 | 100 | 100 | 50 | 65 |
|  | 31.2 | 90 | 30 | 80 | 100 | 50 | 80 | 80 | 100 | 98 | 98 | 35 | 85 | 70 | 80 | 20 | 100 | 98 | 30 | 50 |
| 214 | 62.5 | 75 | — | 90 | 100 | 70 | — | 70 | 100 | 98 | 90 | 30 | 100 | 20 | 80 | 80 | 100 | 98 | 50 | 80 |
| 215 | 62.5 | 80 | — | 90 | 80 | 70 | 80 | 50 | 100 | 80 | 90 | 30 | 85 | 40 | 90 | 80 | 85 | 100 | 40 | 65 |
| 216 | 62.5 | 80 | — | 85 | 100 | 40 | 80 | 50 | 100 | 85 | 90 | 0 | 50 | 0 | 80 | 20 | 80 | 80 | 50 | 70 |
| 217 | 31.2 | 0 | — | 75 | — | 40 | 60 | 95 | 100 | 85 | 80 | 30 | 70 | 0 | 80 | 80 | 60 | 75 | 0 | 35 |
| 218 | 62.5 | 20 | — | 90 | 98 | 60 | 80 | 70 | 100 | 90 | 0 | 0 | 30 | 0 | 0 | 100 | 25 | 0 | 0 | 0 |
| 219 | 62.5 | 80 | — | 90 | 90 | 40 | — | 80 | 100 | 98 | 90 | 0 | 60 | 25 | 60 | 80 | 85 | 85 | 0 | 0 |
| 220 | 15.6 | 65 | — | 80 | — | 35 | — | 40 | 100 | 85 | 0 | 55 | 50 | 0 | 0 | 70 | 60 | 70 | 0 | — |
| 221 | 62.5 | — | 50 | 50 | — | 45 | 50 | 50 | 100 | — | 90 | 0 | 30 | 0 | 80 | 50 | 85 | 60 | 50 | 0 |
| 222 | 62.5 | — | — | 80 | — | 60 | 80 | 80 | 100 | — | 75 | 0 | — | 0 | 50 | 90 | 75 | 90 | 70 | 70 |
| 223 | 125 | 65 | 98 | 80 | 100 | 30 | 100 | 100 | 100 | 100 | 75 | 0 | — | 0 | 0 | 0 | 50 | 50 | 0 | 70 |
|  |  |  |  |  |  |  |  |  |  |  | 100 |  | 100 | 100 | 100 | 100 | 100 | 100 | 80 | 70 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 227 | 15.6 | 50 | 90 | 80 | 80 | 40 | 100 | 90 | 100 | 90 | 98 | 80 | 100 | 80 | 98 | 45 | 100 | 100 | 70 | 55 |
|  | 250 | 0 | — | 0 | — | 80 | 70 | 80 | 100 | 50 | 40 | 30 | 25 | 0 | 0 | 0 | 80 | 50 | 40 | 50 |
| 228 | 31.2 | 0 | — | 0 | 20 | 50 | 50 | 50 | 100 | 0 | 0 | 0 | 20 | 0 | 0 | 80 | 40 | 30 | 0 | 0 |
| 229 | 125 | 0 | 50 | 0 | 80 | 90 | 50 | 70 | 100 | 40 | 20 | 0 | 0 | — | 0 | 20 | 70 | 60 | 0 | 20 |
|  | 125 | 30 | 100 | 80 | 100 | 100 | 60 | 70 | 100 | 98 | 0 | 0 | 0 | 0 | 0 | 0 | 50 | 50 | 0 | 20 |
| 230 | 31.2 | 0 | 98 | 70 | 75 | 98 | 40 | 50 | 100 | 75 | 80 | 50 | 55 | 90 | 0 | 0 | 55 | 0 | 0 | 50 |
| 231 | 125 | 25 | 70 | 50 | 80 | 70 | 80 | 35 | 100 | 85 | 0 | 0 | 100 | 70 | 0 | 100 | 100 | 70 | 60 | 75 |
|  | 125 | 0 | 98 | 65 | 100 | 80 | 100 | 100 | 100 | 85 | 100 | 90 | 100 | 0 | 80 | 50 | 100 | 100 | 40 | 70 |
|  | 31.2 | 0 | 90 | 50 | 100 | 70 | 80 | 80 | 100 | 50 | 95 | 80 | 75 | 0 | 0 | 0 | 100 | 95 | 0 | 80 |
| 232 | 4000 | 50 | — | — | — | — | — | 10 | 0 | 50 | — | — | — | — | 0 | 0 | 0 | — | 0 | 0 |
| 233 | 250 | 0 | 80 | 40 | 0 | 20 | 30 | 0 | 50 | 0 | 0 | 20 | 0 | — | 0 | 0 | 0 | — | 0 | 20 |
| 234 | 4000 | 60 | — | 0 | — | — | — | 0 | 100 | 0 | — | — | — | — | 0 | 0 | 0 | — | 0 | 0 |
| 235 | 1000 | 20 | 70 | 30 | 50 | 70 | 70 | 20 | 100 | 70 | 90 | 20 | 35 | 25 | 75 | 98 | 45 | 75 | 60 | 20 |
| 236 | 1000 | 0 | — | 60 | 80 | 75 | 80 | 70 | 100 | 80 | 0 | 20 | 0 | 0 | 50 | 70 | 80 | 25 | 50 | 0 |
| 237 | 1000 | 50 | 70 | 80 | 30 | 70 | — | 50 | 100 | 90 | 75 | 50 | 45 | 40 | 40 | 20 | 80 | 85 | 65 | 70 |
| 239 | 4000 | 90 | — | 0 | — | — | 60 | 98 | 98 | 80 | 0 | 0 | 20 | — | 20 | 0 | 50 | 0 | 30 | 0 |
| 240 | 2000 | — | — | 50 | 100 | 20 | 0 | 30 | 0 | 30 | 20 | 0 | 0 | 0 | 25 | 70 | 80 | — | 0 | 90 |
| 241 | 2000 | 0 | — | 30 | 50 | 0 | 0 | 20 | 80 | 70 | 0 | 20 | 0 | 20 | 0 | 75 | 75 | 50 | 0 | 65 |
| 242 | 2000 | 0 | — | 0 | 70 | 40 | 0 | 20 | 98 | 90 | 75 | 45 | 75 | 20 | 70 | 15 | 80 | 0 | 0 | 70 |
| 243 | 500 | 80 | 100 | 85 | 95 | 100 | 95 | 80 | 0 | 70 | 0 | 0 | 70 | 0 | 40 | 0 | 0 | 80 | 0 | 0 |
|  | 31.25 | 70 | 90 | 80 | 90 | 100 | 80 | 70 | 80 | 90 | 40 | 40 | 90 | 20 | 0 | 40 | 95 | 30 | 0 | 95 |
| 244 | 500 | 100 | 100 | 45 | 100 | 100 | 100 | 90 | 40 | 100 | 0 | 0 | 80 | 20 | 0 | 0 | 80 | 80 | 0 | 95 |
|  | 125 | 90 | 100 | 30 | 100 | 100 | 90 | 80 | 85 | 95 | 0 | 0 | 0 | 10 | 0 | 75 | 0 | 65 | 0 | 90 |
| 245 | 4000 | 0 | — | — | — | — | — | 50 | 0 | 30 | — | — | — | 0 | 0 | 0 | 0 | — | 0 | 80 |
| 246 | 500 | 80 | 70 | 85 | 100 | 90 | 80 | 50 | 100 | 70 | 0 | 70 | 95 | 0 | 50 | 75 | 90 | 75 | 0 | 0 |
| 247 | 500 | 0 | 70 | 70 | 70 | 20 | 20 | 50 | 70 | 40 | 0 | 0 | 0 | 0 | 0 | 0 | 0 | 0 | 0 | 80 |
| 248 | 500 | 80 | 100 | 40 | 75 | 0 | 0 | 0 | 40 | 100 | 0 | 50 | 80 | 0 | 0 | 0 | 0 | 0 | 0 | 0 |
| 250 | 500 | 50 | 70 | 80 | 30 | 50 | 50 | 25 | 40 | 70 | 0 | 0 | 0 | 0 | 0 | 0 | 0 | 0 | 0 | 0 |
|  | 2000 | 20 | 50 | 45 | 80 | 70 | 0 | 10 | 40 | 0 | 0 | 0 | 0 | 0 | 0 | 0 | 0 | 0 | 0 | 40 |
| 255 | 4000 | 0 | — | 0 | — | — | — | 20 | 0 | 60 | 0 | 0 | 0 | — | 0 | 0 | 0 | 0 | 0 | 0 |
| 257 | 4000 | 0 | — | 0 | — | — | — | 20 | 45 | 20 | 0 | 20 | 0 | — | 50 | 10 | 0 | 95 | 0 | 80 |
| 258 | 500 | 80 | 95 | 90 | 100 | — | 95 | 40 | 65 | 90 | 0 | 45 | 25 | 0 | 20 | 95 | 90 | 100 | 0 | 15 |
| 260 | 500 | 60 | 95 | 95 | 90 | — | 95 | 90 | 100 | 95 | 50 | 40 | 30 | 10 | 100 | 65 | 95 | 100 | 0 | 0 |
| 261 | 500 | 100 | 100 | 90 | 100 | — | 100 | 100 | 100 | 100 | 0 | 85 | 90 | 0 | 80 | 90 | 100 | 100 | 0 | 0 |
| 262 | 500 | 80 | 100 | 0 | 100 | 80 | 80 | 80 | 90 | 40 | 0 | 0 | 75 | 0 | 40 | 0 | 95 | 10 | 0 | 40 |
|  | 31.25 | 50 | 50 | 70 | 80 | 80 | 80 | 80 | 50 | 0 | 0 | 0 | 20 | 0 | 20 | 0 | 60 | 0 | 0 | 0 |
| 263 | 500 | 0 | 60 | 40 | 80 | 0 | 0 | 50 | 70 | 0 | 0 | 40 | 0 | 0 | 0 | 75 | 80 | 75 | 0 | 0 |
| 264 | 250 | 0 | 75 | 80 | 80 | 20 | 90 | 85 | 25 | 75 | 0 | 40 | 65 | 0 | 75 | 0 | 70 | 0 | 0 | 40 |
| 265 | 500 | 10 | 80 | 45 | 30 | 50 | 80 | 90 | 60 | 95 | 0 | 10 | 75 | 0 | 35 | 90 | 85 | 70 | 0 | 95 |
| 266 | 500 | 0 | 100 | 10 | 80 | 0 | 80 | 90 | 100 | 100 | 0 | 0 | 50 | 0 | 100 | 0 | 0 | 0 | 0 | 50 |
| 267 | 500 | 100 | 90 | 0 | — | 30 | 80 | 90 | 30 | 70 | 0 | 0 | 50 | 0 | 60 | 70 | 70 | 75 | 0 | 0 |
| 268 | 31.25 | 80 | 80 | 0 | 100 | 60 | 80 | 55 | 100 | 55 | 35 | 0 | 50 | 0 | 20 | 0 | 85 | 0 | 0 | 50 |
| 269 | 62.5 | 70 | 80 | 10 | 100 | 20 | 80 | 20 | 60 | 80 | 0 | 0 | 10 | 0 | 85 | 0 | 0 | 70 | 40 | 45 |
| 270 | 62.5 | 45 | 70 | 0 | 55 | 50 | — | 60 | 20 | 60 | 0 | 0 | 50 | 0 | 30 | 0 | 70 | 30 | 0 | 20 |
| 271 | 3.9 | 65 | 80 | 40 | 100 | 0 | — | 0 | 50 | 70 | 0 | 0 | 0 | 0 | 85 | 80 | 0 | 0 | 0 | 40 |
|  | 1000 | 50 | 70 | 0 | 60 | 30 | 50 | 0 | 100 | 50 | 0 | 20 | 35 | 0 | 30 | 0 | 50 | 30 | 0 | 80 |
| 272 | 62.5 | 45 | 60 | 0 | 80 | 40 | 100 | 80 | 20 | 80 | 0 | 0 | 0 | 0 | 20 | 20 | 75 | 0 | 0 | 60 |
| 273 | 62.5 | — | 100 | 40 | 100 | 75 | 80 | 80 | 50 | 70 | 50 | 20 | 40 | 0 | 20 | 100 | 98 | 30 | 0 | 40 |
| 274 | 500 | 80 | 90 | 46 | 100 | 80 | 98 | 60 | 100 | 50 | 60 | 70 | 100 | 0 | 100 | 98 | 90 | 80 | 0 | 80 |
| 275 | 2000 | — | — | 0 | — | — | — | — | 100 | — | — | — | — | 0 | 20 | 100 | — | 80 | 30 | 60 |

-continued

POSTEMERGENT CONTROL OF PLANT SPECIES

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 276 | 125 | 0 | — | 0 | — | 70 | 100 | 65 | 100 | — | 80 | 0 | — | 40 | 90 | 90 | 80 | 90 | 0 | 70 |
| 277 | 125 | 0 | — | 50 | — | 60 | 80 | 20 | 100 | — | 75 | 80 | — | 20 | 25 | 70 | 80 | — | 0 | 25 |
| 278 | 31.2 | — | — | 20 | — | 0 | 80 | 0 | 100 | — | 0 | 20 | — | 0 | 0 | 0 | 100 | — | 0 | 80 |
| 279 | 125 | — | — | 30 | — | 60 | 70 | 60 | 100 | — | 0 | 0 | — | 0 | 70 | 100 | 90 | — | 0 | 80 |
| 280 | 125 | — | — | 20 | — | 70 | 98 | 60 | 100 | — | 0 | 35 | — | — | 60 | 95 | 80 | — | 0 | 80 |
| 281 | 250 | — | — | 0 | — | 60 | — | 60 | 100 | — | 75 | 0 | 70 | 0 | 70 | 85 | 90 | 100 | 0 | 50 |
| 282 | 125 | 70 | 80 | 50 | 80 | 70 | 100 | 80 | 100 | 80 | — | 0 | 80 | 0 | 70 | 100 | 98 | 98 | 0 | 70 |
|  | 125 | 60 | 80 | 20 | — | 50 | 80 | 50 | 100 | 85 | 0 | 30 | 50 | 0 | 80 | 90 | 80 | 90 | 0 | 75 |
|  | 31.2 | 50 | — | 80 | 80 | 70 | 70 | 80 | 100 | 80 | 0 | 50 | 80 | 0 | 80 | 70 | 75 | 90 | 0 | 20 |
| 283 | 125 | — | — | 0 | — | 50 | 100 | 80 | 100 | — | 20 | 0 | — | 0 | 80 | 80 | 80 | 100 | 30 | 25 |
| 284 | 125 | 80 | 90 | 70 | 90 | 70 | 100 | 50 | 100 | 98 | 0 | 60 | 50 | 0 | 80 | 80 | 85 | 70 | 0 | 70 |
| 285 | 125 | — | 80 | 0 | 80 | 50 | 100 | 40 | 100 | 80 | 0 | 0 | 20 | 0 | 80 | 0 | 75 | 100 | 0 | 60 |
|  | 7.8 | 30 | 100 | 65 | 85 | 30 | 90 | 80 | 100 | 80 | 0 | 80 | 50 | 0 | 20 | 90 | 85 | 90 | 0 | 0 |
| 286 | 125 | 70 | 80 | 70 | 80 | 40 | 80 | 70 | 100 | 80 | 0 | 0 | 30 | 0 | 70 | 80 | 80 | 80 | 0 | 60 |
| 287 | 125 | 30 | 95 | 70 | 85 | 40 | — | 80 | 100 | 80 | 0 | 35 | 30 | 0 | 80 | 100 | 80 | 80 | 50 | 0 |
| 288 | 125 | 50 | 98 | 55 | 90 | 70 | 100 | 80 | 100 | 90 | 0 | 30 | 80 | 0 | 80 | 90 | 85 | 80 | 0 | 30 |
| 289 | 1000 | 30 | 80 | 50 | 85 | 40 | 100 | 80 | 100 | 80 | 0 | 35 | 50 | 0 | 80 | 100 | 70 | 80 | 50 | 25 |
| 290 | 125 | 30 | 80 | 40 | 85 | 60 | 100 | 30 | 100 | 80 | 0 | 50 | 50 | 0 | 80 | 95 | 80 | 85 | 50 | 20 |
| 291 | 125 | 40 | 85 | 0 | 85 | 0 | 50 | 30 | 100 | 60 | 0 | 20 | 0 | 0 | 80 | 0 | 20 | 20 | 0 | 0 |
|  | 7.8 | 20 | 60 | 50 | — | 90 | 80 | 80 | 100 | 100 | 35 | 70 | 50 | 0 | 80 | 65 | 98 | 100 | 50 | 60 |
| 292 | 125 | 60 | 100 | 0 | — | 60 | 70 | 80 | 100 | 95 | 0 | 60 | 40 | 0 | 20 | 20 | 98 | 75 | — | 20 |
|  | 31.2 | 40 | 95 | 30 | 10 | 90 | 80 | 0 | 100 | 98 | 0 | 60 | 80 | 0 | 70 | 80 | 100 | 80 | 50 | 0 |
| 293 | 125 | 90 | 100 | 10 | 80 | 60 | 50 | 0 | 100 | 85 | 0 | 60 | 50 | 0 | 20 | 50 | 95 | 50 | 20 | 0 |
|  | 31.2 | 50 | 80 | 55 | 85 | 90 | 80 | 70 | 100 | 98 | 0 | 50 | 80 | 0 | 70 | 85 | 98 | 90 | 0 | 0 |
| 294 | 125 | 60 | 98 | 50 | — | 98 | 80 | 0 | 100 | 95 | 0 | 50 | 80 | 0 | 20 | 80 | 95 | 100 | 20 | 0 |
| 297 | 125 | 70 | 100 | 30 | 80 | 80 | 80 | 70 | 100 | 85 | 70 | 50 | 60 | 20 | 90 | 65 | 75 | 60 | 40 | 20 |
| 298 | 2000 | 35 | 95 | 0 | 85 | 90 | 80 | 50 | 100 | 80 | 65 | 50 | 40 | 20 | 50 | 25 | 0 | 50 | — | 0 |
| 299 | 500 | 35 | 50 | 0 | — | 50 | 50 | 40 | 100 | 50 | 0 | 40 | 20 | 0 | 70 | 0 | 85 | 70 | 0 | 0 |
| 300 | 2000 | 0 | 98 | 15 | 80 | 70 | 0 | 60 | 0 | 85 | 0 | 30 | 50 | 40 | 65 | 75 | 50 | 70 | 0 | 0 |
|  | 125 | 60 | 98 | 0 | 85 | 50 | 85 | 50 | — | 85 | 0 | 30 | 25 | 30 | 30 | 50 | 0 | 50 | 0 | 60 |
|  | 62.5 | 50 | 98 | 15 | 80 | 60 | 85 | 50 | 100 | 90 | 0 | 0 | 20 | 0 | 50 | 70 | 100 | — | 0 | 40 |
| 301 | 2000 | 30 | 90 | 80 | 85 | 95 | — | 80 | 100 | 90 | 0 | 40 | 95 | 30 | 25 | 55 | 90 | 97 | 0 | 70 |
| 304 | 62.5 | 90 | 95 | 98 | 98 | 98 | 95 | 85 | 100 | 100 | 0 | 90 | 60 | 80 | 30 | 15 | 90 | 50 | 80 | 35 |
| 305 | 250 | 90 | 98 | 98 | 90 | — | 90 | 70 | 100 | 90 | 0 | 60 | 70 | 80 | 50 | 80 | 98 | 30 | 30 | 80 |
| 306 | 125 | 50 | — | 40 | 35 | — | — | 80 | — | 50 | 0 | 60 | 30 | 0 | 25 | 25 | — | 0 | 80 | 0 |
| 307 | 250 | 70 | 95 | 75 | 30 | 90 | 80 | 90 | 100 | 60 | 70 | 90 | 70 | 40 | 75 | 50 | 98 | 75 | 0 | 0 |
| 308 | 1000 | 30 | 80 | 40 | 98 | 98 | 25 | 80 | 100 | 40 | 65 | 30 | 0 | 30 | 0 | 0 | 0 | 30 | 0 | 0 |
| 312 | 2000 | 0 | 70 | 40 | 80 | 0 | 95 | 0 | 100 | 98 | 0 | 0 | 50 | 0 | 50 | — | 100 | 0 | 0 | 0 |
| 313 | 1000 | 100 | 100 | 40 | 30 | — | 80 | 80 | 0 | 80 | 90 | 60 | 20 | 40 | 20 | 80 | 0 | 75 | 0 | 80 |
| 314 | 2000 | 40 | 80 | 15 | 98 | — | 80 | 80 | — | 75 | 98 | 40 | 60 | 0 | 60 | 0 | 100 | 80 | 75 | 80 |
| 315 | 1000 | 70 | 80 | 0 | 80 | — | 80 | 90 | 100 | 85 | 60 | 30 | 40 | 0 | 20 | 80 | 75 | 50 | 95 | 80 |
| 316 | 2000 | 80 | 100 | 80 | 80 | 75 | 25 | 80 | 90 | 95 | 90 | 80 | 25 | 0 | 60 | 0 | 90 | 80 | 0 | 80 |
| 317 | 31.3 | 75 | 80 | 95 | 90 | 100 | 98 | 98 | 90 | 85 | 98 | 90 | 30 | 60 | 80 | 50 | 80 | 100 | 75 | 80 |
| 318 | 7.8 | 80 | 100 | 98 | 100 | 98 | 80 | 98 | 80 | 95 | 60 | 90 | 80 | 0 | 30 | 80 | 75 | 80 | 95 | 80 |
| 319 | 31.3 | 100 | 100 | 98 | 80 | 98 | 95 | 100 | 80 | 98 | 95 | 98 | 75 | 30 | 50 | 98 | 90 | 75 | 0 | 30 |
| 320 | 7.8 | 70 | 98 | 95 | 80 | 70 | — | 90 | 100 | 95 | 100 | 98 | 80 | 80 | 25 | — | 80 | 90 | 95 | 80 |
| 321 | 7.8 | 40 | 95 | 95 | 90 | 90 | 85 | 98 | 90 | 98 | 100 | 98 | 90 | 80 | 30 | — | 98 | 100 | 80 | 80 |
| 322 | 7.8 | 98 | 95 | 80 | 100 | 70 | 100 | 80 | 100 | 85 | 100 | 98 | 90 | 100 | 50 | — | 98 | 100 | 98 | 70 |
| 323 | 7.8 | 50 | 95 | 90 | 100 | 90 | — | 75 | 100 | 95 | 80 | — | 90 | 70 | 35 | 0 | 98 | 98 | 80 | 30 |
| 324 | 7.8 | 80 | 100 | 90 | 80 | 100 | — | 75 | 100 | 98 | 90 | 95 | 98 | 100 | 40 | 70 | 100 | 100 | 90 | 0 |

-continued

POSTEMERGENT CONTROL OF PLANT SPECIES
Plant Species

| Compound | Dosage (ppm) | A | B | C | D | E | F | G | H | I | J | K | L | M | N | O | P | Q | R | T |
|---|---|---|---|---|---|---|---|---|---|---|---|---|---|---|---|---|---|---|---|---|
| 325 | 15.6 | 90 | 98 | 90 | 90 | 100 | 90 | 90 | 100 | 100 | 30 | 0 | 0 | 70 | 0 | 90 | 90 | 0 | 0 | 80 |
| 326 | 7.8 | 40 | 100 | 90 | 100 | 80 | 80 | 95 | 98 | 80 | 98 | 80 | 90 | 98 | 70 | — | 98 | 100 | 80 | 70 |
| 327 | 15.6 | 90 | 90 | 95 | 90 | 100 | 80 | 90 | 95 | 100 | 95 | 98 | 98 | 90 | 95 | 95 | 98 | 100 | 80 | 90 |
| 328 | 15.6 | 35 | 98 | 85 | 95 | — | 95 | 60 | 98 | 80 | 98 | 95 | 90 | 100 | 85 | 100 | 100 | 100 | 90 | 80 |
| 329 | 31.3 | 95 | 90 | 95 | 80 | 90 | 85 | 90 | 100 | 90 | 98 | 100 | 90 | 98 | 90 | 98 | 95 | 100 | 98 | 0 |
| 330 | 31.3 | 100 | 95 | 100 | 98 | — | 90 | 90 | 100 | 90 | 100 | 98 | 90 | 98 | 80 | 95 | 45 | 90 | 98 | 0 |
| 331 | 3.9 | 90 | 98 | 85 | 90 | 90 | 30 | 80 | 50 | 98 | 0 | 20 | 0 | 0 | 0 | — | 100 | 0 | 0 | 80 |
| 332 | 15.6 | 90 | 98 | 100 | 90 | 100 | 98 | 80 | 98 | 95 | 98 | 70 | 95 | 100 | 98 | 0 | 90 | 100 | 98 | 80 |
| 333 | 7.8 | 60 | 100 | 98 | 80 | 95 | 100 | 100 | 50 | 98 | 100 | 95 | 98 | 90 | 98 | 95 | 100 | 100 | 0 | 0 |
| 334 | 3.9 | 60 | 100 | 95 | 85 | 80 | 100 | 30 | 30 | 95 | 98 | 98 | 70 | 100 | 60 | 40 | 100 | 100 | 20 | 10 |
| 335 | 3.9 | 50 | 100 | 90 | 100 | 90 | 100 | 20 | 100 | 100 | 100 | 100 | 100 | 100 | 98 | 100 | 100 | 90 | 98 | 45 |
| 336 | 62.5 | 60 | 80 | 98 | 85 | 100 | 100 | 100 | 100 | 100 | 100 | 98 | 80 | — | 80 | 50 | 100 | 80 | 98 | 65 |
| 337 | 31.3 | 60 | 80 | 98 | 75 | 95 | 80 | 70 | 98 | 50 | 50 | 20 | 98 | 100 | 70 | — | 100 | 60 | 0 | 80 |
| 338 | 31.3 | 50 | 100 | 100 | 70 | 100 | 100 | 100 | 90 | 100 | 80 | 80 | 70 | 50 | 75 | 0 | 90 | 0 | 20 | 50 |
| 339 | 15.6 | 90 | 90 | 100 | 90 | — | 80 | 80 | 100 | 80 | 50 | 90 | 20 | 50 | 0 | 90 | 20 | 0 | 30 | 0 |
| 340 | 31.3 | 80 | 80 | 60 | 30 | 70 | 20 | 8 | 20 | 55 | 20 | 20 | 50 | 70 | 60 | 0 | 98 | 30 | 0 | 90 |
| 341 | 31.3 | 90 | 90 | 95 | 90 | 80 | — | 70 | 100 | 95 | 95 | 40 | 45 | 0 | 10 | 0 | 0 | 90 | 0 | 70 |
| 342 | 31.3 | 60 | 90 | 60 | 40 | 95 | 50 | 10 | 30 | 100 | 98 | 90 | 10 | 60 | 0 | — | 0 | 90 | 0 | 35 |
| 343 | 15.6 | 55 | 100 | 95 | 80 | 0 | 0 | 0 | 40 | 40 | 0 | 25 | 50 | 0 | 0 | 0 | 0 | 0 | 30 | 0 |
| 347 | 2000 | 0 | 70 | 45 | 50 | 0 | 0 | 0 | — | 30 | 0 | 90 | 0 | 0 | 0 | 0 | 15 | 0 | 0 | 0 |
| 348 | 125 | 0 | 90 | 0 | 60 | 0 | 90 | 30 | 100 | 0 | 0 | 40 | 20 | 0 | 0 | 0 | 100 | 60 | 0 | 0 |
| 350 | 125 | 50 | 40 | 75 | — | 0 | 40 | 70 | — | 0 | 0 | 0 | 0 | 0 | 0 | 0 | 50 | 25 | 0 | 20 |
| 351 | 2000 | 55 | 90 | 90 | 80 | 60 | 40 | 70 | — | 35 | 75 | 40 | 40 | 0 | 20 | — | 0 | 80 | 30 | 45 |

So as to clearly illustrate the phytotoxic properties of the various active ingredients of the present invention applied preemergently, a controlled greenhouse experiment is described below.

EXAMPLE 119

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control at at least one dosage are set forth in the table below. Control refers to the reduction in growth compared to the observed results of the same untreated species.

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| 1 | 10 | — | — | — | — | — | 90 | 100 | 90 | — | — | — | — | 70 | 10 | — | 70 | 100 | — |
| 2 | 0.5 | 0 | 95 | 30 | 70 | 0 | 100 | 30 | 95 | 15 | 20 | 60 | 0 | 80 | 95 | 50 | 30 | 95 | 0 |
| 4 | 10 | 98 | — | — | — | — | 90 | 100 | 90 | — | — | — | — | 100 | 80 | — | 90 | 100 | — |
| 6 | 0.5 | 100 | 100 | 95 | 95 | 0 | 30 | 70 | 60 | 10 | 90 | 50 | 50 | 90 | 70 | 10 | — | 50 | 40 |
|   | 0.25 | 70 | 100 | 10 | 95 | 0 | 0 | 100 | 60 | 0 | 80 | 50 | 0 | 80 | 0 | 0 | — | — | 50 |
| 7 | 1.0 | 95 | 98 | 95 | 98 | 100 | 80 | 100 | 95 | 90 | 98 | 95 | 100 | 98 | 80 | 80 | 20 | 70 | 90 |
|   | 0.125 | 20 | 98 | 20 | 90 | 0 | 40 | 50 | 40 | 0 | 70 | 70 | 0 | 30 | 0 | 10 | 0 | 20 | 0 |
| 8 | 1.0 | 100 | 100 | 95 | 100 | 100 | 60 | 100 | 90 | 95 | 100 | — | 55 | 95 | 95 | 95 | 70 | 95 | 95 |
|   | 0.25 | 90 | 100 | 95 | 90 | 100 | 25 | 95 | 60 | 80 | 90 | — | 0 | 75 | 70 | 80 | 15 | 60 | 75 |
| 9 | 0.5 | 0 | 100 | 40 | 100 | 100 | 0 | 30 | 0 | 0 | 50 | 20 | 0 | 98 | 40 | 0 | — | 20 | 0 |
| 10 | 1.0 | 0 | 98 | 0 | 90 | 0 | 0 | 95 | 75 | 0 | 80 | — | 0 | 0 | 40 | 0 | 0 | 0 | 0 |
| 12 | 0.25 | 95 | 95 | 95 | 98 | 0 | 50 | 60 | 30 | 50 | 10 | — | 0 | 40 | 10 | 80 | 0 | 0 | 50 |
|   | 0.125 | 80 | 95 | 40 | 95 | 0 | 0 | 0 | 20 | 0 | 0 | — | 0 | 10 | 0 | 50 | 0 | 0 | 30 |
| 13 | 0.25 | 95 | 98 | 95 | 98 | 70 | 90 | 95 | 95 | 80 | 95 | 98 | 20 | 95 | 80 | 95 | 10 | 90 | 98 |
|   | 0.062 | 90 | 98 | 80 | 90 | 50 | 90 | 20 | 95 | 0 | 60 | 95 | 0 | 50 | 0 | 90 | 0 | 50 | 80 |
| 14 | 4.0 | 90 | 95 | 20 | 99 | 10 | 0 | 90 | 10 | 10 | 10 | 15 | 0 | 10 | 95 | 60 | 20 | 0 | 0 |
| 15 | 1.0 | 90 | 95 | 60 | 70 | 0 | 30 | 30 | 80 | 10 | 15 | — | 0 | 10 | 15 | 20 | 0 | 10 | 5 |
| 16 | 1.0 | 100 | 0 | 15 | 0 | 0 | 15 | 35 | 0 | 15 | 20 | — | 0 | 0 | 0 | 0 | 0 | 0 | 0 |
| 17 | 1.0 | 0 | 90 | 0 | 40 | 0 | 0 | 70 | 0 | 10 | 50 | 10 | 0 | 0 | 0 | 0 | 0 | 0 | 0 |
| 19 | 1.0 | 95 | 98 | 95 | 95 | 80 | 80 | 98 | 85 | 35 | 50 | 60 | 0 | 40 | 70 | 30 | 80 | 60 | 90 |
|   | 0.25 | 90 | 95 | 20 | 90 | 0 | 50 | 90 | 70 | 0 | 20 | 0 | 0 | 0 | 20 | 0 | 0 | 0 | 40 |
| 21 | 2.0 | 80 | 95 | 70 | 98 | 70 | 60 | 100 | 75 | 50 | 80 | — | 0 | 0 | 60 | 40 | 0 | 0 | 60 |
| 22 | 0.25 | 95 | 100 | 95 | 98 | 100 | 70 | 100 | 98 | 50 | 90 | 95 | 50 | 95 | 95 | 98 | 90 | 98 | 98 |
|   | 0.062 | 80 | 100 | 95 | 95 | 100 | 30 | 80 | 80 | 0 | 10 | 60 | 0 | 40 | 90 | 40 | 90 | 95 | 90 |
| 24 | 10 | 95 | — | — | — | — | 80 | 100 | 98 | — | — | — | — | 70 | 70 | — | 10 | 70 | — |
| 25 | 0.25 | 98 | 100 | 98 | 100 | 98 | 80 | 100 | 98 | 100 | 100 | — | 70 | 98 | 100 | 98 | 95 | 100 | 95 |
|   | 0.062 | 95 | 98 | 95 | 95 | 70 | 40 | 0 | 70 | 98 | 95 | — | 0 | 60 | 20 | 90 | 0 | 50 | 50 |
| 26 | 0.25 | 95 | 98 | 98 | 100 | 100 | 95 | 100 | 95 | 100 | 100 | — | 0 | 98 | 100 | 98 | 40 | 100 | 100 |
|   | 0.062 | 95 | 98 | 95 | 98 | 95 | 80 | 100 | 90 | 95 | 90 | — | 0 | 30 | 95 | 60 | 0 | 60 | 100 |
| 29 | 10 | 90 | — | — | — | — | 0 | 60 | 0 | — | — | — | — | 0 | 20 | 20 | 0 | — | — |
| 30 | 1.0 | 0 | 0 | 95 | 0 | 100 | 0 | 100 | 0 | 0 | 0 | 0 | 0 | 0 | 90 | 0 | 90 | 30 | 0 |
| 31 | 0.25 | 80 | 98 | 95 | 100 | 100 | 65 | 100 | 95 | 95 | 95 | 98 | 50 | 98 | 100 | 100 | 100 | 98 | 100 |
|   | 0.062 | 70 | 60 | 90 | 90 | 100 | 0 | 95 | 90 | 0 | 10 | 50 | 0 | 98 | 95 | 90 | 0 | 98 | 80 |
| 32 | 0.5 | 50 | 100 | 90 | 100 | 100 | 98 | 95 | 100 | 20 | 60 | 40 | 40 | 100 | 98 | 100 | 100 | 98 | 50 |
|   | 0.125 | 20 | 0 | 60 | 50 | 40 | 30 | 95 | 90 | 0 | 0 | 50 | 0 | 30 | 95 | 65 | 0 | 0 | 0 |
| 33 | 1.0 | 90 | 98 | 90 | 50 | 95 | 60 | 95 | 80 | 95 | 95 | 70 | 80 | 98 | 98 | 95 | 40 | 98 | 98 |
|   | 0.25 | 20 | 80 | 10 | 50 | 40 | 0 | 0 | 10 | 0 | 0 | 0 | 0 | 70 | 50 | 10 | 0 | 40 | 0 |
| 34 | 1.0 | 95 | 100 | 95 | 95 | 95 | 80 | 98 | 95 | 60 | 70 | 80 | 0 | 70 | 20 | 95 | 30 | 40 | 90 |
|   | 0.25 | 80 | 95 | 80 | 90 | 0 | 20 | 50 | 80 | 0 | 40 | 90 | 0 | 20 | 0 | 80 | 0 | 0 | 70 |
| 35 | 2.0 | 60 | 80 | 60 | 98 | 0 | 10 | — | 50 | 0 | 0 | 0 | 0 | 0 | 60 | 80 | 0 | 0 | 40 |
| 36 | 1.0 | 0 | 30 | 0 | 50 | 100 | 0 | 0 | 0 | 0 | 0 | 0 | 0 | 0 | 0 | 0 | 0 | 0 | 0 |
| 37 | 0.25 | 95 | 95 | 95 | 97 | 100 | 90 | 100 | 95 | 95 | 97 | 95 | 0 | 97 | 70 | 95 | 0 | 97 | 100 |
|   | 0.062 | 95 | 93 | 35 | 100 | 40 | 30 | 100 | 90 | 20 | 50 | 30 | 0 | 30 | 0 | 50 | 0 | 20 | 97 |
| 39 | 0.25 | 95 | 95 | 95 | 97 | 100 | 90 | 100 | 95 | 95 | 97 | 95 | 0 | 97 | 70 | 95 | 0 | 97 | 100 |
|   | 0.031 | 90 | 93 | 30 | 97 | 0 | 30 | 100 | 50 | 0 | 0 | 0 | 0 | 0 | 0 | 0 | 0 | 0 | 60 |
| 40 | 4 | 20 | 100 | 50 | 60 | 100 | 0 | — | 20 | 0 | 50 | — | 0 | 0 | — | 0 | 0 | 0 | 70 |
| 41 | 0.25 | 40 | 80 | 25 | 80 | 0 | 10 | 0 | 10 | 0 | 0 | 20 | 0 | 80 | 10 | 35 | 0 | 30 | 70 |
| 42 | 0.016 | 0 | 100 | 100 | 70 | 0 | 0 | — | 30 | 0 | 0 | — | 0 | 0 | — | 0 | 100 | 0 | 0 |
| 43 | 4.0 | 30 | 40 | 20 | 95 | 0 | 60 | 70 | 30 | 0 | 0 | 0 | 0 | 20 | 40 | 40 | 0 | 0 | 0 |
| 44 | 0.25 | 85 | 93 | 80 | 97 | 100 | 20 | 95 | 0 | 10 | 70 | 93 | 70 | 40 | 90 | 80 | 40 | 70 | 90 |
| 46 | 0.125 | 95 | 95 | 97 | 97 | 100 | 90 | 100 | 97 | 60 | 0 | 50 | 60 | 70 | 97 | 10 | 60 | 95 | 99 |
|   | 0.031 | 95 | 95 | 93 | 97 | 100 | 70 | 100 | 80 | 0 | 0 | 0 | 0 | 0 | 70 | 0 | 0 | 30 | 97 |
| 47 | 2.0 | 97 | 97 | 97 | 100 | 97 | 70 | 99 | 99 | 0 | 0 | 0 | 30 | — | 40 | 20 | 30 | — | 97 |
|   | 0.5 | 50 | 90 | 85 | 97 | 90 | 20 | 99 | 90 | 0 | 0 | 0 | 0 | — | 40 | 10 | 0 | — | 90 |
| 49 | 0.062 | 100 | 100 | 100 | 99 | 100 | 99 | — | 90 | 90 | 10 | — | 0 | 85 | — | 50 | 0 | 90 | 100 |
| 48 | 1.0 | 30 | 20 | 0 | 50 | 60 | 60 | 0 | 0 | 0 | 0 | 0 | 20 | 20 | 10 | 0 | 70 | 20 | 0 |
| 50 | 0.25 | 80 | 95 | 95 | 100 | 100 | 80 | 100 | 93 | 99 | 97 | 100 | 100 | 95 | 25 | 95 | 60 | 95 | 99 |
|   | 0.062 | 0 | 93 | 85 | 97 | 75 | 40 | 80 | 90 | 90 | 100 | 80 | 0 | 97 | 0 | 90 | 10 | 93 | 99 |
| 51 | 0.25 | 93 | 95 | 90 | 95 | 95 | 80 | 100 | 95 | 97 | 80 | 97 | 97 | 97 | 95 | 95 | 100 | 97 | 100 |
|   | 0.062 | 50 | 95 | 10 | 93 | 90 | 70 | 70 | 20 | 45 | 10 | 55 | 0 | 90 | 10 | 0 | 0 | 45 | 80 |
| 52 | 2.0 | 30 | 80 | — | 30 | 0 | 50 | 0 | 35 | 0 | 0 | 0 | 0 | 0 | 25 | 0 | 0 | 0 | 10 |
| 53 | 0.125 | 90 | 95 | 90 | 100 | 97 | 85 | 100 | 90 | 97 | 97 | 97 | 30 | 95 | 95 | 93 | 99 | 93 | 100 |
|   | 0.031 | 20 | 93 | 20 | 100 | 85 | 40 | 95 | 0 | 20 | 80 | 15 | 0 | 10 | 80 | 75 | 0 | 60 | 97 |
| 54 | 0.125 | 95 | 93 | 95 | 97 | 99 | 70 | 100 | 90 | 95 | 99 | 97 | 0 | 93 | 95 | 95 | 40 | 95 | 97 |

-continued

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
|  | 0.031 | 85 | 93 | 35 | 97 | 90 | 0 | 100 | 20 | 0 | 93 | 50 | 0 | 15 | 10 | 40 | 0 | 45 | 55 |
| 56 | 0.25 | 0 | 100 | 0 | 100 | 0 | 90 | — | 50 | 30 | 0 | — | 0 | 0 | — | 0 | 0 | 20 | 70 |
| 57 | 4.0 | 100 | 100 | 100 | 100 | 0 | 0 | — | 0 | 40 | 0 | — | 0 | 20 | — | 80 | 0 | 50 | 0 |
| 58 | 0.062 | 0 | 100 | 0 | 100 | 100 | 80 | — | 100 | 70 | 0 | — | 0 | 30 | — | 80 | 50 | 90 | 100 |
| 59 | 20.0 | 0 | 100 | 60 | 100 | 90 | 35 | — | 50 | 0 | 0 | — | 0 | 0 | — | 0 | 0 | 0 | 0 |
| 60 | 0.5 | 0 | 50 | 20 | 0 | 0 | 100 | — | 0 | 50 | 0 | — | 0 | 0 | — | 0 | 40 | 0 | 0 |
| 61 | 5.0 | 100 | 100 | 100 | 100 | 100 | 100 | — | 70 | 85 | 100 | — | 0 | 65 | — | 90 | 0 | 100 | 90 |
| 62 | 0.5 | 0 | 90 | 50 | 50 | 0 | 0 | — | 20 | 0 | 80 | — | 0 | 20 | — | 0 | 0 | 20 | 60 |
| 63 | 0.125 | 100 | 100 | 100 | 100 | 100 | 0 | — | 100 | 30 | 90 | — | 40 | 10 | — | 0 | 0 | 30 | 100 |
| 64 | 0.062 | 50 | 100 | 100 | 90 | 100 | 70 | — | 90 | 60 | 0 | 30 | 0 | 0 | — | 40 | 0 | 90 | 90 |
| 65 | 0.25 | 0 | 20 | 100 | 100 | 90 | 50 | — | 20 | 0 | 30 | — | 0 | 70 | — | 95 | 0 | 95 | 95 |
| 66 | 10.0 | 100 | — | — | — | — | 100 | 100 | 100 | — | — | — | — | 80 | 100 | — | 50 | 100 | — |
| 67 | 10.0 | 30 | — | — | — | — | 100 | 30 | 30 | — | — | — | — | 70 | — | — | 40 | — | — |
| 68 | 1.0 | 100 | 100 | 80 | 90 | 100 | 0 | — | 90 | 80 | 0 | 90 | 20 | 70 | — | 50 | 20 | 80 | 50 |
| 69 | 0.5 | 100 | 100 | 50 | 100 | 0 | 30 | — | 40 | 93 | 0 | 100 | 70 | 0 | — | 20 | 0 | 70 | 100 |
| 70 | 1.0 | 90 | 100 | 70 | 95 | 100 | 30 | — | 80 | 100 | 40 | 90 | 80 | 40 | — | 90 | 60 | 90 | 95 |
| 71 | 10.0 | 98 | — | — | — | — | 50 | 100 | 70 | — | — | — | — | 50 | 98 | — | 70 | 100 | — |
| 72 | 0.25 | 40 | 100 | 90 | 100 | 90 | 10 | — | 60 | 90 | 70 | 80 | 90 | 30 | — | 50 | 90 | 50 | 100 |
| 73 | 0.125 | 0 | 30 | 0 | 0 | 0 | 0 | 0 | 0 | 0 | 0 | 40 | 0 | 0 | 0 | 0 | 0 | 0 | 0 |
| 74 | 0.125 | 90 | 100 | 100 | 100 | 100 | 0 | — | 70 | 0 | 0 | 100 | 0 | 30 | — | 70 | 0 | 70 | 100 |
| 75 | 0.5 | 0 | 100 | 0 | 90 | 0 | 20 | — | 90 | 0 | 0 | 0 | — | 20 | — | 0 | 0 | 80 | 0 |
| 76 | 0.25 | 60 | 100 | 95 | 100 | 100 | 50 | — | 100 | 100 | 70 | 90 | 100 | 70 | — | 80 | 90 | 90 | 100 |
| 77 | 0.25 | 0 | 80 | 80 | 50 | 90 | 60 | — | 0 | 70 | 40 | 50 | 0 | 20 | — | 0 | 0 | 80 | 90 |
| 78 | 0.25 | 0 | 100 | 30 | 70 | 0 | 0 | — | 30 | 10 | 40 | 0 | 40 | 20 | — | 0 | 30 | 20 | 50 |
| 79 | 0.5 | 40 | 100 | 40 | 70 | 90 | 10 | — | 30 | 50 | 30 | 10 | 0 | 0 | — | 0 | — | 0 | 0 |
| 80 | 10.0 | 0 | — | — | — | — | — | 100 | 80 | — | — | — | — | 0 | 0 | — | — | 0 | — |
| 82 | 0.125 | 0 | 90 | 0 | 90 | 0 | 0 | 0 | 0 | 0 | 0 | 0 | 0 | 0 | — | 0 | 0 | 0 | 0 |
| 83 | 0.5 | 0 | 98 | 0 | 30 | 50 | 0 | — | 20 | 0 | 0 | 0 | 0 | 0 | — | 0 | 0 | 0 | 0 |
| 84 | 10.0 | 30 | — | — | — | — | 20 | 90 | 98 | — | — | — | — | 0 | 0 | — | 0 | 0 | — |
| 85 | 0.125 | 90 | 100 | 100 | 100 | 100 | 90 | — | 100 | 70 | 0 | 0 | 0 | 20 | — | 30 | 0 | 60 | 100 |
|  | 0.015 | 70 | 100 | 30 | — | 90 | 20 | — | 60 | 0 | 0 | 0 | 0 | 0 | — | 0 | 0 | 0 | 0 |
| 86 | 0.25 | 0 | 100 | 20 | 100 | 100 | 0 | — | 0 | 0 | 0 | 0 | 0 | 0 | — | 0 | 0 | 0 | 0 |
| 87 | 4.0 | 80 | 90 | 65 | — | 20 | 70 | — | 0 | 0 | 0 | 70 | 0 | 0 | — | 50 | 0 | 40 | 100 |
| 90 | 2.0 | 100 | 100 | 70 | 100 | 100 | 70 | — | 95 | 80 | 90 | 70 | 20 | 50 | — | 40 | 30 | 80 | 90 |
|  | 1.0 | 90 | 100 | 50 | 100 | 60 | 30 | — | 30 | 70 | 20 | 40 | 0 | 0 | — | 30 | 0 | 80 | 100 |
| 91 | 0.25 | 100 | 100 | 100 | 100 | 100 | 40 | — | 100 | 60 | 30 | 50 | 0 | 20 | — | 40 | 0 | 70 | 100 |
|  | 0.062 | 20 | 100 | 90 | 90 | 100 | 0 | — | 50 | 0 | 0 | 20 | 0 | 0 | — | 0 | 0 | 20 | 20 |
| 92 | 0.5 | 10 | 100 | 0 | 70 | — | 0 | — | 0 | 0 | 0 | 40 | 0 | 0 | — | 0 | 0 | 0 | 0 |
| 93 | 0.5 | 70 | 40 | 20 | 0 | 0 | 0 | — | 0 | 0 | 10 | 0 | — | 0 | — | 0 | 0 | 0 | 0 |
| 94 | 0.25 | 60 | 100 | 50 | 0 | 0 | 0 | — | 0 | 0 | 0 | 0 | — | 0 | — | 0 | 0 | 0 | 0 |
| 97 | 1.0 | 30 | 100 | 0 | 20 | 80 | 0 | — | 0 | 0 | 0 | 10 | 40 | 0 | — | 0 | 0 | 0 | 100 |
| 98 | 10.0 | 80 | — | — | — | — | 40 | 100 | 98 | — | — | — | — | 90 | 90 | — | 40 | 90 | — |
| 101 | 10.0 | 40 | — | — | — | — | 0 | 40 | 70 | — | — | — | — | 0 | 60 | — | 20 | 0 | — |
| 104 | 0.25 | 100 | 100 | 100 | 100 | 100 | 100 | — | 100 | 100 | 100 | 100 | 100 | 100 | 100 | 100 | 100 | 100 | 100 |
|  | 0.016 | 100 | 100 | 80 | 100 | 80 | 100 | — | 100 | 95 | 95 | 100 | 100 | 100 | — | 100 | 90 | 95 | 100 |
| 106 | 1.0 | 95 | 95 | 95 | 100 | 100 | 85 | — | 98 | 98 | 70 | 98 | 98 | 70 | 20 | 95 | 98 | 70 | 80 |
| 108 | 0.5 | 95 | 95 | 100 | 80 | 80 | 70 | 80 | 98 | 95 | 100 | 70 | 98 | 85 | 95 | 98 | 50 | 50 | 90 |
|  | 0.125 | 40 | 95 | 30 | 70 | 70 | 50 | 40 | 90 | 60 | 80 | 10 | 30 | 0 | 0 | 50 | 0 | 0 | 60 |
| 110 | 2.0 | 0 | 50 | 0 | 0 | 0 | 0 | — | 0 | 90 | 40 | 50 | 0 | 80 | 0 | 0 | 0 | 0 | 0 |
| 111 | 0.25 | 20 | 95 | 10 | 90 | 95 | 20 | 50 | 80 | 35 | 65 | 65 | 0 | 15 | 90 | 75 | 0 | 30 | 93 |
| 112 | 0.25 | 80 | 85 | 0 | 99 | 0 | 80 | 90 | 20 | 50 | 25 | 20 | 0 | 0 | 97 | 30 | 90 | 0 | 90 |
| 113 | 0.25 | 30 | 90 | 0 | 100 | 0 | 0 | 100 | 60 | 0 | 40 | 0 | 0 | 20 | 90 | 50 | 0 | 50 | 50 |
| 114 | 0.5 | 95 | 95 | 15 | 50 | 100 | 50 | 100 | 60 | 0 | 80 | 40 | 0 | 0 | 0 | 10 | 0 | 10 | 80 |
| 116 | 0.5 | 90 | 100 | 10 | 100 | 100 | 20 | — | 60 | 0 | 0 | 0 | — | 0 | — | 0 | 0 | 0 | 30 |
| 117 | 0.5 | 90 | 100 | 20 | 90 | 90 | 20 | — | 90 | 0 | 0 | 0 | 0 | 0 | — | 60 | 0 | 40 | 0 |
| 118 | 0.5 | 30 | 90 | 0 | 60 | 0 | 0 | — | 0 | 0 | 0 | 0 | — | 0 | — | 0 | 0 | 0 | 0 |
| 119 | 0.5 | 90 | 100 | 0 | 90 | 100 | 0 | — | 20 | 0 | 0 | 50 | 0 | 0 | — | 0 | 0 | 0 | 70 |
| 120 | 0.25 | 70 | 90 | 0 | 80 | 95 | 100 | — | 10 | 20 | 0 | 0 | 75 | 0 | 50 | 30 | 0 | 80 | — |
| 128 | 1.0 | 20 | 100 | 0 | 90 | 100 | 0 | — | 30 | 0 | 0 | 50 | 0 | 0 | — | 0 | 0 | 0 | 0 |
| 136 | 1.0 | 30 | 65 | 0 | 0 | 0 | 0 | — | 98 | 0 | 0 | 0 | — | 0 | 0 | 80 | — | 0 | 10 |
| 137 | 0.25 | 80 | — | 0 | 100 | 10 | 70 | — | 80 | 0 | 50 | 30 | 30 | 20 | — | 20 | — | 20 | 100 |
| 138 | 0.25 | 100 | 100 | 50 | 90 | 20 | 20 | — | 90 | 30 | 50 | 50 | 10 | 0 | — | 90 | — | 90 | 80 |
| 139 | 0.25 | 100 | 100 | 50 | 100 | 100 | 90 | — | 100 | 70 | 90 | 100 | 80 | 80 | — | 100 | — | 100 | 100 |
| 140 | 0.125 | 100 | 100 | 50 | 100 | 60 | 80 | — | 90 | 0 | — | 70 | 10 | 70 | — | 100 | 0 | 80 | 100 |
| 141 | 0.25 | 100 | 100 | 100 | 100 | 100 | 100 | — | 100 | 100 | 100 | 100 | 95 | 95 | — | 100 | — | 100 | 75 |
| 142 | 0.5 | 20 | 20 | 0 | 100 | 100 | 0 | 100 | 40 | 0 | 0 | 50 | 0 | 0 | 0 | 0 | 0 | 0 | 25 |
| 143 | 0.25 | 100 | 95 | 70 | 100 | 100 | 90 | 100 | 97 | 95 | 97 | 99 | 50 | 97 | 100 | 100 | 50 | 97 | 100 |
|  | 0.062 | 95 | 95 | 25 | 100 | 100 | 80 | 100 | 95 | 60 | 80 | 99 | 0 | 97 | 50 | 85 | 0 | 95 | 100 |
|  | 0.016 | 95 | 95 | 25 | 100 | 40 | 0 | 40 | 90 | 0 | 70 | 20 | 0 | 75 | 0 | 75 | 0 | 50 | 75 |
| 144 | 0.25 | 100 | 100 | 60 | 100 | 100 | 95 | — | 100 | 70 | 40 | — | 0 | 80 | — | 100 | 70 | 100 | 100 |
|  | 0.062 | 100 | 90 | 70 | 100 | 100 | 0 | — | 60 | 0 | 0 | — | 0 | 60 | — | 60 | 0 | 93 | 80 |
| 145 | 0.125 | 100 | 100 | 40 | 100 | 100 | 60 | — | 100 | 0 | 0 | — | 0 | 0 | — | 50 | 0 | 20 | 80 |
|  | 0.062 | 90 | 90 | 0 | 100 | 50 | 100 | — | 90 | 0 | 0 | — | 0 | 0 | — | 20 | 0 | 0 | 40 |
| 146 | 0.125 | 100 | 85 | 0 | 100 | — | 90 | — | 90 | 60 | 60 | — | 0 | 100 | — | 97 | 0 | 95 | 100 |
|  | 0.062 | 60 | 30 | 0 | 90 | — | 0 | — | 20 | 0 | 30 | — | 0 | 95 | — | 90 | 0 | 85 | 100 |
| 147 | 0.031 | 70 | 100 | 0 | 100 | 100 | 20 | — | 100 | 20 | 20 | 0 | 30 | 0 | — | 0 | 90 | 0 | 100 |
| 148 | 0.125 | 30 | 90 | 0 | 100 | 100 | 0 | — | 50 | 20 | 0 | — | 0 | 30 | — | 90 | 0 | 70 | 100 |

-continued

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| 149 | 10 | 30 | — | — | — | — | 40 | 40 | 50 | — | — | — | — | 50 | 50 | — | 20 | 20 | — |
| 150 | 0.5 | 90 | 100 | 30 | 90 | 100 | 80 | — | 20 | 80 | 0 | 95 | 50 | 30 | — | 70 | 50 | 80 | 95 |
| 151 | 0.031 | 100 | 100 | 0 | 100 | 100 | 30 | — | 90 | 30 | 30 | 40 | 50 | 60 | — | 50 | 30 | 60 | 100 |
| 152 | 0.031 | 90 | 100 | 0 | 100 | 100 | 60 | — | 100 | 0 | 0 | 40 | 0 | 40 | — | 30 | 0 | 90 | 100 |
| 153 | 0.031 | 100 | 100 | 0 | 100 | 100 | 20 | — | 100 | 30 | 20 | 20 | 0 | 65 | — | 30 | 0 | 70 | 100 |
| 154 | 0.125 | 30 | 100 | 0 | 90 | 100 | 0 | — | 20 | 0 | 0 | 10 | 0 | 0 | — | 0 | 0 | 0 | 100 |
| 156 | 0.125 | 90 | 100 | 0 | 100 | 100 | 70 | — | 90 | 0 | 50 | 90 | 0 | 60 | — | 20 | 30 | 20 | 95 |
| 157 | 0.031 | 100 | 100 | 0 | 100 | 90 | 50 | — | 100 | 0 | 20 | 50 | 0 | 10 | — | 90 | 0 | 80 | 30 |
| 158 | 0.031 | 90 | 100 | 0 | 100 | 80 | 20 | — | 100 | 0 | 20 | 30 | 0 | 40 | — | 0 | 0 | 30 | 0 |
| 159 | 0.062 | 100 | 100 | 0 | 100 | 100 | 60 | — | 100 | 50 | 90 | 70 | 0 | 80 | — | 80 | 0 | 75 | 70 |
| 160 | 0.62 | 100 | 100 | 0 | 100 | 100 | 80 | — | 100 | 35 | 0 | 60 | 0 | 0 | — | 0 | 0 | 30 | 100 |
|  | 0.015 | 90 | 100 | 0 | 100 | 100 | 80 | — | 80 | 0 | 0 | 0 | 0 | 0 | — | 0 | 0 | 0 | 100 |
| 161 | 10 | 100 | — | — | — | — | 100 | 100 | 100 | — | — | — | — | 100 | 100 | — | 100 | 100 | — |
| 162 | 0.125 | 80 | 100 | 10 | 100 | 0 | 0 | — | 90 | 0 | 0 | 50 | 0 | 40 | — | 30 | 30 | 80 | 100 |
| 163 | 2 | 100 | 100 | 0 | 100 | 100 | 0 | — | 60 | 40 | 0 | 0 | 0 | 0 | — | 0 | 0 | 0 | 60 |
| 164 | 0.125 | 90 | 100 | 10 | 100 | 100 | 20 | — | 100 | 0 | 0 | 20 | 0 | 0 | — | 0 | 0 | 60 | 90 |
|  | 0.031 | 70 | 100 | 0 | 90 | 70 | 0 | — | 100 | 0 | 0 | 0 | 0 | 0 | — | 0 | 0 | 20 | 90 |
| 165 | 0.25 | 90 | 75 | 10 | 90 | 90 | 60 | — | 30 | 0 | 0 | 60 | 0 | 60 | — | 0 | 0 | 90 | 90 |
| 166 | 0.25 | 100 | 100 | 80 | 100 | 90 | 95 | — | 100 | 10 | 40 | 80 | 20 | 80 | — | 20 | 30 | 80 | 100 |
|  | 0.062 | 80 | 90 | 40 | 100 | 70 | 0 | — | 90 | 0 | 0 | 0 | 0 | 70 | — | 0 | 0 | 50 | 100 |
| 169 | 10 | 90 | — | — | — | — | 100 | 100 | 98 | — | — | — | — | 50 | 40 | — | — | 50 | — |
| 170 | 0.25 | 70 | 100 | 0 | 90 | 0 | 30 | — | 85 | 20 | 30 | 80 | 10 | 40 | — | 90 | — | 70 | 0 |
| 171 | 0.25 | 70 | 100 | 20 | 100 | 20 | 50 | — | 90 | 40 | 90 | 100 | 50 | 100 | — | 100 | — | 100 | 80 |
| 172 | 0.25 | 100 | — | 90 | 100 | 100 | 90 | — | 100 | 80 | 100 | 100 | 90 | 100 | — | 90 | — | 100 | 100 |
|  | 0.31 | 80 | — | 0 | 100 | 40 | 80 | — | 90 | 20 | 0 | 90 | 60 | 0 | — | 70 | 0 | 0 | 100 |
| 173 | 0.25 | 50 | 80 | 0 | 90 | 0 | 0 | — | 0 | 30 | 70 | 30 | 20 | 30 | — | 70 | — | 50 | 0 |
| 175 | 0.125 | 100 | 100 | 100 | 100 | 100 | 100 | — | 100 | 100 | 100 | 100 | 100 | 100 | — | 100 | — | 100 | 100 |
|  | 0.016 | 70 | 100 | 0 | 100 | 60 | 0 | — | 60 | 0 | 0 | 30 | 0 | 50 | — | 50 | 0 | 80 | 70 |
| 178 | 0.25 | 65 | 80 | 0 | 95 | 0 | 10 | 60 | 40 | 0 | 0 | 0 | — | 25 | 0 | 0 | — | 0 | 0 |
| 181 | 0.25 | 98 | 100 | 80 | 98 | 98 | 80 | — | 98 | 0 | 30 | 95 | 0 | 20 | — | 60 | 40 | 80 | 50 |
| 182 | 0.12 | 98 | 98 | 98 | 98 | 99 | 98 | — | 98 | 0 | 0 | 20 | 0 | 0 | — | 70 | 0 | 90 | 100 |
| 183 | 0.5 | 98 | 98 | 0 | 100 | 98 | 0 | — | 100 | 0 | 0 | 90 | 0 | 0 | — | 0 | 0 | 0 | 0 |
| 184 | 0.25 | 100 | 98 | 50 | 100 | 98 | 80 | — | 100 | 0 | 0 | 95 | 0 | 0 | — | 30 | 0 | 80 | 80 |
| 185 | 0.25 | 98 | 100 | 70 | 98 | 90 | 80 | — | 100 | 0 | 20 | 90 | 0 | 20 | — | 90 | 0 | — | 0 |
| 186 | 0.062 | 90 | 98 | 20 | 90 | 90 | 0 | — | 95 | 0 | 0 | 30 | 0 | 30 | — | 40 | 0 | 50 | 30 |
| 187 | 10 | 100 | — | — | — | — | 100 | 100 | 100 | — | — | — | — | 100 | 100 | — | 100 | 100 | — |
| 188 | 10 | 98 | — | — | — | — | 100 | 100 | 100 | — | — | — | — | 100 | 100 | — | 100 | 100 | — |
| 189 | 0.25 | 100 | 100 | 80 | 100 | 80 | 50 | — | 100 | 80 | 90 | 100 | 80 | 80 | — | 70 | — | 80 | 100 |
|  | 0.063 | 80 | 100 | 60 | 80 | 0 | 50 | 0 | 70 | 0 | 10 | 10 | 50 | 70 | — | 50 | — | 40 | 100 |
| 190 | 0.25 | 90 | — | 90 | 100 | 90 | 50 | — | 50 | 10 | 20 | 95 | 20 | 30 | — | 30 | — | 70 | 100 |
| 191 | 0.25 | 100 | 100 | 100 | 100 | 100 | 100 | — | 100 | 95 | — | 100 | 100 | 100 | — | 100 | — | 100 | 100 |
| 192 | 0.25 | 95 | 100 | 90 | 100 | 100 | 97 | — | 100 | 10 | 0 | — | 0 | 0 | — | 0 | 0 | 70 | 90 |
| 193 | 0.125 | 90 | 100 | 0 | 100 | 100 | 40 | — | 60 | 0 | 0 | 0 | 0 | 0 | — | 20 | 0 | 0 | 0 |
| 194 | 0.25 | 90 | 100 | 70 | 100 | 95 | 90 | — | 90 | 0 | 0 | 30 | 0 | 0 | — | 0 | 0 | 0 | 95 |
| 195 | 0.125 | 30 | 100 | 0 | 95 | 100 | 60 | — | 70 | 10 | 0 | 0 | 0 | 0 | — | 0 | 0 | 20 | 100 |
| 196 | 0.125 | 95 | 100 | 0 | 95 | 100 | 60 | — | 70 | 0 | 0 | 0 | 0 | 0 | — | 0 | 0 | 0 | 20 |
| 197 | 0.125 | 99 | 99 | 30 | 99 | 99 | 80 | — | 99 | 0 | 40 | 20 | 10 | 50 | — | 80 | 10 | 98 | 90 |
| 198 | 4 | 90 | 100 | 0 | 100 | 0 | 0 | — | 80 | 10 | 70 | 20 | 50 | 0 | — | 70 | 70 | 0 | 30 |
| 199 | 0.25 | 20 | 100 | 70 | 90 | 0 | 20 | — | 70 | 0 | 0 | — | — | — | — | 0 | 0 | 0 | 0 |
| 200 | 0.5 | 100 | 100 | 100 | 100 | 100 | 60 | — | 90 | 50 | 0 | 10 | 0 | 0 | — | 0 | 0 | 0 | 60 |
| 202 | 4 | 0 | 20 | 40 | 100 | 0 | 100 | — | 0 | 0 | 0 | — | 0 | 0 | — | 0 | 0 | 0 | 0 |
| 203 | 1.0 | 40 | 100 | 0 | 80 | 0 | 0 | — | 0 | 0 | 0 | 0 | 0 | 0 | — | 0 | 0 | 0 | 0 |
| 204 | 0.25 | 80 | 40 | 0 | 90 | — | 0 | — | 0 | 40 | 0 | 60 | 0 | 0 | — | 0 | 0 | 0 | 0 |
| 205 | 0.25 | 100 | 100 | 90 | 100 | 100 | 75 | — | 100 | 95 | 50 | — | 0 | 50 | — | 0 | 50 | 0 | 70 |
| 206 | 0.5 | 100 | 100 | 100 | 100 | 50 | 35 | — | 100 | 0 | 0 | — | 0 | 40 | — | 40 | 0 | 60 | 97 |
| 208 | 0.25 | 100 | 100 | 45 | 100 | 90 | 40 | — | 90 | 0 | 0 | 30 | 0 | 0 | — | 0 | 0 | 0 | 60 |
| 209 | 10 | 100 | — | — | — | — | 100 | 100 | 90 | — | — | — | — | 70 | 100 | — | 70 | 50 | — |
| 211 | 10 | 90 | — | — | — | — | 80 | 80 | 95 | — | — | — | — | — | 80 | — | 50 | 90 | — |
| 212 | 1 | 30 | 30 | 70 | 90 | 30 | 0 | — | 40 | 10 | 0 | 0 | 0 | 0 | — | 0 | 0 | 0 | 0 |
| 213 | 0.125 | 100 | — | 70 | 100 | 90 | 80 | — | 100 | 100 | 10 | 100 | 70 | 80 | — | 80 | 50 | 100 | — |
|  | 0.031 | 50 | — | 0 | 60 | 90 | 50 | — | 100 | 10 | 0 | 50 | 0 | 0 | — | 50 | 0 | 0 | — |
| 214 | 0.25 | 100 | 100 | 100 | 100 | 100 | 100 | — | 100 | 100 | 100 | 100 | 100 | 100 | — | 100 | 100 | 100 | 100 |
|  | 0.031 | 100 | 100 | 50 | 100 | 100 | 70 | — | 100 | 90 | 80 | 100 | 100 | 70 | — | 90 | 100 | 100 | 70 |
| 215 | 0.25 | 100 | 100 | 100 | 100 | 100 | 100 | — | 100 | 100 | 100 | 100 | 100 | 100 | — | 100 | 100 | 100 | 100 |
|  | 0.031 | 70 | 100 | 70 | 100 | 100 | 100 | — | 100 | 70 | 60 | 100 | 50 | 10 | — | 90 | 50 | 90 | 95 |
| 216 | 0.25 | 100 | 20 | 70 | 100 | 100 | 90 | — | 100 | 100 | 90 | 100 | 100 | 75 | — | 100 | 100 | 100 | 70 |
|  | 0.063 | 50 | 0 | 10 | 70 | 100 | 50 | — | 70 | 50 | 50 | 50 | 100 | 70 | — | 70 | 90 | 100 | 70 |
| 217 | 0.25 | 100 | 100 | 100 | 100 | 100 | 100 | — | 100 | 50 | 90 | 100 | 100 | 90 | — | 100 | — | 50 | 70 |
|  | 0.125 | 100 | 100 | 100 | 100 | 100 | 100 | — | 100 | 0 | 0 | 100 | 50 | 30 | — | 90 | — | 30 | 70 |
| 218 | 0.25 | 100 | 100 | 100 | 100 | 100 | 100 | — | 100 | 0 | 0 | 95 | 0 | 0 | — | 50 | — | 50 | 50 |
| 219 | 0.25 | 100 | 100 | 100 | 100 | 100 | 100 | — | 100 | 100 | 50 | 100 | 100 | 100 | — | 100 | — | 100 | 100 |
|  | 0.031 | 100 | 100 | 30 | 100 | 100 | 100 | — | 100 | 70 | 10 | 70 | 100 | 0 | — | 100 | — | 70 | 70 |
| 220 | 0.25 | 100 | 100 | 90 | 100 | 100 | 70 | — | 100 | 100 | 50 | 100 | 100 | 90 | — | 100 | — | 100 | 100 |
|  | 0.063 | 50 | 80 | 0 | 100 | 90 | 30 | — | 100 | 50 | 50 | 10 | 100 | 90 | — | 90 | — | 100 | 50 |
| 221 | 0.25 | 100 | 100 | 100 | 100 | 100 | 100 | — | 100 | 90 | 100 | 100 | 90 | 100 | — | 70 | — | 100 | 100 |
|  | 0.031 | 70 | 60 | 0 | 70 | 75 | 90 | — | 100 | 0 | 0 | 30 | 0 | 90 | — | 0 | — | 50 | 70 |
| 222 | 0.25 | 100 | 100 | 100 | 100 | 100 | 90 | — | 100 | 40 | 90 | 50 | 0 | 0 | — | 100 | — | 30 | 50 |

-continued
PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| | 0.125 | 100 | 100 | 60 | 100 | 100 | 90 | — | 100 | 0 | 100 | 30 | 0 | 0 | — | 70 | — | 30 | 50 |
| 223 | 0.25 | 100 | 100 | 100 | 100 | 100 | 100 | — | 100 | 100 | 95 | 100 | 100 | 100 | — | 100 | 80 | 100 | 100 |
| | 0.031 | 95 | 100 | 100 | 100 | 100 | 100 | — | 100 | 90 | 100 | 100 | 90 | 100 | — | 100 | 80 | 75 | 75 |
| 227 | 0.25 | 60 | 100 | 0 | 100 | 100 | 70 | — | 30 | 40 | 50 | 100 | 90 | 50 | — | 70 | — | 90 | 100 |
| 228 | 0.25 | 90 | 80 | 20 | 100 | 100 | 70 | — | 90 | 50 | — | 100 | 50 | 90 | — | 90 | — | 50 | 50 |
| 229 | 0.25 | 100 | 100 | 30 | 100 | 90 | 100 | — | 90 | 40 | 10 | 90 | 0 | 0 | — | 0 | — | 0 | 100 |
| 230 | 0.25 | 100 | 90 | 20 | 100 | 100 | 90 | — | 90 | 90 | 50 | 100 | 30 | 100 | — | 90 | — | 80 | 100 |
| | 0.063 | 80 | 30 | 0 | 100 | 100 | 30 | — | 90 | 40 | 50 | 70 | 30 | 0 | — | 70 | — | 30 | 50 |
| 231 | 0.063 | 100 | 100 | 20 | 100 | 100 | 100 | — | 75 | 100 | — | 100 | 80 | 95 | — | 100 | 50 | 95 | 90 |
| 232 | 10 | 90 | — | — | — | — | 80 | 98 | 98 | — | — | — | — | 40 | 90 | — | 40 | 98 | — |
| 233 | 1 | 80 | 100 | 20 | 80 | 90 | 70 | — | 70 | 0 | 0 | 0 | 0 | 0 | — | 0 | 0 | 0 | 0 |
| 234 | 2 | 80 | 100 | 0 | 0 | 40 | 0 | — | 0 | 10 | 0 | 30 | 0 | 0 | — | 30 | 0 | 0 | 100 |
| 235 | 0.25 | 50 | — | 0 | 50 | 50 | 90 | — | 20 | 50 | 10 | 50 | 50 | — | — | 0 | — | 20 | 0 |
| 236 | 10 | 100 | — | — | — | — | 100 | 100 | 100 | — | — | — | — | 100 | 100 | — | 100 | 100 | — |
| 237 | 0.25 | 50 | — | 40 | 50 | 10 | 20 | — | 0 | 20 | 20 | 20 | 100 | 10 | — | 10 | — | 30 | 30 |
| 238 | 10 | 0 | — | — | — | — | 0 | 80 | 60 | — | — | — | — | 0 | 0 | — | 0 | 0 | — |
| 239 | 10 | 90 | — | — | — | — | 100 | 100 | 100 | — | — | — | — | 95 | 98 | — | 98 | 98 | — |
| 243 | 0.125 | 90 | 100 | 100 | 100 | 100 | 80 | — | 60 | 75 | 0 | 90 | 0 | 70 | — | 80 | 0 | 80 | 100 |
| 244 | 0.125 | 70 | 100 | 20 | 100 | 100 | 0 | — | 100 | 0 | 0 | 0 | 0 | 0 | — | 0 | 0 | 0 | 95 |
| 245 | 10 | 0 | — | — | — | — | 100 | 0 | 60 | — | — | — | — | 0 | 0 | — | 0 | 0 | — |
| 246 | 0.25 | 80 | 80 | 90 | 90 | 0 | 0 | — | 30 | 20 | 20 | 95 | 10 | 0 | — | 20 | 40 | 20 | 20 |
| 247 | 2.0 | 80 | 100 | 100 | 100 | 100 | 0 | — | 80 | 85 | 70 | 80 | 70 | 60 | — | 90 | 90 | 70 | 30 |
| 250 | 0.5 | 0 | 100 | 0 | 30 | 0 | 10 | — | 0 | 0 | 0 | 50 | 40 | 10 | — | 30 | 100 | 0 | 0 |
| 252 | 10 | 0 | 100 | 100 | 100 | 100 | 50 | — | 0 | 80 | 100 | — | 30 | 60 | — | 50 | 50 | 80 | 90 |
| 255 | 4.0 | 60 | 90 | 15 | 80 | 40 | 0 | 95 | 0 | 0 | 10 | 30 | 0 | 0 | 0 | 40 | 60 | 0 | 15 |
| 257 | 10 | 90 | — | — | — | — | 80 | 100 | 90 | — | — | — | — | 0 | 30 | — | 0 | 30 | 0 |
| 258 | 2.0 | 0 | 10 | 20 | 0 | 100 | 0 | 90 | 20 | 0 | 30 | 0 | 0 | 0 | 60 | 0 | 0 | 0 | 0 |
| 260 | 1.0 | 20 | 80 | 0 | 80 | 90 | 50 | — | 70 | 0 | 0 | — | 0 | 0 | — | 40 | 0 | 30 | 70 |
| 261 | 2.0 | 0 | 100 | 100 | 90 | — | 90 | — | 80 | 0 | 0 | — | 0 | 0 | — | 10 | 70 | 50 | 0 |
| 262 | 0.25 | 90 | 100 | 100 | 100 | 100 | 90 | — | 100 | 80 | 95 | — | 0 | 90 | — | 60 | 50 | 95 | 100 |
| 263 | 0.5 | 0 | 40 | 0 | 100 | 0 | 50 | — | 20 | 0 | 0 | — | 0 | 0 | — | 0 | 50 | 50 | 0 |
| 264 | 2.0 | 0 | 60 | 0 | 40 | 100 | 0 | — | 0 | 10 | 0 | — | 0 | 0 | — | 0 | 0 | 0 | 0 |
| 265 | 10 | 0 | — | — | — | — | 60 | 60 | 30 | — | — | — | — | 0 | 0 | — | 0 | 0 | — |
| 266 | 4.0 | 50 | 100 | 50 | 90 | 80 | 0 | — | 0 | 0 | 0 | 30 | 40 | 0 | — | 0 | 50 | 90 | 80 |
| 267 | 4.0 | 0 | 100 | 30 | 80 | 90 | 0 | — | 90 | 70 | 30 | 30 | 50 | 20 | — | 10 | 50 | 90 | 0 |
| 268 | 0.25 | 100 | 100 | 0 | 100 | 100 | 90 | — | 100 | 80 | 100 | 100 | — | 90 | — | 80 | 30 | 100 | 100 |
| | 0.015 | 70 | 100 | 0 | 90 | 90 | 0 | — | 20 | 0 | 0 | 60 | 0 | 40 | — | 40 | 0 | 60 | 97 |
| 269 | 0.062 | 100 | 100 | 0 | 90 | 90 | 0 | — | 90 | 0 | 0 | 70 | 0 | 20 | — | 10 | 0 | 70 | 90 |
| 270 | 2.0 | 100 | 100 | 0 | 100 | 100 | 95 | — | 98 | 90 | 100 | 98 | 70 | 98 | — | 98 | 80 | 100 | 100 |
| | 0.125 | 98 | 98 | 0 | 98 | 100 | 90 | — | 98 | 30 | 70 | 90 | 0 | 95 | — | 90 | 20 | 95 | 100 |
| 272 | 0.5 | 90 | 100 | 0 | 100 | 100 | 60 | — | 100 | 50 | 40 | 50 | 0 | 75 | — | 60 | 0 | 95 | 100 |
| | 0.25 | 80 | 100 | 0 | 100 | 90 | 40 | — | 100 | 0 | 30 | 40 | 0 | 60 | — | 40 | 0 | 90 | 100 |
| 273 | 10 | 98 | — | — | — | — | 98 | 100 | 98 | — | — | — | — | 95 | 98 | — | 90 | 100 | — |
| 274 | 2 | 100 | 100 | 20 | 100 | 100 | 90 | — | 100 | 80 | 95 | 100 | 30 | 90 | — | 80 | 20 | 100 | 100 |
| | 0.25 | 95 | 100 | 0 | 100 | 90 | 80 | — | 100 | 60 | 80 | 90 | 0 | 80 | — | 70 | 0 | 95 | 100 |
| 275 | 0.25 | 100 | 100 | 20 | 100 | 100 | 90 | — | 100 | 80 | 90 | 100 | 100 | 100 | — | 100 | — | 100 | 100 |
| | 0.063 | 80 | 100 | 0 | 95 | 50 | 50 | — | 100 | 30 | 0 | 60 | 20 | 50 | — | 90 | — | 90 | 0 |
| 276 | 0.25 | 80 | 100 | 10 | 100 | 100 | 90 | — | 100 | 60 | 90 | 100 | 80 | 100 | — | 90 | — | 100 | 100 |
| | 0.063 | 70 | 100 | 0 | 100 | 100 | 80 | — | 100 | 0 | 10 | 90 | 50 | 70 | — | 80 | — | 90 | 100 |
| 277 | 0.25 | 50 | 100 | 20 | 100 | 100 | 30 | — | 100 | 40 | 80 | 90 | 80 | 90 | — | 100 | — | 100 | 100 |
| 278 | 0.25 | 100 | 100 | 70 | 100 | 100 | 100 | — | 100 | 60 | 90 | 100 | 70 | 100 | — | 90 | — | 100 | 100 |
| | 0.063 | 100 | 100 | 0 | 100 | 60 | 100 | — | 100 | 0 | 50 | 70 | 30 | 50 | — | 90 | — | 80 | 100 |
| 279 | 0.25 | 90 | 100 | 20 | 100 | 100 | 90 | — | 100 | 80 | 100 | 100 | 90 | 100 | — | 100 | — | 100 | 100 |
| | 0.063 | 100 | 100 | 0 | 100 | 100 | 90 | — | 100 | 0 | 40 | 90 | 60 | 50 | — | 80 | — | 100 | 100 |
| 280 | 0.25 | 80 | 100 | 10 | 100 | 100 | 90 | — | 100 | 50 | 50 | 100 | 60 | 100 | — | 90 | — | 100 | 100 |
| | 0.063 | 80 | 100 | 0 | 100 | 100 | 70 | — | 100 | 10 | 50 | 50 | 90 | 50 | — | 80 | — | 100 | 100 |
| 282 | 0.25 | 100 | 100 | 50 | 100 | 100 | 80 | — | 100 | 95 | 100 | 100 | 70 | 70 | — | 100 | 100 | 100 | 100 |
| | 0.063 | 100 | 100 | 10 | 100 | 70 | 80 | — | 100 | 0 | 50 | 90 | 50 | 70 | — | 100 | 100 | 80 | 70 |
| 283 | 0.25 | 100 | 100 | 20 | 100 | 95 | 80 | — | 100 | 40 | 100 | 100 | 100 | 100 | — | 100 | — | 100 | 100 |
| | 0.063 | 100 | 100 | 0 | 100 | 70 | 70 | — | 100 | 0 | 80 | 90 | 50 | 85 | — | 90 | — | 70 | 90 |
| 284 | 0.25 | 100 | 100 | 20 | 100 | 100 | 80 | — | 100 | 85 | 100 | 100 | 100 | 100 | — | 100 | 90 | 100 | 100 |
| | 0.063 | 70 | 100 | 0 | 100 | 85 | 70 | — | 100 | 0 | 70 | 90 | 50 | 100 | — | 70 | 10 | 70 | 100 |
| 286 | 0.25 | 100 | 100 | 30 | 100 | 100 | 100 | — | 100 | 50 | 100 | 100 | 70 | 100 | — | 100 | — | 100 | 100 |
| | 0.063 | 100 | 100 | 0 | 100 | 100 | 100 | — | 100 | 0 | 95 | 30 | 0 | 95 | — | 80 | — | 100 | 85 |
| 287 | 0.25 | 100 | 100 | 30 | 100 | 100 | 100 | — | 100 | 60 | 100 | 100 | 70 | 100 | — | 100 | — | 100 | 100 |
| | 0.063 | 100 | 100 | 0 | 100 | 100 | 50 | — | 100 | 0 | 80 | 70 | 100 | 100 | — | 80 | — | 100 | 70 |
| 288 | 0.25 | 100 | 100 | 40 | 100 | 100 | 100 | — | 100 | 80 | 100 | 100 | 60 | 100 | — | 100 | 90 | 100 | 100 |
| | 0.063 | 100 | 100 | 0 | 100 | 50 | 100 | — | 100 | 0 | 100 | 95 | 0 | 75 | — | 100 | 80 | 100 | 60 |
| 289 | 0.25 | 100 | 100 | 50 | 100 | 100 | 100 | — | 100 | 95 | — | 100 | 80 | 100 | — | 100 | 100 | 100 | 100 |
| | 0.063 | 100 | 100 | 0 | 100 | 80 | 70 | — | 100 | 60 | — | 95 | 50 | 60 | — | 95 | 50 | 100 | 50 |
| 290 | 0.25 | 100 | 100 | 70 | 100 | 100 | 100 | — | 100 | 90 | 100 | 100 | 95 | 100 | — | 100 | 70 | 100 | 80 |
| | 0.063 | 100 | 100 | 20 | 100 | 100 | 40 | — | 100 | 60 | 50 | 100 | 20 | 70 | — | 100 | 20 | 90 | 50 |
| 291 | 0.25 | 100 | 100 | 20 | 100 | 100 | 90 | — | 100 | 55 | 100 | 100 | 100 | 100 | — | 100 | 70 | 100 | 100 |
| | 0.063 | 100 | 100 | 0 | 100 | 100 | 0 | — | 100 | 0 | 70 | 100 | 30 | 75 | — | 100 | 70 | 90 | 100 |
| 293 | 0.25 | 100 | 100 | 10 | 100 | 100 | 70 | — | 100 | 60 | 90 | 100 | 60 | 100 | — | 95 | 95 | 100 | 100 |
| | 0.063 | 100 | 75 | 0 | 100 | 95 | 20 | — | 80 | 0 | 100 | 60 | 0 | 20 | — | 50 | 50 | 65 | 0 |
| 297 | 0.025 | 100 | 100 | 50 | 100 | 100 | 95 | — | 100 | 80 | 100 | 100 | 60 | 100 | — | 100 | 80 | 100 | 100 |

| | | | | | | | PREEMERGENT CONTROL OF PLANT SPECIES | | | | | | | | | | | | |
|---|---|---|---|---|---|---|---|---|---|---|---|---|---|---|---|---|---|---|---|
| Com-<br>pound | Dosage<br>(lb/-<br>acre) | A | B | C | D | F | G | H | I | J | K | L | M | N | O | Q | R | P | T |
| | 0.063 | 100 | 100 | 0 | 100 | 90 | 85 | — | 100 | 0 | 50 | 90 | 20 | 65 | — | 70 | 50 | 40 | 90 |
| 298 | 0.25 | 100 | 100 | 0 | 100 | 100 | 70 | — | 100 | 40 | 95 | 95 | 50 | 100 | — | 95 | 50 | 100 | 100 |
| | 0.063 | 90 | 100 | 0 | 85 | 0 | 0 | — | 70 | 0 | 50 | 60 | 20 | 50 | — | 75 | 20 | 20 | 40 |
| 304 | 0.125 | 100 | 97 | 90 | 100 | 95 | 40 | 100 | 95 | 90 | 95 | 97 | 0 | 55 | 20 | 95 | 0 | 93 | 97 |
| | 0.031 | 70 | 95 | 40 | 100 | 20 | 0 | 100 | 60 | 0 | 10 | 10 | 0 | 0 | 0 | 10 | 0 | 20 | 35 |
| 305 | 1.0 | 97 | 97 | 95 | 100 | 80 | 90 | 100 | 95 | 90 | 98 | 100 | 0 | 93 | 50 | 95 | 0 | 50 | 100 |
| 306 | 0.125 | 90 | 100 | 70 | 90 | 100 | 40 | — | 100 | 0 | 0 | 40 | 0 | 0 | — | 80 | 0 | 20 | 70 |
| 307 | 0.250 | 70 | 100 | 60 | 85 | 55 | 100 | — | 0 | 0 | 10 | 30 | 100 | 0 | 60 | 100 | 10 | 60 | — |
| 313 | 0.250 | 90 | 0 | 0 | 0 | 0 | — | — | 0 | 0 | 0 | 0 | 0 | 0 | 0 | 50 | 0 | 0 | — |
| 314 | 0.250 | 50 | 90 | 0 | 0 | 0 | 0 | — | 0 | 60 | 0 | 0 | 0 | 0 | 0 | 0 | 0 | 0 | — |
| 317 | 0.250 | 95 | 100 | 95 | 95 | 95 | 80 | 95 | 85 | 100 | 100 | 100 | 100 | 80 | 70 | 95 | 95 | 90 | 100 |
| 318 | 0.125 | 100 | 100 | 90 | 100 | 90 | 98 | 90 | 90 | 100 | 90 | 95 | 98 | 70 | 90 | 95 | 70 | 90 | 100 |
| 319 | 0.125 | 80 | 100 | 90 | 90 | 95 | 80 | 100 | 100 | 80 | 0 | 0 | 0 | 0 | 20 | 100 | 0 | 50 | 90 |
| 320 | 0.063 | 100 | 100 | 80 | 100 | 90 | 50 | 60 | 90 | 90 | 100 | 100 | 100 | 100 | 90 | 90 | 50 | 100 | 95 |
| 321 | 0.125 | 90 | 100 | 50 | 80 | 90 | 80 | 100 | 80 | 95 | 100 | 90 | 90 | 90 | 90 | 90 | 75 | 90 | 100 |
| 322 | 0.125 | 80 | 80 | 20 | 80 | 90 | 60 | 55 | 30 | 90 | 90 | 90 | 90 | 50 | 85 | 80 | 60 | 90 | 100 |
| 323 | 0.125 | 90 | 90 | 90 | 90 | 90 | 90 | 75 | 80 | 80 | 100 | 100 | 100 | 100 | 80 | 90 | 40 | 90 | 100 |
| 324 | 0.063 | 50 | 90 | 90 | 100 | 85 | 60 | 90 | 20 | 90 | 95 | 40 | 50 | 50 | 0 | 85 | 50 | 90 | 20 |
| 325 | 0.125 | 90 | 90 | 90 | 90 | 95 | 95 | 80 | 80 | 90 | 0 | 40 | 0 | 0 | 0 | 0 | 0 | 0 | 100 |
| 326 | 10 | — | — | — | — | — | 80 | 100 | 80 | — | — | — | — | 100 | 100 | — | 100 | 100 | — |
| 327 | 10 | — | — | — | — | — | 90 | 100 | 90 | — | — | — | — | 100 | 100 | — | 100 | 100 | — |
| 328 | 0.063 | 75 | 100 | 95 | 100 | 90 | 90 | 75 | 85 | 70 | 95 | 90 | 95 | 100 | 90 | 100 | 80 | 100 | 70 |
| 329 | 0.063 | 90 | 90 | 95 | 95 | 90 | 75 | 80 | 0 | 90 | 98 | 100 | 95 | 90 | 90 | 100 | 90 | 90 | 100 |
| 330 | 0.063 | 90 | 100 | 80 | 100 | 0 | 100 | 90 | 70 | 90 | 50 | 15 | 60 | 75 | 60 | 90 | 20 | 70 | 100 |
| 331 | 0.063 | 60 | 100 | 90 | 95 | 90 | 50 | 100 | 60 | 90 | 25 | 0 | 20 | 0 | 0 | 0 | 0 | 50 | 95 |
| 332 | 0.063 | 90 | 0 | 100 | 90 | 90 | 100 | 100 | 75 | 85 | 90 | 70 | 95 | 100 | 100 | 90 | 60 | 90 | 90 |
| 333 | 10 | — | — | — | — | — | 100 | 100 | 100 | — | — | — | — | 100 | 100 | — | 100 | 100 | — |
| 334 | 0.063 | 90 | 100 | 90 | 100 | 90 | 80 | 100 | 0 | 100 | 100 | 90 | 95 | 100 | 90 | 90 | 60 | 90 | 0 |
| 335 | 0.063 | 100 | 100 | 90 | 90 | 80 | 70 | 60 | 20 | 50 | 100 | 30 | 75 | 80 | 80 | 70 | 70 | 60 | 90 |
| 336 | 0.063 | 75 | 95 | 95 | 98 | 90 | 50 | 90 | 80 | 90 | 95 | 100 | 70 | 95 | 60 | 100 | 40 | 90 | 100 |
| 337 | 0.063 | 0 | 90 | 40 | 0 | 75 | 100 | 90 | 30 | 50 | 80 | 0 | 0 | 0 | 50 | 0 | 0 | 75 | 85 |
| 338 | 0.063 | 0 | 0 | 60 | 70 | 70 | 100 | 75 | 50 | 20 | 75 | 40 | 75 | 30 | 60 | 0 | 0 | 0 | 100 |
| 339 | 0.125 | 80 | 100 | 50 | 90 | 80 | — | 70 | 20 | 90 | 35 | 0 | 25 | 0 | 25 | — | 0 | 55 | 100 |
| 341 | 10 | — | — | — | — | — | 70 | 100 | 80 | — | — | — | — | 95 | 100 | — | 50 | 80 | — |
| 342 | 0.125 | 0 | — | 0 | 25 | 50 | 0 | 90 | 0 | 50 | 0 | 0 | 0 | 0 | 0 | 60 | 0 | 90 | 95 |
| 343 | 0.125 | 0 | 70 | 15 | 0 | 35 | 0 | 0 | 0 | 0 | 0 | 30 | 20 | 0 | 45 | 50 | 0 | 70 | 95 |

Certain of the compounds of this invention have been found to be useful for the control of aquatic weeds and some of these are useful for the selective control of, e.g., barnyardgrass and yellow nutsedge in paddy fields in the presence of rice. The following example illustrate the utility of the compounds of this invention in aquatic weed control.

EXAMPLE 120

In testing for such utility, the plant species to be tested were transplanted into 16 oz. containers into about 2 inches of soil when they were in the 1-2 inch stage and then flooded to a depth of about 1 inch. An acetone concentrate of the chemical to be tested was then injected into the paddy water, the volume injected being varied as desired to provide the desired concentration. Percent control was evaluated nine days after application. The results were as follows:

| CONTROL OF AQUATIC PLANT SPECIES | | | | | |
|---|---|---|---|---|---|
| | Dosage | Plant Species | | | |
| Compound | (Kg/Ha) | K | N | S | T |
| 1 | 2.0 | 97 | 95 | 90 | 70 |
| 2 | 2.0 | 97 | 97 | 99 | 93 |
| 4 | 2.0 | 90 | 95 | 45 | 80 |
| 6 | 1.0 | 93 | 99 | 20 | 90 |
| 7 | 1.0 | 97 | 99 | 93 | 90 |
| 8 | 1.0 | 97 | 99 | 0 | 93 |
| 9 | 1.0 | 25 | 99 | 97 | 85 |
| | 0.25 | 0 | 93 | 80 | 30 |
| 10 | 1.0 | 93 | 90 | 50 | 90 |
| 12 | 1.0 | 70 | 97 | 0 | 95 |
| 13 | 0.25 | 97 | 93 | 10 | 93 |
| 15 | 4.0 | 35 | 25 | 0 | 70 |
| 17 | 4.0 | 97 | 40 | 0 | 90 |
| 22 | 0.25 | 97 | 97 | 30 | 97 |
| 25 | 0.25 | 97 | 95 | 0 | 90 |
| 26 | 0.125 | 93 | 90 | 0 | 95 |
| 31 | 0.125 | 90 | 97 | 45 | 97 |
| 32 | 0.5 | 93 | 97 | 95 | 95 |
| 33 | 1.0 | 97 | 97 | 90 | 97 |
| 38 | 0.25 | 97 | 99 | 85 | 97 |
| | 0.031 | 0 | 80 | 0 | 95 |
| 39 | 0.25 | 75 | 99 | 75 | 99 |
| | 0.031 | 0 | 20 | 0 | 85 |
| 41 | 1.0 | 97 | 99 | 95 | 80 |
| 49 | 0.5 | 97 | 97 | 97 | 99 |
| | 0.016 | 0 | 50 | 0 | 95 |
| 50 | 0.125 | 97 | 97 | 97 | 97 |
| 51 | 1.0 | 95 | 97 | 70 | 97 |
| | 0.031 | 0 | 35 | 0 | 93 |
| 53 | 0.5 | 99 | 99 | 97 | 99 |
| | 0.031 | 0 | 80 | 10 | 95 |
| 54 | 0.5 | 97 | 97 | 0 | 95 |
| 108 | 1.0 | 97 | 97 | 97 | 90 |
| 111 | 4.0 | 93 | 99 | 80 | 99 |
| 114 | 1.0 | 70 | 95 | 0 | 90 |
| | 0.25 | 0 | 80 | 0 | 65 |
| 143 | 0.5 | 95 | 99 | 97 | 97 |
| | 0.031 | 0 | 95 | 0 | 93 |
| 178 | 2.0 | 50 | 20 | 0 | 90 |
| 180 | 1.0 | 80 | 97 | 97 | 97 |
| | 0.25 | 0 | 90 | 0 | 90 |

EXAMPLE 121

A post-emergence test comparing the herbicidal activity of Compound 157 (acid) with various of its amine salts was conducted using the protocol of Example 118 except that aqueous solutions of the amine salts and a wettable powder formulation of Compound 157 were employed and only lambsquarters, morning glory, and soybeans were tested. In each case, 0.25 percent v/v of X-77 non-ionic surfactant was added. The following results were obtained at the application rates given:

| Compound | Application rates g/Ha | Percent Control |  |  |
|---|---|---|---|---|
|  |  | lambsquarters | morning glory | soybean |
| acid | 280 | 100 | 50 | 20 |
|  | 70 | 90 | 20 | 10 |
| ethanolamine | 280 | 100 | 80 | 60 |
| salt | 70 | 100 | 50 | 25 |
| ammonium salt | 280 | 100 | 70 | 60 |
|  | 70 | 80 | 50 | 40 |
| triethanolamine | 280 | 100 | 80 | 65 |
| salt | 70 | 100 | 60 | 40 |
| dimethylamine | 280 | 100 | 50 | 50 |
| salt | 70 | 100 | 60 | 20 |
| piperidine salt | 280 | 100 | 80 | 45 |
|  | 70 | 70 | 50 | 15 |

We claim:
1. A compound having the formula:

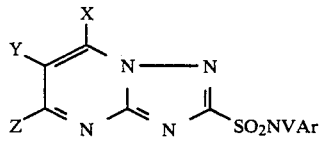

wherein Ar represents an aromatic or heteroaromatic ring chosen among phenyl; 1- or 2- naphthyl; 2-, 3-, or 4-pyridyl; 2- or 3- thienyl; 2- or 3-furyl; 2-, 4-, or 5-thiazoyl; 2, 4, or 5-imidazoyl; 2-, 4- or 5-oxazoyl; 3-, 4-, or 5-isothiazoyl; 3-, 4-, or 5-isoxazoyl; 3-, 4-, or 5-pyrazoyl; 2-benzthiazoyl; 2-benzoxazoyl; 2-benzimidazoyl; or 1-benztriazoyl; and Ar is unsubstituted except in the case of where Ar is phenyl or Ar is substituted with one to four substituents chosen from among $C_1$–$C_6$ alkyl; benzyl; halo; $C_1$–$C_6$ mono- or polyhaloalkyl; phenyl; phenyl substituted with one or more groups chosen from halo, $C_1$–$C_6$ alkyl, or $C_1$–$C_4$ haloalkyl; hydroxy; $C_1$–$C_6$ alkoxy; $C_1$–$C_6$ mono- or polyhaloalkoxy; phenoxy; phenoxy substituted with one or more groups chosen from halo, $C_1$–$C_6$ alkyl, or $C_1$–$C_4$ haloalkyl; 2-pyridyloxy; 2-pyridyloxy substituted with one or more groups chosen from halo, $C_1$–$C_6$ alkyl, or $C_1$–$C_4$ haloalkyl; amino; $C_1$–$C_6$ alkylamino; $C_1$–$C_6$ dialkylamino; nitro; $C_1$–$C_6$ alkylthio; $C_1$–$C_6$ polyhaloalkylthio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more groups chosen from halo, $C_1$–$C_6$ alkyl, or $C_1$–$C_4$ haloalkyl; phenylsulfinyl; phenysulfinyl substituted with one or more groups chosen from halo, $C_1$–$C_6$ alkyl, or $C_1$–$C_4$ haloalkyl; phenylsulfonyl; phenylsulfonyl substituted with one or more groups chosen from halo, $C_1$–$C_6$ alkyl, or $C_1$–$C_4$ haloalkyl; cyano; carboxyl; $C_1$–$C_{10}$ alkoxycarbonyl; phenoxycarbonyl; phenoxycarbonyl substituted with one or more groups chosen from halo, $C_1$–$C_6$ alkyl, or $C_1$–$C_4$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_3$–$C_6$ alkenyloxycarbonyl; COON=C($R^{14}$)($R^{14}$) wherein $R^{14}$ independently represents hydrogen, $C_1$–$C_6$ alkyl or phenyl; amino-, $C_1$–$C_6$ alkylamino- or di $C_1$–$C_6$ alkylaminocarbonyl; $C_1$–$C_{10}$ alkoxysulfonyl; $C_1$–$C_4$ polyhaloalkoxysulfonyl; di $C_1$–$C_6$ alkylaminosulfonyl; formyl; $C_1$–$C_6$ alkylcarbonyl; $C_1$–$C_6$ mono- or polyhaloalkylcarbonyl; phenylcarbonyl; phenylcarbonyl substituted with one or more groups chosen from halo, $C_1$–$C_6$ alkyl, or $C_1$–$C_4$ haloalkyl; or C($R^{15}$)($R^{15}$)O$R^{16}$ wherein each $R^{15}$ independently represents hydrogen or $C_1$–$C_6$ alkyl and $R^{16}$ represents hydrogen, $C_1$–$C_6$ alkyl, benzyl, phenylcarbonyl, or $C_1$–$C_6$ alkylcarbonyl; (except in the cases of thio, sulfinyl, and sulfonyl substituents where if one of these substituents is present the other one to three Ar substituents may not be chosen from among the other two; oxycarbonyl substituents where the other one to three Ar substituents may not be chosen from among different oxycarbonyl substituents or aminocarbonyl substituents where the other one to three Ar substituents may not be chosen from among different aminocarbonyl substituents); X, Y, and Z independently represent hydroxyl; carboxyl; hydrogen; $C_1$–$C_6$ alkyl; $C_1$–$C_6$ mono- or polyhaloalkyl; $C_1$–$C_6$ alkoxy; $C_1$–$C_6$ mono- or polyhaloalkoxy; amino; $C_1$–$C_4$ alkylamino; or di $C_1$–$C_4$ alkylamino; phenyl; phenyl substituted with one or more groups chosen from halo, nitro, $C_1$–$C_6$ alkyl, or $C_1$–$C_6$ mono- or polyhaloalkyl; $C_1$–$C_6$ alkylthio; or halo; or two adjacent substituents (i.e. X and Y or Y and Z) are joined together to form a five, six, or seven-membered saturated cyclic structure of carbon atoms or one said carbon atom of X,Y or Y,Z is replaced by a heteroatom chosen from among nitrogen, oxygen, and sulfur (i.e. X,Y or Y,Z is —(CH$_2$)$_n$ wherein n is 3, 4, or 5; or X,Y or Y,Z is —(CH$_2$)$_n$—A—(CH$_2$)—$_m$ wherein n is 0–4, the value of m is equal to the ring size minus (n+3) and A is NH, O, or S); and V is H or R and R represents $C_1$–$C_{10}$ alkyl, $C_3$–$C_{10}$ alkenyl, $C_3$–$C_{10}$ alkynyl, phenylalkyl, $C_2$–$C_{10}$ alkanoyl, $C_1$–$C_{10}$ alkoxycarbonyl, phenoxycarbonyl, di $C_1$–$C_6$ alkylaminocarbonyl, $C_1$–$C_6$ alkylsulfonyl, phenylsulfonyl, $C_1$–$C_{10}$ alkoxythiocarbonyl or phenoxythiocarbonyl wherein alkyl, alkenyl, alkynyl and alkoxy in each instance is optionally substituted by halo and each phenyl moiety is optionally substituted by one or two groups selected from halo, nitro, $C_1$–$C_4$ alkyl, and $C_1$–$C_4$ haloalkyl; and, when V represents hydrogen, agriculturally acceptable salts thereof.

2. A compound of claim 1 wherein Ar represents substituted phenyl; or substituted or unsubstituted 1- or 2-naphthyl, 2-, 3- or 4-pyridyl 2- or 3-thienyl, or 3-, 4- or 5-pyrazolyl.

3. A compound of claim 2 wherein Ar represents substituted phenyl, substituted 1-naphthyl or substituted 3-, 4-, or 5-pyrazolyl.

4. A compound of claim 3 wherein Ar is

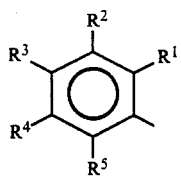

wherein $R^1$, $R^2$, $R^3$, $R^4$ and $R^5$ independently represent hydrogen; $C_1$–$C_6$ alkyl; benzyl; halo; $C_1$–$C_6$ mono- or polyhaloalkyl; phenyl; phenyl substituted with one or more groups chosen from halo, $C_1$–$C_6$ alkyl, or $C_1$–$C_4$ haloalkyl; hydroxy, $C_1$–$C_6$ alkoxy; $C_1$–$C_6$ mono- or polyhaloalkoxy; phenoxy; phenoxy substituted with one or more groups chosen from halo, $C_1$–$C_6$ alkyl, or $C_1$–$C_4$ haloalkyl; 2-pyridyloxy; 2-pyridyloxy substituted with one or more groups chosen from halo, $C_1$–$C_6$ alkyl, or $C_1$–$C_4$ haloalkyl; amino; $C_1$–$C_6$ alkylamino; $C_1$–$C_6$ dialkylamino; nitro; $C_1$–$C_6$ alkylthio; $C_1$–$C_6$ polyhaloalkylthio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more groups chosen from halo, $C_1$–$C_6$ alkyl; or $C_1$–$C_4$ haloalkyl; phenylsulfinyl; phenylsulfinyl substituted with one or more groups chosen from halo, $C_1$–$C_6$ alkyl, or $C_1$–$C_4$ haloalkyl; phenylsulfonyl; phenylsulfonyl substituted with one or more groups chosen from halo, $C_1$–$C_6$ alkyl, or $C_1$–$C_4$ haloalkyl; cyano; carboxyl; $C_1$–$C_{10}$ alkoxycarbonyl; phenoxycarbonyl; phenoxycarbonyl substituted with one or more groups chosen from halo, $C_1$–$C_6$ alkyl, or $C_1$–$C_4$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_3$–$C_6$ alkenyloxycarbonyl; $COON=C(R^{14})(R^{14})$ wherein each $R^{14}$ independently represents hydrogen, $C_1$–$C_6$ alkyl or phenyl; amino-, $C_1$–$C_6$ alkylamino- or di $C_1$–$C_6$ alkylaminocarbonyl; $C_1$–$C_{10}$ alkoxysulfonyl; $C_1$–$C_4$ polyhaloalkoxysulfonyl; di $C_1$–$C_6$ alkylaminosulfonyl; formyl; $C_1$–$C_6$ alkylcarbonyl; $C_1$–$C_6$ mono- or polyhaloalkylcarbonyl; phenylcarbonyl; phenylcarbonyl substituted with one or more groups chosen from halo, $C_1$–$C_6$ alkyl, or $C_1$–$C_4$ haloalkyl; or $C(R^{15})(R^{15})OR^{16}$ wherein each $R^{15}$ independently represents hydrogen or $C_1$–$C_6$ alkyl and $R^{16}$ represents hydrogen, $C_1$–$C_6$ alkyl, benzyl, phenylcarbonyl, or $C_1$–$C_6$ alkylcarbonyl (except in the case of thio, sulfinyl, or sulfonyl substituents where if one of these substituents is present the other one to three Ar substituents may not be chosen from among the other two; oxycarbonyl substituents where other Ar the substituents may not be chosen from among different oxycarbonyl substituents or aminocarbonyl substituents where the other substituents may not be chosen from among different aminocarbonyl substituents) with the proviso that at least 1, but no more than 4 of $R^1$, $R^2$, $R^3$, $R^4$, and $R^5$ represents hydrogen.

5. A compound of claim 4 wherein Ar is

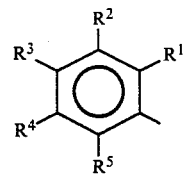

wherein $R^1$ represents F, Cl, Br, I, $-NO_2$, phenyl, phenoxy, (optionally substituted by one or more groups selected from F, Cl, Br, I, $C_1$–$C_4$ alkyl, and $C_1$–$C_4$ haloalkyl), $-CF_3$, $-OCF_3$, $-OCF_2CF_2H$, $-OCF_2CCl_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $-COOR^7$, $-CONH_2$, $-CONHR^8$, $-CONR^8R_8$, $-SO_3R^8$ and $-SO_3CH_2CF_3$; $R^2$ and $R^4$ represent H, F, Cl, Br, I, $C_1$–$C_4$ alkyl, $-COOR^7$ or $-OR^8$; $R^3$ is H; and $R^5$ represents H, phenyl, $C_1$–$C_4$ alkyl, $C_1$–$C_4$ alkoxy, F, Cl, Br, I, $NO_2$, $CF_3$, $-OCF_3$, $-OCF_2CF_2H$, $-OCF_2CCL_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $-COOR^7$, $-CONH_2$, $-CONHR^8$, $-CONR^8R^8$, $-SO_3R^8$, $-SO_3CH_2CF_3$, or $-CR^6R^6OR^6$, wherein $R^6$ represents H or $C_1$–$C_4$ alkyl, $R^7$ represents $C_1$–$C_6$ alkyl, $C_3$–$C_4$ alkenyl, $C_3$–$C_4$ alkynyl, $C_1$–$C_4$ alkoxy-$C_2$–$C_3$ alkyl, phenyl (optionally substituted by one or two groups selected from F, Cl, Br, I, $C_1$–$C_4$ alkyl, and $C_1$–$C_4$ haloalkyl), or 2-pyridylmethyl and $R^8$ represents $C_1$–$C_4$ alkyl; with the proviso that when $R^1$ and $R^5$ both represent a sulfur-containing substituent, the sulfur atoms in both are in the same oxidation state.

6. A compound of claim 5 wherein Ar is

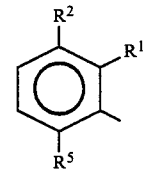

wherein $R^1$ represents $C_1$–$C_4$ alkyl, F, Cl, Br, I, $NO_2$, $SR^6$, $SOR^6$, $SO_2R^6$, $COOR^7$ or $CF_3$; $R^2$ represents H, F, Cl, Br, I, $C_1$–$C_4$ alkyl or $COOR^7$ and $R^5$ represents H, $C_1$–$C_4$ alkyl, $C_1$–$C_4$ alkoxy, F, Cl, Br, I, $-CH_2OR^6$, phenyl, $NO_2$ or $COOR^7$, wherein $R^6$ represents $C_1$–$C_4$ alkyl and $R7$ represents $C_1$–$C_4$ alkyl, $C_3$–$C_4$ alkenyl, $C_3$–$C_4$ alkynyl, 2-ethoxyethyl or 2-pyridylmethyl.

7. A compound of claim 3 wherein Ar is

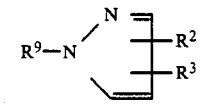

wherein $R^9$ is H or $C_1$–$C_6$ alkyl and $R^2$ and $R^3$ independently represent hydrogen; $C_1$–$C_6$ alkyl; benzyl; halo; $C_1$–$C_6$ mono- or polyhaloalkyl; phenyl; phenyl substituted with one or more groups selected from halo, $C_1$–$C_6$ alkyl, and $C_1$–$C_6$ haloalkyl; hydroxy; $C_1$–$C_6$ alkoxy; $C_1$–$C_6$ mono- or polyhaloalkoxy; phenoxy; phenoxy substituted with one or more groups chosen from halo, $C_1$–$C_6$ alkyl, or $C_1$–$C_6$ haloalkyl; 2-pyridyloxy; 2-pyridyloxy substituted with one or more groups chosen from halo, $C_1$–$C_6$ alkyl, or $C_1$–$C_6$ haloalkyl; amino; $C_1$–$C_6$ alkylamino, $C_1$–$C_6$ dialkylamino, nitro; $C_1$–$C_6$ alkythio; $C_1$–$C_6$ polyhaloalkythio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more groups chosen from halo, $C_1$–$C_6$ alkyl, or $C_1$–$C_6$ haloalkyl; phenylsulfinyl; phenylsulfinyl substituted with one or more groups chosen from halo, $C_1$–$C_6$ alkyl, or $C_1$–$C_6$ haloalkyl; phenylsulfonyl; phenylsulfonyl substituted with one or more of groups chosen from halo, $C_1$–$C_6$ alkyl, or $C_1$–$C_6$ haloalkyl; cyano; carboxyl; $C_1$–$C_{10}$ alkoxycarbonyl; phenoxycarbonyl; phenoxycarbonyl substituted with one or more groups chosen from halo, $C_1$–$C_6$ alkyl, or $C_1$–$C_6$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_3$–$C_6$ alkenyloxycarbonyl; $COON=C(R^{14})(R^{14})$ wherein each $R^{14}$ independently represents hydrogen, $C_1$–$C_6$ alkyl or phenyl; amino-, $C_1$–$C_6$ alkylamino- or di $C_1$–$C_6$ alkylaminocarbonyl; $C_1$–$C_{10}$ alkoxysulfonyl; $C_1$–$C_4$ polyhaloalkoxysulfonyl; $C_1$–$C_6$ dialkylaminosulfonyl; formyl $C_1$–$C_6$ alkylcarbonyl; $C_1$–$C_6$ mono- or polyhaloalkylcarbonyl; phenylcarbonyl; phenylcarbonyl substituted with one or more groups chosen from halo, $C_1$–$C_6$ alkyl, or $C_1$–$C_6$ haloalkyl; or $C(R^{15})OR^{16}$ wherein each $R^{15}$ independently represents hydrogen or $C_1$–$C_6$ alkyl and $R^{16}$ represents hydrogen, $C_1$–$C_6$ alkyl, benzyl, phenylcarbonyl, or $C_1$–$C_6$ alkylcarbonyl (except in the case of thio, sulfinyl, or sulfonyl substituents where if one of these substituents is present the other Ar substituent may not be chosen from among the other two; oxycarbonyl substituents where the substituents may not be chosen from among different oxycarbonyl substituents or aminocarbonyl substituents where the substituents may not be chosen from among different aminocarbonyl substituents).

8. A compound of claim 7 wherein $R^9$ represents $C_1$–$C_4$ alkyl and $R^2$ and $R^3$ each, independently, represents hydrogen, $C_1$–$C_4$ alkyl, benzyl, F, Cl, Br, I, $NO_2$, $CF_3$, $OCF_3$, $C_1$–$C_4$ alkoxy, $C_1$–$C_{10}$ alkyloxycarbonyl, $C_3$–$C_6$ alkenyloxycarbonyl, benzyloxycarbonyl, or amino-, $C_1$–$C_4$ alkylamino-, or di $C_1$–$C_4$ alkylaminocarbonyl.

9. A compound of claim 1 wherein X, Y, and independently represent H, F, Cl, Br, I, $C_1$–$C_4$ alkyl, $C_1$–$C_4$ alkoxy, $C_1$–$C_4$ alkylthio, or $C_1$–$C_4$ haloalkyl.

10. A compound of claim 9 wherein X represents hydrogen, $CH_3$, $CF_3$, $OCH_3$, $OC_2H_5$, or $SCH_3$.

11. A compound of claim 9 wherein Y represents hydrogen, Cl, or $CH_3$.

12. A compound of claim 9 wherein Z represents hydrogen, $CH_3$ or $OCH_3$.

13. A compound of claim 6 wherein $R^1$ represents F, Cl, Br, $CF_3$, $NO_2$, or $C_1$–$C_4$ alkoxycarbonyl.

14. A compound of claim 6 wherein $R^2$ represents hydrogen or $CH_3$.

15. A compound of claim 6 wherein $R^5$ represents hydrogen, F, Cl, Br, $OCH_3$, or $CH_3$.

16. A compound of claim 6 wherein X represents hydrogen, $CH_3$, $CF_3$, $OCH_3$, $OC_2H_5$, or $SCH_3$; Y represents hydrogen, Cl, or $CH_3$; Z represents hydrogen, $CH_3$, or $OCH_3$; $R^1$ represents F, Cl, Br, $CF_3$, $NO_2$, or $C_1$–$C_4$ alkoxycarbonyl; $R^2$ represents hydrogen or $CH_3$; and $R^5$ represents hydrogen, F, Cl, Br, $OCH_3$, or $CH_3$.

17. A compound of claim 8 wherein $R^9$ represents $CH_3$ or $C_2H_5$.

18. A compound of claim 8 wherein $R^2$ and $R^3$ independently represent hydrogen, $CH_3$, $CF_3$, Cl, Br or $C_1$–$C_4$ alkoxycarbonyl.

19. A compound of claim 8 wherein $R^9$ represents $CH_3$ or $C_2H_5$, $R^2$ and $R^3$ independently represent hydrogen, $CH_3$, $CF_3$, Cl, Br or $C_1$–$C_4$ alkoxycarbonyl, X represents hydrogen, $CH_3$, $CF_3$, $OCH_3$, $OC_2H_5$ or $SCH_3$; Y represents hydrogen Cl, or $CH_3$; and Z represents hydrogen, $CH_3$, or $OCH_3$.

20. A compound of claim 1 wherein V represents hydrogen.

21. A compound of claim 1 wherein V represents $C_1$–$C_4$ alkyl, allyl, benzyl, $C_2$–$C_4$ alkanoyl, $C_2$–$C_3$ haloalkanoyl, benzoyl, $C_1$–$C_4$ alkoxycarbonyl, phenoxycarbonyl, di $C_1$–$C_4$ alkylaminocarbonyl, $C_1$–$C_4$ alkoxythiocarbonyl, $C_1$–$C_4$ alkylsulfonyl, $C_1$–$C_2$ haloalkylsulfonyl, or phenylsulfonyl, sulfonyl, each phenyl optionally substituted by one or two groups chosen from among halo, nitro, methyl, and trifluoromethyl.

22. A compound according to claim 21 wherein V represents $C_2$–$C_4$ alkanoyl, $C_1$–$C_4$ alkoxycarbonyl, or di $C_1$–$C_4$ alkylaminocarbonyl.

23. A compound according to claim 3 wherein V represents hydrogen.

24. A compound according to claim 3 wherein V represents $C_2$–$C_4$ alkanoyl, $C_1$–$C_4$ alkoxycarbonyl, or di $C_1$–$C_4$ alkylaminocarbonyl.

25. A compound according to claim 6 wherein V represents hydrogen.

26. A compound according to claim 6 wherein V represents $C_2$–$C_4$ alkanoyl, $C_1$–$C_4$ alkoxycarbonyl, or di $C_1$–$C_4$ alkylaminocarbonyl.

27. A compound according to claim 8 wherein V represents hydrogen.

28. A compound according to claim 8 wherein V represents $C_2$–$C_4$ alkanoyl, $C_1$–$C_4$ alkoxycarbonyl, or di $C_1$–$C_4$ alkylaminocarbonyl.

29. A compound of claim 1 wherein the salt comprises a cation selected from the group consisting of sodium, potassium, magnesium, and ammonium of the formula

$$R^{10}R^{11}R^{12}N^{\oplus}H$$

wherein $R^{10}$, $R^{11}$, and each, independently represents hydrogen or $C_1$–$C_{12}$ alkyl, $C_3$–$C_{12}$ cycloalkyl, or $C_3$–$C_{12}$ alkenyl, each of which is optionally substituted by one or more hydroxy, $C_1$–$C_8$ alkoxy, $C_1$–$C_8$ alkylthio or phenyl groups; or wherein any two of $R^{10}$, $R^{11}$, and $R^{12}$ taken together represent an aliphatic difunctional moiety containing 1 to 12 carbon atoms and up to two oxygen or sulfur atoms.

30. A compound of claim 29 wherein the cation is sodium or potassium.

31. A compound of claim 29 wherein the cation is ammonium or triethanolaminium.

32. A compound of claim 3 wherein the salt comprises a cation selected from the group consisting of sodium, potassium, magnesium, and ammonium of the formula

$$R^{10}R^{11}R^{12}N^{\oplus}H$$

wherein $R^{10}$, $R^{11}$, and $R^{12}$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups; or wherein any two of $R^{10}$, and $R^{11}$, and $R^{12}$ taken together represent an aliphatic difunctional moiety containing 1 to 12 carbon atoms and up to two oxygen or sulfur atoms.

33. A compound of claim 32 wherein the cation is sodium or potassium.

34. A compound of claim 32 wherein the cation is ammonium or triethanolaminium.

35. A compound of claim 6 wherein the salt comprises a cation selected from the group consisting of sodium, potassium, magnesium, and aminium of the formula

wherein $R^{10}$, $R^{11}$, and $R^{12}$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups; or wherein any two of $R^{10}$, $R^{11}$, and $R^{12}$ taken together represent an aliphatic difunctional moiety containing 1 to 12 carbon atoms and up to two oxygen or sulfur atoms.

36. A compound of claim 35 wherein the cation is sodium or potassium.

37. A compound of claim 35 wherein the cation is ammonium or triethanolaminium.

38. A compound of claim 8 wherein the salt comprises a cation selected from the group consisting of sodium, potassium, magnesium, and aminium of the formula

wherein $R^{10}$, $R^{11}$, and $R^{12}$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups; or wherein any two of $R^{10}$, $R^{11}$, and $R^{12}$ taken together represent an aliphatic difunctional moiety containing 1 to 12 carbon atoms and up to two oxygen or sulfur atoms.

39. A compound of claim 38 wherein the cation is sodium or potassium.

40. A compound of claim 39 wherein the cation is ammonium or triethanolaminium.

41. A compound of claim 16 which is 5,7-di-methyl-N-(2,6-dichlorophenyl)-1,2,4-triazolo[1,5-a]pyrimidine-2-sulfonamide or an agriculturally acceptable salt thereof.

42. A compound of claim 16 which is 5-methyl-N-(2,6-dichlorophenyl)-1,2,4-triazolo[1,5-a]pyrimidine-2-sulfonamide or an agriculturally acceptable salt thereof.

43. A compound of claim 16 which is 5-methyl-N-(2-bromo-6-chlorophenyl)-1,2,4-triazolo[1,5-a]pyrimidine-2-sulfonamide or an agriculturally acceptable salt thereof.

44. A compound of claim 16 which is 5-methyl-N-(2,6-difluoro-3-methylphenyl)-1,2,4-triazolo-[1,5-a]pyrimidine-2-sulfonamide or an agriculturally acceptable salt thereof.

45. A compound of claim 16 which is 5-methyl-N-(2,6-difluorophenyl)-1,2,4-triazolo[1,5-a]-pyrimidine-2-sulfonamide or an agriculturally acceptable salt thereof.

46. A compound of claim 16 which is 5,7-dimethoxy-N-(2,6-dichloro-3-methylphenyl)-1,2,4-triazolo-[1,5-a]pyrimidine-2-sulfonamide or an agriculturally acceptable salt thereof.

47. A compound of claim 16 which is 5,7-dimethoxy-N-(2-methoxy-6-trifluoromethylphenyl)-1,2,4-triazolo-[1,5-a]pyrimidine-2-sulfonamide or an agriculturally acceptable salt thereof.

48. A compound of claim 16 which is 5-methyl-7-methylthio-N-(2,6-dichlorophenyl)-1,2,4-triazolo-[1,5-a]-pyrimidine-2-sulfonamide or an agriculturally acceptable salt thereof.

49. A compound of claim 16 which is 5-methyl-7-methylthio-N-(2-trifluoromethylphenyl)-1,2,4-triazolo-[1,5-a]pyrimidine-2-sulfonamide or an agriculturally acceptable salt thereof.

50. A compound of claim 16 which is 7-ethoxy-5-methyl-N-(2,6-dichloro-3-methylphenyl)-1,2,4-triazolo-[1,5-a]pyrimidine-2-sulfonamide or an agriculturally acceptable salt thereof.

51. A compound of claim 16 which is 5,7-dimethyl-N-(2-chloro-6-phenylphenyl)-1,2,4-triazolo[1,5-a]-pyrimidine-2-sulfonamide or an agriculturally acceptable salt thereof.

52. A compound of claim 16 which is 5-methyl-N-(2-methyl-6-nitrophenyl)-1,2,4-triazolo[1,5-a]pyrimidine-2-sulfonamide or an agriculturally acceptable salt thereof.

53. A compound of claim 16 which is 5-methyl-N-(2-chloro-6-methylphenyl)-1,2,4-triazolo[1,5-a]pyrimidine-2-sulfonamide or an agriculturally acceptable salt thereof.

54. A compound of claim 16 which is methyl 3-methyl-N-(5,7-dimethyl-1,2,4-triazolo[1,5-a]pyrimidine-2-sulfonyl)anthranilate or an agriculturally acceptable salt thereof.

55. A compound of claim 16 which is methyl 3-methyl-N-(5-methyl-7-ethoxy-1,2,4-triazolo[1,5-a]pyrimidine-2-sulfonyl)anthranilate or an agriculturally acceptable salt thereof.

56. The compound of claim 16 which is isopropyl 3-methyl-N-(5-methyl-1,2,4-triazolo[1,5-a]pyrimidine-2-sulfonyl)anthranilate or an agriculturally acceptable salt thereof.

57. A compound of claim 16 which is 6-methyl-N-(2-bromo-6-methylphenyl)-1,2,4-triazolo[1,5-a]pyrimidine-2-sulfonamide or an agriculturally acceptable salt thereof.

58. A compound of claim 16 which is 6-methyl-N-(2-fluoro-6-chlorophenyl)-1,2,4-triazolo[1,5-a]pyrimidine-2-sulfonamide or an agriculturally acceptable salt thereof.

59. A compound of claim 16 which is 6-methyl-N-(2-chloro-6-methylphenyl)-1,2,4-triazolo[1,5-a]pyrimidine-2-sulfonamide or an agriculturally acceptable salt thereof.

60. A compound of claim 16 which is 6-methyl-N-(2-methyl-6-nitrophenyl)-1,2,4-triazolo[1,5-a]pyrimidine-2-sulfonamide or an agriculturally acceptable salt thereof.

61. A compound of claim 16 which is 7-ethoxy-5-methyl-N-(2-trifluoromethylphenyl)-1,2,4-triazolo-[1,5-a]pyrimidine-2-sulfonamide or an agriculturally acceptable salt thereof.

62. A compound of claim 16 which is 7-methoxy-5-methyl-N-(2,6-dichloro-3-methylphenyl)-1,2,4-triazolo-[1,5-a]pyrimidine-2-sulfonamide or an agriculturally acceptable salt thereof.

63. A compound of claim 16 which is 7-ethoxy-5-methyl-N-(2-bromo-6-chloro-3-methylphenyl)-1,2,4-triazolo[1,5-a]pyrimidine-2-sulfonamide or an agriculturally acceptable salt thereof.

64. A compound of claim 16 which is 5,7-dimethoxy-N-(2,6-dibromo-3-methylphenyl)-1,2,4-triazolo-[1,5-a]pyrimidine-2-sulfonamide or an agriculturally acceptable salt thereof.

65. A compound of claim 16 which is 5,7-dimethoxy-N-(2,6-dichlorophenyl)-1,2,4-triazolo[1,5-a]-pyrimidine-2-sulfonamide or an agriculturally acceptable salt thereof.

66. A compound of claim 16 which is 7-methyl-N-(2,6-dichlorophenyl)-1,2,4-triazolo[1,5-a]pyrimidine-2-sulfonamide or an agriculturally acceptable salt thereof.

67. A compound of claim 16 which is N-(2,6-dichlorophenyl)-1,2,4-triazolo[1,5-a]pyrimidine-2-sulfonamide or an agriculturally acceptable salt thereof.

68. A compound of claim 16 which is 7-ethoxy-5-methyl-N-(2,6-dibromo-3-methylphenyl)-1,2,4-triazolo-[1,5-a]pyrimidine-2-sulfonamide or an agriculturally acceptable salt thereof.

69. A compound of claim 16 which is 6-chloro-N-(2,6-difluorophenyl)-1,2,4-triazolo[1,5-a]pyrimidine-2-sulfonamide or an agriculturally acceptable salt thereof.

70. A compound of claim 16 which is 5-methyl-7-trifluoromethyl-N-(2-methoxy-6-trifluoromethylphenyl)-1,2,4-triazolo[1,5-a]pyrimidine-2-sulfonamide or an agriculturally acceptable salt thereof.

71. A compound of claim 16 which is methyl 3-fluoro-N-(6-chloro-1,2,4-triazolo[1,5-a]pyrimidine-2-sulfonyl)anthranilate or an agriculturally acceptable salt thereof.

72. A compound of claim 19 which is 5,7-dimethyl-N-(1,3-dimethyl-5-trifluoromethyl-4-pyrazolyl)-1,2,4-triazolo[1,5-a]pyrimidine-2-sulfonamide or an agriculturally acceptable salt thereof.

73. A compound of claim 19 which is 5-methyl-N-(1,3-dimethyl-5-trifluoromethyl-4-pyrazolyl)-1,2,4-triazolo[1,5-a]pyrimidine-2-sulfonamide or an agriculturally acceptable salt thereof.

74. A compound of claim 19 which is 5,7-dimethyl-N-(1-methyl-4-ethoxycarbonyl-5-pyrazolyl)-1,2,4-triazolo[1,5-a]pyrimidine-2-sulfonamide or an agriculturally acceptable salt thereof.

75. A compound of claim 3 which is 5,7-dimethoxy-N-(2-chloro-1-napthyl)-1,2,4-triazolo[1,5-a]-pyrimidine-2-sulfonamide or an agriculturally acceptable salt thereof.

76. A compound of claim 3 which is 5-methyl-7-methoxy-N-(2-chloro-1-naphthyl)-1,2,4-triazolo[1,5-a]-pyrimidine-2-sulfonamide or an agriculturally acceptable salt thereof.

77. The compound of claim 3 which is 5-methyl-7-ethoxy-N-(2-chloro-1-naphthyl)-1,2,4-triazolo[1,5-a]pyrimidine-2-sulfonamide or an agriculturally acceptable salt thereof.

78. A compound of claim 26 which is 5-methyl-N-(2-methylpropanoyl)-N-(2,6-difluorophenyl)-1,2,4-triazolo[1,5-a]pyrimidine-2-sulfonamide.

79. A compound of claim 26 which is 5-methyl-N-acetyl-N-(2,6-dichlorophenyl)-1,2,4-triazolo[1,5-a]pyrimidine-2-sulfonamide.

80. A compound having the formula

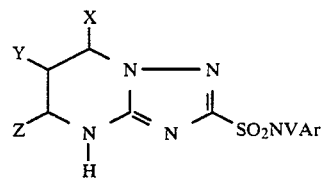

wherein Ar, X, Y, Z, and V are as defined in claim 1.

81. A compound of claim 80 wherein Ar is as defined in claim 2.

82. A compound of claim 81 wherein Ar is as defined in claim 3.

83. A compound of claim 82 wherein Ar is as defined in claim 4.

84. A compound of claim 83 wherein Ar is as defined in claim 5.

85. A compound of claim 84 wherein Ar is as defined in claim 6.

86. A compound of claim 85 wherein Ar is as defined in claim 7.

87. A compound of claim 80 wherein X, Y, and Z are as defined in claim 9.

88. A compound of claim 85 wherein X, Y, and Z and $R^1$, $R^2$, and $R^5$ of Ar are as defined in claim 16.

89. A compound of claim 86 wherein X, Y, and Z and $R^2$, $R^3$, and $R^9$ of Ar are as defined in claim 19.

90. A compound of claim 80 wherein V represents hydrogen.

91. A compound of claim 80 wherein V represents $C_1$–$C_4$ alkyl, allyl, benzyl, $C_2$–$C_4$ alkanoyl, $C_2$–$C_3$ haloalkanoyl, benzoyl, $C_1$–$C_4$ alkoxycarbonyl, phenoxycarbonyl, di $C_1$–$C_4$ alkylaminocarbony, $C_1$–$C_4$ alkyloxythiocarbonyl, $C_1$–$C_4$ alkylsulfonyl, $C_1$–$C_2$ haloalkylsulfonyl, or phenylsulfonyl, each phenyl optionally substituted by one or two groups chosen from among halo, nitro, methyl, and trifluoromethyl.

92. A compound of claim 91 wherein V represents $C_1$–$C_4$ alkanoyl, $C_1$–$C_4$ alkoxycarbonyl, or di $C_1$–$C_4$ alkylaminocarbonyl.

93. A composition comprising an inert carrier in admixture with an herbicidally effective amount of a compound of claim 1.

94. A composition comprising an inert carrier in admixture with an herbicidally effective amount of a compound of claim 2.

95. A composition comprising an inert carrier in admixture with an herbicidally effective amount of a compound of claim 3.

96. A composition comprising an inert carrier in admixture with an herbicidally effective amount of a compound of claim 4.

97. A composition comprising an inert carrier in admixture with an herbicidally effective amount of a compound of claim 5.

98. A composition comprising an inert carrier in admixture with an herbicidally effective amount of a compound of claim 6.

99. A composition comprising an inert carrier in admixture with an herbicidally effective amount of a compound of claim 7.

100. A composition comprising an inert carrier in admixture with an herbicidally effective amount of a compound of claim 8.

101. A composition comprising an inert carrier in admixture with an herbicidally effective amount of a compound of claim 9.

102. A composition comprising an inert carrier in admixture with an herbicidally effective amount of a compound of claim 10.

103. A composition comprising an inert carrier in admixture with an herbicidally effective amount of a compound of claim 11.

104. A composition comprising an inert carrier in admixture with an herbicidally effective amount of a compound of claim 12.

105. A composition comprising an inert carrier in admixture with an herbicidally effective amount of a compound of claim 13.

106. A composition comprising an inert carrier in admixture with an herbicidally effective amount of a compound of claim 14.

107. A composition comprising an inert carrier in admixture with an herbicidally effective amount of a compound of claim 15.

108. A composition comprising an inert carrier in admixture with an herbicidally effective amount of a compound of claim 16.

109. A composition comprising an inert carrier in admixture with an herbicidally effective amount of a compound of claim 17.

110. A composition comprising an inert carrier in admixture with an herbicidally effective amount of a compound of claim 18.

111. A composition comprising an inert carrier in admixture with an herbicidally effective amount of a compound of claim 19.

112. A composition comprising an inert carrier in admixture with an herbicidally effective amount of a compound of claim 20.

113. A composition comprising an inert carrier in admixture with an herbicidally effective amount of a compound of claim 21.

114. A composition comprising an inert carrier in admixture with an herbicidally effective amount of a compound of claim 22.

115. A composition comprising an inert carrier in admixture with an herbicidally effective amount of a compound of claim 23.

116. A composition comprising an inert carrier in admixture with an herbicidally effective amount of a compound of claim 24.

117. A composition comprising an inert carrier in admixture with an herbicidally effective amount of a compound of claim 25.

118. A composition comprising an inert carrier in admixture with an herbicidally effective amount of a compound of claim 26.

119. A composition comprising an inert carrier in admixture with an herbicidally effective amount of a compound of claim 27.

120. A composition comprising an inert carrier in admixture with an herbicidally effective amount of a compound of claim 28.

121. A composition comprising an inert carrier in admixture with an herbicidally effective amount of a compound of claim 29.

122. A composition comprising an inert carrier in admixture with an herbicidally effective amount of a compound of claim 30.

123. A composition comprising an inert carrier in admixture with an herbicidally effective amount of a compound of claim 31.

124. A composition comprising an inert carrier in admixture with an herbicidally effective amount of a compound of claim 32.

125. A composition comprising an inert carrier in admixture with an herbicidally effective amount of a compound of claim 33.

126. A composition comprising an inert carrier in admixture with an herbicidally effective amount of a compound of claim 34.

127. A composition comprising an inert carrier in admixture with an herbicidally effective amount of a compound of claim 35.

128. A composition comprising an inert carrier in admixture with an herbicidally effective amount of a compound of claim 36.

129. A composition comprising an inert carrier in admixture with an herbicidally effective amount of a compound of claim 37.

130. A composition comprising an inert carrier in admixture with an herbicidally effective amount of a compound of claim 38.

131. A composition comprising an inert carrier in admixture with an herbicidally effective amount of a compound of claim 39.

132. A composition comprising an inert carrier in admixture with an herbicidally effective amount of a compound of claim 40.

133. A composition comprising an inert carrier in admixture with an herbicidally effective amount of a compound of claim 80.

* * * * *

UNITED STATES PATENT AND TRADEMARK OFFICE
CERTIFICATE OF CORRECTION

PATENT NO. : 4,954,163
DATED : September 4, 1990
INVENTOR(S) : Kleschik et al.

It is certified that error appears in the above-identified patent and that said Letters Patent is hereby corrected as shown below:

Cover Page, in the Title, before "SUBSTITUTED" insert -- NOVEL --;

Col. 1, line 2, before "SUBSTITUTED" insert -- NOVEL --;

Col. 5, line 4, delete the second reference to "--$SOR^6$" and insert -- --$SO_2R^6$ --;

Col. 7, line 41, delete "6-N-" and insert -- 6-Methyl-N- --;

Col. 14, line 61, delete ($<m^{VII}$) and insert -- ($Mn^{VII}$) --;

Col. 16, line 35, delete "halo FF" and insert -- halo $CF$ --;

Col. 20, line 63, delete "Compounds38" and insert -- Compounds --;

Col. 22, line 28, after "Formula" insert -- I --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 24, line 49, delete "613.9" and insert -- 13.9 --;

Col. 24, line 52, delete "cm1" and insert -- $cm^{-1}$ --;

Col. 24, line 53, delete "ocetir";

Col. 24, line 57, delete "$C_7C_8N_4S$" and insert -- $C_7H_8N_4S$ --;

Col. 25, line 30, delete "δ0-7.6" and insert -- δ7.0-7.6 --;

Col. 26, line 61, delete "°C" and insert -- 65°C --;

Col. 31, line 56, delete "$C_{14}H_{14}N_4S$:" and insert -- $C_{14}H_{14}N_4OS$: --;

Col. 34, line 5, after "cyclopentano-" insert -- 7-methyl-1, --;

UNITED STATES PATENT AND TRADEMARK OFFICE
CERTIFICATE OF CORRECTION

PATENT NO. : 4,954,163
DATED : September 4, 1990
INVENTOR(S) : Kleschik et al.

Page 3 of 9

It is certified that error appears in the above-identified patent and that said Letters Patent is hereby corrected as shown below:

Col. 34, line 31, delete "20" --;

Col. 36, line 15, after "-methyl-" insert --1,2,4-triazolo--.

Col. 37, line 44, delete "tri-azoloa]" and insert -- triazolo[1,5-a] --;

Col. 38, line 58, delete "$C_8H_9ClN_4O_2S$:" and insert -- $C_7H_7ClN_4O_3S$: --;

Col. 40, line 52, after "58" insert -- Preparation --;

Col. 40, line 55, delete "of chloroaniline" and insert -- of o-chloroaniline --;

Col. 44, line 38, delete "1.5.41" and insert -- 15.41 --;

Col. 46, line 10, after "(51%)" insert -- of --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 46, line 10, "desired" is misspelled;

Col. 46, line 24, delete "[1,5-apyrimiine-2-" and insert -- [1,5-a]pyrimidine-2- --;

Col. 53, line 60, delete "Example 9" and insert -- Example 94 --;

Col. 54, line 16, delete "0.55" and insert -- 0.65 --;

Col. 54, line 36, delete "2S.9" and insert -- 28.9 --;

Col. 57, line 36, after "Kugelrohr" insert -- distilled to yield the desired product as a liquid, bp --;

Col. 59, line 54, after "hours" insert -- . It was then allowed to cool to ambient temperature, --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 66, in Table I under the heading "Elemental Analysis", reference 54, delete "16.61" and insert -- 19.41 --;

Col. 69, in Table I, under the heading "Melting Point" reference 87, delete "2088" and insert -- 208 --;

Col. 69, in Table I, under the heading "Elemental Analysis" reference 87, delete "14.15" and insert -- 14.51 --;

Col. 70, in Table I, reference 96, delete "$C_{19}H_{17}N_5O_4S$:" and insert -- $C_{19}H_{17}N_5O_4S_2$: --;

Col. 76, in Table V, under the heading "Elemental Analysis" for reference 136, delete "$C_{12}H_8F_3O_2S$:" and insert -- $C_{12}H_8F_3N_5O_2S$: --;

Col. 78, in Table VI, reference 156, under the heading "Elemental Analysis" delete "$C_{14}H_{15}$" and insert -- $C_{15}H_{14}$ --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 77, in Table VI, reference 163, under the heading "Melting Point" delete "209°OC" and insert -- 209°C --;

Col. 78, in Table VI, reference 163, under the heading "Elemental Analysis" delete "$C_{12}H_7F_4N_4O_2S:$" and insert -- $C_{12}H_7F_4N_5O_2S:$ --;

Col. 77, in Table VI. reference 169, under the heading "$R^1$", delete "$CH_3$" and insert -- $CF_3$ --;

Col. 80, in Table VIII, reference 183, under the subheading "C", delete "42.70" and insert -- 43.70 --;

Col. 86, in Table XVI, under the heading "Elemental Analysis" delete, "C N H" and insert -- C H N --;

Col. 88, in Table XX, under the heading "Elemental Analysis" delete "C N H S" and insert -- C H N S --;

Col. 88, in Table XXI, reference 217, under the heading "Elemental Analysis" delete "41.64  3.28   17.56" and insert -- 42.90  3.21, and 18.48 --;

UNITED STATES PATENT AND TRADEMARK OFFICE
CERTIFICATE OF CORRECTION

PATENT NO. :  4,954,163

DATED :  September 4, 1990

INVENTOR(S) :  Kleschik et al.

Page 7 of 9

It is certified that error appears in the above-identified patent and that said Letters Patent is hereby corrected as shown below:

Col. 104, in Table XLIV, reference 286, under the sub-heading "Analysis" delete "$C_{16}H_{13}F_2O_3S$:" and insert --$C_{16}H_{13}F_2N_5O_3S$: --;

Col. 110, in Table XLVIII, reference 333, under the subheading "Analysis" after "$C_{15}H_{14}F_3N_5O_3$" insert -- S --;

Col. 113, line 63, delete "alkylalyl" and insert -- alkylaryl --;

Col. 126, in the Table "Postemergent Control of Plant Species", reference 200, under the subheading "T" delete "0" and insert -- 35 --;

Col. 129, in the Table "Postemergent Control of Plant Species", reference 293, under the subheading "D" delete "10" and insert -- 100 --;

Col. 131, in the Table "Postemergent Control of Plant Species", reference 341, under the subheading "G", delete "8" and insert -- 80 --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 134, in the Table "Postemergent Control of Plant Species" under the subheading "O" for reference 1, delete "10" and insert -- 100 --;

Col. 146, line 18, delete "CONR$^8$R$_8$" and insert --CONR$^8$R$^8$--;

Col. 146, lines 55-60, change the formula as follows:

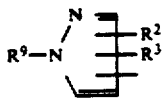

Col. 147, line 52, after "Y and" insert -- Z --;

Col. 148, line 47, delete "ammonium" and insert -- aminium --;

Col. 148, line 51, after "and" insert -- R$^{12}$ --;

UNITED STATES PATENT AND TRADEMARK OFFICE
CERTIFICATE OF CORRECTION

PATENT NO. : 4,954,163

DATED : September 4, 1990

INVENTOR(S) : Kleschik et al.

It is certified that error appears in the above-identified patent and that said Letters Patent is hereby corrected as shown below:

Col. 148, line 65, delete "ammonium" and insert -- aminium --;

Col. 152, line 34, "alkylaminocarbonyl" has been misspelled.

Signed and Sealed this

Seventh Day of July, 1992

Attest:

DOUGLAS B. COMER

*Attesting Officer*   *Acting Commissioner of Patents and Trademarks*